US008975471B2

(12) United States Patent
Reyes Taboada et al.

(10) Patent No.: US 8,975,471 B2
(45) Date of Patent: Mar. 10, 2015

(54) MICRORNAS

(75) Inventors: Jose L. Reyes Taboada, Mexico City (MX); Xiuren Zhang, New York, NY (US); Takashi Soyano, New York, NY (US); Nam-Hai Chua, New York, NY (US); Qi-Wen Niu, Staten Island, NY (US); Shih-Shun Lin, New York, NY (US)

(73) Assignee: The Rockefeller University, New York, NY (US)

( * ) Notice: Subject to any disclaimer, the term of this patent is extended or adjusted under 35 U.S.C. 154(b) by 402 days.

(21) Appl. No.: 11/247,587

(22) Filed: Oct. 12, 2005

(65) Prior Publication Data

US 2006/0130176 A1    Jun. 15, 2006

Related U.S. Application Data

(63) Continuation-in-part of application No. PCT/US2004/033379, filed on Oct. 12, 2004.

(60) Provisional application No. 60/671,089, filed on Apr. 14, 2005.

(51) Int. Cl.
*C12N 15/82* (2006.01)
*C12N 15/113* (2010.01)
*A01H 5/00* (2006.01)

(52) U.S. Cl.
CPC ........ *C12N 15/8218* (2013.01); *C12N 15/8216* (2013.01); *C12N 15/8261* (2013.01); *C12N 15/827* (2013.01); *C12N 15/8283* (2013.01)
USPC ........... 800/279; 800/285; 800/312; 800/317; 800/317.3; 800/317.4; 800/320.1; 800/320.2; 800/320.3; 800/320; 800/301; 435/468

(58) Field of Classification Search
None
See application file for complete search history.

(56) References Cited

U.S. PATENT DOCUMENTS

| 6,506,559 | B1 | 1/2003 | Fire et al. | |
|---|---|---|---|---|
| 7,071,380 | B1 * | 7/2006 | Lough et al. | 800/290 |
| 7,166,771 | B2 | 1/2007 | Eenennaam | |
| 2002/0086356 | A1 | 7/2002 | Tuschl et al. | |
| 2003/0051263 | A1 | 3/2003 | Fire et al. | |
| 2003/0055020 | A1 | 3/2003 | Fire et al. | |
| 2003/0056235 | A1 | 3/2003 | Fire et al. | |
| 2003/0108923 | A1 | 6/2003 | Tuschl et al. | |
| 2004/0053411 | A1 | 3/2004 | Cullen et al. | |
| 2004/0098761 | A1 | 5/2004 | Trick et al. | |
| 2004/0265839 | A1 | 12/2004 | Mello et al. | |
| 2004/0268441 | A1 * | 12/2004 | Vance et al. | 800/288 |
| 2005/0037988 | A1 | 2/2005 | Zamore et al. | |
| 2005/0120415 | A1 | 6/2005 | Aukerman | |
| 2005/0138689 | A1 | 6/2005 | Aukerman | |
| 2005/0144669 | A1 | 6/2005 | Reinhart et al. | |
| 2005/0181382 | A1 | 8/2005 | Zamore et al. | |
| 2005/0186586 | A1 | 8/2005 | Zamore et al. | |
| 2006/0009402 | A1 | 1/2006 | Zamore et al. | |

FOREIGN PATENT DOCUMENTS

| WO | WO 99/53050 A1 | 10/1999 |
|---|---|---|
| WO | WO 03/006477 A1 | 1/2003 |
| WO | WO 03/012052 A2 | 2/2003 |
| WO | WO 03/070918 A2 | 8/2003 |
| WO | WO 2004/066183 A2 | 8/2004 |

OTHER PUBLICATIONS

Lu et al. 2008, Biochemical and biophysical Research Communication 368:458-462.*
Bengert et al. 2005, Briefing in Bioinformatics 6:72-85.*
Vanitharani et al. 2003 PNAS 100:9632-9636.*
Kasschau et al. 2003, Developmental Cell 4:205-217.*
Tenllado et al. 2004, Virus Rearch 102 :85-96.*
Llave et al (Plant Cell, 14, pp. 1605-1619, 2002).*
Tsao et al (AF394601, 2001).*
Tomimura et al (AB093611, 2003).*
Bologna et al (EMBO, 28, pp. 3646-3656, 2009).*
Shi (Trends in Genetics, 19(1), pp. 9-12, 2003).*
Fire, A., et al., "Potent and specific genetic interference by double-stranded RNA in *Caenorhabditis elegans*", Nature, vol. 391, Feb. 19, 1998, pp. 806-811.
Ashraft, K., et al., "Genome-wide RNAi analysis of *Caenorhabditis elegans* fat regulatory genes", Nature, vol. 421, Jan. 16, 2003, pp. 268-272.
Aukerman, M., "Regulation of Flowering Time and Floral Organ Identity by a MicroRNA and Its *APETALA2*-Like Target Genes", The Plant Cell, vol. 15, Nov. 2003, pp. 2730-2741.
B77795, Rounsley, S.D, et al., A BAC End Sequence Database for Identifying Minimal Overlaps in Arabidopsis Genomic Sequencing, 1998, 1 page.
Banerjee, D., et al., "Control of developmental timing by small temporal RNAs: a paradigm for RNA-mediated regulation of gene expression", BioEssays, vol. 24, 2002, pp. 119-129.
Carrington, J.C., "Role of MicroRNAs in Plant and Animal Development", Science, vol. 301, Jul. 18, 2003, pp. 336-338.
Elbashir, S.M., "RNA interference is mediated by 21- and 22-nucleotide RNAs", Genes & Development, vol. 15, 2001, pp. 188-200.
M. Fagard, et al., "(Trans)Gene Silencing in Plants: How Many Mechanisms?", Annu. Rev. Plant Physiol. Plant Biol., 2000, vol. 51, pp. 167-194.

(Continued)

*Primary Examiner* — Elizabeth McElwain
*Assistant Examiner* — Stephen Uyeno
(74) *Attorney, Agent, or Firm* — Rothwell, Figg, Ernst & Manbeck P.C.

(57) ABSTRACT

The invention provides methods and compositions useful in target sequence suppression, target sequence validation and target sequence down regulation. The invention provides polynucleotide constructs useful for gene silencing or RNA down regulation, as well as cells, plants and seeds comprising the polynucleotides. The invention also provides a method for using microRNA to silence a target sequence or to down regulate RNA.

33 Claims, 29 Drawing Sheets

(56) References Cited

OTHER PUBLICATIONS

Hutvágner, G., et al., "A microRNA in a Multiple-Turnover RNAi Enzyme Complex", Science, vol. 297, Sep. 20, 2002, pp. 2056-2060.
Kamath, R.S., "Systematic functional analysis of the *Caenorhabditis elegans* genome using RNAi", Nature, vol. 421, Jan. 16, 2003, pp. 231-237.
Kidner, C.A., et al., "Macro effects of microRNAs in plants", Trends in Genetics, vol. 19, No. 1, Jan. 2003, pp. 13-16.
Lagos-Quinta, M., et al., "Identification of Novel Genes Coding for Small Expressed RNAs", Science, vol. 294, Oct. 26, 2001, pp. 853-857.
Lau, N.C., et al., "An Abundant Class of Tiny RNAs with Probable Regulatory Roles in *Caenorhabditis elegans*", Science, vol. 294, Oct. 26, 2001, pp. 858-862.
Lee, R.C., et al., "An Extensive Class of Small RNAs in *Caenorhabditis elegans*", Science, Vo. 294, Oct. 26, 2001, pp. 862-864.
Lee, Y., et al., "The nuclear RNase III Drosha initiates microRNA processing", Nature, vol. 425, Sep. 25, 2003, pp. 415-419.
Lim, L.P., et al., "Vertebrate MicroRNA Genes", Science, vol. 299, Mar. 7, 2003, p. 1540.
Llave, C., et al., "Cleavage of *Scarecrow-like* mRNA Targets Directed by a Class of Arabidopsis miRNA", Science, vol. 297, Sep. 20, 2002, pp. 2053-2056.
Llave, C., et al., "Endogenous and Silencing-Associated Small RNAs in Plants", The Plant Cell, vol. 14, Jul. 2002, pp. 1605-1619.
McHale, N.A., "MicroRNA-Directed Cleavage of *Nicotiana sylvestris Phavoluta* mRNA Regulates the Vascular Cambium and Structure of Apical Meristems", The Plant Cell, vol. 16, Jul. 2004, pp. 1730-1740.
Moss, E.G., et al., "MicroRNAs: Something New Under Dispatch the Sun", Current Biology, vol. 12, Oct. 15, 2002, pp. R688-R690.
Myers, J.W., "Recombinant Dicer efficiently converts large dsRNAs into siRNAs suitable for gene silencing", Nature Biotechnology, vol. 21, Mar. 2003, pp. 324-328.
Park, W., et al., "Carpel Factory, A Dicer Homolog, and HEN1, a Novel Protein, Act in microRNA Metabolism in *Arabidopsis thaliana*", Current Biology, vol. 12, Sep. 3, 2002, pp. 1484-1495.
Parizotto, E.A., et al., "In vivo investigation of the transcription, processing, endonucleolytic activity, and functional relevance of the spatial distribution of a plant miRNA", Genes & Development, vol. 18, 2oo4, pp. 2237-2242.
Pasquinelli, A.E., et al., "Control of Developmental Timing by MicroRNAs and Their Targets", Annu. Rev. Cell Dev. Biol., vol. 18, pp. 2002, pp. 495-513.
Reinhart, B.J., et al., "MicroRNAs in plants", Genes & Development, vol. 16, 2002, pp. 1616-1626.
Reinhart, B.J., et al., "The 21-nucleotide let-7 RNA regulates developmental timing in *Caenorhabditis elegans*", Nature, vol. 403, Feb. 24, 2000, pp. 901-906.
Reynolds, A., et al., "Rational siRNA design for RNA interference", Nature Biotechnology, vol. 22, No. 3, Mar. 2004, pp. 326-330.
Rhoades, M.W., "Prediction of Plant MicroRNA Targets", Cell, vol. 110, Aug. 23, 2002, pp. 513-520.

Tang, G., et al., "A biochemical framework for RNA silencing in plants", Genes & Development, vol. 17, 2003, pp. 49-63.
Tuschl, T., "RNA Interference and Small Interfering RNAs", Chembiochem, vol. 2, 2001, pp. 239-245.
Vaucheret, H., et al., "The action of *ARGONAUTE1* in the miRNA pathway and its regulation by the miRNA pathway are crucial for plant development", Genes & Development, vol. 18, 2004, pp. 1187-1197.
Voinnet, O., "RNA silencing as a plant immune system against viruses", Trends in Genetics, vol. 17, No. 8, Aug. 2001, pp. 449-459.
Waterhouse, P.M., et al., "Gene silencing as an adaptive defence against viruses", Nature vol. 411, Jun. 14, 2001, pp. 834-842.
Yoo, B.C., et al., "A systemic Small RNA Signaling System in Plants", The Plant Cell, vol. 16, Aug. 2004, pp. 1979-2000.
Zeng, Y., et al., "Both Natural and Designed Micro RNAs Can Inhibit the Expression of Cognate mRNAs when Expressed in Human Cells", Molecular Cell, vol. 9, , Jun. 2002, pp. 1327-1333.
Zeng, Y., et a., "Structural requirements for pre-microRNA binding and nuclear export by Exportin 5", Nucleic Acids Research, vol. 32, No. 16, 2004, pp. 4776-4785.
Pooggin, M., et al., "RNAi targeting of DNA virus in plants", Nature Biotechnology, vol. 21, Feb. 2003, pp. 131-132.
"RNA Goes Mobile", The Plant Cell, vol. 14, Jul. 2002, pp. 1433-1436.
Boden, D., et al. "Enhanced gene silencing of HIV-1 specific siRNA using microRNA designed hairpins", Feb. 2004, pp. 1154-1158, vol. 32(3), *Nucleic Acids Research*.
Hunter, C., et al. "miSSING Links: miRNAs and plant development", 2003, pp. 372-378, vol. 13, *Current Opinion in Genetics & Development*.
Khvorova, A., et al. "Functional siRNAs and miRNAs Exhibit Strand Bias", Oct. 2003, pp. 209-216, vol. 115, *Cell*.
McManus, M., et al. "Gene silencing using micro-RNA designed hairpins", 2002, pp. 842-850, vol. 8, *RNA*.
Mallory, A.C. et al., "MicroRNAs: something important between the genes," Current Opinion in Plant Biology, Quadrant Subscription Services, GB, vol. 7, No. 2, Apr. 1, 2004, pp. 120-125, XP002387506.
Niu, Qi-Wen et al., "Expression of artificial microRNAs in transgenic *Arabidopsis thaliana* confers virus resistance," Nature Biotechnology, vol. 24, No. 11, Nov. 2006, pp. 1420-1428, XP002514067.
Chapman, E.J., et al., "Viral RNA silencing suppressors inhibit the microRNA pathway at an intermediate step," Genes Dev. 2004, vol. 18, pp. 1179-1186.
Savenkov, E.I., "Silencing of a viral RNA silencing suppressor in transgenic plants," Journal of General Virology, 2002, vol. 83, pp. 2325-2335.
Anandalakshmi, R. et al., "A viral suppressor of gene silencing in plants," Proc. Natl. Acad. Sci., USA, vol. 95, pp. 13079-13084, Oct. 1998, Genetics, copyright 1998 by The National Academy of Sciences.
Mallory, A.C. et al., "HC-Pro suppression of transgene silencing eliminates the small RNAs but not transgene methylation or the mobile signal," The Plant Cell, vol. 13, pp. 571-583, Mar. 2001, www.plantcell.org, copyright 2001 American Society of Plant Physiologists.

* cited by examiner

Figure 6
A
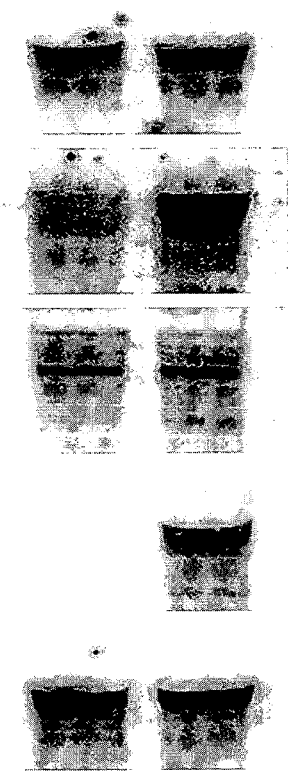
B
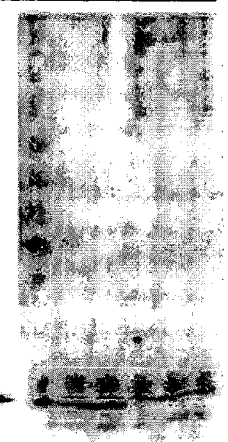

Figure 7
A
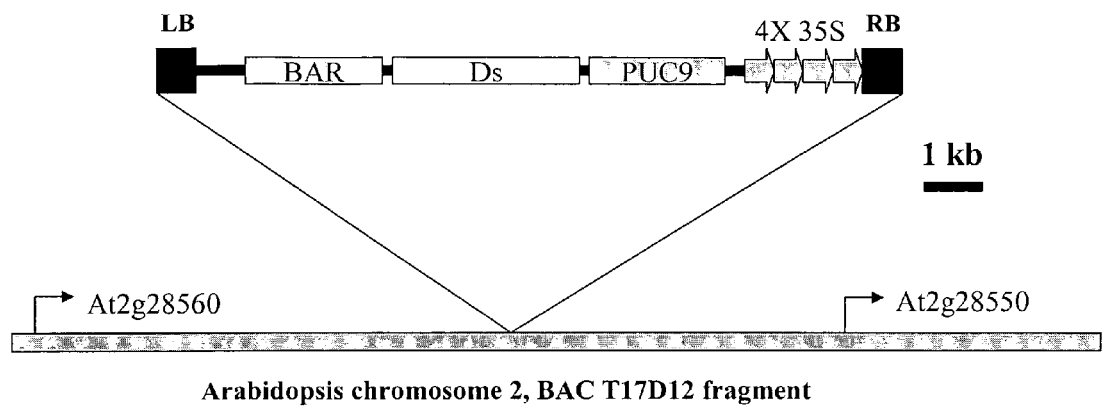
B
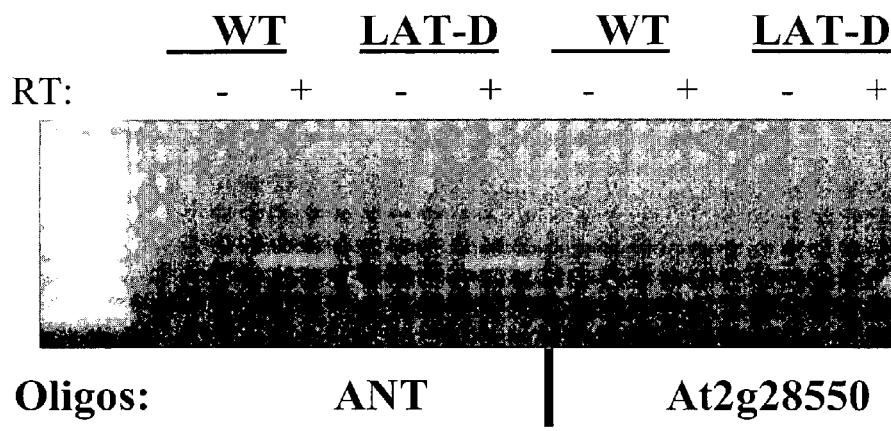

Figure 10
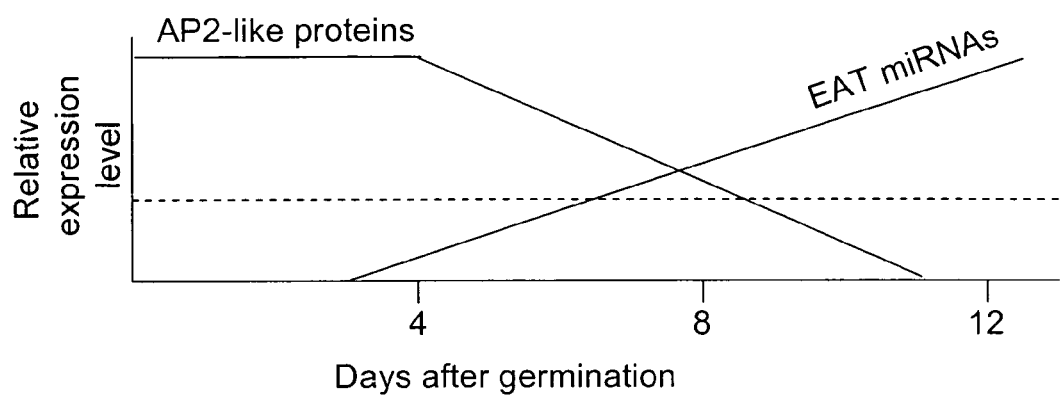
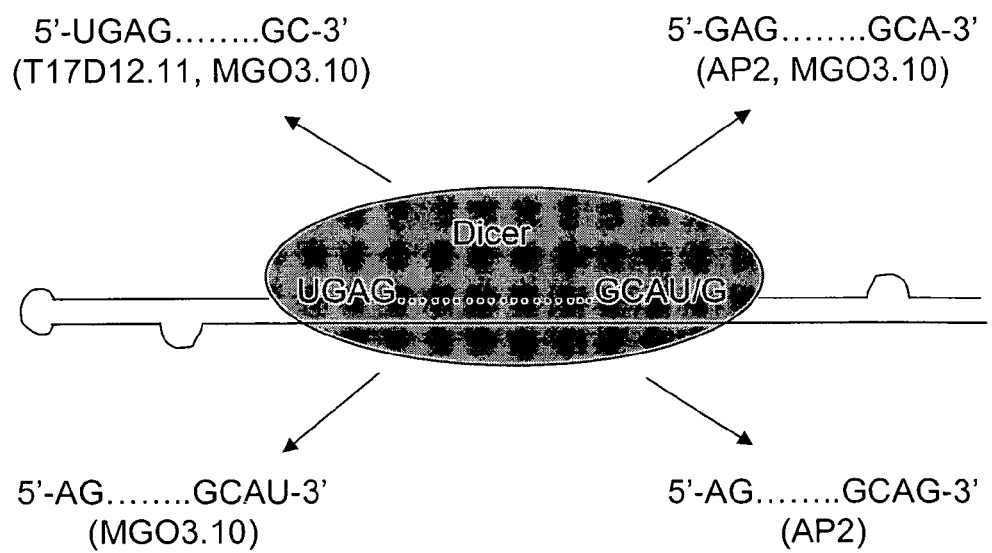

FIG. 13A
```
miR169           GAGCCAAGGAUGACUUGCCGG
miR-PDSa169g     GAGUUUAGUCUGACUUGGCCA
miR-PDSb169g     GAUCUCUUUCCAGUCUUCAGG
```
FIG. 13B
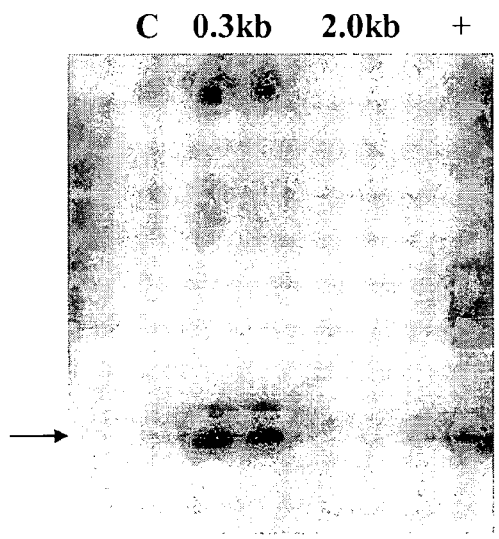
FIG. 13C
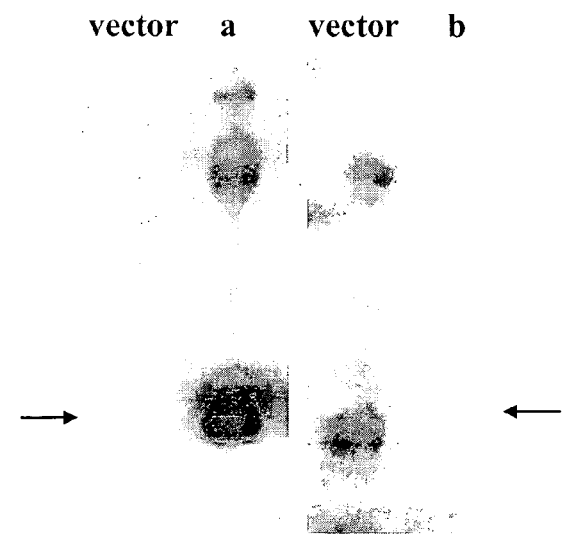
FIG. 13D
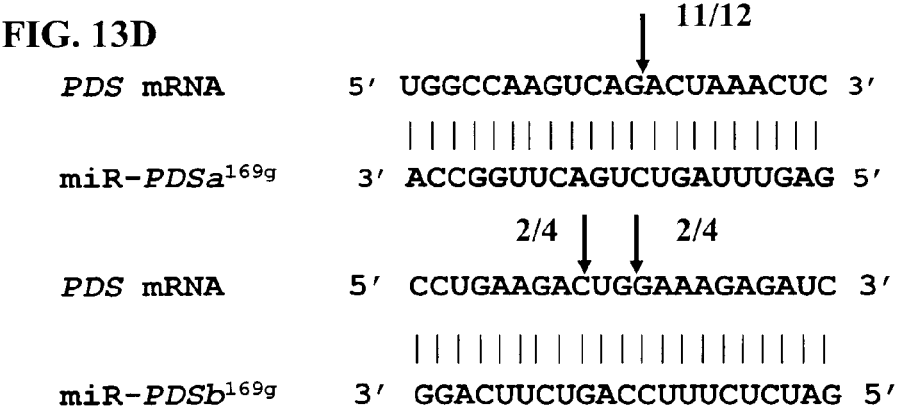
FIG. 13E

Fig. 14 A
```
miR159a          5' UUUGGAUUGAAGGGAGCUCUA 3'
                     ↓ ↓  ↓↓      ↓ ↓↓↓↓
miRrbcS^159a-A   5' UUUCGAAUCCGGGCGAGGAA 3'
                    |:|||||||::||:|||||
rbcS mRNA        3' AGAGCUUAAGGUUCGUUCCUU 5'
```
FIG. 14B
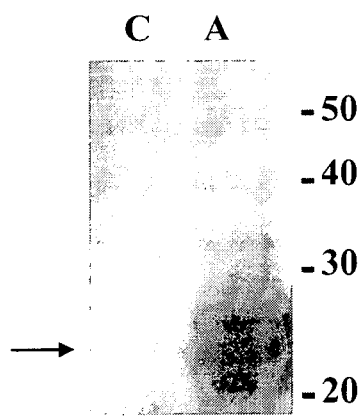
FIG. 14C
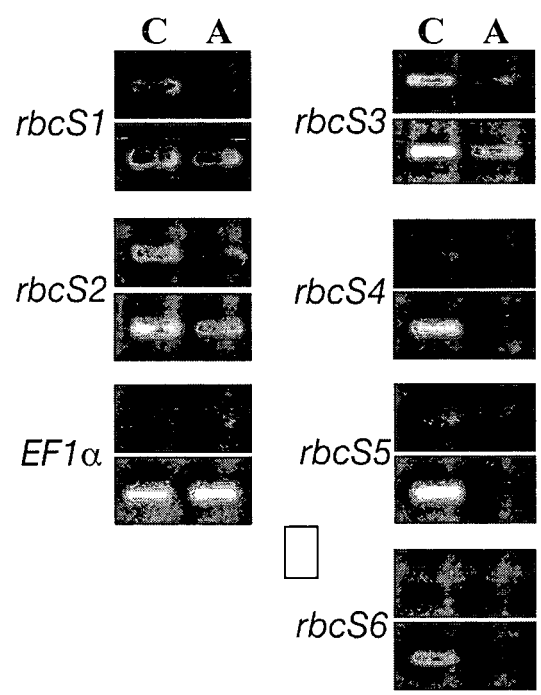

FIG. 16A

| | | |
|---|---|---|
| miR159a | 5' | UUUGGAUUGAAGGGAGCUCUA 3' |
| miR-PDS<sup>159a</sup> | 5' | UUUGGA<u>AAU</u>A<u>U</u>GGGA<u>U</u>CUCU<u>U</u> 3' |
| miR-rbcS<sup>159a</sup>-A | 5' | UUU<u>C</u>GA<u>AU</u>CCGGG<u>C</u>GAGGA<u>A</u> 3' |
| | | \*\*\* \*\*    \*\*\* |

FIG. 16B

| | |
|---|---|
| miR169g | 5' GAGCCAAGGAUGACUUGCCGG 3' |
| miR-PDSa<sup>169g</sup> | 5' GAG<u>UUU</u>A<u>G</u>U<u>C</u>GACUUGG<u>C</u>C<u>A</u> 3' |
| miR-PDSb<sup>169g</sup> | 5' GA<u>U</u>C<u>U</u>CUUUCCAGUCUUCAGG 3' |
| | \*\* \*                \* \* \*\* |

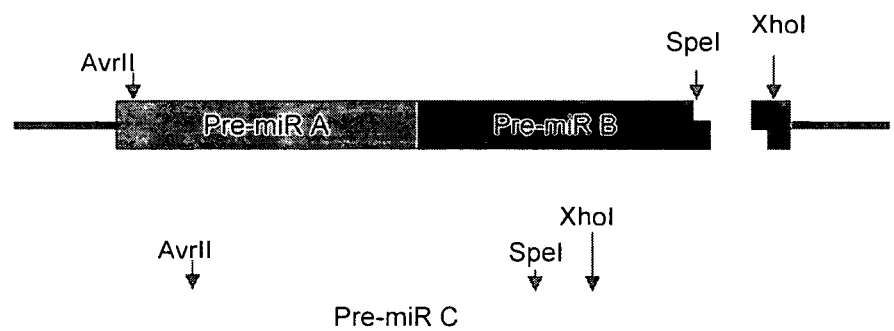
FIG. 21D
FIG. 21E
Figure 22
FIG. 23A  FIG. 23B

Expt. 2
A
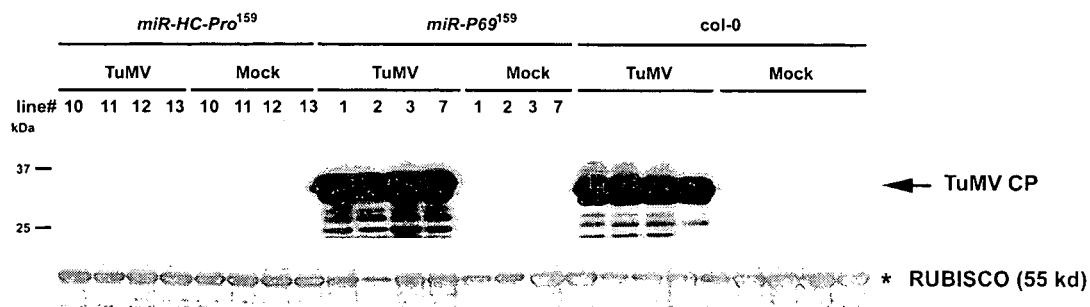
B
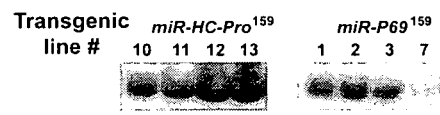
Figure 33
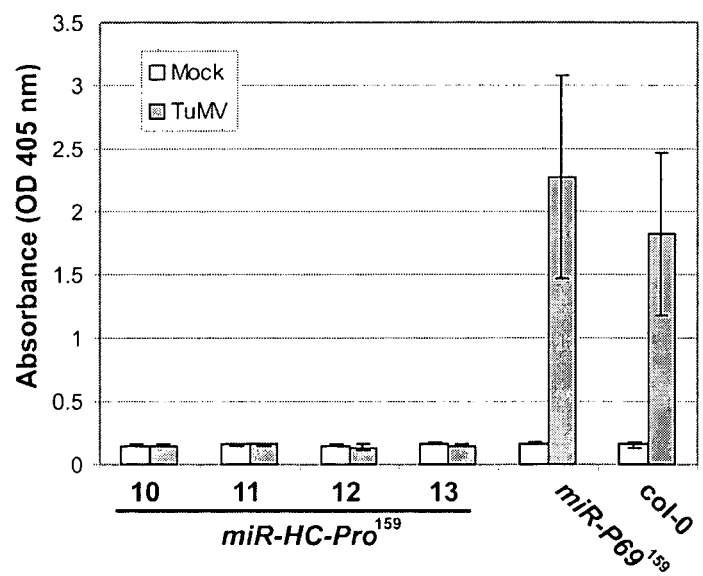
Figure 34

SEQUENCE LISTING

<160> NUMBER OF SEQ ID NOS: 189

<210> SEQ ID NO 1
<211> LENGTH: 1417
<212> TYPE: DNA
<213> ORGANISM: Arabidopsis thaliana

<400> SEQUENCE: 1

| | | | | | |
|---|---|---|---|---|---|
| gcacctctca | ctcccttcct | ctaactagtc | ttgtgtgcac | ccatttatgt | gtacgtacta | 60 |
| ttatctcata | aataaatatt | tttaaaatta | gatgcattta | ttgatatgaa | aaagttacaa | 120 |
| gattagtttg | ttgtgtgtga | gactttggat | cgacagatcg | aaaaattaac | taaccggtca | 180 |
| gtattgaata | tcaactatta | tatgctccat | gcattcgctt | atagtttcac | acaatttgtt | 240 |
| ttcttcacgg | tctaaaatca | gaagattcca | tatattttct | tatgacgtaa | aaggaccact | 300 |
| tataagttga | cacgtcagcc | cttggattcg | tgaggttttt | ctctctactt | cacctatcta | 360 |
| cttttcctca | tatcccactg | cttttctcct | tcttgttctt | gttttctcg | ttttttttctt | 420 |
| cttcttctcc | aagaaaatag | agatcgaaaa | gattagatct | attttgtgta | gcaagaaatt | 480 |
| atcattttcg | tttcttcatt | catatattgt | tctattatgt | tgtacaataa | tagatactcg | 540 |
| atctcttgtg | cgtgcgtaaa | ttttatacaa | gttgtcggcg | gatccatgga | agaaagctca | 600 |
| tctgtcgttg | tttgtaggcg | cagcaccatt | aagattcaca | tggaaattga | taaatacctc | 660 |
| aaattagggt | tttgatatgt | atatgagaat | cttgatgatg | ctgcatcaac | aatcgacggc | 720 |
| tacaaatacc | taaagcttga | gaaagaaact | tgaagatatt | gattgaagtc | tggatcgatc | 780 |
| tttggtaaat | ctctctcttg | attagtttta | agaatcactt | ttttttttct | gtgtttgaac | 840 |
| atgtttacat | atatcatcta | tgtctcaata | tatatatttt | cttaatctag | ggtcaatgac | 900 |
| ggattagggc | gttaattaca | atgaatatgg | aaaaactatt | ttgcctttga | tcttgacttg | 960 |
| agtgttgatg | aacagatgta | taatgttatg | tagtatgtac | tgtatttttt | ctagaatcat | 1020 |
| tctttagtct | ccaactctcc | attaatcaaa | tgaggtcctt | ataggtaatg | ctatgatcaa | 1080 |
| gaacaacaag | atcgtgagca | cagatcggcc | agttcggtca | cttttaaaa | gagagatgtt | 1140 |
| atattgttaa | tttgttatta | tcaggtataa | taaatacaga | atagttcgtc | cagagaccag | 1200 |
| acattttata | gtttcaattt | tatgacagtc | ttgtaataat | atttgtttaa | tagtgtgtca | 1260 |
| ccttctatt | ctgggttatt | acttggtccc | gaaattttct | tattgttcta | attttgtaat | 1320 |
| attagaaatt | tggttttctt | gccaaatcaa | atcaaacatt | acggtgtgtt | gtacattgta | 1380 |
| ccagaacttt | tgttttcaag | tgctcaactt | gagaacc | | | 1417 |

<210> SEQ ID NO 2
<211> LENGTH: 95
<212> TYPE: DNA
<213> ORGANISM: Arabidopsis thaliana

<400> SEQUENCE: 2

| | | | | | |
|---|---|---|---|---|---|
| aggcgcagca | ccattaagat | tcacatggaa | attgataaat | accctaaatt | agggttttga | 60 |
| tatgtatatg | agaatcttga | tgatgctgca | tcaac | | | 95 |

<210> SEQ ID NO 3
<211> LENGTH: 159
<212> TYPE: DNA
<213> ORGANISM: Artificial Sequence
<220> FEATURE:
<223> OTHER INFORMATION: miRNA template cassette

<400> SEQUENCE: 3

```
ggatccatgg aagaaagctc atctgtcgtt gtttgtaggc gcagcaccat taagattcac      60
atggaaattg ataaataccc taaattaggg ttttgatatg tatatgagaa tcttgatgat     120
gctgcatcaa caatcgacgg ctacaaatac ctaaagctt                            159
```

<210> SEQ ID NO 4
<211> LENGTH: 21
<212> TYPE: DNA
<213> ORGANISM: Artificial Sequence
<220> FEATURE:
<223> OTHER INFORMATION: miRNA template to target At4g18960

<400> SEQUENCE: 4

```
taggttgtaa tgccgcgact t                                                21
```

<210> SEQ ID NO 5
<211> LENGTH: 21
<212> TYPE: DNA
<213> ORGANISM: Artificial Sequence
<220> FEATURE:
<223> OTHER INFORMATION: miRNA template to target At3g54340

<400> SEQUENCE: 5

```
ggtggaaatg aagagcgtaa g                                                21
```

<210> SEQ ID NO 6
<211> LENGTH: 21
<212> TYPE: DNA
<213> ORGANISM: Artificial Sequence
<220> FEATURE:
<223> OTHER INFORMATION: miRNA template to target At3g54340

<400> SEQUENCE: 6

```
agagcgtaag cacgtgaccc t                                                21
```

<210> SEQ ID NO 7
<211> LENGTH: 21
<212> TYPE: DNA
<213> ORGANISM: Artificial Sequence
<220> FEATURE:
<223> OTHER INFORMATION: miRNA template to target maize phytoene
      desaturase

<400> SEQUENCE: 7

```
tgctggcaga agtccgattg c                                                21
```

<210> SEQ ID NO 8
<211> LENGTH: 21
<212> TYPE: DNA
<213> ORGANISM: Artificial Sequence
<220> FEATURE:
<223> OTHER INFORMATION: miRNA template to target maize phytoene
      desaturase

<400> SEQUENCE: 8

```
agcttcctgg ataggactgc a                                                21
```

<210> SEQ ID NO 9
<211> LENGTH: 21
<212> TYPE: DNA
<213> ORGANISM: Artificial Sequence
<220> FEATURE:
<223> OTHER INFORMATION: miRNA template to target is maize IPPK2

<400> SEQUENCE: 9

```
aagttgtggt taatcacccc a                                              21

<210> SEQ ID NO 10
<211> LENGTH: 21
<212> TYPE: DNA
<213> ORGANISM: Artificial Sequence
<220> FEATURE:
<223> OTHER INFORMATION: miRNA template to target is maize ITPK5

<400> SEQUENCE: 10
gaggacagtt tcgtatcctg g                                              21

<210> SEQ ID NO 11
<211> LENGTH: 21
<212> TYPE: DNA
<213> ORGANISM: Artificial Sequence
<220> FEATURE:
<223> OTHER INFORMATION: miRNA template to target is maize Milps3

<400> SEQUENCE: 11
gagcgtttac caccggtgtg c                                              21

<210> SEQ ID NO 12
<211> LENGTH: 77
<212> TYPE: DNA
<213> ORGANISM: Artificial Sequence
<220> FEATURE:
<223> OTHER INFORMATION: Synthetic oligo1/4 for At4g18960 target

<400> SEQUENCE: 12
gatccatgga agaaagctca tctgtcgttg tttgtaggca gtcgcggcac tacaaccaaa    60
tggaaattga taaatac                                                   77

<210> SEQ ID NO 13
<211> LENGTH: 77
<212> TYPE: DNA
<213> ORGANISM: Artificial Sequence
<220> FEATURE:
<223> OTHER INFORMATION: Synthetic oligo2/4 for At4g18960 target

<400> SEQUENCE: 13
tagggtattt atcaatttcc atttggttgt agtgccgcga ctgcctacaa acaacgacag    60
atgagctttc ttccatg                                                   77

<210> SEQ ID NO 14
<211> LENGTH: 76
<212> TYPE: DNA
<213> ORGANISM: Artificial Sequence
<220> FEATURE:
<223> OTHER INFORMATION: Synthetic oligo3/4 for At4g18960 target

<400> SEQUENCE: 14
cctaaattag gttttgata tgtatattag gttgtaatgc cgcgactttc aacaatcgac    60
ggctacaaat acctaa                                                    76

<210> SEQ ID NO 15
<211> LENGTH: 76
<212> TYPE: DNA
<213> ORGANISM: Artificial Sequence
<220> FEATURE:
<223> OTHER INFORMATION: Synthetic oligo4/4 for At4g18960 target

<400> SEQUENCE: 15
agctttaggt atttgtagcc gtcgattgtt gaaagtcgcg gcattacaac ctaatataca    60
```
tatcaaaacc ctaatt                                              76

<210> SEQ ID NO 16
<211> LENGTH: 77
<212> TYPE: DNA
<213> ORGANISM: Artificial Sequence
<220> FEATURE:
<223> OTHER INFORMATION: Synthetic oligo1/4 for At3g54340 target

<400> SEQUENCE: 16
gatccatgga agaaagctca tctgtcgttg tttgtaggat tacgcccttc attaccaca    60 tggaaattga taaatac                                             77

<210> SEQ ID NO 17
<211> LENGTH: 77
<212> TYPE: DNA
<213> ORGANISM: Artificial Sequence
<220> FEATURE:
<223> OTHER INFORMATION: Synthetic oligo2/4 for At3g54340 target

<400> SEQUENCE: 17
tagggtattt atcaatttcc atggtggtaa tgaagggcgt aatcctacaa acaacgacag    60
atgagctttc ttccatg                                             77

<210> SEQ ID NO 18
<211> LENGTH: 76
<212> TYPE: DNA
<213> ORGANISM: Artificial Sequence
<220> FEATURE:
<223> OTHER INFORMATION: Synthetic oligo3/4 for At3g54340 target

<400> SEQUENCE: 18
cctaaattag ggttttgata tgtatatggt ggaaatgaag agcgtaagtc aacaatcgac    60
ggctacaaat acctaa                                              76

<210> SEQ ID NO 19
<211> LENGTH: 76
<212> TYPE: DNA
<213> ORGANISM: Artificial Sequence
<220> FEATURE:
<223> OTHER INFORMATION: Synthetic oligo4/4 for At3g54340 target

<400> SEQUENCE: 19
agctttaggt atttgtagcc gtcgattgtt gacttacgct cttcatttcc accatataca    60
tatcaaaacc ctaatt                                              76

<210> SEQ ID NO 20
<211> LENGTH: 77
<212> TYPE: DNA
<213> ORGANISM: Artificial Sequence
<220> FEATURE:
<223> OTHER INFORMATION: Synthetic oligo1/4 for At3g54340 target

<400> SEQUENCE: 20
gatccatgga agaaagctca tctgtcgttg tttgtaggcg gtcacgcgct tacgctcaca    60
tggaaattga taaatac                                             77

<210> SEQ ID NO 21
<211> LENGTH: 77
<212> TYPE: DNA
<213> ORGANISM: Artificial Sequence
<220> FEATURE:

<223> OTHER INFORMATION: Synthetic oligo2/4 for At3g54340 target

<400> SEQUENCE: 21
tagggtattt atcaatttcc atgtgagcgt aagcgcgtga ccgcctacaa acaacgacag    60
atgagctttc ttccatg                                                 77

<210> SEQ ID NO 22
<211> LENGTH: 76
<212> TYPE: DNA
<213> ORGANISM: Artificial Sequence
<220> FEATURE:
<223> OTHER INFORMATION: Synthetic oligo3/4 for At3g54340 target

<400> SEQUENCE: 22
cctaaattag ggttttgata tgtatatgag agcgtaagca cgtgaccctc aacaatcgac    60
ggctacaaat acctaa                                                  76

<210> SEQ ID NO 23
<211> LENGTH: 76
<212> TYPE: DNA
<213> ORGANISM: Artificial Sequence
<220> FEATURE:
<223> OTHER INFORMATION: Synthetic oligo4/4 for At3g54340 target

<400> SEQUENCE: 23
agctttaggt atttgtagcc gtcgattgtt gagggtcacg tgcttacgct ctcatataca    60
tatcaaaacc ctaatt                                                  76

<210> SEQ ID NO 24
<211> LENGTH: 77
<212> TYPE: DNA
<213> ORGANISM: Artificial Sequence
<220> FEATURE:
<223> OTHER INFORMATION: Synthetic oligo1/4 for phytoene desaturase
      target

<400> SEQUENCE: 24
gatccatgga agaaagctca tctgtcgttg tttgtaggca atcggacttc tgccagcaca    60
tggaaattga taaatac                                                 77

<210> SEQ ID NO 25
<211> LENGTH: 77
<212> TYPE: DNA
<213> ORGANISM: Artificial Sequence
<220> FEATURE:
<223> OTHER INFORMATION: Synthetic oligo2/4 for phytoene desaturase
      target

<400> SEQUENCE: 25
tagggtattt atcaatttcc atgtgctggc agaagtccga ttgcctacaa acaacgacag    60
atgagctttc ttccatg                                                 77

<210> SEQ ID NO 26
<211> LENGTH: 76
<212> TYPE: DNA
<213> ORGANISM: Artificial Sequence
<220> FEATURE:
<223> OTHER INFORMATION: Synthetic oligo3/4 for phytoene desaturase
      target

<400> SEQUENCE: 26
cctaaattag ggttttgata tgtatatgtg ctggcagaag tccgattgcc aacaatcgac    60
ggctacaaat acctaa 76

<210> SEQ ID NO 27
<211> LENGTH: 76
<212> TYPE: DNA
<213> ORGANISM: Artificial Sequence
<220> FEATURE:
<223> OTHER INFORMATION: Synthetic oligo4/4 for phytoene desaturase
      target

<400> SEQUENCE: 27
agctttaggt atttgtagcc gtcgattgtt ggcaatcgga cttctgccag cacatataca    60
tatcaaaacc ctaatt                                                    76

<210> SEQ ID NO 28
<211> LENGTH: 77
<212> TYPE: DNA
<213> ORGANISM: Artificial Sequence
<220> FEATURE:
<223> OTHER INFORMATION: Synthetic oligo1/4 for phytoene desaturase
      target

<400> SEQUENCE: 28
gatccatgga agaaagctca tctgtcgttg tttgtagtac agtcccatcc aggaagcaca    60
tggaaattga taaatac                                                   77

<210> SEQ ID NO 29
<211> LENGTH: 77
<212> TYPE: DNA
<213> ORGANISM: Artificial Sequence
<220> FEATURE:
<223> OTHER INFORMATION: Synthetic oligo2/4 for phytoene desaturase
      target

<400> SEQUENCE: 29
tagggtattt atcaatttcc atgtgcttcc tggatgggac tgtactacaa acaacgacag    60
atgagctttc ttccatg                                                   77

<210> SEQ ID NO 30
<211> LENGTH: 76
<212> TYPE: DNA
<213> ORGANISM: Artificial Sequence
<220> FEATURE:
<223> OTHER INFORMATION: Synthetic oligo3/4 for phytoene desaturase
      target

<400> SEQUENCE: 30
cctaaattag ggttttgata tgtatatgag cttcctggat aggactgcac aacaatcgac    60
ggctacaaat acctaa                                                    76

<210> SEQ ID NO 31
<211> LENGTH: 76
<212> TYPE: DNA
<213> ORGANISM: Artificial Sequence
<220> FEATURE:
<223> OTHER INFORMATION: Synthetic oligo4/4 for phytoene desaturase
      target

<400> SEQUENCE: 31
agctttaggt atttgtagcc gtcgattgtt gtgcagtcct atccaggaag ctcatataca    60
tatcaaaacc ctaatt                                                    76

<210> SEQ ID NO 32

-continued

<210> SEQ ID NO 32
<211> LENGTH: 77
<212> TYPE: DNA
<213> ORGANISM: Artificial Sequence
<220> FEATURE:
<223> OTHER INFORMATION: Synthetic oligo1/4 for IPPK2 target

<400> SEQUENCE: 32
gatccatgga agaaagctca tctgtcgttg tttgtaggcg gggtgataaa ccacaacata    60
tggaaattga taaatac                                                  77

<210> SEQ ID NO 33
<211> LENGTH: 77
<212> TYPE: DNA
<213> ORGANISM: Artificial Sequence
<220> FEATURE:
<223> OTHER INFORMATION: Synthetic oligo2/4 for IPPK2 target

<400> SEQUENCE: 33
tagggtattt atcaatttcc atatgttgtg gtttatcacc ccgcctacaa acaacgacag    60
atgagctttc ttccatg                                                  77

<210> SEQ ID NO 34
<211> LENGTH: 76
<212> TYPE: DNA
<213> ORGANISM: Artificial Sequence
<220> FEATURE:
<223> OTHER INFORMATION: Synthetic oligo3/4 for IPPK2 target

<400> SEQUENCE: 34
cctaaattag ggttttgata tgtatataag ttgtggttaa tcaccccatc aacaatcgac    60
ggctacaaat acctaa                                                   76

<210> SEQ ID NO 35
<211> LENGTH: 76
<212> TYPE: DNA
<213> ORGANISM: Artificial Sequence
<220> FEATURE:
<223> OTHER INFORMATION: Synthetic oligo4/4 for IPPK2 target

<400> SEQUENCE: 35
agctttaggt atttgtagcc gtcgattgtt gatggggtga ttaaccacaa cttatataca    60
tatcaaaacc ctaatt                                                   76

<210> SEQ ID NO 36
<211> LENGTH: 77
<212> TYPE: DNA
<213> ORGANISM: Artificial Sequence
<220> FEATURE:
<223> OTHER INFORMATION: Synthetic oligo1/4 for ITPK5 target

<400> SEQUENCE: 36
gatccatgga agaaagctca tctgtcgttg tttgtaggac aggatacgta actgtccaca    60
tggaaattga taaatac                                                  77

<210> SEQ ID NO 37
<211> LENGTH: 77
<212> TYPE: DNA
<213> ORGANISM: Artificial Sequence
<220> FEATURE:
<223> OTHER INFORMATION: Synthetic oligo2/4 for ITPK5 target

<400> SEQUENCE: 37
tagggtattt atcaatttcc atgtggacag ttacgtatcc tgtcctacaa acaacgacag    60
atgagctttc ttccatg 77

<210> SEQ ID NO 38
<211> LENGTH: 76
<212> TYPE: DNA
<213> ORGANISM: Artificial Sequence
<220> FEATURE:
<223> OTHER INFORMATION: Synthetic oligo3/4 for ITPK5 target

<400> SEQUENCE: 38
cctaaattag ggttttgata tgtatatgag gacagtttcg tatcctggtc aacaatcgac 60
ggctacaaat acctaa 76

<210> SEQ ID NO 39
<211> LENGTH: 76
<212> TYPE: DNA
<213> ORGANISM: Artificial Sequence
<220> FEATURE:
<223> OTHER INFORMATION: Synthetic oligo4/4 for ITPK5 target

<400> SEQUENCE: 39
agctttaggt atttgtagcc gtcgattgtt gaccaggata cgaaactgtc ctcatataca 60
tatcaaaacc ctaatt 76

<210> SEQ ID NO 40
<211> LENGTH: 77
<212> TYPE: DNA
<213> ORGANISM: Artificial Sequence
<220> FEATURE:
<223> OTHER INFORMATION: Synthetic oligo1/4 for mi1ps target

<400> SEQUENCE: 40
gatccatgga agaaagctca tctgtcgttg tttgtaggac acaccggcgg taaacgcaca 60
tggaaattga taaatac 77

<210> SEQ ID NO 41
<211> LENGTH: 77
<212> TYPE: DNA
<213> ORGANISM: Artificial Sequence
<220> FEATURE:
<223> OTHER INFORMATION: Synthetic oligo2/4 for mi1ps target

<400> SEQUENCE: 41
tagggtattt atcaatttcc atgtgcgttt accgccggtg tgtcctacaa acaacgacag 60
atgagctttc ttccatg 77

<210> SEQ ID NO 42
<211> LENGTH: 76
<212> TYPE: DNA
<213> ORGANISM: Artificial Sequence
<220> FEATURE:
<223> OTHER INFORMATION: Synthetic oligo3/4 for mi1ps target

<400> SEQUENCE: 42
cctaaattag ggttttgata tgtatatgag cgtttaccac cggtgtgctc aacaatcgac 60
ggctacaaat acctaa 76

<210> SEQ ID NO 43
<211> LENGTH: 76
<212> TYPE: DNA
<213> ORGANISM: Artificial Sequence
<220> FEATURE:

<223> OTHER INFORMATION: Synthetic oligo4/4 for mi1ps target

<400> SEQUENCE: 43

| | |
|---|---|
| agctttaggt atttgtagcc gtcgattgtt gagcacaccg gtggtaaacg ctcatataca | 60 |
| tatcaaaacc ctaatt | 76 |

<210> SEQ ID NO 44
<211> LENGTH: 4426
<212> TYPE: DNA
<213> ORGANISM: Artificial Sequence
<220> FEATURE:
<223> OTHER INFORMATION: Plasmid

<400> SEQUENCE: 44

| | |
|---|---|
| ctaaattgta agcgttaata ttttgttaaa attcgcgtta aattttttgtt aaatcagctc | 60 |
| attttttaac caataggccg aaatcggcaa atcccttat aaatcaaaag aatagaccga | 120 |
| gataggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta atcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgcgtaata cgactcacta tagggcgaat gggtaccgg | 660 |
| gccctctaga tgcatgctcg agcggccgcc agtgtgatgg atatctgcag aattcgccct | 720 |
| tgactactcg agcacctctc actccctttc tctaactagt cttgtgtgca cccatttatg | 780 |
| tgtacgtact attatctcat aaataaatat ttttaaaatt agatgcattt attgatatga | 840 |
| aaaagttaca agattagttt gttgtgtgtg agactttgga tcgacagatc gaaaaattaa | 900 |
| ctaaccggtc agtattgaat atcaactatt atatgctcca tgcattcgct tatagtttca | 960 |
| cacaatttgt tttcttcacg gtctaaaatc agaagattcc atatattttc ttatgacgta | 1020 |
| aaaggaccac ttataagttg acacgtcagc ccttggattc gtgaggtttt tctctctact | 1080 |
| tcacctatct acttttcctc atatcccact gcttttctcc ttcttgttct tgttttctc | 1140 |
| gtttttttct tcttcttctc caagaaaata gagatcgaaa agattagatc tatttttgtgt | 1200 |
| agcaagaaat tatcattttc gtttcttcat tcatatattg ttctattatg ttgtacaata | 1260 |
| atagatactc gatctcttgt gcgtgcgtaa attttataca agttgtcggc ggatccatgg | 1320 |
| aagaaagctc atctgtcgtt gtttgtaggc gcagcaccat taagattcac atggaaattg | 1380 |
| ataaataccc taattaggg ttttgatatg tatatgagaa tcttgatgat gctgcatcaa | 1440 |
| caatcgacgg ctacaaatac ctaaagcttg agaaagaaac ttgaagatat tgattgaagt | 1500 |
| ctggatcgat ctttggtaaa tctctctctt gattagtttt aagaatcact ttttttttc | 1560 |
| tgtgtttgaa catgtttaca tatcatct atgtctcaat atatatttt tcttaatcta | 1620 |
| gggtcaatga cggattaggg cgttaattac aatgaatatg gaaaactat tttgcctttg | 1680 |
| atcttgactt gagtgttgat gaacagatgt ataatgttat gtagtatgta ctgtattttt | 1740 |
| tctagaatca ttctttagtc tccaactctc cattaatcaa atgaggtcct tataggtaat | 1800 |
| gctatgatca agaacaacaa gatcgtgagc acagatcggc cagttcggtc acttttaaa | 1860 |

```
agagagatgt tatattgtta atttgttatt atcaggtata ataaatacag aatagttcgt    1920
ccagagacca gacattttat agtttcaatt ttatgacagt cttgtaataa tatttgttta    1980
atagtgtgtc accttctatt tctgggttat tacttggtcc cgaaattttc ttattgttct    2040
aattttgtaa tattagaaat ttggttttct tgccaaatca aatcaaacat tacggtgtgt    2100
tgtacattgt accagaactt tgttttcaa gtgctcaact tgagaacctc gagtagtcaa     2160
gggcgaattc cagcacactg gcggccgtta ctagttctag agcggccgcc accgcgtgg     2220
agctccagct tttgttccct ttagtgaggg ttaattgcgc gcttggcgta atcatggtca    2280
tagctgtttc ctgtgtgaaa ttgttatccg ctcacaattc cacacaacat acgagccgga    2340
agcataaagt gtaaagcctg gggtgcctaa tgagtgagct aactcacatt aattgcgttg    2400
cgctcactgc ccgctttcca gtcgggaaac ctgtcgtgcc agctgcatta atgaatcggc    2460
caacgcgcgg ggagaggcgg tttgcgtatt gggcgctctt ccgcttcctc gctcactgac    2520
tcgctgcgct cggtcgttcg gctgcggcga gcggtatcag ctcactcaaa ggcggtaata    2580
cggttatcca cagaatcagg ggataacgca ggaaagaaca tgtgagcaaa aggccagcaa    2640
aaggccagga accgtaaaaa ggccgcgttg ctggcgtttt tccataggct ccgcccccct    2700
gacgagcatc acaaaaatcg acgctcaagt cagaggtggc gaaacccgac aggactataa    2760
agataccagg cgtttccccc tggaagctcc ctcgtgcgct ctcctgttcc gaccctgccg    2820
cttaccggat acctgtccgc ctttctccct tcgggaagcg tggcgctttc tcatagctca    2880
cgctgtaggt atctcagttc ggtgtaggtc gttcgctcca agctgggctg tgtgcacgaa    2940
ccccccgttc agcccgaccg ctgcgcctta tccggtaact atcgtcttga gtccaacccg    3000
gtaagacacg acttatcgcc actggcagca gccactggta acaggattag cagagcgagg    3060
tatgtaggcg gtgctacaga gttcttgaag tggtggccta actacggcta cactagaagg    3120
acagtatttg gtatctgcgc tctgctgaag ccagttacct tcggaaaaag agttggtagc    3180
tcttgatccg gcaaacaaac caccgctggt agcggtggtt ttttgtttg caagcagcag     3240
attacgcgca gaaaaaaagg atctcaagaa gatcctttga tcttttctac ggggtctgac    3300
gctcagtgga acgaaaactc acgttaaggg attttggtca tgagattatc aaaaaggatc    3360
ttcacctaga tccttttaaa ttaaaaatga agttttaaat caatctaaag tatatatgag    3420
taaacttggt ctgacagtta ccaatgctta atcagtgagg cacctatctc agcgatctgt    3480
ctatttcgtt catccatagt tgcctgactc ccgtcgtgt agataactac gatacgggag     3540
ggcttaccat ctggccccag tgctgcaatg ataccgcgag acccacgctc accggctcca    3600
gatttatcag caataaacca gccagccgga agggccgagc gcagaagtgg tcctgcaact    3660
ttatccgcct ccatccagtc tattaattgt tgccgggaag ctagagtaag tagttcgcca    3720
gttaatagtt tgcgcaacgt tgttgccatt gctacaggca tcgtggtgtc acgctcgtcg    3780
tttggtatgg cttcattcag ctccggttcc caacgatcaa ggcgagttac atgatccccc    3840
atgttgtgca aaaaagcggt tagctccttc ggtcctccga tcgttgtcag aagtaagttg    3900
gccgcagtgt tatcactcat ggttatggca gcactgcata attctcttac tgtcatgcca    3960
tccgtaagat gcttttctgt gactggtgag tactcaacca agtcattctg agaatagtgt    4020
atgcggcgac cgagttgctc ttgcccggcg tcaatacggg ataataccgc gccacatagc    4080
agaactttaa aagtgctcat cattggaaaa cgttcttcgg ggcgaaaact ctcaaggatc    4140
ttaccgctgt tgagatccag ttcgatgtaa cccactcgtg cacccaactg atcttcagca    4200
```

-continued

```
tcttttactt tcaccagcgt ttctgggtga gcaaaaacag gaaggcaaaa tgccgcaaaa      4260
aagggaataa gggcgacacg gaaatgttga atactcatac tcttcctttt tcaatattat      4320
tgaagcattt atcagggtta ttgtctcatg agcggataca tatttgaatg tatttagaaa      4380
aataaacaaa taggggttcc gcgcacattt ccccgaaaag tgccac                    4426
```

```
<210> SEQ ID NO 45
<211> LENGTH: 29
<212> TYPE: DNA
<213> ORGANISM: Artificial Sequence
<220> FEATURE:
<223> OTHER INFORMATION: EAT 3' PCR primer

<400> SEQUENCE: 45
ctgtgctcac gatcttgttg ttcttgatc                                         29

<210> SEQ ID NO 46
<211> LENGTH: 29
<212> TYPE: DNA
<213> ORGANISM: Artificial Sequence
<220> FEATURE:
<223> OTHER INFORMATION: EAT 5' PCR primer

<400> SEQUENCE: 46
gtcggcggat ccatggaaga aagctcatc                                         29

<210> SEQ ID NO 47
<211> LENGTH: 21
<212> TYPE: RNA
<213> ORGANISM: Arabidopsis thaliana
<220> FEATURE:
<223> OTHER INFORMATION: AP2 RNA

<400> SEQUENCE: 47
cugcagcauc aucaggauuc u                                                 21

<210> SEQ ID NO 48
<211> LENGTH: 21
<212> TYPE: RNA
<213> ORGANISM: Arabidopsis thaliana
<220> FEATURE:
<221> NAME/KEY: misc_feature
<222> LOCATION: (0)...(0)
<223> OTHER INFORMATION: EAT miRNA

<400> SEQUENCE: 48
agaaucuuga ugaugcugca u                                                 21

<210> SEQ ID NO 49
<211> LENGTH: 59
<212> TYPE: DNA
<213> ORGANISM: Arabidopsis thaliana

<400> SEQUENCE: 49
accaagtgtt gacaaatgct gcagcatcat caggattctc tcctcatcat cacaatcag        59

<210> SEQ ID NO 50
<211> LENGTH: 59
<212> TYPE: DNA
<213> ORGANISM: Arabidopsis thaliana

<400> SEQUENCE: 50
caccgccact gttttcaaat gcagcatcat caggattctc actctcagct acacgccct        59
```

```
<210> SEQ ID NO 51
<211> LENGTH: 59
<212> TYPE: DNA
<213> ORGANISM: Arabidopsis thaliana

<400> SEQUENCE: 51
caccattgtt ctcagttgca gcagcatcat caggattctc acatttccgg ccacaacct        59

<210> SEQ ID NO 52
<211> LENGTH: 59
<212> TYPE: DNA
<213> ORGANISM: Arabidopsis thaliana

<400> SEQUENCE: 52
gaaatcgagt ggtgggaatg gcagcatcat caggattctc cctcaacct tcccttac         59

<210> SEQ ID NO 53
<211> LENGTH: 59
<212> TYPE: DNA
<213> ORGANISM: Zea mays

<400> SEQUENCE: 53
acgtgccgtt gcaccactct gcagcatcat caggattctc taccgccgcc ggggccaac        59

<210> SEQ ID NO 54
<211> LENGTH: 59
<212> TYPE: DNA
<213> ORGANISM: Zea mays

<400> SEQUENCE: 54
acgccagcag cgccgccgct gcagcatcat caggattccc actgtggcag ctgggtgcg        59

<210> SEQ ID NO 55
<211> LENGTH: 35
<212> TYPE: DNA
<213> ORGANISM: Artificial Sequence
<220> FEATURE:
<223> OTHER INFORMATION: EAT PCR primer

<400> SEQUENCE: 55
gactactcga gcacctctca ctcccttct ctaac                                   35

<210> SEQ ID NO 56
<211> LENGTH: 36
<212> TYPE: DNA
<213> ORGANISM: Artificial Sequence
<220> FEATURE:
<223> OTHER INFORMATION: EAT PCR primer

<400> SEQUENCE: 56
gactactcga ggttctcaag ttgagcactt gaaaac                                 36

<210> SEQ ID NO 57
<211> LENGTH: 77
<212> TYPE: DNA
<213> ORGANISM: Artificial Sequence
<220> FEATURE:
<223> OTHER INFORMATION: EAT deletion oligonucleotide

<400> SEQUENCE: 57
gatccatgga agaaagctca tctgtcgttg tttgtaggcg cagcaccatt aagattcaca       60
tggaaattga taaatac                                                      77

<210> SEQ ID NO 58
```

```
<211> LENGTH: 55
<212> TYPE: DNA
<213> ORGANISM: Artificial Sequence
<220> FEATURE:
<223> OTHER INFORMATION: EAT deletion oligonucleotide

<400> SEQUENCE: 58
cctaaattag ggttttgata tgtatattca acaatcgacg gctacaaata cctaa          55

<210> SEQ ID NO 59
<211> LENGTH: 77
<212> TYPE: DNA
<213> ORGANISM: Artificial Sequence
<220> FEATURE:
<223> OTHER INFORMATION: EAT deletion oligonucleotide

<400> SEQUENCE: 59
tagggtattt atcaatttcc atgtgaatct taatggtgct gcgcctacaa acaacgacag     60
atgagctttc ttccatg                                                   77

<210> SEQ ID NO 60
<211> LENGTH: 55
<212> TYPE: DNA
<213> ORGANISM: Artificial Sequence
<220> FEATURE:
<223> OTHER INFORMATION: EAT deletion oligonucleotide

<400> SEQUENCE: 60
agctttaggt atttgtagcc gtcgattgtt gaatatacat atcaaaaccc taatt          55

<210> SEQ ID NO 61
<211> LENGTH: 30
<212> TYPE: DNA
<213> ORGANISM: Artificial Sequence
<220> FEATURE:
<223> OTHER INFORMATION: S1 probe

<400> SEQUENCE: 61
atgcagcatc atcaagattc tcatatacat                                     30

<210> SEQ ID NO 62
<211> LENGTH: 29
<212> TYPE: DNA
<213> ORGANISM: Artificial Sequence
<220> FEATURE:
<223> OTHER INFORMATION: mir172a-2 PCR primer

<400> SEQUENCE: 62
gtcggcggat ccatggaaga aagctcatc                                      29

<210> SEQ ID NO 63
<211> LENGTH: 30
<212> TYPE: DNA
<213> ORGANISM: Artificial Sequence
<220> FEATURE:
<223> OTHER INFORMATION: mir172a-2 PCR primer

<400> SEQUENCE: 63
caaagatcga tccagacttc aatcaatatc                                     30

<210> SEQ ID NO 64
<211> LENGTH: 27
<212> TYPE: DNA
<213> ORGANISM: Artificial Sequence
<220> FEATURE:
<223> OTHER INFORMATION: mir172a-1 PCR primer
```

-continued

<210> SEQ ID NO 64
<211> LENGTH: 27
<212> TYPE: DNA
<213> ORGANISM: Artificial Sequence
<220> FEATURE:
<223> OTHER INFORMATION: mir172a-1 PCR primer

<400> SEQUENCE: 64
taatttccgg agccacggtc gttgttg                                      27

<210> SEQ ID NO 65
<211> LENGTH: 28
<212> TYPE: DNA
<213> ORGANISM: Artificial Sequence
<220> FEATURE:
<223> OTHER INFORMATION: mir172a-1 PCR primer

<400> SEQUENCE: 65
aatagtcgtt gattgccgat gcagcatc                                     28

<210> SEQ ID NO 66
<211> LENGTH: 24
<212> TYPE: DNA
<213> ORGANISM: Artificial Sequence
<220> FEATURE:
<223> OTHER INFORMATION: Actin PCR primer

<400> SEQUENCE: 66
atggcagatg gtgaagacat tcag                                         24

<210> SEQ ID NO 67
<211> LENGTH: 26
<212> TYPE: DNA
<213> ORGANISM: Artificial Sequence
<220> FEATURE:
<223> OTHER INFORMATION: Actin PCR primer

<400> SEQUENCE: 67
gaagcacttc ctgtggacta ttgatg                                       26

<210> SEQ ID NO 68
<211> LENGTH: 26
<212> TYPE: DNA
<213> ORGANISM: Artificial Sequence
<220> FEATURE:
<223> OTHER INFORMATION: AP2 PCR primer

<400> SEQUENCE: 68
tttccgggca gcagcaacat tggtag                                       26

<210> SEQ ID NO 69
<211> LENGTH: 29
<212> TYPE: DNA
<213> ORGANISM: Artificial Sequence
<220> FEATURE:
<223> OTHER INFORMATION: AP2 PCR primer

<400> SEQUENCE: 69
gttcgcctaa gttaacaaga ggatttagg                                    29

<210> SEQ ID NO 70
<211> LENGTH: 30
<212> TYPE: DNA
<213> ORGANISM: Artificial Sequence
<220> FEATURE:
<223> OTHER INFORMATION: ANT PCR primer

<400> SEQUENCE: 70
gatcaacttc aatgactaac tctggttttc                                   30

<210> SEQ ID NO 71

```
<211> LENGTH: 30
<212> TYPE: DNA
<213> ORGANISM: Artificial Sequence
<220> FEATURE:
<223> OTHER INFORMATION: ANT PCR primer

<400> SEQUENCE: 71
gttatagaga gattcattct gtttcacatg                                    30

<210> SEQ ID NO 72
<211> LENGTH: 21
<212> TYPE: DNA
<213> ORGANISM: Artificial Sequence
<220> FEATURE:
<223> OTHER INFORMATION: miRNA template to EAT

<400> SEQUENCE: 72
agaatcttga tgatgctgca t                                             21

<210> SEQ ID NO 73
<211> LENGTH: 175
<212> TYPE: DNA
<213> ORGANISM: Artificial Sequence
<220> FEATURE:
<223> OTHER INFORMATION: Synthetic oligonucleotide 1 for EAT with attB
      sites

<400> SEQUENCE: 73
ttaaacaagt ttgtacaaaa aagcaggctg tcgttgtttg taggcgcagc accattaaga   60
ttcacatgga aattgataaa taccctaaat tagggttttg atatgtatat gagaatcttg  120
atgatgctgc atcaacaatc gacggcaccc agctttcttg tacaaagtgg tttaa        175

<210> SEQ ID NO 74
<211> LENGTH: 175
<212> TYPE: DNA
<213> ORGANISM: Artificial Sequence
<220> FEATURE:
<223> OTHER INFORMATION: Synthetic oligonucleotide 2 for EAT with attB
      sites

<400> SEQUENCE: 74
ttaaaccact ttgtacaaga aagctgggtg ccgtcgattg ttgatgcagc atcatcaaga   60
ttctcatata catatcaaaa ccctaattta gggtatttat caatttccat gtgaatctta  120
atggtgctgc gcctacaaac aacgacagcc tgcttttttg tacaaacttg tttaa        175

<210> SEQ ID NO 75
<211> LENGTH: 21
<212> TYPE: DNA
<213> ORGANISM: Artificial Sequence
<220> FEATURE:
<223> OTHER INFORMATION: miRNA template for FAD2

<400> SEQUENCE: 75
agataagacc aactgtgtca t                                             21

<210> SEQ ID NO 76
<211> LENGTH: 175
<212> TYPE: DNA
<213> ORGANISM: Artificial Sequence
<220> FEATURE:
<223> OTHER INFORMATION: Synthetic oligonucleotide 1 for FAD2

<400> SEQUENCE: 76
ttaaacaagt ttgtacaaaa aagcaggctg tcgttgtttg taggcgacac agctggtctt   60
```

```
atcacatgga aattgataaa taccctaaat tagggttttg atatgtatat gagataagac      120
caactgtgtc atcaacaatc gacggcaccc agctttcttg tacaaagtgg tttaa          175

<210> SEQ ID NO 77
<211> LENGTH: 175
<212> TYPE: DNA
<213> ORGANISM: Artificial Sequence
<220> FEATURE:
<223> OTHER INFORMATION: Synthetic oligonucleotide 2 for FAD2

<400> SEQUENCE: 77
ttaaaccact ttgtacaaga aagctgggtg ccgtcgattg ttgatgacac agttggtctt      60
atctcatata catatcaaaa ccctaattta gggtatttat caatttccat gtgataagac      120
cagctgtgtc gcctacaaac aacgacagcc tgctttttg tacaaacttg tttaa           175

<210> SEQ ID NO 78
<211> LENGTH: 21
<212> TYPE: DNA
<213> ORGANISM: Artificial Sequence
<220> FEATURE:
<223> OTHER INFORMATION: miRNA template for PDS

<400> SEQUENCE: 78
agaaactctt aaccgtgcca t                                                21

<210> SEQ ID NO 79
<211> LENGTH: 175
<212> TYPE: DNA
<213> ORGANISM: Artificial Sequence
<220> FEATURE:
<223> OTHER INFORMATION: Synthetic oligonucleotide 1 to target PDS

<400> SEQUENCE: 79
ttaaacaagt ttgtacaaaa aagcaggctg tcgttgtttg taggcggcac ggtcaagagt      60
ttcacatgga aattgataaa taccctaaat tagggttttg atatgtatat gagaaactct      120
taaccgtgcc atcaacaatc gacggcaccc agctttcttg tacaaagtgg tttaa          175

<210> SEQ ID NO 80
<211> LENGTH: 175
<212> TYPE: DNA
<213> ORGANISM: Artificial Sequence
<220> FEATURE:
<223> OTHER INFORMATION: Synthetic oligonucleotide 2 to target PDS

<400> SEQUENCE: 80
ttaaaccact ttgtacaaga aagctgggtg ccgtcgattg ttgatggcac ggttaagagt      60
ttctcatata catatcaaaa ccctaattta gggtatttat caatttccat gtgaaactct      120
tgaccgtgcc gcctacaaac aacgacagcc tgctttttg tacaaacttg tttaa           175

<210> SEQ ID NO 81
<211> LENGTH: 907
<212> TYPE: DNA
<213> ORGANISM: Zea mays

<400> SEQUENCE: 81
ttaaaaaaat agcgatttgt ttgaagaaag gatcatggcc gagcatcatt caacgtacct      60
ctgtagggcg tatgaatcgt tggattagga tcaaagtcgg caacggttaa attcaaggaa      120
gaaaacaacg ggcgtggggt cctgtccacg tcatcaggtg accaggcagg caggcatgcg      180
```

```
cgccatgcgg cattgcttct gtccccgtgc ccgggcagct tttggcagcg gatccggacg    240
gaacaccacg cgcggcagcg cgcggcaggc acgcaccggc caacttaatc ttgcctccac    300
tctgcactag tggggttatt aacaatttga ttaatccgac actgacgtac tgtgtcaacc    360
aatggcaccg cctatatatt aatcgaacca ttcagctcgt cttaattgcc acccacccac    420
ccaccgccat tgccatggtt cacctcattc attctaagct tagacgatgc agtgatagaa    480
attaatactg caaatcagtc agtgtttgcg ggcgtggcat catcaagatt cacaacccat    540
caatccgaac cactgatttg gaatgcatgt atgagaatct tgatgatgct gcatccgcca    600
acaagcgcct acgaacgttt gtgtgctcat cttcgccatc aatcgagatt ttgtatcttc    660
acgtttagct aaggtgaaag atcgtcatcc catccgccta aagctagctt tgcaaatttt    720
tattcgaaac aacgaccatt tctatatatt tcctttctct gttatagtct ctaattaacg    780
cctgtaaact gttgcaccct gcttctgcat cttcttatta attagttttg tctcttatgg    840
atgctaaaca gccatgacgt tcggacaatg gttcagctcg tacttccttc aatcgggagc    900
gccaaaa                                                              907

<210> SEQ ID NO 82
<211> LENGTH: 1128
<212> TYPE: DNA
<213> ORGANISM: Zea mays

<400> SEQUENCE: 82
tcgtcgatct gatttgcctg ctttatttct tcttcttctt cacaccgagc tagctagcta    60
tcttgcttta atttgcctag aacgaataga tccaccgtac tagcttcttg ctcgatctgc    120
agcttctcgc ttgtgagcca agagcccggc cagcagtgtc ggccgtgcag tggcactctc    180
tccatcaaca atcaaccctc tctccgtcga catgtggaaa ggtaggtaga gatagatggt    240
gtgtgtaatc cggttccttg gttcttgtgt ttccgatctc ctctaattaa tcgatctctc    300
tacctggcca gctcacttca cccatgcttg catctagctg ttccaatctg atgcatgata    360
tagatgatgc ttgcggcctc tcttcttgga ttcataggct catcatctat gcctctgtca    420
tgcacacact cgtgtctttc ttcttgatgg atacacgtac gggggggttgg gttgttcaca    480 tatatagtag tatagctagt ttattagatg caggtataca gatcatgagg aagcaagaaa    540
ttatgcaaaa cagtcggtgc ttgcaggtgc agcaccatca agattcacat ccccagctcg    600
atctgtgcat gatgagatga gaatcttgat gatgctgcat cagcaaacac tcacttacat    660
cgatctcacc cctggacaag ctggacagtg aaaccggact gagcaatcga gtactactaa    720
aaacttgtcc tcagctcttt atgttttact ttcaattacc ttgcttatat taattttctt    780
tcacttaatt tagttaatta ctgctctctc tctctctctc tgtctctctc tctctctctc    840
tggttttttc atcttgcaaa aaaaatgcag aaattaatat gtatatgtgt acctcatgat    900
tattaaggcc gctgcaccat gattttatgg tatattatta tcagcttaaa acaggctttc    960 cctttttgatt atatttcaat aattcgttta gcatcattag tttctgcatt tgccgatgat   1020
ctcgaggttc tgtttgcaag aagtggctgc actgcagccc tgcagctata tatacacagg   1080
ttcaagttac taattttgtg cttctacaat aatcctatca gtccgcag               1128

<210> SEQ ID NO 83
<211> LENGTH: 912
<212> TYPE: DNA
<213> ORGANISM: Zea mays

<400> SEQUENCE: 83
```

```
cactaatagc tttctatctg atcgattcat catcatccgg gcatgcatga gcatcatcgt    60
ctccagatcg ttgggctctc gcagctacct acattcaaca ttcaagctcg ctctacatat   120
gcatgcaaat ctgcaacact cgctcttggc agggatacat tcacgccgag agagagagag   180
agagagagag agagagagag agagagagag atgtgtgtgc tgtagtcatc agccagccgg   240
tgatttctgg agtggcatca tcaagattca cacactgcat gccaacataa tgcgcgtgtt   300
catgcatcca tcgccgccgc tgcatcatgc atcatatata atatatatat atgtgtatgt   360
gtgggaatct tgatgatgct gcattggata tcaagggcta tatatatata tggatcaagc   420
atatatatat atatatcaga tcaccagtca tatcgagttc ttccttccag gcttgctagg   480
taatttataa cttaaacctt gttgctgaac taactaattt tacttagcta gctagctact   540
actatacttc attgttagta gtagctagca agaaggaaag taggcatccc ggccggttcg   600
taccttcttt ttttttgcac agcaggatct gaccttctgt ataaaatgca ttttgccttt   660 gagtttttt gttttccac agtaggaggt agctgattct gatctgctgt ataaaaatgc   720 attttttcc ttttcatttc atggcagaag gcaatatata ataagaaaag actgaaagga   780
aaaggcacca ctgccatgat ggatcgcatc agtgcatctg ttttgttctt ctaaacgatt   840
caggtcatca ggtgagctag gtgggctaat aagtatatag attaatttct attttgcaca   900
tgatttatat gg                                                       912

<210> SEQ ID NO 84
<211> LENGTH: 1063
<212> TYPE: DNA
<213> ORGANISM: Zea mays

<400> SEQUENCE: 84
catgcatgct gccttacacc taagctagct agctgttgaa tttgatgcat gacgcatgct    60
ttcctcctcc tccgttcgta gtcgttgtcg ttgtctcagt aatccatcct ctctcttttt   120
ttcttgctaa tacataaaag gggttcagat ggtagctgct agtggttatt cttcttctta   180
gacgatgcaa gtatatgtat atggaccacc aaattagctt ctcgtcttgc cgccggaccg   240
ccatcatgca ccttggagaa gcaacagaac gaagctcgct gctatgctat ctatggatta   300
ttgtattgta tatgaatgaa gcagcaagca aacgtagttc agtacagtcg gtgcttgcag   360
gtgcagcacc atcaagattc acatcgtcca actcatgcat catgcatata tgcatcttca   420
atgatgcgtg cctcgcatgt gtgtgtatat atatatgatg agatgagaat cttgatgatg   480
ctgcatcagc agacactcac tagctcatgc atcacctcca agtaataaga gatgaattga   540
attaacgacc atgcagctac tagctctrgt acgtaccact tcgttctcct ctaatttctt   600
tttccattca gtctaccttg tttgctaatc aacttgttct catataatat atggttccca   660
atgcgataag ggttggcctg caggcttagc tctgcagcag gtagcaccca tgcatggccc   720
atgatacata acatattgat ggatatatac tagcataaaa acatgatgat gcagagcagc   780
agcatccatc tcatagctag cataaaaaca tgcatgagct agcagcggca gttgacgatg   840
actcttcgag aggaaggaag gaagcagcag atcgatggac gcgagacatg agcagtgaca   900
gatgcataat gtagcagtac atacagcatt attgctatta tttgtgccca agcaaattaa   960
ggaaggggac caaattgaaa tatactaatg acattgcaga cggcaccagc agagtccaca  1020
gctcgtgaac ctgtgtaggc tgcctgccga tggtacaatg caa                    1063

<210> SEQ ID NO 85
```

<211> LENGTH: 1738
<212> TYPE: DNA
<213> ORGANISM: Zea mays

<400> SEQUENCE: 85

```
ccatcagcaa ctgctcgtag ctccgtcctc atcacttaaa ccttatcatc atcactctct      60
cttcctctct cttctggccg gccggtcctt tcacctcact catcttctca gttcattcca     120
tggagagcgt cgttcctata tatcatgcat catccaccaa ggccctagct aagctgctac     180
tacctgctag gggttttatt agttgctcaa ccttcgctgg ccggccttat atatacctag     240
ctatagctgt cttgcttgca tagatcatcg atccatgttg ctagctagct agctccctca     300
gttcagttca gttcagttca gctcagctag ctagctcact cctctcttga gtcgtggtgt     360
ccatcacaat cttctctata tcgatacagg tgaggaggta gctagacaga tcaacaccaa     420
tcctctcaac gacatcccct tgttcttgta gagagagttg gtgtaggtcg aaaggcagat     480
agatcatata tagagggaga gatgcatata tggtgtaggg ttcttcaatt tgtttctatg     540
atcgattcat tcgccctgca gccccccctg cgcatctagt tatgtctcca tccctcctcc     600
cttgttcctg atacatatat atatatgtag gtagtggctc tgtatatacc catgccatct     660
ctctcaatct catctatatc atatatatccc atgctttgca tctagctgtt tcatttcttt     720
tcactcgtgc tttgaaagat ctggtacagt ccggcctgta ttagtaagaa cgagttagaa     780
aaatacacac gtacgcgcga gaaccatgca tcatcagcta gctcctctct ttcctctttt     840
tttttgttaa tgcatacatt catatatata ttcccatgaa tgaatgcttt aagcatgagg     900
caagcaaaca tcgacagtgg gtgcttgcag gtgcagcacc accaagattc acatccaact     960
ctcacgcatc ttcagtgatg catgcatgct ctgtgatgtc tcgcagcagc tatatgcata    1020
tgtgatgaga tgagaatctt gatgatgctg catcagcaga cactcactca tcacaccaac    1080
gtaccccaac aagggtgaga gacgacgaat cggctgctgg tatatacata caactgagaa    1140
gtcggattac ctttgctgat tattaacttg tttccattgc tgtgaaatga aactttcaat    1200
gcaaggggggc tggcctacca gctggtacta gcaggaatga agagcatata tatgaaca     1260
tgatgatgca tatatgcaga gcagcaacag cagcatcgtc gtaccatctc atatatatca    1320
ttgcaaacat gagcagtagt ggtagttcat gaatcatgat gaaagcaagg aagaggaagc    1380
tagcagtgct ggacgcggat cagatgcaga tcgatggagg ccggggccgg gggtgtacct    1440
acgtagtaca ttgctattat tgtgtccatg aaggggggac caaagtatgt aatgcgttgc    1500
acaccacaca ccagagctgg ctcagcagct agcagcagcc tgtggtggtg gtggtacaat    1560
gcagcgtgta ctgctgtcgt cccagcagca agttgaaagg taaaagagag aaatatttca    1620
gctgacttta ctcatcacgc actctgcctg catgctggct gcaggcctgc tgtgagtctg    1680
tgtgtgtgtg cttgttctct tgctttagtg gtggtgtaga tcttctattt gctagttt      1738
```

<210> SEQ ID NO 86
<211> LENGTH: 21
<212> TYPE: DNA
<213> ORGANISM: Arabidopsis thaliana

<400> SEQUENCE: 86

```
agaatcttga tgatgctgca t                                                21
```

<210> SEQ ID NO 87
<211> LENGTH: 26
<212> TYPE: DNA
<213> ORGANISM: Artificial Sequence

```
<220> FEATURE:
<223> OTHER INFORMATION: Forward PCR primer for maize miR172a

<400> SEQUENCE: 87
ggatcctctg cactagtggg gttatt                                              26

<210> SEQ ID NO 88
<211> LENGTH: 26
<212> TYPE: DNA
<213> ORGANISM: Artificial Sequence
<220> FEATURE:
<223> OTHER INFORMATION: Reverse PCR primer for maize miR172a

<400> SEQUENCE: 88
gatatctgca acagtttaca ggcgtt                                              26

<210> SEQ ID NO 89
<211> LENGTH: 26
<212> TYPE: DNA
<213> ORGANISM: Artificial Sequence
<220> FEATURE:
<223> OTHER INFORMATION: Forward PCR primer for maize miR172b

<400> SEQUENCE: 89
ggatcccatg atatagatga tgcttg                                              26

<210> SEQ ID NO 90
<211> LENGTH: 26
<212> TYPE: DNA
<213> ORGANISM: Artificial Sequence
<220> FEATURE:
<223> OTHER INFORMATION: Reverse PCR primer for maize miR172b

<400> SEQUENCE: 90
gatatcaaga gctgaggaca agtttt                                              26

<210> SEQ ID NO 91
<211> LENGTH: 170
<212> TYPE: DNA
<213> ORGANISM: Zea mays

<400> SEQUENCE: 91
tatacagatc atgaggaagc aagaaattat gcaaaacagt cggtgcttgc aggtgcagca         60
ccatcaagat tcacatcccc agctcgatct gtgcatgatg agatgagaat cttgatgatg        120
ctgcatcagc aaacactcac ttacatcgat ctcacccctg acaagctgg                    170

<210> SEQ ID NO 92
<211> LENGTH: 21
<212> TYPE: DNA
<213> ORGANISM: Zea mays

<400> SEQUENCE: 92
agaatcttga tgatgctgca t                                                   21

<210> SEQ ID NO 93
<211> LENGTH: 21
<212> TYPE: DNA
<213> ORGANISM: Zea mays

<400> SEQUENCE: 93
gtgcagcacc atcaagattc a                                                   21

<210> SEQ ID NO 94
```

```
<211> LENGTH: 170
<212> TYPE: DNA
<213> ORGANISM: Artificial Sequence
<220> FEATURE:
<223> OTHER INFORMATION: miRNA precursor template to target PDS

<400> SEQUENCE: 94
tatacagatc atgaggaagc aagaaattat gcaaaacagt cggtgcttgc agatcctgcc      60
tcgcaggttg tcacatcccc agctcgatct gtgcatgatg agatgagaca acctgcaagg    120
caggatcagc aaacactcac ttacatcgat ctcaccctg gacaagctgg                170

<210> SEQ ID NO 95
<211> LENGTH: 21
<212> TYPE: DNA
<213> ORGANISM: Artificial Sequence
<220> FEATURE:
<223> OTHER INFORMATION: miRNA  template to PDS target

<400> SEQUENCE: 95
agacaacctg caaggcagga t                                                21

<210> SEQ ID NO 96
<211> LENGTH: 21
<212> TYPE: DNA
<213> ORGANISM: Artificial Sequence
<220> FEATURE:
<223> OTHER INFORMATION: miRNA template backside to PDS target

<400> SEQUENCE: 96
atcctgcctc gcaggttgtc a                                                21

<210> SEQ ID NO 97
<211> LENGTH: 178
<212> TYPE: DNA
<213> ORGANISM: Artificial Sequence
<220> FEATURE:
<223> OTHER INFORMATION: Oligonucleotide 1 for maize miR172b

<400> SEQUENCE: 97
gatctataca gatcatgagg aagcaagaaa ttatgcaaaa cagtcggtgc ttgcaggtgc      60
agcaccatca agattcacat ccccagctcg atctgtgcat gatgagatga gaatcttgat    120
gatgctgcat cagcaaacac tcacttacat cgatctcacc cctggacaag ctgggtac      178

<210> SEQ ID NO 98
<211> LENGTH: 170
<212> TYPE: DNA
<213> ORGANISM: Artificial Sequence
<220> FEATURE:
<223> OTHER INFORMATION: Oligonucleotide 2 for maize miR172b

<400> SEQUENCE: 98
ccagcttgtc caggggtgag atcgatgtaa gtgagtgttt gctgatgcag catcatcaag      60
attctcatct catcatgcac agatcgagct ggggatgtga atcttgatgg tgctgcacct    120
gcaagcaccg actgttttgc ataatttctt gcttcctcat gatctgtata                170

<210> SEQ ID NO 99
<211> LENGTH: 178
<212> TYPE: DNA
<213> ORGANISM: Artificial Sequence
<220> FEATURE:
<223> OTHER INFORMATION: Oligonucleotide 1 for maize PDS target

<400> SEQUENCE: 99
```

```
gatctataca gatcatgagg aagcaagaaa ttatgcaaaa cagtcggtgc ttgcagatcc      60
tgcctcgcag gttgtcacat ccccagctcg atctgtgcat gatgagatga dacaacctgc    120
aaggcaggat cagcaaacac tcacttacat cgatctcacc cctggacaag ctgggtac     178
```

<210> SEQ ID NO 100
<211> LENGTH: 170
<212> TYPE: DNA
<213> ORGANISM: Artificial Sequence
<220> FEATURE:
<223> OTHER INFORMATION: Oligonucleotide 2 for maize PDS target

<400> SEQUENCE: 100

```
ccagcttgtc caggggtgag atcgatgtaa gtgagtgttt gctgatcctg ccttgcaggt      60
tgtctcatct catcatgcac agatcgagct ggggatgtga caacctgcga ggcaggatct    120
gcaagcaccg actgttttgc ataatttctt gcttcctcat gatctgtata                170
```

<210> SEQ ID NO 101
<211> LENGTH: 26
<212> TYPE: DNA
<213> ORGANISM: Artificial Sequence
<220> FEATURE:
<223> OTHER INFORMATION: oligonucleotide

<400> SEQUENCE: 101

```
caccacagtt tgcttatgtc ggatcc                                           26
```

<210> SEQ ID NO 102
<211> LENGTH: 30
<212> TYPE: DNA
<213> ORGANISM: Artificial Sequence
<220> FEATURE:
<223> OTHER INFORMATION: oligonucleotide

<400> SEQUENCE: 102

```
tgacccggga tgtagagctc ccttcaatcc                                       30
```

<210> SEQ ID NO 103
<211> LENGTH: 46
<212> TYPE: DNA
<213> ORGANISM: Artificial Sequence
<220> FEATURE:
<223> OTHER INFORMATION: oligonucleotide

<400> SEQUENCE: 103

```
atagatcttg atctgacgat ggaagaagag atcctaactt ttcaaa                     46
```

<210> SEQ ID NO 104
<211> LENGTH: 33
<212> TYPE: DNA
<213> ORGANISM: Artificial Sequence
<220> FEATURE:
<223> OTHER INFORMATION: oligonucleotide

<400> SEQUENCE: 104

```
tgacccggga tgaagagatc ccatatttcc aaa                                   33
```

<210> SEQ ID NO 105
<211> LENGTH: 29
<212> TYPE: DNA
<213> ORGANISM: Artificial Sequence
<220> FEATURE:
<223> OTHER INFORMATION: oligonucleotide

```
<400> SEQUENCE: 105
caccaatgat gattacgatg atgagagtc                              29

<210> SEQ ID NO 106
<211> LENGTH: 23
<212> TYPE: DNA
<213> ORGANISM: Artificial Sequence
<220> FEATURE:
<223> OTHER INFORMATION: oligonucleotide

<400> SEQUENCE: 106
caaagtttga tcacgattca tga                                    23

<210> SEQ ID NO 107
<211> LENGTH: 48
<212> TYPE: DNA
<213> ORGANISM: Artificial Sequence
<220> FEATURE:
<223> OTHER INFORMATION: oligonucleotide

<400> SEQUENCE: 107
gagaatgagg ttgagtttag tctgacttgg ccagttttt taccaatg          48

<210> SEQ ID NO 108
<211> LENGTH: 46
<212> TYPE: DNA
<213> ORGANISM: Artificial Sequence
<220> FEATURE:
<223> OTHER INFORMATION: oligonucleotide

<400> SEQUENCE: 108
ctgattctgg tgttggccaa gtcagactaa actctgtttc cttctc           46

<210> SEQ ID NO 109
<211> LENGTH: 48
<212> TYPE: DNA
<213> ORGANISM: Artificial Sequence
<220> FEATURE:
<223> OTHER INFORMATION: oligonucleotide

<400> SEQUENCE: 109
gagaatgagg ttgatctctt tccagtcttc agggttttt taccaatg          48

<210> SEQ ID NO 110
<211> LENGTH: 47
<212> TYPE: DNA
<213> ORGANISM: Artificial Sequence
<220> FEATURE:
<223> OTHER INFORMATION: oligonucleotide

<400> SEQUENCE: 110
gattctggtg tcctgaagac tggaaagaga tctgtttcct tctcttc          47

<210> SEQ ID NO 111
<211> LENGTH: 44
<212> TYPE: DNA
<213> ORGANISM: Artificial Sequence
<220> FEATURE:
<223> OTHER INFORMATION: oligonucleotide

<400> SEQUENCE: 111
tctgacgatg gaagttcctc gcccgacatt cgaaaatgag ttga             44

<210> SEQ ID NO 112
<211> LENGTH: 45
```

```
<212> TYPE: DNA
<213> ORGANISM: Artificial Sequence
<220> FEATURE:
<223> OTHER INFORMATION: oligonucleotide

<400> SEQUENCE: 112
aaacccggga tgttcctcgc ccggaattcg aaagaagagt aaaag          45

<210> SEQ ID NO 113
<211> LENGTH: 272
<212> TYPE: DNA
<213> ORGANISM: Artificial Sequence
<220> FEATURE:
<223> OTHER INFORMATION: miR159a precursor template

<400> SEQUENCE: 113
acagtttgct tatgtcggat ccataatata tttgacaaga tactttgttt ttcgatagat    60
cttgatctga cgatggaagt agagctcctt aaagttcaaa catgagttga gcagggtaaa   120
gaaaagctgc taagctatgg atcccataag ccctaatcct tgtaaagtaa aaaaggattt   180
ggttatatgg attgcatatc tcaggagctt taacttgccc tttaatggct tttactcttc   240
tttggattga agggagctct acatcccggg tc                                 272

<210> SEQ ID NO 114
<211> LENGTH: 21
<212> TYPE: DNA
<213> ORGANISM: Artificial Sequence
<220> FEATURE:
<223> OTHER INFORMATION: miR159a mature template

<400> SEQUENCE: 114
tttggattga agggagctct a                                              21

<210> SEQ ID NO 115
<211> LENGTH: 21
<212> TYPE: DNA
<213> ORGANISM: Artificial Sequence
<220> FEATURE:
<223> OTHER INFORMATION: miRPDS(159a) mature template

<400> SEQUENCE: 115
tttggaaata tgggatctct t                                              21

<210> SEQ ID NO 116
<211> LENGTH: 222
<212> TYPE: DNA
<213> ORGANISM: Artificial Sequence
<220> FEATURE:
<223> OTHER INFORMATION: miR169g precursor template

<400> SEQUENCE: 116
aatgatgatt acgatgatga gagtctctag ttgtatcaga gggtcttgca tggaagaata    60
gagaatgagg ttgagccaag gatgacttgc cgggtttttt taccaatgaa tctaattaac   120
tgattctggt gtccggcaag ttgaccttgg ctctgtttcc ttctcttctt ttggatgtca   180
gactccaaga tatctatcat catgaatcgt gatcaaactt tg                      222

<210> SEQ ID NO 117
<211> LENGTH: 21
<212> TYPE: DNA
<213> ORGANISM: Artificial Sequence
<220> FEATURE:
<223> OTHER INFORMATION: miR169 mature template
```

<400> SEQUENCE: 117
gagccaagga tgacttgccg g					21

<210> SEQ ID NO 118
<211> LENGTH: 21
<212> TYPE: DNA
<213> ORGANISM: Artificial Sequence
<220> FEATURE:
<223> OTHER INFORMATION: miRPDSa(169g) mature template

<400> SEQUENCE: 118
gagtttagtc tgacttggcc a					21

<210> SEQ ID NO 119
<211> LENGTH: 21
<212> TYPE: DNA
<213> ORGANISM: Artificial Sequence
<220> FEATURE:
<223> OTHER INFORMATION: miR169 mature template

<400> SEQUENCE: 119
gagccaagga tgacttgccg g					21

<210> SEQ ID NO 120
<211> LENGTH: 21
<212> TYPE: DNA
<213> ORGANISM: Artificial Sequence
<220> FEATURE:
<223> OTHER INFORMATION: miRPDSb(169g) mature template

<400> SEQUENCE: 120
gatctctttc cagtcttcag g					21

<210> SEQ ID NO 121
<211> LENGTH: 2470
<212> TYPE: DNA
<213> ORGANISM: Artificial Sequence
<220> FEATURE:
<223> OTHER INFORMATION: miR169 precursor template

<400> SEQUENCE: 121
aagctttgat ctttagctct tgccaaagc ttcttttgat ttttctattt ctctaatcta		60 tccattgacc atttggggtg atgatattct tcaatttatg ttgttgttta ttgcccatcc	120 acagacccac gtttgatttg tttaatcaaa atatataaac tgacagttgt gccactagtc	180 acttgccaat taagcattcc aaagctcctt cctttacatt agtatcaagt gagactagca	240 caagctttta agtccagata aaaagcccca tggaagggaa gctttcaaga acgagattta	300 accgtaaaac ccaatttcga tttccgctaa taatttggat ccaaaaatct agacaaaatc	360 tgataaaatt agacaaagaa atggataaaa ccccaaaacc cataatcgtc gttgttcttg	420 tttgcttcaa tatcactctt tcccctccaa cgagttagtt agagtgacgt ggcagctgaa	480 ctagatttgg agtaacggga tagattaccc ataaagccca ataatgatca ttacgtgaga	540 cataacttgc ttagataacc tcattttatg ggcttagatg gggtctctag tgttagtcat	600 aagctcttaa ataccatttc tagttatata tcaatcttta gcttggaatt ggatcgttgt	660 cctatagtaa aaaaactttt actattttat gttagcaatc ccacttaaca ttcaatatgt	720 ttaaaatgaa agagtttacc aaaaggaaag aaaaaaaggt tggtaatgaa tttatctaat	780 cggatacgat atttcataat ctaatgatgg gatctatcaa taaatagaat caaagttaac	840 tttaacgctt ttgttaccctg ttttctttct ttagcaatta atattaaacg agttttagta	900

```
atataaatat gtttccagtt ataaccaaa ctttatgtaa tattcataag cttgccaaaa    960
tttacaagag tttttggaac gcgcacaaaa ttctcatata tttcttaccc aaaaataaat   1020
ttttttttttt tttttacttg tttataatcc tatatgaaca ttgctcatct tccccatttg   1080
atggtaattt ttctattcct atatgtaatt aaatcctaac taatgaaatt gaaaacataa   1140
tttgaagata atcaatccta atatctcccg tcttagatct atttaaatgg tcttatttaa   1200
tttcctatat ttttggcctaa ttattttattt gatatagtga atttatggaa gcttcatgtt   1260
gatggaataa aaccggctta tcccaattaa tcgatcggga gctataacac aaatcgaaac   1320
tctagtagct ataaagagtg tgtaatagct ttggatcaca tgtattacta tttatttact   1380
agctcgtgca acaattggct ttgggaaaaa atttatttac tagtactccc ccttcacaat   1440
gtgatgagtc tccaaatgat atattctcaa cccaaaggac aatctgaaat ttcaatata   1500
tattccatttt tatccgcaac atttgaaatt tgtggcaatg ttttaaaaa gactatttat   1560
aaagaatctt tctaaattgt ttctacgaca atcgataaca cctttttgttg atcaaccca   1620
cacaagacta tgattccaat cctaagaaac atacgacacg tggatttta tgtcacacta   1680
gtacgatgcg tcgatgcctt cagagtacga atatttattca cataaaattc ttattcgaat   1740
ttgataatat aaggtcagcc aatcttttaa agtaattata ttcttcaata tacggttgtg   1800
gtcaaaattc cattttattt tgtagcttgc atgcactact agtttaaaac catgcatgga   1860
tttattgcat ataataacat tatatgaatt ttcaattaaa ttaatccaca catttcccat   1920
ttcaatatgc ctataaatac cttcatcacg agtatgacaa gatcacaaga caagaaaaga   1980
aaggtagaga aaacatgata atgatgatta cgatgatgag agtctctagt tgtatcagag   2040
ggtcttgcat ggaagaatag agaatgaggt tgagccaagg atgacttgcc gggttttttt   2100
accaatgaat ctaattaact gattctggtg tccggcaagt tgaccttggc tctgtttcct   2160
tctcttcttt tggatgtcag actccaagat atctatcatc atgaatcgtg atcaaacttt   2220
gtaatttcat tgaaatgtgt ttttcttgat gcgaatttttt tggcttacgg ttttttcgatt   2280
tgaatgatca gattttttgtt tttgcactca aactatagtt tcacttaggt tctatttttt   2340
tcaggtttat gaatgataaa acaagtaaga ttttatgcta gttttagttc attttttcgat   2400
tcaaattcaa acatcttggt tttggtttag ttaagtttga tttttcaagt caaatgctat   2460
gttttcttgt                                                          2470

<210> SEQ ID NO 122
<211> LENGTH: 268
<212> TYPE: DNA
<213> ORGANISM: Nicotiana benthamiana

<400> SEQUENCE: 122
atgcctcaaa ttggacttgt ttctgctgtt aacttgagag tccaaggtag ttcagcttat     60
ctttggagct cgaggtcgtc ttctttggga actgaaagtc gagatggttg cttgcaaagg    120
aattcgttat gttttgctgg tagcgaatca atgggtcata agttaaagat tcgtactccc    180
catgccacga ccagaagatt ggttaaggac ttggggcctt taaaggtcgt atgcattgat    240
tatccaagac cagagctgga caatacag                                      268

<210> SEQ ID NO 123
<211> LENGTH: 657
<212> TYPE: DNA
<213> ORGANISM: Nicotiana benthamiana
```

<400> SEQUENCE: 123

```
ggcactcaac tttataaacc ctgacgagct ttcgatgcag tgcattttga ttgctttgaa    60
cagatttctt caggagaaac atggttcaaa atggccttt ttagatggta accctcctga   120
gagactttgc atgccgattg tggaacatat tgagtcaaaa ggtggccaag tcagactaaa   180
ctcacgaata aaaagatcg agctgaatga ggatggaagt gtcaaatgtt ttatactgaa    240
taatggcagt acaattaaag gagatgcttt tgtgtttgcc actccagtgg atatcttgaa   300
gcttcttttg cctgaagact ggaaagagat cccatatttc caaagttgg agaagctagt    360
gggagttcct gtgataaatg tccatatatg gtttgacaga aaactgaaga acacatctga   420
taatctgctc ttcagcagaa gcccgttgct cagtgtgtac gctgacatgt ctgttacatg   480
taaggaatat tacaaccca atcagtctat gttggaattg gtatttgcac ccgcagaaga    540
gtggataaat cgtagtgact cagaaattat tgatgctaca atgaaggaac tagcgaagct   600
tttccctgat gaaatttcgg cagatcagag caaagcaaaa atattgaagt accatgt      657
```

<210> SEQ ID NO 124
<211> LENGTH: 781
<212> TYPE: DNA
<213> ORGANISM: Nicotiana benthamiana

<400> SEQUENCE: 124

```
ggagaaagag aaactttctg tcttaagagt aattagcaat ggcttcctca gttctttcct    60
cagcagcagt tgccacccgc agcaatgttg ctcaagctaa catggttgca cctttcacag   120
gtcttaagtc tgctgcctca ttccctgttt caagaaagca aaaccttgac atcacttcca   180
ttgccagcaa cggcggaaga gtgcaatgca tgcaggtgtg gccaccaatt aacatgaaga   240
agtatgagac tctctcatac cttcccgatt gagccagga gcaattgctc tccgaaattg    300
agtaccttt gaaaaatgga tgggttcctt gcttggaatt cgagactgag aaaggatttg   360
tctaccgtga acaccacaag tcaccaggat actatgatgg cagatactgg accatgtgga   420
agctacctat gttcggatgc actgatgcca cccaagtgtt ggctgaggtg ggagaggcga   480
agaaggaata cccacaggcc tgggtccgta tcattggatt tgacaacgtg cgtcaagtgc   540
agtgcatcag tttcattgcc tccaagcctg acggctactg agtttcatat taggacaact   600
taccctattg tctgtcttta ggggcagttt gtttgaaatg ttacttagct tcttttttt    660
ccttcccata aaaactgttt atgttccttc tttttattcg gtgtatgttt tggattccta   720
ccaagttatg agacctaata attatgattt tgtgctttgt ttgtaaaaaa aaaaaaaaa    780
a                                                                   781
```

<210> SEQ ID NO 125
<211> LENGTH: 762
<212> TYPE: DNA
<213> ORGANISM: Nicotiana benthamiana

<400> SEQUENCE: 125

```
tctttctgtc ttaagtgtaa ttaacaatgg cttcctcagt tctttcctca gcagcagttg    60
ccacccgcag caatgttgct caagctaaca tggttgcacc tttcactggt cttaagtcag   120
ctgcctcgtt ccctgtttca aggaagcaaa accttgacat cacttccatt gccagcaacg   180
gcggaagagt gcaatgcatg caggtgtggc caccaattaa caagaagaag tacgagactc   240
tctcatacct tcctgatctg agcgtggagc aattgcttag cgaaattgag tacctcttga   300
aaaatggatg ggttccttgc ttggaattcg agactgagcg cggatttgtc taccgtgaac   360
```

```
accacaagtc accgggatac tatgacggca gatactggac catgtggaag ttgcctatgt    420
tcggatgcac tgatgccacc caagtgttgg ccgaggtgga agaggcgaag aaggcatacc    480
cacaggcctg gatccgtatt attggattcg acaacgtgcg tcaagtgcag tgcatcagtt    540
tcattgccta caagccagaa ggctactaag tttcatatta ggacaactta ccctattgtc    600
cgactttagg ggcaatttgt ttgaaatgtt acttggcttc tttttttttt aattttccca    660
caaaaactgt ttatgtttcc tactttctat tcggtgtatg ttttgcatt cctaccaagt     720
tatgagacct aataactatg atttggtgct ttgtttgtaa at                      762
```

<210> SEQ ID NO 126
<211> LENGTH: 683
<212> TYPE: DNA
<213> ORGANISM: Nicotiana benthamiana

<400> SEQUENCE: 126

```
tagcaatagc tttaagctta gaaattattt tcagaaatgg cttcctcagt tatgtcctca     60
gcagctgctg ttgcgaccgg cgccaatgct gctcaagcca acatggttgc acccttcact   120
ggcctcaagt ccgcctcctc cttccctgtt accaggaaac aaaaccttga cattacctcc   180
attgctagca atggtggaag agttcaatgc atgcaggtgt ggccaccaat aacatgaag    240
aagtacgaga cactctcata ccttcctgat ttgagccagg agcaattgct tagtgaagtt   300
gagtaccttt tgaaaaatgg atgggttcct tgcttggaat tcgagactga gcgtggattc   360
gtctaccgtg aacaccacaa ctcaccagga tactacgatg cagatactg gaccatgtgg    420
aagttgccca tgttcgggtg cactgatgcc actcaggtgt tggctgaggt cgaggaggca   480
aagaaggctt acccacaagc ctgggttaga atcattggat tcgacaacgt ccgtcaagtg   540
caatgcatca gttttatcgc ctccaagcca gaaggctact aaaatctcca tttttaaggc   600
aacttatcgt atgtgttccc cggagaaact gttttggttt tcctgcttcc ttatattatt   660
caatgtatgt ttttgaattc caa                                            683
```

<210> SEQ ID NO 127
<211> LENGTH: 700
<212> TYPE: DNA
<213> ORGANISM: Nicotiana benthamiana

<400> SEQUENCE: 127

```
aatggcttcc tcagttatgt cctcagctgc cgctgttgcc accggcgcca atgctgctca     60
agccagtatg gttgcacctt tcactggcct caagtccgca acctccttcc ctgtttccag   120
aaaacaaaac cttgacatta cttccattgc tagcaacggc ggaagagttc aatgcatgca   180
ggtgtggcca ccaattaaca agaagaagta cgagacactc tcataccttc cgatttgag    240
ccaggagcaa ttgcttagtg aagttgagta cctgttgaaa aatggatggg ttccttgctt   300
ggaattcgag actgagcgtg gattcgtcta ccgtgaacac cacagctcac caggatatta   360
tgatggcaga tactggacca tgtggaagtt gcccatgttc gggtgcactg atgccactca   420
ggtgttggct gaggtcgagg aggcaaagaa ggcttaccca caagcctggg ttagaatcat   480
tggattcgac aatgtccgtc aagtgcaatg catcagtttt atcgcctaca gccagaagg    540
ctactagaat ctccatttt aaggcaactt atcgtatgtg ttccccggag aaactgtttt     600
ggtttttcct gcttcattat attattcaat gtatgttttt gaattccaat caaggttatg   660
agaactaata atgacattta atttgttcct tttctatata                         700
```

<210> SEQ ID NO 128
<211> LENGTH: 698
<212> TYPE: DNA
<213> ORGANISM: Nicotiana benthamiana

<400> SEQUENCE: 128

| | | | | | |
|---|---|---|---|---|---|
| taaataatta | attgcaacaa | tggcttcctc | tgtgatttcc | tcagctgctg | ccgttgccac | 60 |
| cggcgctaat | gctgctcaag | ccagcatggt | tgcacccttc | actggcctca | aatctgcttc | 120 |
| ctccttccct | gttaccagaa | acaaaacct | tgacattaca | tccattgcta | gcaatggtgg | 180 |
| aagagtccaa | tgcatgcagg | tgtggccacc | aattaacatg | aagaagtacg | agacactctc | 240 |
| ataccttcct | gatttgagcc | aggagcaatt | gcttagtgaa | gttgagtatc | ttttgaaaaa | 300 |
| tggatgggtt | ccttgcttgg | aattcgagac | tgagcgtgga | tttgtctacc | gtgaacatca | 360 |
| cagctcacca | ggatactacg | atggcagata | ctggaccatg | tggaagttgc | ccatgttcgg | 420 |
| gtgcactgat | gccactcagg | tgttggctga | ggtcgaggag | gcaaagaagg | cttacccaca | 480 |
| agcctgggtt | agaatcattg | gattcgacaa | cgtccgtcaa | gtgcaatgca | tcagttttat | 540 |
| cgcctccaag | ccagaaggct | actaaaatct | ccatttttaa | ggcaacttat | cgtatgtgtt | 600 |
| ccccggagaa | actgttttgg | ttttcctgct | tcattatatt | attcaatgta | tgttttgaa | 660 |
| ttccaatcaa | ggttatgaga | actaataatg | acatttaa | | | 698 |

<210> SEQ ID NO 129
<211> LENGTH: 727
<212> TYPE: DNA
<213> ORGANISM: Nicotiana benthamiana

<400> SEQUENCE: 129

| | | | | | |
|---|---|---|---|---|---|
| gcacgaggct | tcctcagtta | tgtcctcagc | tgccgctgtt | ccaccggcg | ccaatgctgt | 60 |
| tcaagccagc | atggtcgcac | ccttcactgg | cctcaaggcc | gcctcctcct | tccggttc | 120 |
| caggaaacaa | aaccttgaca | ttacttccat | tgctagaaat | ggtggaagag | tccaatgcat | 180 |
| gcaggtgtgg | ccgccaatta | caagaagaa | gtacgagaca | ctctcatacc | ttcctgattt | 240 |
| gagcgtggag | caattgctta | gcgaaattga | gtaccttttg | aaaatggat | gggttccttg | 300 |
| cttggaattc | gagactgagc | atggattcgt | ctaccgtgaa | caccaccact | caccaggata | 360 |
| ctacgatggc | agatactgga | cgatgtggaa | gttgccatg | ttcgggtgca | ccgatgccac | 420 |
| tcaggtcttg | gctgaggtag | aggaggccaa | gaaggcttac | ccacaagcct | gggtcagaat | 480 |
| cattggattc | gacaacgtcc | gtcaagtgca | atgcatcagt | ttcatcgcct | acaagcccga | 540 |
| aggctattaa | aatctccatt | tttaggacag | cttaccctat | gtattcaggg | gaagtttgtt | 600 |
| tgaattctcc | tggagaaact | gttttggttt | tcctttgttt | taatcttctt | tctattatat | 660 |
| ttttggattt | tactcaagtt | tataagaact | aataataatc | atttgtttcg | ttactaaaaa | 720 |
| aaaaaaa | | | | | | 727 |

<210> SEQ ID NO 130
<211> LENGTH: 25
<212> TYPE: DNA
<213> ORGANISM: Artificial Sequence
<220> FEATURE:
<223> OTHER INFORMATION: oligonucleotide

<400> SEQUENCE: 130

| | |
|---|---|
| ccactcttct gcaggtgcaa aaacc | 25 |

```
<210> SEQ ID NO 131
<211> LENGTH: 28
<212> TYPE: DNA
<213> ORGANISM: Artificial Sequence
<220> FEATURE:
<223> OTHER INFORMATION: oligonucleotide

<400> SEQUENCE: 131
acatggtact tcaatatttt tgctttgc                                              28

<210> SEQ ID NO 132
<211> LENGTH: 28
<212> TYPE: DNA
<213> ORGANISM: Artificial Sequence
<220> FEATURE:
<223> OTHER INFORMATION: oligonucleotide

<400> SEQUENCE: 132
gatctttgta aaggccgaca gggttcac                                              28

<210> SEQ ID NO 133
<211> LENGTH: 29
<212> TYPE: DNA
<213> ORGANISM: Artificial Sequence
<220> FEATURE:
<223> OTHER INFORMATION: oligonucleotide

<400> SEQUENCE: 133
ttcctcagtt ctttcctcag cagcagttg                                             29

<210> SEQ ID NO 134
<211> LENGTH: 24
<212> TYPE: DNA
<213> ORGANISM: Artificial Sequence
<220> FEATURE:
<223> OTHER INFORMATION: oligonucleotide

<400> SEQUENCE: 134
ctcagttatg tcctcagcag ctgc                                                  24

<210> SEQ ID NO 135
<211> LENGTH: 24
<212> TYPE: DNA
<213> ORGANISM: Artificial Sequence
<220> FEATURE:
<223> OTHER INFORMATION: oligonucleotide

<400> SEQUENCE: 135
tcctcagtta tgtcctcagc tgcc                                                  24

<210> SEQ ID NO 136
<211> LENGTH: 22
<212> TYPE: DNA
<213> ORGANISM: Artificial Sequence
<220> FEATURE:
<223> OTHER INFORMATION: oligonucleotide

<400> SEQUENCE: 136
tgtgatttcc tcagctgctg cc                                                    22

<210> SEQ ID NO 137
<211> LENGTH: 23
<212> TYPE: DNA
<213> ORGANISM: Artificial Sequence
<220> FEATURE:
<223> OTHER INFORMATION: oligonucleotide
```

```
<400> SEQUENCE: 137
aactcagtag ccgtcaggct tgg                                           23

<210> SEQ ID NO 138
<211> LENGTH: 30
<212> TYPE: DNA
<213> ORGANISM: Artificial Sequence
<220> FEATURE:
<223> OTHER INFORMATION: oligonucleotide

<400> SEQUENCE: 138
aatatgaaac ttagtagcct tctggcttgt                                    30

<210> SEQ ID NO 139
<211> LENGTH: 23
<212> TYPE: DNA
<213> ORGANISM: Artificial Sequence
<220> FEATURE:
<223> OTHER INFORMATION: oligonucleotide

<400> SEQUENCE: 139
gtttctccgg ggaacacata cga                                           23

<210> SEQ ID NO 140
<211> LENGTH: 27
<212> TYPE: DNA
<213> ORGANISM: Artificial Sequence
<220> FEATURE:
<223> OTHER INFORMATION: oligonucleotide

<400> SEQUENCE: 140
aaacaaactt cccctgaata cataggg                                       27

<210> SEQ ID NO 141
<211> LENGTH: 21
<212> TYPE: RNA
<213> ORGANISM: Artificial Sequence
<220> FEATURE:
<223> OTHER INFORMATION: oligonucleotide

<400> SEQUENCE: 141
uuuggauuga agggagcucu a                                             21

<210> SEQ ID NO 142
<211> LENGTH: 21
<212> TYPE: RNA
<213> ORGANISM: Artificial Sequence
<220> FEATURE:
<223> OTHER INFORMATION: oligonucleotide

<400> SEQUENCE: 142
uuuggaaaua ugggaucucu u                                             21

<210> SEQ ID NO 143
<211> LENGTH: 21
<212> TYPE: RNA
<213> ORGANISM: Artificial Sequence
<220> FEATURE:
<223> OTHER INFORMATION: oligonucleotide

<400> SEQUENCE: 143
aagagauccc auauuuccaa a                                             21

<210> SEQ ID NO 144
<211> LENGTH: 21
```

```
<212> TYPE: RNA
<213> ORGANISM: Artificial Sequence
<220> FEATURE:
<223> OTHER INFORMATION: oligonucleotide

<400> SEQUENCE: 144
gagccaagga ugacuugccg g                                              21

<210> SEQ ID NO 145
<211> LENGTH: 21
<212> TYPE: RNA
<213> ORGANISM: Artificial Sequence
<220> FEATURE:
<223> OTHER INFORMATION: oligonucleotide

<400> SEQUENCE: 145
gaguuuaguc ugacuuggcc a                                              21

<210> SEQ ID NO 146
<211> LENGTH: 21
<212> TYPE: RNA
<213> ORGANISM: Artificial Sequence
<220> FEATURE:
<223> OTHER INFORMATION: oligonucleotide

<400> SEQUENCE: 146
gaucucuuuc cagucuucag g                                              21

<210> SEQ ID NO 147
<211> LENGTH: 21
<212> TYPE: RNA
<213> ORGANISM: Artificial Sequence
<220> FEATURE:
<223> OTHER INFORMATION: oligonucleotide

<400> SEQUENCE: 147
uggccaaguc agacuaaacu c                                              21

<210> SEQ ID NO 148
<211> LENGTH: 21
<212> TYPE: RNA
<213> ORGANISM: Artificial Sequence
<220> FEATURE:
<223> OTHER INFORMATION: oligonucleotide

<400> SEQUENCE: 148
ccugaagacu ggaaagagau c                                              21

<210> SEQ ID NO 149
<211> LENGTH: 21
<212> TYPE: RNA
<213> ORGANISM: Artificial Sequence
<220> FEATURE:
<223> OTHER INFORMATION: oligonucleotide

<400> SEQUENCE: 149
uuucgaauuc cgggcgagga a                                              21

<210> SEQ ID NO 150
<211> LENGTH: 21
<212> TYPE: RNA
<213> ORGANISM: Nicotiana benthamiana

<400> SEQUENCE: 150
uuccuugcuu ggaauucgag a                                              21
```

<210> SEQ ID NO 151
<211> LENGTH: 273
<212> TYPE: DNA
<213> ORGANISM: Artificial
<220> FEATURE:
<223> OTHER INFORMATION: miRCPC1(159) precursor template

<400> SEQUENCE: 151
acagtttgct tatgtcggat ccataatata tttgacaaga tactttgttt ttcgatagat    60
cttgatctga cgatggaaga agaggtgagt aatgttgaaa catgagttga gcagggtaaa   120
gaaaagctgc taagctatgg atcccataag ccctaatcct tgtaaagtaa aaaaggattt   180
ggttatatgg attgcatatc tcaggagctt aacttgccc tttaatggct tttactcttc    240
tttcgatact actcacctct tcatcccggg tca                                273

<210> SEQ ID NO 152
<211> LENGTH: 21
<212> TYPE: DNA
<213> ORGANISM: Artificial
<220> FEATURE:
<223> OTHER INFORMATION: miRCPC1(159) mature template

<400> SEQUENCE: 152
tttcgatact actcacctct t                                              21

<210> SEQ ID NO 153
<211> LENGTH: 273
<212> TYPE: DNA
<213> ORGANISM: Artificial
<220> FEATURE:
<223> OTHER INFORMATION: miRCPC3(159) precursor template

<400> SEQUENCE: 153
acagtttgct tatgtcggat ccataatata tttgacaaga tactttgttt ttcgatagat    60
cttgatctga cgatggaagc tcgttggcga caggtgggag catgagttga gcagggtaaa   120
gaaaagctgc taagctatgg atcccataag ccctaatcct tgtaaagtaa aaaaggattt   180
ggttatatgg attgcatatc tcaggagctt aacttgccc tttaatggct tttactcttc    240
ctcccacctg acgccaacga gcatcccggg tca                                273

<210> SEQ ID NO 154
<211> LENGTH: 21
<212> TYPE: DNA
<213> ORGANISM: Artificial
<220> FEATURE:
<223> OTHER INFORMATION: miRCPC3(159) mature template

<400> SEQUENCE: 154
ctcccacctg acgccaacga g                                              21

<210> SEQ ID NO 155
<211> LENGTH: 273
<212> TYPE: DNA
<213> ORGANISM: Artificial
<220> FEATURE:
<223> OTHER INFORMATION: miRP69(159) precursor template

<400> SEQUENCE: 155
acagtttgct tatgtcggat ccataatata tttgacaaga tactttgttt ttcgatagat    60
cttgatctga cgatggaagc cacaagacaa tcgagacttt catgagttga gcagggtaaa   120
gaaaagctgc taagctatgg atcccataag ccctaatcct tgtaaagtaa aaaaggattt   180

```
ggttatatgg attgcatatc tcaggagctt aacttgccc tttaatggct tttactcttc      240
aaagtctcga ttgtcttgtg gcatcccggg tca                                 273

<210> SEQ ID NO 156
<211> LENGTH: 21
<212> TYPE: DNA
<213> ORGANISM: Artificial
<220> FEATURE:
<223> OTHER INFORMATION: miRP69(159) mature template

<400> SEQUENCE: 156
aaagtctcga ttgtcttgtg g                                               21

<210> SEQ ID NO 157
<211> LENGTH: 222
<212> TYPE: DNA
<213> ORGANISM: Artificial
<220> FEATURE:
<223> OTHER INFORMATION: miRPDS1(169) precursor template

<400> SEQUENCE: 157
aatgatgatt acgatgatga gagtctctag ttgtatcaga gggtcttgca tggaagaata     60
gagaatgagg ttgagtttag tctgacttgg ccagtttttt taccaatgaa tctaattaac    120
tgattctggt gttggccaag tcagactaaa ctctgtttcc ttctcttctt ttggatgtca    180
gactccaaga tatctatcat catgaatcgt gatcaaactt tg                       222

<210> SEQ ID NO 158
<211> LENGTH: 21
<212> TYPE: DNA
<213> ORGANISM: Artificial
<220> FEATURE:
<223> OTHER INFORMATION: miRPDS1(169) mature template

<400> SEQUENCE: 158
gagtttagtc tgacttggcc a                                               21

<210> SEQ ID NO 159
<211> LENGTH: 552
<212> TYPE: DNA
<213> ORGANISM: Artificial
<220> FEATURE:
<223> OTHER INFORMATION: miRPDS1(169)-CPC3(159) precursor template

<400> SEQUENCE: 159
cacctaggaa tgatgattac gatgatgaga gtctctagtt gtatcagagg gtcttgcatg     60
gaagaataga gaatgaggtt gagtttagtc tgacttggcc agttttttta ccaatgaatc    120
taattaactg attctggtgt tggccaagtc agactaaact ctgtttcctt ctcttctttt    180
ggatgtcaga ctccaagata tctatcatca tgaatcgtga tcaaactttg aagggtgggc    240
gactaggaca gtttgcttat gtcggatcca taatatattt gacaagatac tttgtttttc    300
gatagatctt gatctgacga tggaagctcg ttggcgacag gtgggagcat gagttgagca    360
gggtaaagaa aagctgctaa gctatggatc ccataagccc taatccttgt aaagtaaaaa    420
aggatttggt tatatggatt gcatatctca ggagctttaa cttgcccttt aatggctttt    480
actcttcctc ccacctgacg ccaacgagca tcccgggtca aagggtgggc gactagtcta    540
gactcgagta tt                                                        552

<210> SEQ ID NO 160
```

```
<211> LENGTH: 21
<212> TYPE: RNA
<213> ORGANISM: Arabidopsis thaliana

<400> SEQUENCE: 160
uuuggauuga agggagcucu a                                              21

<210> SEQ ID NO 161
<211> LENGTH: 184
<212> TYPE: RNA
<213> ORGANISM: Arabidopsis thaliana

<400> SEQUENCE: 161
guagagcucc uuaaaguuca acaugaguu gagcagggua aagaaaagcu gcuaagcuau      60
ggaucccaua agcccuaauc cuuguaaagu aaaaaaggau uggu uauau ggauugcaua   120 ucucaggagc uuuaacuugc ccuuuaaugg cuuuuacucu ucuuuggauu gaagggagcu   180
cuac                                                                184

<210> SEQ ID NO 162
<211> LENGTH: 21
<212> TYPE: RNA
<213> ORGANISM: Artificial
<220> FEATURE:
<223> OTHER INFORMATION: miRNA

<400> SEQUENCE: 162
acuugcucac gcacucgacu g                                              21

<210> SEQ ID NO 163
<211> LENGTH: 261
<212> TYPE: DNA
<213> ORGANISM: Artificial
<220> FEATURE:
<223> OTHER INFORMATION: miRNA precursor

<400> SEQUENCE: 163
cagtttgctt atgtcggatc cataatatat ttgacaagat actttgtttt tcgatagatc    60
ttgatctgac gatggaagca gtcgagtgcg tgagcaagtc atgagttgag cagggtaaag   120
aaaagctgct aagctatgga tcccataagc cctaatcctt gtaaagtaaa aaggatttg    180 gttatatgga ttcatatct caggagcttt aacttgccct ttaatggctt ttactcttca   240
cttgctcacg cactcgactg c                                             261

<210> SEQ ID NO 164
<211> LENGTH: 21
<212> TYPE: RNA
<213> ORGANISM: Artificial
<220> FEATURE:
<223> OTHER INFORMATION: miRNA

<400> SEQUENCE: 164
aaagucucga uugucuugug g                                              21

<210> SEQ ID NO 165
<211> LENGTH: 261
<212> TYPE: DNA
<213> ORGANISM: Artificial
<220> FEATURE:
<223> OTHER INFORMATION: miRNA precursor

<400> SEQUENCE: 165
cagtttgctt atgtcggatc cataatatat ttgacaagat actttgtttt tcgatagatc    60
```

```
ttgatctgac gatggaagcc acaagacaat cgagactttc atgagttgag cagggtaaag      120
aaaagctgct aagctatgga tcccataagc cctaatcctt gtaaagtaaa aaaggatttg      180
gttatatgga ttgcatatct caggagcttt aacttgccct ttaatggctt ttactcttca      240
aagtctcgat tgtcttgtgg c                                                261

<210> SEQ ID NO 166
<211> LENGTH: 551
<212> TYPE: DNA
<213> ORGANISM: Artificial
<220> FEATURE:
<223> OTHER INFORMATION: homo-polymeric pre-miRNA

<400> SEQUENCE: 166
cagtttgctt atgtcggatc cataatatat ttgacaagat actttgtttt tcgatagatc       60
ttgatctgac gatggaagcc acaagacaat cgagactttc atgagttgag cagggtaaag      120
aaaagctgct aagctatgga tcccataagc cctaatcctt gtaaagtaaa aaaggatttg      180
gttatatgga ttgcatatct caggagcttt aacttgccct ttaatggctt ttactcttca      240
aagtctcgat tgtcttgtgg catcccgggt caaaggtgg gcgactagga cagtttgctt      300
atgtcggatc cataatatat ttgacaagat actttgtttt tcgatagatc ttgatctgac      360
gatggaagca gtcgagtgcg tgagcaagtc atgagttgag cagggtaaag aaaagctgct      420
aagctatgga tcccataagc cctaatcctt gtaaagtaaa aaaggatttg gttatatgga      480
ttgcatatct caggagcttt aacttgccct ttaatggctt ttactcttca cttgctcacg      540
cactcgactg c                                                           551

<210> SEQ ID NO 167
<211> LENGTH: 23
<212> TYPE: DNA
<213> ORGANISM: Turnip mosaic virus

<400> SEQUENCE: 167
cgatttaggc ggcagataca gcg                                               23

<210> SEQ ID NO 168
<211> LENGTH: 35
<212> TYPE: DNA
<213> ORGANISM: Turnip mosaic virus

<400> SEQUENCE: 168
attctcaatg gtttaatggt ctggtgcatt gagaa                                  35

<210> SEQ ID NO 169
<211> LENGTH: 26
<212> TYPE: DNA
<213> ORGANISM: Turnip mosaic virus

<400> SEQUENCE: 169
ataaacggaa tgtgggtgat gatgga                                            26

<210> SEQ ID NO 170
<211> LENGTH: 21
<212> TYPE: DNA
<213> ORGANISM: Turnip mosaic virus

<400> SEQUENCE: 170
gatcaggtgg aattcccgat c                                                 21
```

```
<210> SEQ ID NO 171
<211> LENGTH: 32
<212> TYPE: DNA
<213> ORGANISM: Turnip mosaic virus

<400> SEQUENCE: 171
cacgccaaac ccacatttag gcaaataatg gc                              32

<210> SEQ ID NO 172
<211> LENGTH: 68
<212> TYPE: DNA
<213> ORGANISM: Turnip mosaic virus

<400> SEQUENCE: 172
gctgaagcgt acattgaaaa gcgtaaccaa gaccgaccat acatgccacg atatggtctt  60
cagcgcaa                                                         68

<210> SEQ ID NO 173
<211> LENGTH: 80
<212> TYPE: DNA
<213> ORGANISM: Turnip mosaic virus

<400> SEQUENCE: 173
gaaatgactt ctagaactcc aatacgtgcg agagaagcac acatccagat gaaagcagca  60
gcactgcgtg gcgcaaataa                                            80

<210> SEQ ID NO 174
<211> LENGTH: 26
<212> TYPE: DNA
<213> ORGANISM: Turnip mosaic virus

<400> SEQUENCE: 174
acaacggtag agaacacgga gaggca                                     26

<210> SEQ ID NO 175
<211> LENGTH: 117
<212> TYPE: RNA
<213> ORGANISM: Arabidopsis thaliana

<400> SEQUENCE: 175
gucguuguuu guaggcgcag caccauuaag auucacaugg aaauugauaa auacccuaaa  60 uuagggguuuu gauauguaua ugagaaucuu gaugaugcug caucaacaau cgacggc    117

<210> SEQ ID NO 176
<211> LENGTH: 60
<212> TYPE: DNA
<213> ORGANISM: Arabidopsis thaliana

<400> SEQUENCE: 176
tagggttttg atatgtatat gagaatcttg atgatgctgc atcaacaatc gacggctaca  60

<210> SEQ ID NO 177
<211> LENGTH: 60
<212> TYPE: DNA
<213> ORGANISM: Arabidopsis thaliana

<400> SEQUENCE: 177
acaaagttct ctatgaaaat gagaatcttg atgatgctgc atcggcaatc aacgactatt  60

<210> SEQ ID NO 178
<211> LENGTH: 60
```

```
<212> TYPE: DNA
<213> ORGANISM: Arabidopsis thaliana

<400> SEQUENCE: 178
gagcctttat tttttggttt gagaatcttg atgatgctgc agcggcaatt aaatggctta    60

<210> SEQ ID NO 179
<211> LENGTH: 60
<212> TYPE: DNA
<213> ORGANISM: Arabidopsis thaliana

<400> SEQUENCE: 179 tagattttg atgtatgtat gagaatcttg atgatgctgc agctgcaatc agtggcttac     60

<210> SEQ ID NO 180
<211> LENGTH: 60
<212> TYPE: DNA
<213> ORGANISM: Arabidopsis thaliana

<400> SEQUENCE: 180
aaaagggttc cttatcgagt gggaatcttg atgatgctgc atcagcaaat acatggctac    60

<210> SEQ ID NO 181
<211> LENGTH: 60
<212> TYPE: DNA
<213> ORGANISM: Solanum lycopersicum

<400> SEQUENCE: 181
gctggctatt tgaaactcac gagaatcttg atgatgctgc atcagcaata aacgactatt    60

<210> SEQ ID NO 182
<211> LENGTH: 60
<212> TYPE: DNA
<213> ORGANISM: Glycine max

<400> SEQUENCE: 182
tccatcggtc tttttgatgt gagaatcttg atgatgctgc atcagccata aacggcttta    60

<210> SEQ ID NO 183
<211> LENGTH: 60
<212> TYPE: DNA
<213> ORGANISM: Solanum tuberosum

<400> SEQUENCE: 183
tgcccaattt ttgaatacat gagaatcttg atgatgctgc attggcaaat tgatgacttg    60

<210> SEQ ID NO 184
<211> LENGTH: 60
<212> TYPE: DNA
<213> ORGANISM: Oryza sativa

<400> SEQUENCE: 184
acgcatgtgt atatatgtgt gggaatcttg atgatgctgc atcggaaatt aatgactaag    60

<210> SEQ ID NO 185
<211> LENGTH: 60
<212> TYPE: DNA
<213> ORGANISM: Oryza sativa

<400> SEQUENCE: 185
gttggctgac tatatgtgat gagaatcttg atgatgctgc atcagcaaac gctcgactac    60

<210> SEQ ID NO 186
```

| | |
|---|---|
| <211> LENGTH: 60 | |
| <212> TYPE: DNA | |
| <213> ORGANISM: Oryza sativa | |

<400> SEQUENCE: 186

| | |
|---|---|
| ttcaagtgta gtcatcgtgc gtgaatcttg atgatgctgc accagcaaag agccggccgt | 60 |

<210> SEQ ID NO 187
<211> LENGTH: 60
<212> TYPE: DNA
<213> ORGANISM: Oryza sativa

<400> SEQUENCE: 187

| | |
|---|---|
| catatacatc cgatttggct gagaatcttg atgatgctgc atccgcagac aagcgccttt | 60 |

<210> SEQ ID NO 188
<211> LENGTH: 1374
<212> TYPE: DNA
<213> ORGANISM: Turnip mosaic virus

<400> SEQUENCE: 188

| | |
|---|---|
| agtgcggcag gagctaattt ctggaaaggc ttcgacagat gcttcctcgc ataccgtagt | 60 |
| gacaatcgcg atcacacatg ctattcaggg ctagatgtca ctgagtgcgg cgaagtagca | 120 |
| gcactaatgt gtttggctat gttcccatgc ggaaagataa cctgtcctga ctgcgtgaca | 180 |
| gacagtgagc tatcccaagg acaagcaagt ggaccatcta tgaagcacag gttgacacag | 240 |
| ctacgcgatg tcatcaagtc aagctaccca cgctttaaac atgcagtgca gatactagat | 300 |
| aggtacgagc aatcactgag tagtgcaaac gagaactacc aagatttcgc agaaatccag | 360 |
| agcataagcg atggagttga aaaagctgca ttcccacatg tcaacaagct aaactcaata | 420 |
| ttgataaagg gagccacagc gacaggagag gaattctcac aggctacgaa gcatttgctc | 480 |
| gagatagcac gctacctgaa gaacagaact gagaatatcg agaagggttc acttaagtct | 540 |
| tttcgtaaca agatttccca gaaggcgcac atcaacccaa cactaatgtg cgacaaccaa | 600 |
| ctcgacagaa atggaaattt catatggggt gagaggggat accacgcgaa acggttcttt | 660 |
| agcaactact ttgagataat cgatccaaag aaaggctaca cccagtacga aacaagagca | 720 |
| gtgccaaatg ggtcacggaa acttgcaatc ggcaaactaa tagtcccaac gaacttcgaa | 780 |
| gttctaaggg aacaaatgaa aggcgaacca gtggaaccat acccagtaac agccgagtgt | 840 |
| gtgagcaaat tacagggtga tttcgtccat gcatgttgct gtgtcacaac agaatcaggc | 900 |
| gatccaatct tgtctgaaat caaaatgcca accaaacacc acctagtgat tggtaacagc | 960 |
| ggcgatccaa agtacataga tctccctgag atcgaggaga ataaaatgta catagcaaaa | 1020 |
| gaaggttatt gctacatcaa tatcttccta gccatgttag tgaatgtcaa ggagtcacag | 1080 |
| gcaaaggagt tcacgaaagt tgtcagagac aaaattagttg gcgaacttgg caagtggcca | 1140 |
| actttgctag atgtagcaac cgcttgttat ttcctgaagg tgtttttaccc agacgttgct | 1200 |
| aacgccgaac tgccacgcat gttagtggac cacaagacaa agataattca tgttgttgat | 1260 |
| tcatatgggt cactgtcaac tggatatcac gtccttaaaa caaacactgt ggaacaactc | 1320 |
| atcaaattca cgagatgcaa tctggaatca agtttgaaac actaccgcgt cgga | 1374 |

<210> SEQ ID NO 189
<211> LENGTH: 1887
<212> TYPE: DNA
<213> ORGANISM: Turnip yellow mosaic virus

<400> SEQUENCE: 189

```
atgagtaatg gccttccaat tagcattgga cgcccttgca cccacgactc acagagatcc      60
ctctctgcac ccaattctcg aatccacagt ggattcaatt cgctcctcga tacagaccta     120
cccatggtcc attccgaagg aacttctacc cctactcaac tcctacggca tcccaacatc     180
tggtttggga acctcccacc accccacgc cgcccacaag acaatcgaga ctttctcct      240
ttgcacccac tggtctttcc aggccaccac tcccagctcc gtcatgttca tgaaacccag     300
caagttcaac aaacttgccc aggtaaactc aaactttcgg gagctgaaga actaccgcct     360
gcacccaac gacagcactc gttacccctt cacatcacca gaccttcccg ttttccccac     420
cattttcatg cacgacgccc tgatgtatta ccatccgtcc cagatcatgg acctgttctt    480
gcggaaacca aacctcgaac gtctgtacgc cagcctcgta gtgccacccg aggcccatct    540
ttccgaccaa tccttctacc caaagttgta cacgtacacg acgacccgcc acactcttca    600
ctacgtccca gagggtcacg aagccggcag ctacaaccaa ccgtccgacg cccactcttg    660
gctccgaatc aattccattc gcctcggcaa ccaccacctc tcagtgacga tcctggaatc    720
ctggggcccc gtccactcgc tcctaattca acgagggacc ccccccccg acccatcact    780
ccaggcccct ccaacactca tggcctcaga cctctttcgg tcttaccaag agcctcgcct    840
cgacgtggtc tccttccgaa tccccgacgc catcgaactt ccacaggcca cattcctcca   900
acaaccactt cgagaccgac tggtccccg agccgtctac aacgccctgt tcacctatac    960
cagagcagtc cgcacactcc gaacttcaga cccagcagca ttcgtaagga tgcactcctc   1020
caaaccggac cacgattggg tcacctcgaa tgcctgggac aacctgcaaa ccttcgcact   1080
tctgaacgtt cccctccgac caaacgtcgt ctaccacgtt cttcagagcc caatcgcctc   1140
cctaagcctt tacctgaggc aacattggcg ccgtcttacc gccaccgccg ttcctatcct   1200
ttccttccta accctcctgc agcgcttcct tccattgcct atacctctag cagaggtaaa   1260
atccatcaca gccttccgaa gggagcttta ccgaaagaag gagcccccacc accccctcga  1320
cgtcttccat ctccagcacc gcatccgcaa ctaccactcc gcgatctcgg ccgtacgccc   1380
ggcttcccca ccccaccaaa aactcccaca cgcactccag aaagccgcat tactgcttct   1440
ccgaccgata tcgcccctct tgacagcgac cccgttcttt cggtccgaac agaagtccat   1500
gctcccgaac gccgaacttt catggaccct gaagcgcttc gctctgccct ggcaagcctc   1560
cctagtcctc ctcgctctgt cggaatcatc catactgctc cacaaactgt tctccccgcc   1620
aaccctccaa gcccaacacg acacctacca ccgacatctc caccctggat cctacagtct   1680
ccagtgggag aggacgccat tgtcgattcc gaggacgaca gcatttcttc cttttactcc   1740
cacgacttcg acagcccctc cggaccgctc cgaagccagt ctccctcccg ctttcgcctc   1800
taccttcgtt cccgtccac ctccagcggc atcgagccct ggagcccagc ctcctacgac    1860
tacggcagcg cccccgacac cgattga                                       1887
```

MICRORNAS

CROSS-REFERENCE TO RELATED APPLICATION

The present application is a continuation-in-part of PCT international application No. PCT/US2004/033379, filed on 12 Oct. 2004. The present application is also related to and claims priority under 35 U.S.C. §119(e) to U.S. provisional patent application Ser. No. 60/671,089, filed on 14 Apr. 2005. Each application is incorporated herein by reference.

FIELD OF THE INVENTION

The field of the present invention relates generally to plant molecular biology and plant biotechnology. More specifically it relates to constructs and methods to suppress the expression of targeted genes or to down regulate targeted genes.

BACKGROUND OF THE INVENTION

RNA interference refers to the process of sequence-specific post-transcriptional gene silencing in animals mediated by short interfering RNAs (siRNAs) (Fire et al. (1998) *Nature* 391:806-811). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire (1999) *Trends Genet.* 15:358-363). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

A new class of small RNA molecules is involved in regulating gene expression in a number of eukaryotic organisms ranging from animals to plants. These short RNAs or microRNAs (miRNAs; miRs) are 20-22 nucleotide-long molecules that specifically base-pair to target messenger-RNAs to repress their translation or to induce their degradation. Recent reports have identified numerous miRNAs from vertebrates, *Caenorhabditis elegans*, *Drosophila* and *Arabidopsis thaliana* (Bartel (2004) *Cell* 116:281-297; He and Hannon (2004) *Nature Reviews Genetics* 5:522-531).

Viruses such as Turnip Mosaic Virus (TuMV) and Turnip Yellow Mosaic Virus (TYMV) cause considerable crop loss world-wide and have serious economic impact on agriculture (Morch et al. (1998) *Nucleic Acids Res* 16:6157-6173; Skotnicki et al. (1992) *Arch Virol* 127:25-35; Tomlinson (1987) *Ann Appl Biol* 110:661-681). Most if not all plant viruses encode one or more proteins that are able to suppress the host's post-transcriptional gene silencing (PTGS) mechanism so as to ensure their successful replication in host cells. The PTGS is a mechanism that a plant host uses to defend against viruses by triggering breakdown of double stranded RNAs which are produced as intermediates in viral genome replication (Bernstein et al. (2001) *Nature* 409:363-366; Hamilton and Baulcombe (1999) *Science* 286:950-952; Zamore et al. (2000) *Cell* 31:25-33).

Reduction of the activity of specific genes (also known as gene silencing, or gene suppression), including virus genes, is desirable for several aspects of genetic engineering in plants. There is still a need for methods and constructs that induce gene suppression against a wide selection of target genes, and that result in effective silencing of the target gene at high efficiency.

SUMMARY OF THE INVENTION

According to one aspect, the present invention provides a method of down regulating a target sequence in a cell and a nucleic acid construct for use in this method, as well as a polynucleotide for use in the nucleic acid construct. The method comprises introducing into the cell a nucleic acid construct capable of producing miRNA and expressing the nucleic acid construct for a time sufficient to produce the miRNA, wherein the miRNA inhibits expression of the target sequence. The nucleic acid construct comprises a polynucleotide encoding a modified miRNA precursor capable of forming a double-stranded RNA or a hairpin, wherein the modified miRNA precursor comprises a modified miRNA and a sequence complementary to the modified miRNA, wherein the modified miRNA is a miRNA modified to be (i) fully complementary to the target sequence or (ii) fully complementary to the target sequence except for GU base pairing. As is well known in the art, the pre-miRNA forms a hairpin which in some cases the double-stranded region may be very short, e.g., not exceeding 21-25 bp in length. The nucleic acid construct may further comprise a promoter operably linked to the polynucleotide. The cell may be a plant cell, either monocot or dicot, including, but not limited to, corn, wheat, rice, barley, oats, sorghum, millet, sunflower, safflower, cotton, soy, canola, alfalfa, *Arabidopsis*, and tobacco. The promoter may be a pathogen-inducible promoter or other inducible promoters. The binding of the modified miRNA to the target RNA leads to cleavage of the target RNA. The target sequence of a target RNA may be a coding sequence, an intron or a splice site.

According to another aspect, the present invention provides an isolated polynucleotide encoding a modified plant miRNA precursor, the modified precursor is capable of forming a double-stranded RNA or a hairpin and comprises a modified miRNA and a sequence complementary to the modified miRNA, wherein the modified miRNA is a miRNA modified to be (i) fully complementary to the target sequence or (ii) fully complementary to the target sequence except for GU base pairing. Expression of the polynucleotide produces a miRNA precursor which is processed in a host cell to provide a mature miRNA which inhibits expression of the target sequence. The polynucleotide may be a nucleic acid construct or may be the modified plant miRNA precursor. The nucleic acid construct may further comprise a promoter operably linked to the polynucleotide. The promoter may be a pathogen-inducible promoter or other inducible promoter. The binding of the modified miRNA to the target RNA leads to cleavage of the target RNA. The target sequence of a target RNA may be a coding sequence, a non-coding sequence or a splice site.

According to another aspect, the present invention provides a nucleic acid construct for suppressing a multiple number of target sequences. The nucleic acid construct comprises at least two and up to 45 or more polynucleotides, each of which encodes a miRNA precursor capable of forming a double-stranded RNA or a hairpin. Each miRNA is substantially complementary to a target or is modified to be complementary to a target as described herein. In some embodiments, each of the polynucleotides encoding precursor miRNAs in the construct is individually placed under control of a single promoter. In some embodiments, the multiple polynucleotides encoding precursor miRNAs are operably linked together such that they can be placed under the control of a single promoter. The promoter may be operably linked to the construct of multiple miRNAs or the construct of multiple miRNAs may be inserted into a host genome such that it is operably linked to a single promoter. The promoter may be a pathogen-inducible promoter or other inducible promoter. In some embodiments, the multiple polynucleotides are linked one to another so as to form a single transcript when expressed. Expression of the polynucleotides in the nucleic acid construct produces multiple miRNA precursors which are processed in a host cell to provide multiple mature miRNAs, each of which inhibits expression of a target sequence. In one embodiment, the binding of each of the mature miRNA to each of the target RNA leads to cleavage of each of the target RNA. The target sequence of a target RNA may be a coding sequence, a non-coding sequence or a splice site.

According to another aspect, the present invention provides a method of down regulating a multiple number of target sequences in a cell. The method comprises introducing into the cell a nucleic acid construct capable of producing multiple miRNAs and expressing the nucleic acid construct for a time sufficient to produce the multiple miRNAs, wherein each of the miRNAs inhibits expression of a target sequence. The nucleic acid construct comprises at least two and up to 45 or more polynucleotides, each of which encodes a miRNA precursor capable of forming a double-stranded RNA or a hairpin. Each miRNA is substantially complementary to a target or is modified to be complementary to a target as described herein. In some embodiments, each of the polynucleotides encoding precursor miRNAs in the construct is individually placed under control of a single promoter. In some embodiments, the multiple polynucleotides encoding precursor miRNAs are linked together such that they can be under the control of a single promoter as described herein. In some embodiments, the multiple polynucleotides are linked one to another so as to form a single transcript when expressed. In some embodiments, the construct may be a hetero-polymeric pre-miRNA or a homo-polymeric pre-miRNA. Expression of the polynucleotides in the nucleic acid construct produces multiple miRNA precursors which are processed in a host cell to provide multiple mature miRNAs, each of which inhibits expression of a target sequence. In one embodiment, the binding of each of the mature miRNA to each of the target RNA leads to cleavage of each of the target RNA. The target sequence of a target RNA may be a coding sequence, a non-coding sequence or a splice site.

According to a further aspect, the present invention provides a cell comprising the isolated polynucleotide or nucleic acid construct of the present invention. In some embodiments, the isolated polynucleotide or nucleic acid construct of the present invention may be inserted into an intron of a gene or a transgene of the cell. The cell may be a plant cell, either a monocot or a dicot, including, but not limited to, corn, wheat, rice, barley, oats, sorghum, millet, sunflower, safflower, cotton, soy, canola, alfalfa, *Arabidopsis*, and tobacco.

According to another aspect, the present invention provides a transgenic plant comprising the isolated polynucleotide or nucleic acid construct. In some embodiments, the isolated polynucleotide or nucleic acid construct of the present invention may be inserted into an intron of a gene or a transgene of the transgenic plant. The transgenic plant may be either a monocot or a dicot, including, but not limited to, corn, wheat, rice, barley, oats, sorghum, millet, sunflower, safflower, cotton, soy, canola, alfalfa, *Arabidopsis*, and tobacco.

According to a further aspect, the present invention provides a method of inhibiting expression of a target sequence in a cell comprising: (a) introducing into the cell a nucleic acid construct comprising a modified plant miRNA precursor comprising a first and a second oligonucleotide, wherein at least one of the first or the second oligonucleotides is heterologous to the precursor, wherein the first oligonucleotide encodes an RNA sequence substantially identical to the target sequence, and the second oligonucleotide encodes a miRNA substantially complementary to the target sequence, whereby the precursor encodes a miRNA; and (b) expressing the nucleic acid construct for a time sufficient to produce the miRNA, wherein the miRNA inhibits expression of the target sequence.

According to another aspect, the present invention provides an isolated polynucleotide comprising a modified plant miRNA precursor, the modified precursor comprising a first and a second oligonucleotide, wherein at least one of the first or the second oligonucleotides is heterologous to the precursor, wherein the first oligonucleotide encodes an RNA sequence substantially identical to a target sequence, and the second oligonucleotide comprises a miRNA substantially complementary to the target sequence, wherein expression of the polynucleotide produces the miRNA which inhibits expression of the target sequence. The present invention also relates to a cell comprising this isolated polynucleotide. The cell may be a plant cell, either monocot or dicot, including, but not limited to, corn, wheat, rice, barley, oats, sorghum, millet, sunflower, safflower, cotton, soy, canola, alfalfa, *Arabidopsis*, and tobacco.

According to a further aspect, the present invention provides for a method of inhibiting expression of a target sequence in a cell, such as any of those herein described that further comprises producing a transformed plant, wherein the plant comprises the nucleic acid construct which encodes the miRNA. The present invention also relates to a plant produced by such methods. The plant may a monocot or a dicot, including, but not limited to, corn, wheat, rice, barley, oats, sorghum, millet, sunflower, safflower, cotton, soy, canola, alfalfa, *Arabidopsis*, and tobacco.

BRIEF DESCRIPTION OF THE FIGURES

FIG. 1 shows the predicted hairpin structure formed by the sequence (SEQ ID NO:175) surrounding miR172a-2. The mature microRNA is indicated by a grey box.

FIG. 6 shows the expression analysis of putative EAT target genes. a, Northern blot analysis of polyA+ RNA isolated from wild type (Col) or EAT-D floral buds. Probes for hybridization are indicated on the right. b, Western blot of proteins from wild type or EAT-D floral buds, probed with AP2 antibody. RbcL, large subunit of ribulose 1,5-bisphosphate carboxylase as loading control.

FIG. 7 shows the identification of LAT-D. a, Location of the T-DNA insert in LAT-D, in between At2g28550 and At2g28560. The 4×35S enhancers are approximately 5 kb from At2g28550. b, RT-PCR analysis of At2g28550 expression in wild type versus LAT-D plants.

FIG. 10 shows the potential function of the miR172 miRNA family. a, Temporal expression of miR172a-2 and its relatives may cause temporal downregulation of AP2 targets (e.g. At2g28550 and At5g60120), which may trigger flowering once the target proteins drop below a critical threshold (dotted line). b, Dicer cleavage at various positions may generate at least four distinct miRNAs from the miR172 family (indicated as a single hairpin with a miRNA consensus sequence). Sequences at the 5' and 3' ends of each miRNA are indicated, with the invariant middle 15 nt shown as ellipses. The putative targets recognized by the individual miRNAs are in parentheses below each.

FIG. 11A shows the structure of the pre-miR159a sequence construct under the control of the CaMV 35S promoter (35S) and NOS terminator (Tnos). The orientation and position of the mature miRNA is indicated by an arrow. FIG. 11B shows that point mutations in miR159a (SEQ ID NO:141) (indicated by arrows) turn it into miR-PDS$^{159a}$ (SEQ ID NO:142) to become fully complementary to a region in *N. benthamiana* PDS miRNA. FIG. 11C shows that Northern blot analysis of *Agrobacterium* infiltrated *N. benthamiana* leaves shows expression of miR-PDS$^{159a}$, miR-PDS$^{159a}$* and miR159 in samples infiltrated with an empty vector (vector) or the artificial miRNA (miR-PDS$^{159a}$) 1, 2, 3 days post infiltration (d.p.i).

FIG. 12A shows Northern blot analysis of PDS miRNA from samples infiltrated with empty vector or miR-PDS$^{159a}$ after 1 or 2 days post infiltration (d.p.i.) (upper panel). The bottom panel shows the EtBr-stained agarose gel from the same samples. FIG. 12B shows the site of cleavage of the miRNA. 5'RACE analysis was conducted on samples infiltrated with miR-PDS$^{159a}$ constructs and the 5'-end sequence of 5 out of 6 clones indicated the site of cleavage of the miRNA as indicated by an arrow.

FIGS. 13A-13E show that the expression of miR-PDS$^{169g}$ results in cleavage of the PDS mRNA. FIG. 13A shows the point mutations (underlined nucleotides) in miR169g (SEQ ID NO:144) that it turn it into miR-PDSa$^{169g}$ (SEQ ID NO:145) or miR-PDSb$^{169g}$ (SEQ ID NO:146) to become fully complementary to two different regions in *N. benthamiana* PDS mRNA. FIG. 13B shows Northern blot analysis of two different miR169g expression constructs. Total RNA was extracted from non-infiltrated leaves (C) or from leaves infiltrated with *Agrobacterium* containing the pre-miR169g sequence in the context of a 0.3 kb (0.3 kb) or 2.0 kb (2.0 kb) fragment, or from control *Arabidopsis* leaves (+). The arrow indicates the position of the miR169 signal. FIG. 13C shows Northern blot showing the expression of miR-PDSa$^{169g}$ (a) and miR-PDSb$^{169g}$ (b) in infiltrated leaves containing the 0.3 kb construct but not in control using the empty plasmid (vector). FIG. 13D shows the sites of cleavage of the miRNA. 5'RACE analysis was conducted on samples infiltrated with miR-PDS$^{169g}$ a (SEQ ID NO:145) and b (SEQ ID NO:146) constructs and the 5'-end sequence identified from independent clones is indicated by an arrow together with the number of clones analyzed. The PDS mRNAs are SEQ ID NO:147 and SEQ ID NO:148. FIG. 13E shows a Northern blot analysis to detect PDS mRNA levels in plants infiltrated with *Agrobacterium* strains carrying the empty vector (C) or constructs expressing miR-PDSa$^{169g}$ (a) or miR-PDSb$^{169g}$ (b).

FIGS. 14A-14C show the microRNA-directed cleavage of *Nicotiana benthamiana* rbcS miRNAs. FIG. 14A shows that point mutations in miR159a (SEQ ID NO:141) (indicated by arrows) turn it into miR-rbcS$^{159a}$-A (SEQ ID NO:149) to become complementary to a region common to all *N. benthamiana* rbcS miRNAs (shown as rbcS miRNA; SEQ ID NO:150). miRNA:miRNA base-pairs are indicated by vertical lines and G:U wobble base-pairs by colons. FIG. 14B shows that Northern blot analysis of *Agrobacterium* infiltrated *N. benthamiana* leaves shows expression of miR-rbcS$^{159a}$-A in samples infiltrated with an empty vector (C) or the artificial miRNA (A) 2 days post infiltration (d.p.i). FIG. 14C shows that RT-PCR analysis was used to detect rbcS miRNA abundance for all six genes in the same samples shown in B. Amplification of EF1α miRNA served as a loading control.

FIG. 15A shows the PDS gene from *Lycopersicum esculetum* that was used as reference sequence since the complete PDS gene from *N. benthamiana* is not known (segments missing are shown as a dashed line). Large grey arrows indicate positions targeted by the miR-PDS constructs described in the text. Small arrowheads indicate primers used for 5'RACE analysis. Known *N. benthamiana* PDS fragments are indicated along with the origin of the sequences. FIG. 15B shows the different reported sequences that were used to assemble the rbcS gene sequence schematized here. The grey arrow indicates the position of the sequence targeted by miR-rbcS$^{159a}$-A, the arrowheads indicate the position of primers used in RT-PCR experiments shown in FIGS. 14A-14C.

FIGS. 16A-16B show a summary of changes introduced to *Arabidopsis* miR159a and miR169g. FIG. 16A shows sequences of miR-PDS$^{159a}$ (SEQ ID NO:142) and miR-rbcS$^{159a}$-A (SEQ ID NO:149) as compared to miR159a (SEQ ID NO:141). The base-changes in each case are underlined while unmodified positions are marked with an asterisk. FIG. 16B shows sequences of miR-PDSa$^{161g}$ (SEQ ID NO:145) and miR-PDSb$^{169g}$ (SEQ ID NO:146) as compared to miR169g (SEQ ID NO:144). The base-changes in each case are underlined while unmodified positions are marked with an asterisk.

FIGS. 21A-21E represent a diagram for a process for designing a polymeric pre-miRNA. FIG. 21A: The products of amplification of three different pre-miRNAs (pre-miR A, pre-miR B and pre-miR C) in which AvrII, SpeI and XhoI sites have been added by amplification. FIG. 21B: Pre-miR A is digested with SpeI and XhoI and pre-miR B is digested with AvrII and XhoI. FIG. 21C: The digested pre-miR A and pre-miR B are ligated to form a dimeric pre-miRNA. FIG. 21D: Pre-miR A-B is digested with SpeI and XhoI and pre-miR C is digested with AvrII and XhoI. FIG. 21E: The digested pre-miR A-B and pre-miR C are ligated to form a trimeric pre-miRNA.

FIG. 22 is a diagram of a dimeric construct containing pre-miRPDS1$^{169g}$ and pre-miRCPC3$^{159a}$.

FIGS. 23A and 23B show that mature miRPDS1$^{169g}$ (FIG. 23A) and miRCPC3$^{159a}$ (FIG. 23B) was successfully produced from the dimeric construct. Lane 1 is 35S::pre-miRPDS1$^{169g}$, lane 2 is 35S::CPC3$^{159a}$ and lane 3 is 35S::pre-miRPDS1$^{169g}$-CPC3$^{159a}$.

FIG. 33B) developed normal inflorescences whereas WT plants and $T_2$ transgenic plants expressing miR-P69$^{159a}$ (line #1; FIG. 33B) showed viral infection symptoms. The bar represents 3 cm.

FIG. 33 shows (A) Western blot analysis of representative plants of 35S::miR-HC-Pro$^{159a}$, 35S::miR-P69$^{159a}$, and WT (Col-o) and (B) Northern blot analysis of miRNAs produced by the transgenic plants.

FIG. 34 shows ELISA detection of TuMV in different transgenic and non-transgenic *Arabidopsis*.

DETAILED DESCRIPTION

Figure 2:
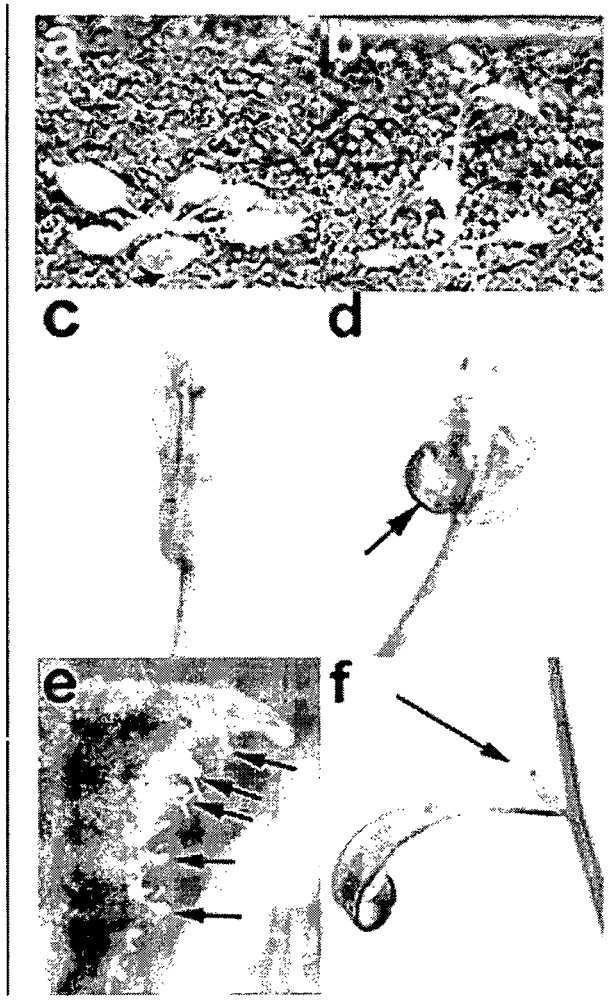
FIG. 2 shows the miR172a-2 overexpression phenotype. a, Wild type (Columbia ecotype) plant, 3.5 weeks old. b, EAT-D plant, 3.5 weeks old. c, Wild type flower. d, EAT-D flower. Note absence of second whorl organs (petals). Arrow indicates sepal with ovules along the margins and stigmatic papillae at the tip. e, Cauline leaf margin from a 35S-EAT plant. Arrows indicate bundles of stigmatic papillae projecting from the margin. f, Solitary gynoecium (arrow) emerging from the axil of a cauline leaf of a 35S-EAT plant.
Figure 3:
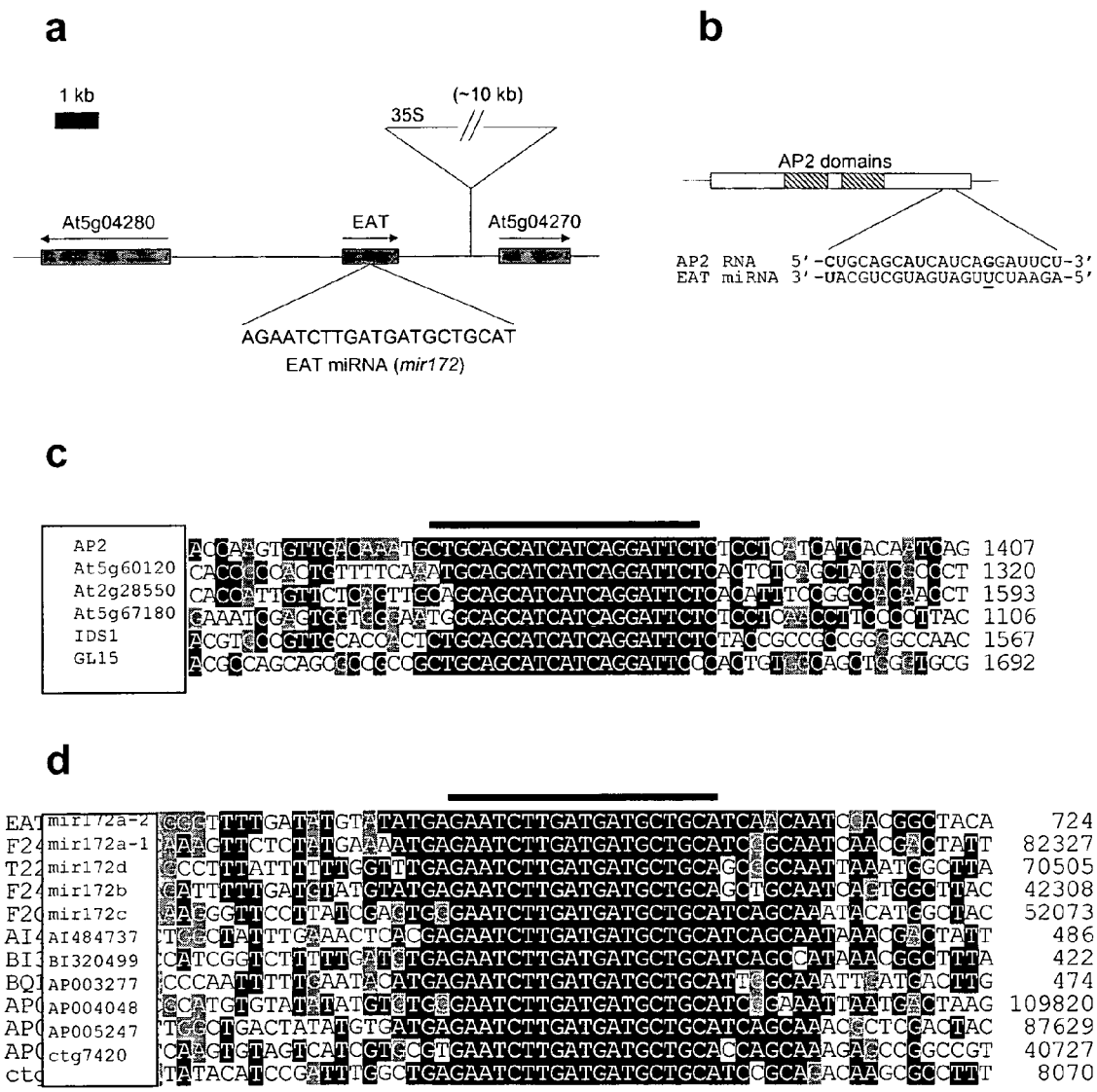
FIG. 3 shows the EAT gene contains a miRNA that is complementary to APETALA2 (AP2). a, Location of the EAT gene on chromosome 5. The T-DNA insertion and orientation of the 35S enhancers is indicated. The 21-nt sequence corresponding to miR172a-2 is shown below the EAT gene (SEQ ID NO:86). b, Putative 21-nt miR172a-2/AP2 RNA duplex is shown below the gene structure of AP2. The GU wobble in the duplex is underlined. The sequence for miR172a-2 is SEQ ID NO:48, and the sequence for APT2 RNA is SEQ ID NO:47. c, Alignment of AP2 21-nt region (black bar) and surrounding sequence with three other *Arabidopsis* AP2 family members, and with two maize AP2 genes (IDS1 and GL15). The sequences are set forth in SEQ ID NO:49 (AP2), SEQ ID NO:50 (At5g60120), SEQ ID NO:51 (At2g28550), SEQ ID NO:52 (At5g67180), SEQ ID NO:53 (IDS1) and SEQ ID NO:54 (GL15). d, Alignment of miR172a-2 miRNA (black bar) and surrounding sequence with miR172-like sequences from *Arabidopsis*, tomato, soybean, potato and rice. The sequences are set forth in SEQ ID NO:176 (mir172-2), SEQ ID NO:177 (mir172a-1), SEQ ID NO:178 (mir172d), SEQ ID NO:179 (mir172b), SEQ ID NO:180 (mir172c), SEQ ID NO:181 (AI484737), SEQ ID NO:182 (BI320499), SEQ ID NO:183 (BQ1), SEQ ID NO:184 (AP003277), SEQ ID NO:185 (AP004048), SEQ ID NO:186 (AP005247), SEQ ID NO:187 (ctg7420)
Figure 4:
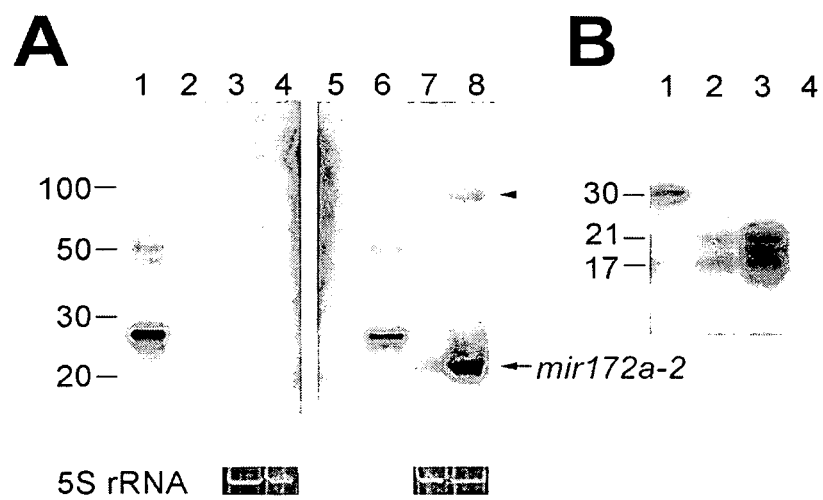
FIG. 4 shows the miR172a-2 miRNA expression. a, Northern blot of total RNA from wild type (lanes 3 and 7) and EAT-D (lanes 4 and 8). Blots were probed with sense (lanes 1-4) or antisense (lanes 5-8) oligo to miR172a-2 miRNA. 100 pg of sense oligo (lanes 2 and 6) and antisense oligo (lanes 1 and 5) were loaded as hybridization controls. Nucleotide size markers are indicated on the left. b, S1 nuclease mapping of miR172a-2 miRNA. A 5'-end-labeled probe undigested (lane 1) or digested after hybridization to total RNA from wild-type (lane 2), EAT-D (lane 3), or tRNA (lane 4).
Figure 5:
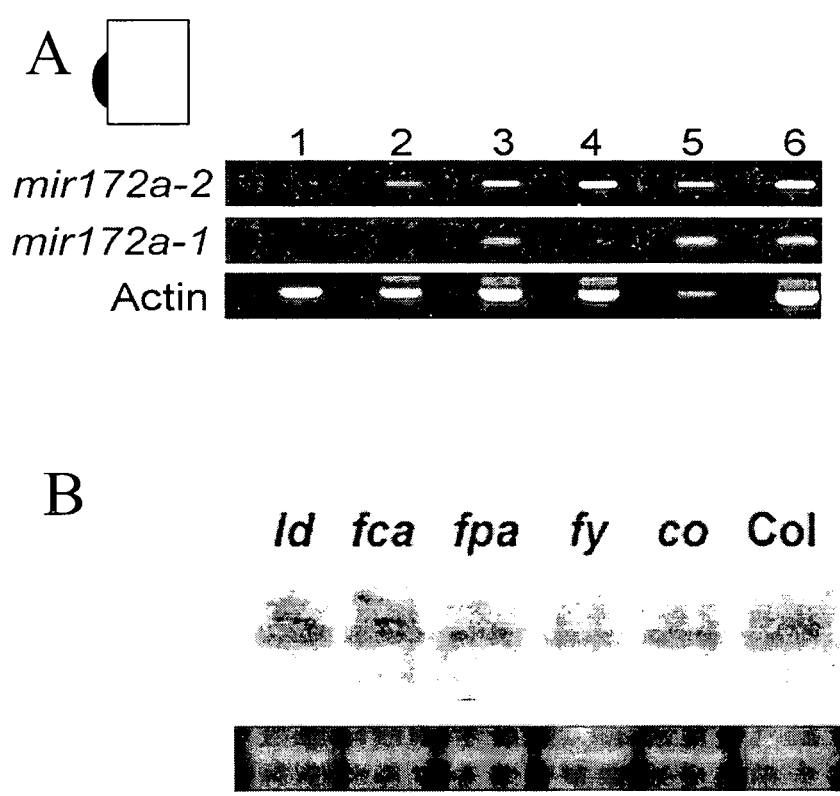
FIG. 5 shows the developmental expression pattern of miR172 family members. a, RT-PCR of total RNA from wild type seedlings harvested at 2, 5, 12, and 21 days after germination (lanes 1-4, respectively), or from mature leaves (lane 5) and floral buds (lane 6). Primers for PCR are indicated on the left. b, Northern analysis of mirR172 expression in the indicated mutants, relative to wild type (Col). Blot was probed with an oligo to miR172a-2; however, all miR172 members should cross hybridize.
Figure 8:
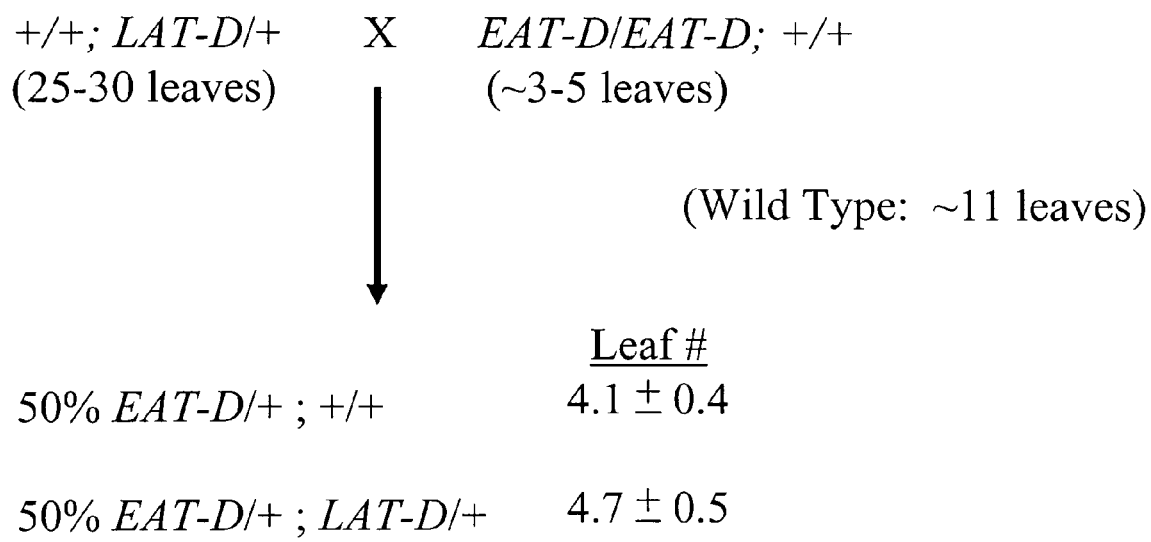
FIG. 8 shows that EAT-D is epistatic to LAT-D. Genetic cross between EAT-D and LAT-D plants, with the resultant F1 plants shown, along with their flowering time (measured as rosette leaf number).
Figure 9:
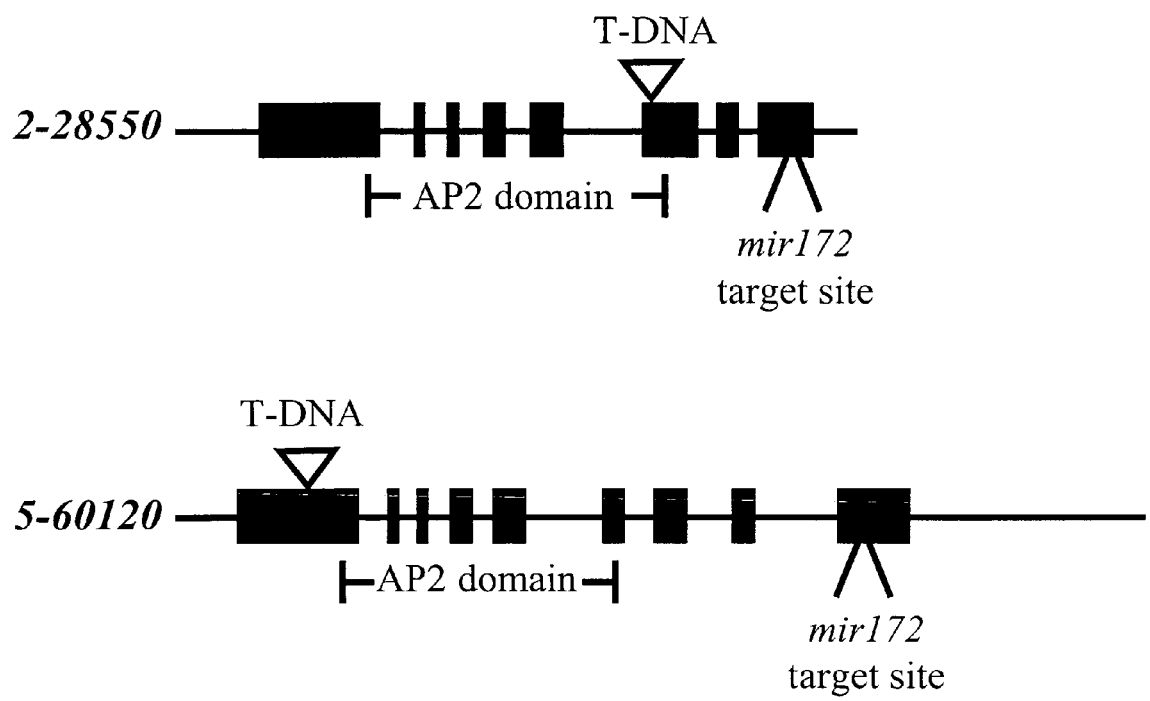
FIG. 9 shows the loss-of-function At2g28550 (2-28550) and At5g60120 (6-60120) mutants. Location of T-DNA in each line is indicated, along with intron/exon structure.

Recently discovered small RNAs play an important role in controlling gene expression. Regulation of many developmental processes including flowering is controlled by small RNAs. It is now possible to engineer changes in gene expression of plant genes by using transgenic constructs which produce small RNAs in the plant.

The invention provides methods and compositions useful for suppressing targeted sequences. The compositions can be employed in any type of plant cell, and in other cells which comprise the appropriate processing components (e.g., RNA interference components), including invertebrate and vertebrate animal cells. The compositions and methods are based on an endogenous miRNA silencing process discovered in *Arabidopsis*, a similar strategy can be used to extend the number of compositions and the organisms in which the methods are used. The methods can be adapted to work in any eukaryotic cell system. Additionally, the compositions and methods described herein can be used in individual cells, cells or tissue in culture, or in vivo in organisms, or in organs or other portions of organisms.

The compositions selectively suppress the target sequence by encoding a miRNA having substantial complementarity to a region of the target sequence. The miRNA is provided in a nucleic acid construct which, when transcribed into RNA, is predicted to form a hairpin structure which is processed by the cell to generate the miRNA, which then suppresses expression of the target sequence.

A nucleic acid construct is provided to encode the miRNA for any specific target sequence. Any miRNA can be inserted into the construct, such that the encoded miRNA selectively targets and suppresses the target sequence.

A method for suppressing a target sequence is provided. The method employs the constructs above, in which a miRNA is designed to a region of the target sequence, and inserted into the construct. Upon introduction into a cell, the miRNA produced suppresses expression of the targeted sequence. The target sequence can be an endogenous plant sequence, or a heterologous transgene in the plant. The target gene may also be a gene from a plant pathogen, such as a pathogenic virus, nematode, insect, or mold or fungus.

A plant, cell, and seed comprising the construct and/or the miRNA is provided. Typically, the cell will be a cell from a plant, but other eukaryotic cells are also contemplated, including but not limited to yeast, insect, nematode, or animal cells. Plant cells include cells from monocots and dicots. The invention also provides plants and seeds comprising the construct and/or the miRNA. Viruses and prokaryotic cells comprising the construct are also provided.

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

As used herein, "nucleic acid construct" or "construct" refers to an isolated polynucleotide which is introduced into a host cell. This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

As used here "suppression" or "silencing" or "inhibition" are used interchangeably to denote the down-regulation of the expression of the product of a target sequence relative to its normal expression level in a wild type organism. Suppression includes expression that is decreased by about 10%, 15%, 20%, 25%, 30%, 35%, 40%, 45%, 50%, 55%, 60%, 65%, 70%, 75%, 80%, 85%, 90%, 95%, or 100% relative to the wild type expression level.

As used herein, "encodes" or "encoding" refers to a DNA sequence which can be processed to generate an RNA and/or polypeptide.

As used herein, "expression" or "expressing" refers to the generation of an RNA transcript from an introduced construct, an endogenous DNA sequence, or a stably incorporated heterologous DNA sequence. The term may also refer to a polypeptide produced from an miRNA generated from any of the above DNA precursors.

As used herein, "heterologous" in reference to a nucleic acid is a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention.

By "host cell" is meant a cell which contains an introduced nucleic acid construct and supports the replication and/or expression of the construct. Host cells may be prokaryotic cells such as *E. coli*, or eukaryotic cells such as fungi, yeast, insect, amphibian, nematode, or mammalian cells. Alternatively, the host cells are monocotyledonous or dicotyledonous plant cells. An example of a monocotyledonous host cell is a maize host cell.

The term "introduced" means providing a nucleic acid or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "miRNA" refers to an oligoribonucleic acid, which suppresses expression of a polynucleotide comprising the target sequence transcript or down regulates a target RNA. A "miRNA precursor" refers to a larger polynucleotide which is processed to produce a mature miRNA, and includes a DNA which encodes an RNA precursor, and an RNA transcript comprising the miRNA. A "mature miRNA" refers to the miRNA generated from the processing of a miRNA precursor. A "miRNA template" is an oligonucleotide region, or regions, in a nucleic acid construct which encodes the miRNA. The "backside" region of a miRNA is a portion of a polynucleotide construct which is substantially complementary to the miRNA template and is predicted to base pair with the miRNA template. The miRNA template and backside may form a double-stranded polynucleotide, including a hairpin structure. As is known for natural miRNAs, the mature miRNA and its complements may contain mismatches and form bulges and thus do not need to be fully complementary.

As used herein, the phrases "target sequence" and "sequence of interest" are used interchangeably. Target sequence is used to mean the nucleic acid sequence that is selected for suppression of expression, and is not limited to polynucleotides encoding polypeptides. The target sequence comprises a sequence that is substantially or completely complementary to the miRNA. The target sequence can be RNA or DNA, and may also refer to a polynucleotide comprising the target sequence.

As used herein, "nucleic acid" means a polynucleotide and includes single or double-stranded polymer of deoxyribonucleotide or ribonucleotide bases. Nucleic acids may also include fragments and modified nucleotides.

By "nucleic acid library" is meant a collection of isolated DNA or RNA molecules which comprise and substantially represent the entire transcribed fraction of a genome of a specified organism or of a tissue from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage of at least two sequences. Operably linked includes linkage between a promoter and a second sequence, wherein the promoter sequence initiates and mediates transcription of the DNA sequence corresponding to the second sequence.

As used herein, "plant" includes plants and plant parts including but not limited to plant cells, plant tissue such as leaves, stems, roots, flowers, and seeds.

As used herein, "polypeptide" means proteins, protein fragments, modified proteins, amino acid sequences and synthetic amino acid sequences. The polypeptide can be glycosylated or not.

As used herein, "promoter" includes reference to a region of DNA that is involved in recognition and binding of an RNA polymerase and other proteins to initiate transcription.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl ((1984) *Anal Biochem* 138:267-284): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C.

lower than the thermal melting point (T$_m$). Using the equation, hybridization and wash compositions, and desired T$_m$, those of ordinary skill will understand that variations in the stringency of hybridization and/or wash solutions are inherently described. If the desired degree of mismatching results in a T$_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

As used herein, "transgenic" includes reference to a plant or a cell which comprises a heterologous polynucleotide. Generally, the heterologous polynucleotide is stably integrated within the genome such that the polynucleotide is passed on to successive generations. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in introduction of a polynucleotide of the invention into a host cell. Expression vectors permit transcription of a nucleic acid inserted therein.

Polynucleotide sequences may have substantial identity, substantial homology, or substantial complementarity to the selected region of the target gene. As used herein "substantial identity" and "substantial homology" indicate sequences that have sequence identity or homology to each other. Generally, sequences that are substantially identical or substantially homologous will have about 75%, 80%, 85%, 90%, 91%, 92%, 93%, 94%, 95%, 96%, 97%, 98%, 99%, or 100% sequence identity wherein the percent sequence identity is based on the entire sequence and is determined by GAP alignment using default parameters (GCG, GAP version 10, Accelrys, San Diego, Calif.). GAP uses the algorithm of Needleman and Wunsch ((1970) *J Mol Biol* 48:443-453) to find the alignment of two complete sequences that maximizes the number of matches and minimizes the number of sequence gaps. Sequences which have 100% identity are identical. "Substantial complementarity" refers to sequences that are complementary to each other, and are able to base pair with each other. In describing complementary sequences, if all the nucleotides in the first sequence will base pair to the second sequence, these sequences are fully complementary.

Through a forward genetics approach, a microRNA that confers a developmental phenotype in *Arabidopsis* was identified. This miRNA, miR172a-2 (Park et al. (2002) *Curr Biol* 12:1484-1495), causes early flowering and defects in floral organ identity when overexpressed. The predicted target of miR172a-2 is a small subfamily of APETALA2-like transcription factors (Okamuro et al. (1997) *Proc Natl Acad Sci USA* 94:7076-7081). Overexpression of miR172a-2 downregulates at least one member of this family. In addition, overexpression of one of the AP2-like target genes, At2g28550, causes late flowering. This result, in conjunction with loss-of-function analyses of At2g28550 and another target gene, At5g60120, indicates that at least some of the AP2-like genes targeted by miR172a-2 normally function as floral repressors. The EAT-D line overexpressing miR172-a2 has a wild-type response to photoperiod. The genomic region encoding the miRNA was also identified (SEQ ID NO:1) and used to produce a cassette into which other miRNAs to target sequences can be inserted (SEQ ID NO:3), and to produce an expression vector (SEQ ID NO:44) useful for cloning the cassettes and expressing the miRNA. The expression vector comprises the 1.4 kb region encoding the miRNA. Expression of this region is processed in the cell to produce the miRNA which suppresses expression of the target gene. Alternatively, the miRNA may be synthetically produced and introduced to the cell directly.

In one embodiment, there is provided a method for the suppression of a target sequence comprising introducing into a cell a nucleic acid construct encoding a miRNA substantially complementary to the target. In some embodiments the miRNA comprises about 10-200 nucleotides, about 10-15, 15-20, 19, 20, 21, 22, 23, 24, 25, 26, 27, 25-30, 30-50, 50-100, 100-150, or about 150-200 nucleotides. In some embodiments the nucleic acid construct encodes the miRNA. In some embodiments the nucleic acid construct encodes a polynucleotide precursor which may form a double-stranded RNA, or hairpin structure comprising the miRNA. In some embodiments, nucleotides 39-59 and 107-127 of SEQ ID NO:3 are replaced by the backside of the miRNA template and the miRNA template respectively. In some embodiments, this new sequence replaces the equivalent region of SEQ ID NO:1. In further embodiments, this new sequence replaces the equivalent region of SEQ ID NO:44.

In some embodiments, the nucleic acid construct comprises a modified endogenous plant miRNA precursor, wherein the precursor has been modified to replace the endogenous miRNA encoding regions with sequences designed to produce a miRNA directed to the target sequence. In some embodiments the miRNA precursor template is a miR172a miRNA precursor. In some embodiments, the miR172a precursor is from a dicot or a monocot. In some embodiments the miR172a precursor is from *Arabidopsis thaliana*, tomato, soybean, rice, or corn. In some embodiments the miRNA precursor is SEQ ID NO:1, SEQ ID NO:3, or SEQ ID NO:44.

In another embodiment the method comprises:

A method of inhibiting expression of a target sequence in a cell comprising:

(a) introducing into the cell a nucleic acid construct comprising a promoter operably linked to a polynucleotide, wherein the polynucleotide comprises in the following order:
  (i) at least about 20 and up to 38 contiguous nucleotides in the region of nucleotides 1-38 of SEQ ID NO:3,
  (ii) a first oligonucleotide of 10 to about 50 contiguous nucleotides, wherein the first oligonucleotide is substantially complementary to a second oligonucleotide
  (iii) at least about 20 and up to 47 contiguous nucleotides in the region of nucleotides 60-106 of SEQ ID NO:3,
  (iv) the second oligonucleotide of about 10 to about 50 contiguous nucleotides, wherein the second oligonucleotide encodes a miRNA, and the second oligonucleotide is substantially complementary to the target sequence, and
  (v) at least about 20 and up to 32 contiguous nucleotides in the region of nucleotides 128-159 of SEQ ID NO:3;

wherein the polynucleotide encodes an RNA precursor capable of forming a hairpin, and (b) expressing the nucleic acid construct for a time sufficient to produce the miRNA, wherein the miRNA inhibits expression of the target sequence.

In another embodiment, the method comprises selecting a target sequence of a gene, and designing a nucleic acid construct comprising polynucleotide encoding a miRNA substantially complementary to the target sequence. In some embodiments, the target sequence is selected from any region of the gene. In some embodiments, the target sequence is selected from an untranslated region. In some embodiments, the target sequence is selected from a coding region of the gene. In some embodiments, the target sequence is selected from a region about 50 to about 200 nucleotides upstream from the stop codon, including regions from about 50-75, 75-100, 100-125, 125-150, or 150-200 upstream from the stop codon. In further embodiments, the target sequence and/or the miRNA is based on the polynucleotides and process of EAT suppression of Apetela2-like genes in *Arabidopsis thaliana*. In some embodiments, nucleotides 39-59 and 107-127 of SEQ ID NO:3 are replaced by the backside of the miRNA template (first oligonucleotide) and the miRNA template (second oligonucleotide) respectively. In some embodiments, this new sequence replaces the equivalent region of SEQ ID NO:1. In further embodiments, this new sequence replaces the equivalent region of SEQ ID NO:44.

In some embodiments, the miRNA template, (i.e. the polynucleotide encoding the miRNA), and thereby the miRNA, may comprise some mismatches relative to the target sequence. In some embodiments the miRNA template has ≥1 nucleotide mismatch as compared to the target sequence, for example, the miRNA template can have 1, 2, 3, 4, 5, or more mismatches as compared to the target sequence. This degree of mismatch may also be described by determining the percent identity of the miRNA template to the complement of the target sequence. For example, the miRNA template may have a percent identity including about at least 70%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to the complement of the target sequence.

In some embodiments, the miRNA template, (i.e. the polynucleotide encoding the miRNA) and thereby the miRNA, may comprise some mismatches relative to the miRNA backside. In some embodiments the miRNA template has ≥1 nucleotide mismatch as compared to the miRNA backside, for example, the miRNA template can have 1, 2, 3, 4, 5, or more mismatches as compared to the miRNA backside. This degree of mismatch may also be described by determining the percent identity of the miRNA template to the complement of the miRNA backside. For example, the miRNA template may have a percent identity including about at least 70%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to the complement of the miRNA backside.

In some embodiments, the target sequence is selected from a plant pathogen. Plants or cells comprising a miRNA directed to the target sequence of the pathogen are expected to have decreased sensitivity and/or increased resistance to the pathogen. In some embodiments, the miRNA is encoded by a nucleic acid construct further comprising an operably linked promoter. In some embodiments, the promoter is a pathogen-inducible promoter.

In another embodiment, the method comprises replacing the miRNA encoding sequence in the polynucleotide of SEQ ID NO:3 with a sequence encoding a miRNA substantially complementary to the target region of the target gene.

In another embodiment a method is provided comprising a method of inhibiting expression of a target sequence in a cell comprising:

(a) introducing into the cell a nucleic acid construct comprising a promoter operably linked to a polynucleotide encoding a modified plant miRNA precursor comprising a first and a second oligonucleotide, wherein at least one of the first or the second oligonucleotides is heterologous to the precursor, wherein the first oligonucleotide is substantially complementary to the second oligonucleotide, and the second oligonucleotide encodes a miRNA substantially complementary to the target sequence, wherein the precursor is capable of forming a hairpin; and (b) expressing the nucleic acid construct for a time sufficient to produce the miRNA, wherein the miRNA inhibits expression of the target sequence.

In another embodiment a method is provided comprising a method of inhibiting expression of a target sequence in a cell comprising:

(a) introducing into the cell a nucleic acid construct comprising a promoter operably linked to a polynucleotide encoding a modified plant miR172 miRNA precursor comprising a first and a second oligonucleotide, wherein at least one of the first or the second oligonucleotides is heterologous to the precursor, wherein the first oligonucleotide is substantially complementary to the second oligonucleotide, and the second oligonucleotide encodes a miRNA substantially complementary to the target sequence, wherein the precursor is capable of forming a hairpin; and (b) expressing the nucleic acid construct for a time sufficient to produce the miRNA, wherein the miRNA inhibits expression of the target sequence.

In some embodiments, the modified plant miR172 miRNA precursor is a modified *Arabidopsis* miR172 miRNA precursor, or a modified corn miR172 miRNA precursor or the like.

In another embodiment, there is provided a nucleic acid construct for suppressing a target sequence. The nucleic acid construct encodes a miRNA substantially complementary to the target. In some embodiments, the nucleic acid construct further comprises a promoter operably linked to the polynucleotide encoding the miRNA. In some embodiments, the nucleic acid construct lacking a promoter is designed and introduced in such a way that it becomes operably linked to a promoter upon integration in the host genome. In some embodiments, the nucleic acid construct is integrated using recombination, including site-specific recombination. See, for example, PCT International published application No. WO 99/25821, herein incorporated by reference. In some embodiments, the nucleic acid construct is an RNA. In some embodiments, the nucleic acid construct comprises at least one recombination site, including site-specific recombination sites. In some embodiments the nucleic acid construct comprises at least one recombination site in order to facilitate integration, modification, or cloning of the construct. In some embodiments the nucleic acid construct comprises two site-specific recombination sites flanking the miRNA precursor. In some embodiments the site-specific recombination sites include FRT sites, lox sites, or att sites, including attB, attL, attP or attR sites. See, for example, PCT International published application No. WO 99/25821, and U.S. Pat. Nos. 5,888,732, 6,143,557, 6,171,861, 6,270,969, and 6,277,608, herein incorporated by reference.

In some embodiments, the nucleic acid construct comprises a modified endogenous plant miRNA precursor, wherein the precursor has been modified to replace the miRNA encoding region with a sequence designed to produce a miRNA directed to the target sequence. In some embodiments the miRNA precursor template is a miR172a miRNA precursor. In some embodiments, the miR172a precursor is from a dicot or a monocot. In some embodiments the miR172a precursor is from *Arabidopsis thaliana*, tomato, soybean, rice, or corn. In some embodiments the miRNA precursor is SEQ ID NO:1, SEQ ID NO:3, or SEQ ID NO:44.

In another embodiment, the nucleic acid construct comprises an isolated polynucleotide comprising a polynucleotide which encodes a modified plant miRNA precursor, the modified precursor comprising a first and a second oligonucleotide, wherein at least one of the first or the second oligonucleotides is heterologous to the precursor, wherein the first oligonucleotide i is substantially complementary to the second oligonucleotide, and the second oligonucleotide comprises a miRNA substantially complementary to the target sequence, wherein the precursor is capable of forming a hairpin.

In another embodiment, the nucleic acid construct comprises an isolated polynucleotide comprising a polynucleotide which encodes a modified plant miR172 miRNA precursor, the modified precursor comprising a first and a second oligonucleotide, wherein at least one of the first or the second oligonucleotides is heterologous to the precursor, wherein the first oligonucleotide is substantially complementary to the second oligonucleotide, and the second oligonucleotide comprises a miRNA substantially complementary to the target sequence, wherein the precursor is capable of forming a hairpin. In some embodiments, the modified plant miR172 miRNA precursor is a modified *Arabidopsis* miR172 miRNA precursor, or a modified corn miR172 miRNA precursor, or the like.

In some embodiments the miRNA comprises about 10-200 nucleotides, about 10-15, 15-20, 19, 20, 21, 22, 23, 24, 25, 26, 27, 25-30, 30-50, 50-100, 100-150, or about 150-200 nucleotides. In some embodiments the nucleic acid construct encodes the miRNA. In some embodiments the nucleic acid construct encodes a polynucleotide precursor which may form a double-stranded RNA, or hairpin structure comprising the miRNA. In some embodiments, nucleotides 39-59 and/or 107-127 of SEQ ID NO:3 are replaced by the backside of the miRNA template and the miRNA template respectively. In some embodiments, this new sequence replaces the equivalent region of SEQ ID NO:1. In further embodiments, this new sequence replaces the equivalent region of SEQ ID NO:44. In some embodiments, the target region is selected from any region of the target sequence. In some embodiments, the target region is selected from a untranslated region. In some embodiments, the target region is selected from a coding region of the target sequence. In some embodiments, the target region is selected from a region about 50 to about 200 nucleotides upstream from the stop codon, including regions from about 50-75, 75-100, 100-125, 125-150, or 150-200 upstream from the stop codon. In further embodiments, the target region and/or the miRNA is based on the polynucleotides and process of EAT suppression of Apetela2-like sequences in *Arabidopsis thaliana*.

In another embodiment the nucleic acid construct comprises an isolated polynucleotide comprising in the following order at least 20 and up to 38 contiguous nucleotides in the region from nucleotides 1-38 of SEQ ID NO:3, a first oligonucleotide of about 10 to about 50 contiguous nucleotides, wherein the first oligonucleotide is substantially complementary to a second oligonucleotide, at least about 20 and up to 47 contiguous nucleotides in the region from nucleotides 60-106 of SEQ ID NO:3, a second oligonucleotide of about 10 to about 50 contiguous nucleotides, wherein the second oligonucleotide encodes a miRNA, and the second oligonucleotide is substantially complementary to the target sequence, and at least about 20 and up to 32 contiguous nucleotides in the region from nucleotides 128-159 of SEQ ID NO:3, wherein the polynucleotide encodes an RNA precursor capable of forming a hairpin structure.

In some embodiments there are provided cells, plants, and seeds comprising the introduced polynucleotides, and/or produced by the methods of the invention. The cells include prokaryotic and eukaryotic cells, including but not limited to bacteria, yeast, fungi, viral, invertebrate, vertebrate, and plant cells. Plants, plant cells, and seeds of the invention include gynosperms, monocots and dicots, including but not limited to, for example, rice, wheat, oats, barley, millet, sorghum, soy, sunflower, safflower, canola, alfalfa, cotton, *Arabidopsis*, and tobacco.

In some embodiments, the cells, plants, and/or seeds comprise a nucleic acid construct comprising a modified plant miRNA precursor, wherein the precursor has been modified to replace the endogenous miRNA encoding regions with sequences designed to produce a miRNA directed to the target sequence. In some embodiments the miRNA precursor template is a miR172a miRNA precursor. In some embodiments, the miR172a precursor is from a dicot or a monocot. In some embodiments the miR172a precursor is from *Arabidopsis thaliana*, tomato, soybean, rice, or corn. In some embodiments the miRNA precursor is SEQ ID NO:1, SEQ ID NO:3, or SEQ ID NO:44. In some embodiments the miRNA precursor is encoded by SEQ ID NO:1, SEQ ID NO:3, or SEQ ID NO:44. In some embodiments, the nucleic acid construct comprises at least one recombination site, including site-specific recombination sites. In some embodiments the nucleic acid construct comprises at least one recombination site in order to facilitate modification or cloning of the construct. In some embodiments the nucleic acid construct comprises two site-specific recombination sites flanking the miRNA precursor. In some embodiments the site-specific recombination sites include FRT sites, lox sites, or att sites, including attB, attL, attP or attR sites. See, for example, PCT International published application No. WO 99/25821, and U.S. Pat. Nos. 5,888,732, 6,143,557, 6,171,861, 6,270,969, and 6,277,608, herein incorporated by reference.

In a further embodiment, there is provided a method for down regulating a target RNA comprising introducing into a cell a nucleic acid construct that encodes a miRNA that is complementary to a region of the target RNA. In some embodiments, the miRNA is fully complementary to the region of the target RNA. In some embodiments, the miRNA is complementary and includes the use of G-U base pairing, i.e. the GU wobble, to otherwise be fully complementary. In some embodiments, the first ten nucleotides of the miRNA (counting from the 5' end of the miRNA) are fully complementary to a region of the target RNA and the remaining nucleotides may include mismatches and/or bulges with the target RNA. In some embodiments the miRNA comprises about 10-200 nucleotides, about 10-15, 15-20, 19, 20, 21, 22, 23, 24, 25, 26, 27, 25-30, 30-50, 50-100, 100-150, or about 150-200 nucleotides. The binding of the miRNA to the complementary sequence in the target RNA results in cleavage of the target RNA. In some embodiments, the miRNA is a miRNA that has been modified such that the miRNA is fully complementary to the target sequence of the target RNA. In some embodiments, the miRNA is an endogenous plant miRNA that has been modified such that the miRNA is fully complementary to the target sequence of the target RNA. In some embodiments, the polynucleotide encoding the miRNA is operably linked to a promoter. In some embodiments, the nucleic acid construct comprises a promoter operably linked to the miRNA.

In some embodiments, the nucleic acid construct encodes the miRNA. In some embodiments, the nucleic acid construct comprises a promoter operably linked to the miRNA. In some embodiments, the nucleic acid construct encodes a polynucleotide which may form a double-stranded RNA, or hairpin structure comprising the miRNA. In some embodiments, the nucleic acid construct comprises a promoter operably linked to the polynucleotide which may form a double-stranded RNA, or hairpin structure comprising the miRNA. In some embodiments, the nucleic acid construct comprises an endogenous plant miRNA precursor that has been modified such that the miRNA is fully complementary to the target sequence of the target RNA. In some embodiments, the nucleic acid construct comprises a promoter operably linked to the miRNA precursor. In some embodiments, the nucleic acid construct comprises about 50 nucleotides to about 3000 nucleotides, about 50-100, 100-150, 150-200, 200-250, 250-300, 300-350, 350-400, 400-450, 450-500, 500-600, 600-700, 700-800, 800-900, 900-1000, 1000-1100, 1100-1200, 1200-1300, 1300-1400, 1400-1500, 1500-1600, 1600-1700, 1700-1800, 1800-1900, 1900-2000, 2000-2100, 2100-2200, 2200-2300, 2300-2400, 2400-2500, 2500-2600, 2600-2700, 2700-2800, 2800-2900 or about 2900-3000 nucleotides.

In some embodiments, the nucleic acid construct lacking a promoter is designed and introduced in such a way that it becomes operably linked to a promoter upon integration in the host genome. In some embodiments, the nucleic acid construct is integrated using recombination, including site-specific recombination. In some embodiments, the nucleic acid construct is an RNA. In some embodiments, the nucleic acid construct comprises at least one recombination site, including site-specific recombination sites. In some embodiments the nucleic acid construct comprises at least one recombination site in order to facilitate integration, modification, or cloning of the construct. In some embodiments the nucleic acid construct comprises two site-specific recombination sites flanking the miRNA precursor.

In another embodiment, the method comprises a method for down regulating a target RNA in a cell comprising introducing into the cell a nucleic acid construct that encodes a miRNA that is complementary to a region of the target RNA and expressing the nucleic acid construct for a time sufficient to produce miRNA, wherein the miRNA down regulates the target RNA. In some embodiments, the miRNA is fully complementary to the region of the target RNA. In some embodiments, the miRNA is complementary and includes the use of G-U base pairing, i.e. the GU wobble, to otherwise be fully complementary.

In another embodiment, the method comprises selecting a target RNA, selecting a miRNA, comparing the sequence of the target RNA (or its DNA) with the sequence of the miRNA, identifying a region of the target RNA (or its DNA) in which the nucleotide sequence is similar to the nucleotide sequence of the miRNA, modifying the nucleotide sequence of the miRNA so that it is complementary to the nucleotide sequence of the identified region of the target RNA and preparing a nucleic acid construct comprising the modified miRNA. In some embodiments, the miRNA is fully complementary to the identified region of the target RNA. In some embodiments, the miRNA is complementary and includes the use of G-U base pairing, i.e. the GU wobble, to otherwise be fully complementary. In some embodiments, a nucleic acid construct encodes a polynucleotide which may form a double-stranded RNA, or hairpin structure comprising the miRNA. In some embodiments, a nucleic acid construct comprises a precursor of the miRNA, i.e., a pre-miRNA that has been modified in accordance with this embodiment.

In another embodiment, the method comprises selecting a target RNA, selecting a nucleotide sequence within the target RNA, selecting a miRNA, modifying the sequence of the miRNA so that it is complementary to the nucleotide sequence of the identified region of the target RNA and preparing a nucleic acid construct comprising the modified miRNA. In some embodiments, the miRNA is fully complementary to the identified region of the target RNA. In some embodiments, the miRNA is complementary and includes the use of G-U base pairing, i.e. the GU wobble, to otherwise be fully complementary. In some embodiments, a nucleic acid construct encodes a polynucleotide which may form a double-stranded RNA, or hairpin structure comprising the miRNA. In some embodiments, a nucleic acid construct comprises a precursor of the miRNA, i.e., a pre-miRNA that has been modified in accordance with this embodiment.

In some embodiments, the miRNA is a miRNA disclosed in the microRNA registry, now also known as the miRBase Sequence Database (Griffiths-Jones (2004) *Nucl Acids Res* 32, Database issue:D109-D111; http colon//microrna dot sanger dot ac dot uk/). In some embodiments, the miRNA is ath-MIR156a, ath-MIR156b, ath-MIR156c, ath-MIR156d, ath-MIR156e, ath-MIR156f, ath-MIR156g, ath-MIR156h, ath-MIR157a, ath-MIR157b, ath-MIR157c, ath-MIR157d, ath-MIR158a, ath-MIR158b, ath-MIR159a, ath-MIR159b, ath-MIR159c, ath-MIR160a, ath-MIR160b, ath-MIR160c, ath-MIR161, ath-MIR162a, ath-MIR162b, ath-MIR163, ath-MIR164a, ath-MIR164b, ath-MIR164c, ath-MIR165a, ath-MIR165b, ath-MIR166a, ath-MIR166b, ath-MIR166c, ath-MIR166d, ath-MIR166e, ath-MIR166f, ath-MIR166g, ath-MIR167a, ath-MIR167b, ath-MIR167c, ath-MIR167d, ath-MIR168a, ath-MIR168b, ath-MIR169a, ath-MIR169b, ath-MIR169c, ath-MIR169d, ath-MIR169e, ath-MIR169f, ath-MIR169g, ath-MIR169h, ath-MIR169i, ath-MIR169j, ath-MIR169k, ath-MIR1691, ath-MIR169m, ath-MIR169n, ath-MIR170, ath-MIR171a, ath-MIR171b, ath-MIR171c, ath-MIR172a, ath-MIR172b, ath-MIR172c, ath-MIR172d, ath-MIR172e, ath-MIR173, ath-MIR319a, ath-MIR319b, ath-MIR319c, ath-MIR390a, ath-MIR390b, ath-MIR393a, ath-MIR393b, ath-MIR394a, ath-MIR394b, ath-MIR395a, ath-MIR395b, ath-MIR395c, ath-MIR395d, ath-MIR395e, ath-MIR395f, ath-MIR396a, ath-MIR396b, ath-MIR397a, ath-MIR397b, ath-MIR398a, ath-MIR398b, ath-MIR398c, ath-MIR399a, ath-MIR399b, ath-MIR399c, ath-MIR399d, ath-MIR399e, ath-MIR399f, ath-MIR400, ath-MIR401, ath-MIR402, ath-MIR403, ath-MIR404, ath-MIR405a, ath-MIR405b, ath-MIR405d, ath-MIR406, ath-MIR407, ath-MIR408, ath-MIR413, ath-MIR414, ath-MIR415, ath-MIR416, ath-MIR417, ath-MIR418, ath-MIR419, ath-MIR420, ath-MIR426, ath-MIR447a, ath-MIR447b, ath-MIR447c, osa-MIR156a, osa-MIR156b, osa-MIR156c, osa-MIR156d, osa-MIR156e, osa-MIR156f, osa-MIR156g, osa-MIR156h, osa-MIR156i, osa-MIR156j, osa-MIR156k, osa-MIR1561, osa-MIR159a, osa-MIR159b, osa-MIR159c, osa-MIR159d, osa-MIR159e, osa-MIR159f, osa-MIR160a, osa-MIR160b, osa-MIR160c, osa-MIR160d, osa-MIR160e, osa-MIR160f, osa-MIR162a, osa-MIR162b, osa-MIR164a, osa-MIR164b, osa-MIR164c, osa-MIR164d, osa-MIR164e, osa-MIR166a, osa-MIR166b, osa-MIR166c, osa-MIR166d, osa-MIR166e, osa-MIR166f, osa-MIR166j, osa-MIR166k, osa-MIR1661, osa-MIR166g, osa-MIR166h, osa-MIR166i, osa-MIR166m, osa-MIR166n, osa-MIR167a, osa-MIR167b, osa-MIR167c, osa-MIR167d, osa-MIR167e, osa-MIR167f, osa-MIR167g, osa-MIR167h, osa-MIR167i, osa-MIR167j, osa-MIR168a, osa-MIR168b, osa-MIR169a, osa-MIR169b, osa-MIR169c, osa-MIR169d, osa-MIR169e, osa-MIR169f, osa-MIR169g, osa-MIR169h, osa-MIR169i, osa-MIR169j, osa-MIR169k, osa-MIR169l, osa-MIR169m, osa-MIR169n, osa-MIR169o, osa-MIR169p, osa-MIR169q, osa-IR171a, osa-MIR171b, osa-MIR171c, osa-MIR171d, osa-MIR171e, osa-MIR171f, osa-MIR171g, osa-MIR171h, osa-MIR171i, osa-MIR172a, osa-MIR172b, osa-MIR172c, osa-MIR173d, osa-MIR390, osa-MIR319a, osa-MIR319b, osa-MIR393, osa-MIR393b, osa-MIR394, osa-MIR395b, osa-MIR395c, osa-MIR395d, osa-MIR395e, osa-MIR395g, osa-MIR395h, osa-MIR395i, osa-MIR395j, osa-MIR395k, osa-MIR395l, osa-MIR395m, osa-MIR395n, osa-MIR395o, osa-MIR395r, osa-MIR395q, osa-MIR395c, osa-MIR395a, osa-MIR395f, osa-MIR395p, osa-MIR396a, osa-MIR396b, osa-MIR396c, osa-MIR397a, osa-MIR397b, osa-MIR398a, osa-MIR398b, osa-MIR399a, osa-MIR399b, osa-MIR399c, osa-MIR399d, osa-MIR399e, osa-MIR399f, osa-MIR399g, osa-MIR399h, osa-MIR399i, osa-MIR399j, osa-MIR399k, osa-MIR408, osa-MIR413, osa-MIR414, osa-MIR415, osa-MIR416, osa-MIR 417, osa-MIR418, osa-MIR419, osa-MIR426, osa-MIR437, osa-MIR439, osa-MIR439c, osa-MIR439d, osa-MIR438e, osa-MIR439f, osa-MIR439g, osa-MIR439h, osa-MIR440, osa-MIR441a, osa-MIR441c, osa-MIR439z, osa-MIR443, osa-MIR445d, osa-MIR446, zma-MIR156a, zma-MIR156b, zma-MIR156c, zma-MIR156d, zma-MIR156e, zma-MIR156f, zma-MIR156g, zma-MIR156h, zma-MIR156i, zma-MIR156j, zma-MIR156k, zma-MIR159a, zma-MIR159b, zma-MIR159c, zma-MIR159d, zma-MIR160a, zma-MIR160b, zma-MIR160c, zma-MIR160d, zma-MIR160e, zma-MIR160f, zma-MIR 1611, zma-MIR162, zma-MIR164a, zma-MIR164b, zma-MIR164c, zma-MIR164d, zma-MIR166a, zma-MIR166b, zma-MIR166c, zma-MIR166d, zma-MIR166e, zma-MIR166e, zma-MIR166f, zma-MIR166g, zma-MIR166h, zma-MIR166i, zma-MIR166j, zma-MIR166k, zma-MIR166m, zma-MIR167a, zma-MIR167b, zma-MIR167c, zma-MIR167d, zma-MIR 167e, zma-MIR167f, zma-MIR167g, zma-MIR167h, zma-MIR168a, zma-MIR168b, zma-MIR169a, zma-MIR169b, zma-MIR169c, zma-MIR169d, zma-MIR169e, zma-MIR169f, zma-MIR169g, zma-MIR169i, zma-MIR169j, zma-MIR169k, zma-MIR171a, zma-MIR171b, zma-MIR171c, zma-MIR171d, zma-MIR171e, zma-MIR171f, zma-MIR171g, zma-MIR171h, zma-MIR171i, zma-MIR171j, zma-MIR171k, zma-MIR172a, zma-MIR172b, zma-MIR172c or zma-MIR172d, zma-MIR172e, zma-MIR319a, zma-MIR319b, zma-MIR319d, zma-MIR393, zma-MIR394a, zma-MIR394b, zma-MIR395a, zma-MIR395b, zma-MIR395c, zma-MIR395d, zma-MIR396a, zma-MIR396b, zma-MIR399a, zma-MIR399b, zma-MIR399c, zma-MIR399d, zma-MIR399e, zma-MIR399f, zma-MIR408.

In some embodiments, the miRNA is a miRNA disclosed in Genbank (USA), EMBL (Europe) or DDBJ (Japan). In some embodiments, the miRNA is selected from one of the following Genbank accession numbers: AJ505003, AJ505002, AJ505001, AJ496805, AJ496804, AJ496803, AJ496802, AJ496801, AJ505004, AJ493656, AJ493655, AJ493654, AJ493653, AJ493652, AJ493651, AJ493650, AJ493649, AJ493648, AJ493647, AJ493646, AJ493645, AJ493644, AJ493643, AJ493642, AJ493641, AJ493640, AJ493639, AJ493638, AJ493637, AJ493636, AJ493635, AJ493634, AJ493633, AJ493632, AJ493631, AJ493630, AJ493629, AJ493628, AJ493627, AJ493626, AJ493625, AJ493624, AJ493623, AJ493622, AJ493621, AJ493620, AY615374, AY615373, AY730704, AY730703, AY730702, AY730701, AY730700, AY730699, AY730698, AY599420, AY551259, AY551258, AY551257, AY551256, AY551255, AY551254, AY551253, AY551252, AY551251, AY551250, AY551249, AY551248, AY551247, AY551246, AY551245, AY551244, AY551243, AY551242, AY551241, AY551240, AY551239, AY551238, AY551237, AY551236, AY551235, AY551234, AY551233, AY551232, AY551231, AY551230, AY551229, AY551228, AY551227, AY551226, AY551225, AY551224, AY551223, AY551222, AY551221, AY551220, AY551219, AY551218, AY551217, AY551216, AY551215, AY551214, AY551213, AY551212, AY551211, AY551210, AY551209, AY551208, AY551207, AY551206, AY551205, AY551204, AY551203, AY551202, AY551201, AY551200, AY551199, AY551198, AY551197, AY551196, AY551195, AY551194, AY551193, AY551192, AY551191, AY551190, AY551189, AY551188, AY501434, AY501433, AY501432, AY501431, AY498859, AY376459, AY376458 AY884233, AY884232, AY884231, AY884230, AY884229, AY884228, AY884227, AY884226, AY884225, AY884224, AY884223, AY884222, AY884221, AY884220, AY884219, AY884218, AY884217, AY884216, AY728475, AY728474, AY728473, AY728472, AY728471, AY728470, AY728469, AY728468, AY728467, AY728466, AY728465, AY728464, AY728463, AY728462, AY728461, AY728460, AY728459, AY728458, AY728457, AY728456, AY728455, AY728454, AY728453, AY728452, AY728451, AY728450, AY728449, AY728448, AY728447, AY728446, AY728445, AY728444, AY728443, AY728442, AY728441, AY728440, AY728439, AY728438, AY728437, AY728436, AY728435 AY728434, AY728433, AY728432, AY728431, AY728430, AY728429, AY728428, AY728427, AY728426, AY728425, AY728424, AY728423, AY728422, AY728421, AY728420, AY728419, AY728418, AY728417, AY728416, AY728415, AY728414, AY728413, AY728412, AY728411, AY728410, AY728409, AY728408, AY728407, AY728406, AY728405, AY728404, AY728403, AY728402, AY728401, AY728400, AY728399, AY728398, AY728397, AY728396, AY728395, AY728394, AY728393, AY728392, AY728391, AY728390, AY728389, AY728388, AY851149, AY851148, AY851147, AY851146, AY851145, AY851144 or AY599420.

In some embodiments, the miRNA is selected from one of the sequences disclosed in U.S. published patent application No. 2005/0144669 A1, incorporated herein by reference.

In some embodiments, the above miRNAs, as well as those disclosed herein, have been modified to be directed to a specific target as described herein.

In some embodiments the target RNA is an RNA of a plant pathogen, such as a plant virus or plant viroid. In some embodiments, the miRNA directed against the plant pathogen RNA is operably linked to a pathogen-inducible promoter. In some embodiments, the target RNA is an mRNA. The target sequence in an mRNA may be a non-coding sequence (such as an intron sequence, 5' untranslated region and 3' untranslated region), a coding sequence or a sequence involved in mRNA splicing. Targeting the miRNA to an intron sequence compromises the maturation of the mRNA. Targeting the miRNA to a sequence involved in mRNA splicing influences the maturation of alternative splice forms providing different protein isoforms.

In some embodiments there are provided cells, plants, and seeds comprising the polynucleotides of the invention, and/or produced by the methods of the invention. In some embodiments, the cells, plants, and/or seeds comprise a nucleic acid construct comprising a modified plant miRNA precursor, as described herein. In some embodiments, the modified plant miRNA precursor in the nucleic acid construct is operably linked to a promoter. The promoter may be any well known promoter, including constitutive promoters, inducible promoters, derepressible promoters, and the like, such as described below. The cells include prokaryotic and eukaryotic cells, including but not limited to bacteria, yeast, fungi, viral, invertebrate, vertebrate, and plant cells. Plants, plant cells, and seeds of the invention include gynosperms, monocots and dicots, including but not limited to, rice, wheat, oats, barley, millet, sorghum, soy, sunflower, safflower, canola, alfalfa, cotton, *Arabidopsis*, and tobacco.

In another embodiment, there is provided a method for down regulating multiple target RNAs comprising introducing into a cell a nucleic acid construct encoding a multiple number of miRNAs. One miRNA in the multiple miRNAs is complementary to a region of one of the target RNAs. In some embodiments, a miRNA is fully complementary to the region of the target RNA. In some embodiments, a miRNA is complementary and includes the use of G-U base pairing, i.e. the GU wobble, to otherwise be fully complementary. In some embodiments, the first ten nucleotides of the miRNA (counting from the 5' end of the miRNA) are fully complementary to a region of the target RNA and the remaining nucleotides may include mismatches and/or bulges with the target RNA. In some embodiments a miRNA comprises about 10-200 nucleotides, about 10-15, 15-20, 19, 20, 21, 22, 23, 24, 25, 26, 27, 25-30, 30-50, 50-100, 100-150, or about 150-200 nucleotides. The binding of a miRNA to its complementary sequence in the target RNA results in cleavage of the target RNA. In some embodiments, the miRNA is a miRNA that has been modified such that the miRNA is fully complementary to the target sequence of the target RNA. In some embodiments, the miRNA is an endogenous plant miRNA that has been modified such that the miRNA is fully complementary to the target sequence of the target RNA. In some embodiments, the miRNA is operably linked to a promoter. In some embodiments, the multiple miRNAs are linked one to another so as to form a single transcript when expressed. In some embodiments, the nucleic acid construct comprises a promoter operably linked to the miRNA.

In some embodiments, the nucleic acid construct encodes miRNAs for suppressing a multiple number of target sequences. The nucleic acid construct encodes at least two miRNAs. In some embodiments, each miRNA is substantially complementary to a target or which is modified to be complementary to a target as described herein. In some embodiments, the nucleic acid construct encodes for 2-30 or more miRNAs, for example 3-40 or more miRNAs, for example 3-45 or more miRNAs, and for further example, multimers of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or more miRNAs. In some embodiments, the multiple miRNAs are linked one to another so as to form a single transcript when expressed.

In some embodiments, polymeric pre-miRNAs that are artificial miRNA precursors consisting of more than one miRNA precursor units are provided. The polymeric pre-miRNAs can either be hetero-polymeric with different miRNA precursors, or homo-polymeric containing several units of the same miRNA precursor. The Examples demonstrate that hetero-polymeric pre-miRNAs are able to produce different mature artificial miRNAs. For example, pre-miR-PDS1$^{169g}$-CPC3$^{159a}$, which is a dimer comprising of pre-miR-CPC3$^{159a}$ and pre-miR-PDS1$^{169g}$ can produce mature miR-PDS1$^{169g}$ and miR-CPC3$^{159a}$ when expressed in plant cells. The Examples also demonstrate that homo-polymeric miRNA precursors are able to produce different mature artificial miRNAs. For example, pre-miR-P69$^{159a}$-HC-Pro$^{159a}$, which is a dimer comprising pre-miR-P69$^{159a}$ and pre-miR-HC-Pro$^{159a}$, can produce mature miR-P69$^{159a}$ and miR-HC-Pro$^{159a}$. In a similar manner, hetero- or homo-polymeric pre-miRNAs are produced that contain any number of monomer units, such as described herein. An exemplary method for preparing a nucleic acid construct comprising multiple pre-miRNAs under the control of a single promoter is shown in Examples 21 and 27. Each mature miRNA is properly processed from the nucleic acid construct as demonstrated in Examples 22 and 27.

In some embodiments, the nucleic acid construct comprises multiple polynucleotides, each polynucleotide encoding a separate miRNA precursor, i.e., a separate pre-miRNA. The polynucleotides are operably linked one to another such that they may be placed under the control of a single promoter. In some embodiments, the multiple polynucleotides are linked one to another so as to form a single transcript containing the multiple pre-miRNAs when expressed. The single transcript is processed in the host cells to produce multiple mature miRNAs, each capable of downregulating its target gene. As many polynucleotides encoding the pre-miRNAs as desired can be linked together, with the only limitation being the ultimate size of the transcript. It is well known that transcripts of 8-10 kb can be produced in plants. Thus, it is possible to form a nucleic acid construct comprising multimeric polynucleotides encoding 2-30 or more pre-miRNAs, for example 3-40 or more pre-miRNAs, for example 3-45 or more pre-miRNAs, and for further example, multimers of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or more pre-miRNAs.

In some embodiments, the nucleic acid construct further comprises a promoter operably linked to the polynucleotide encoding the multiple number of miRNAs. In some embodiments, the nucleic acid construct lacking a promoter is designed and introduced in such a way that it becomes operably linked to a promoter upon integration in the host genome. In some embodiments, the nucleic acid construct is integrated using recombination, including site-specific recombination. See, for example, PCT International published application No. WO 99/25821, herein incorporated by reference. In some embodiments, the nucleic acid construct is an RNA. In some embodiments, the nucleic acid construct comprises at least one recombination site, including site-specific recombination sites. In some embodiments the nucleic acid construct comprises at least one recombination site in order to facilitate integration, modification, or cloning of the construct. In some embodiments the nucleic acid construct comprises two site-specific recombination sites flanking the miRNA precursor. In some embodiments the site-specific recombination sites include FRT sites, lox sites, or att sites, including attB, attL, attP or attR sites. See, for example, PCT International published application No. WO 99/25821, and U.S. Pat. Nos. 5,888,732, 6,143,557, 6,171,861, 6,270,969, and 6,277,608, herein incorporated by reference.

In some embodiments, the pre-miRNA is inserted into an intron in a gene or a transgene of a cell or plant. If the gene has multiple introns, a pre-miRNA, which can be the same or different, can be inserted into each intron. In some embodiments the pre-miRNA inserted into an intron is a polymeric pre-miRNA, such as described herein. During RNA splicing, introns are released from primary RNA transcripts and therefore, as illustrated herein, can serve as precursors for miR-NAs. Most introns contain a splicing donor site at the 5' end, splicing acceptor site at the 3' end and a branch site within the intron. The branch site is important for intron maturation—without it, an intron can not be excised and released from the primary RNA transcript. A branch site is usually located 20-50 nt upstream of the splicing acceptor site, whereas distances between the splice donor site and the branch site are largely variable among different introns. Thus, in some embodiments, the pre-miRNA is inserted into an intron between the splicing donor site and the branch site.

In some embodiments the target RNA is an RNA of a plant pathogen, such as a plant virus or plant viroid. In some embodiments, the miRNA directed against the plant pathogen RNA is operably linked to a pathogen-inducible promoter. In some embodiments, the target RNA is an mRNA. The target sequence in an mRNA may be an intron sequence, a coding sequence or a sequence involved in mRNA splicing. Targeting the mRNA to an intron sequence compromises the maturation of the mRNA. Targeting the mRNA to a sequence involved in mRNA splicing influences the maturation of alternative splice forms providing different protein isoforms. In some embodiments, the target includes genes affecting agronomic traits, insect resistance, disease resistance, herbicide resistance, sterility, grain characteristics, and commercial products.

In some embodiments there are provided cells, plants, and seeds comprising the nucleic acid construct encoding multiple miRNAs of the invention, and/or produced by the methods of the invention. In some embodiments, the cells, plants, and/or seeds comprise a nucleic acid construct comprising multiple polynucleotides, each encoding a plant miRNA precursor, as described herein. In some embodiments, the multiple polynucleotides are operably linked to a promoter. The promoter may be any well known promoter, including constitutive promoters, inducible promoters, derepressible promoters, and the like, such as described below. The polynucleotides encoding the miRNA precursors are linked together. In some embodiments, the multiple polynucleotides are linked one to another so as to form a single transcript containing the multiple pre-miRNAs when expressed in the cells, plants or seeds. The cells include prokaryotic and eukaryotic cells, including but not limited to bacteria, yeast, fungi, viral, invertebrate, vertebrate, and plant cells. Plants, plant cells, and seeds of the invention include gynosperms, monocots and dicots, including but not limited to, rice, wheat, oats, barley, millet, sorghum, soy, sunflower, safflower, canola, alfalfa, cotton, *Arabidopsis*, and tobacco.

The present invention concerns methods and compositions useful in suppression of a target sequence and/or validation of function. The invention also relates to a method for using microRNA (miRNA) mediated RNA interference (RNAi) to silence or suppress a target sequence to evaluate function, or to validate a target sequence for phenotypic effect and/or trait development. Specifically, the invention relates to constructs comprising small nucleic acid molecules, miRNAs, capable of inducing silencing, and methods of using these miRNAs to selectively silence target sequences.

RNA interference refers to the process of sequence-specific post-transcriptional gene silencing in animals mediated by short interfering RNAs (siRNAs) (Fire et al. (1998) *Nature* 391:806-810). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al. (1999) *Trends Genet.* 15:358-363). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Bernstein et al. (2001) *Nature* 409:363-366). Short interfering RNAs derived from dicer activity are typically about 21 to about 23 nucleotides in length and comprise about 19 base pair duplexes (Elbashir et al. (2001) *Genes Dev* 15:188-200). Dicer has also been implicated in the excision of 21- and 22-nucleotide small temporal RNAs (stRNAs) from precursor RNA of conserved structure that are implicated in translational control (Hutvagner et al. (2001) *Science* 293:834-838). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir et al. (2001) *Genes Dev* 15:188-200). In addition, RNA interference can also involve small RNA (e.g., microRNA, or miRNA) mediated gene silencing, presumably through cellular mechanisms that regulate chromatin structure and thereby prevent transcription of target gene sequences (see, e.g., Allshire, *Science* 297:1818-1819 2002; Volpe et al. (2002) *Science* 297:1833-1837; Jenuwein (2002) *Science* 297:2215-2218; Hall et al. (2002) *Science* 297:2232-2237). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. ((1998) *Nature* 391:806-811) were the first to observe RNAi in *C. elegans*. Wianny and Goetz ((1999) *Nature Cell Biol* 2:70) describe RNAi mediated by dsRNA in mouse embryos. Hammond et al. ((2000) *Nature* 404:293-296) describe RNAi in *Drosophila* cells transfected with dsRNA. Elbashir et al. ((2001) *Nature* 411:494-498) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

It is thought that sequence complementarity between small RNAs and their RNA targets helps to determine which mechanism, RNA cleavage or translational inhibition, is employed. It is believed that siRNAs, which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level. Again, without being held to a particular theory on the mechanism of action, a general rule is emerging that perfect or near-perfect complementarity favors RNA cleavage, especially within the first ten nucleotides (counting from the 5'end of the miRNA), whereas translational inhibition is favored when the miRNA/target duplex contains many mismatches. The apparent exception to this is microRNA 172 (miR172) in plants. One of the targets of miR172 is APETALA2 (AP2), and although miR172 shares near-perfect complementarity with AP2 it appears to cause translational inhibition of AP2 rather than RNA cleavage.

MicroRNAs (miRNAs) are noncoding RNAs of about 19 to about 24 nucleotides (nt) in length that have been identified in both animals and plants (Lagos-Quintana et al. (2001) *Science* 294:853-858, Lagos-Quintana et al. (2002) *Curr Biol* 12:735-739; Lau et al. (2002) *Science* 294:858-862; Lee and Ambros (2001) *Science* 294:862-864; Llave et al. (2002) *Plant Cell* 14:1605-1619; Mourelatos et al. (2002) *Genes Dev* 16:720-728; Park et al. (2002) *Curr Biol* 12:1484-1495; Reinhart et al. (2002) *Genes Dev* 16:1616-1626). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (Grishok et al. (2001) *Cell* 106:23-34; Hutvagner et al. (2001) *Science* 293:834-838; Ketting et al. (2001) *Genes Dev* 15:2654-2659). Plants also have a Dicer-like enzyme, DCL1 (previously named CARPEL FACTORY/SHORT INTEGUMENTS1/SUSPENSOR1), and recent evidence indicates that it, like Dicer, is involved in processing the hairpin precursors to generate mature miRNAs (Park et al. (2002) *Curr Biol* 12:1484-1495; Reinhart et al. (2002) *Genes Dev* 16:1616-1626). Furthermore, it is becoming clear from recent work that at least some miRNA hairpin precursors originate as longer polyadenylated transcripts, and several different miRNAs and associated hairpins can be present in a single transcript (Lagos-Quintana et al. (2001) *Science* 294:853-858; Lee et al. (2002) *EMBO J.* 21:4663-4670). Recent work has also examined the selection of the miRNA strand from the dsRNA product arising from processing of the hairpin by DICER (Schwartz et al. (2003) *Cell* 115:199-208). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

In animals, there is direct evidence indicating a role for specific miRNAs in development. The lin-4 and let-7 miRNAs in *C. elegans* have been found to control temporal development, based on the phenotypes generated when the genes producing the lin-4 and let-7 miRNAs are mutated (Lee et al. (1993) *Cell* 75:843-854; Reinhart et al. (2000) *Nature* 403:901-906). In addition, both miRNAs display a temporal expression pattern consistent with their roles in developmental timing. Other animal miRNAs display developmentally regulated patterns of expression, both temporal and tissue-specific (Lagos-Quintana et al. (2001) *Science* 294:853-853, Lagos-Quintana et al. (2002) *Curr Biol* 12:735-739; Lau et al. (2001) *Science* 294:858-862; Lee and Ambros (2001) *Science* 294:862-864), leading to the hypothesis that miRNAs may, in many cases, be involved in the regulation of important developmental processes. Likewise, in plants, the differential expression patterns of many miRNAs suggests a role in development (Llave et al. (2002) *Plant Cell* 14:1605-1619; Park et al. (2002) *Curr Biol* 12:1484-1495; Reinhart et al. (2002) *Genes Dev* 16:1616-1626), which has now been shown (e.g., Guo et al. (2005) *Plant Cell* 17:1376-1386).

MicroRNAs appear to regulate target genes by binding to complementary sequences located in the transcripts produced by these genes. In the case of lin-4 and let-7, the target sites are located in the 3' UTRs of the target mRNAs (Lee et al. (1993) *Cell* 75:843-854; Wightman et al. (1993) *Cell* 75:855-862; Reinhart et al. (2000) *Nature* 403:901-906; Slack et al. (2000) *Mol Cell* 5:659-669), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros (1999) *Dev Biol* 216:671-680). On the other hand, recent evidence suggests that miRNAs can, in some cases, cause specific RNA cleavage of the target transcript within the target site, and this cleavage step appears to require 100% complementarity between the miRNA and the target transcript (Hutvagner and Zamore (2002) *Science* 297:2056-2060; Llave et al. (2002) *Plant Cell* 14:1605-1619), especially within the first ten nucleotides (counting from the 5' end of the miRNA). It seems likely that miRNAs can enter at least two pathways of target gene regulation. Protein downregulation when target complementarity is <100%, and RNA cleavage when target complementarity is 100%. MicroRNAs entering the RNA cleavage pathway are analogous to the 21-25 nt short interfering RNAs (siRNAs) generated during RNA interference (RNAi) in animals and posttranscriptional gene silencing (PTGS) in plants (Hamilton and Baulcombe (1999) *Science* 286:950-952; Hammond et al., (2000) *Nature* 404:293-296; Zamore et al., (2000) *Cell* 31:25-33; Elbashir et al., (2001) *Nature* 411:494-498), and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al. (2002) *Plant Cell* 14:1605-1619; Park et al. (2002) *Curr Biol* 12:1484-1495; Rhoades et al. (2002) *Cell* 110:513-520), and thus it appears that plant miRNAs have higher overall complementarity with their putative targets than do animal miRNAs. Most of these predicted target transcripts of plant miRNAs encode members of transcription factor families implicated in plant developmental patterning or cell differentiation. Nonetheless, biological function has not been directly demonstrated for any plant miRNA. Although Llave et al. ((2002) *Science* 297:2053-2056) have shown that a transcript for a SCARECROW-like transcription factor is a target of the *Arabidopsis* miRNA mir171, these studies were performed in a heterologous species and no plant phenotype associated with mir171 was reported.

The methods provided can be practiced in any organism in which a method of transformation is available, and for which there is at least some sequence information for the target sequence, or for a region flanking the target sequence of interest. It is also understood that two or more sequences could be targeted by sequential transformation, co-transformation with more than one targeting vector, or the construction of a DNA construct comprising more than one miRNA sequence. The methods of the invention may also be implemented by a combinatorial nucleic acid library construction in order to generate a library of miRNAs directed to random target sequences. The library of miRNAs could be used for high-throughput screening for gene function validation.

General categories of sequences of interest include, for example, those genes involved in regulation or information, such as zinc fingers, transcription factors, homeotic genes, or cell cycle and cell death modulators, those involved in communication, such as kinases, and those involved in housekeeping, such as heat shock proteins.

virus in this selected region may render the encoded protein inactive, thus preventing mutation of the virus as a way to escape the resistance mechanism. In some embodiments, an artificial miRNA directed towards a conserved sequence of a family of viruses would confer resistance to members of the entire family. In some embodiments, an artificial miRNA directed towards a sequence conserved amongst members of would confer resistance to members of the different viral families (e.g, see Table 1).

TABLE 1

Conserved Viral Genome Sequence of TuMV for Artificial miRNA Design

TuMV CY5

| No | Region[a] | Gene | Sequence[b] (SEQ ID NO:) | length |
|----|-----------|------|--------------------------|--------|
| 1 | 3207 to 3229 | P3 | 5'-cgatttaggcggcagatacagcg-3' (167) | 23 |
| 2 | 9151 to 9185 | CP | 5'-attctcaatggtttaatggtctggtgcattgagaa-3' (168) | 35 |
| 3 | 9222 to 9227 | CP | 5'-ataaacggaatgtgggtgatgatgga-3' (169) | 26 |
| 4 | 9235 to 9255 | CP | 5'-gatcaggtggaattcccgatc-3' (170) | 21 |
| 5 | 9270 to 9302 | CP | 5'-cacgccaaacccacatttaggcaaataatggc-3' (171) | 32 |
| 6 | 9319 to 9386 | CP | 5'-gctgaagcgtacattgaaaagcgtaaccaagaccgaccatac atgccacgatatggtcttcagcgcaa-3' (172) | 68 |
| 7 | 9430 to 9509 | CP | 5'-gaaatgacttctagaactccaatacgtgcgagagaagcacac atccagatgaaagcagcagcactgcgtggcgcaaataa-3' (173) | 80 |
| 8 | 9541 to 9566 | CP | 5'-acaacggtagagaacacggagaggca-3' (174) | 26 |

[a]The region of genome sequence is according to TuMV CY5 strain (AF530055).
[b]The highly conserved of TuMV sequence from 21 different TuMV strains was alignment by Vector NTI Advance 10.0.1 software (Invitrogen Corp).
The full-length sequence of 21 different TuMV strains were obtained from the GenBank database under the following accession numbers including AB093596, AB093598, AB093599, AB093600, AB093615, AB093616, AB093617, AB093618, AB093619, AB093611, AB093612, AY227024, AB093609, AF394601, AF169561, AF530055, AF394602, AB093623, AB093624, AY090660, D83184.

Target sequences further include coding regions and non-coding regions such as promoters, enhancers, terminators, introns and the like, which may be modified in order to alter the expression of a gene of interest. For example, an intron sequence can be added to the 5' region to increase the amount of mature message that accumulates (see for example Buchman and Berg (1988) Mol Cell Biol 8:4395-4405); and Callis et al. (1987) Genes Dev 1:1183-1200).

The target sequence may be an endogenous sequence, or may be an introduced heterologous sequence, or transgene. For example, the methods may be used to alter the regulation or expression of a transgene, or to remove a transgene or other introduced sequence such as an introduced site-specific recombination site. The target sequence may also be a sequence from a pathogen, for example, the target sequence may be from a plant pathogen such as a virus, a mold or fungus, an insect, or a nematode. A miRNA can be expressed in a plant which, upon infection or infestation, would target the pathogen and confer some degree of resistance to the plant. The Examples herein demonstrate the techniques to design artificial miRNAs to confer virus resistance/tolerance to plants. In some embodiments, two or more artificial miRNA sequences directed against different sequences of the virus can be used to prevent the target virus from mutating and thus evading the resistance mechanism. In some embodiments, sequences of artificial miRNAs can be selected so that they target a critical region of the viral RNA (e.g. active site of a silencing gene suppressor). In this case, mutation of the In plants, other categories of target sequences include genes affecting agronomic traits, insect resistance, disease resistance, herbicide resistance, sterility, grain characteristics, and commercial products. Genes of interest also include those involved in oil, starch, carbohydrate, or nutrient metabolism as well as those affecting, for example, kernel size, sucrose loading, and the like. The quality of grain is reflected in traits such as levels and types of oils, saturated and unsaturated, quality and quantity of essential amino acids, and levels of cellulose. For example, genes of the phytic acid biosynthetic pathway could be suppressed to generate a high available phosphorous phenotype. See, for example, phytic acid biosynthetic enzymes including inositol polyphosphate kinase-2 polynucleotides, disclosed in WO 02/059324, inositol 1,3,4-trisphosphate 5/6-kinase polynucleotides, disclosed in WO 03/027243, and myo-inositol 1-phosphate synthase and other phytate biosynthetic polynucleotides, disclosed in WO 99/05298, all of which are herein incorporated by reference. Genes in the lignification pathway could be suppressed to enhance digestibility or energy availability. Genes affecting cell cycle or cell death could be suppressed to affect growth or stress response. Genes affecting DNA repair and/or recombination could be suppressed to increase genetic variability. Genes affecting flowering time could be suppressed, as well as genes affecting fertility. Any target sequence could be suppressed in order to evaluate or confirm its role in a particular trait or phenotype, or to dissect a molecular, regulatory, biochemical, or proteomic pathway or network.

A number of promoters can be used, these promoters can be selected based on the desired outcome. It is recognized that different applications will be enhanced by the use of different promoters in plant expression cassettes to modulate the timing, location and/or level of expression of the miRNA. Such plant expression cassettes may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608, 144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the PEP (phophoenol pyruvate) carboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT International published application No. WO 02/04699). Other examples of inducible promoters include the GVG and XVE promoters, which are induced by glucocorticoids and estrogen, respectively (U.S. Pat. No. 6,452, 068).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter (Boronat et al. (1986) *Plant Sci* 47:95-102; Reina et al. (1990) *Nucl Acids Res* 18(21):6426; Kloesgen et al. (1986) *Mol. Gen. Genet.* 203:237-244). Promoters that express in the embryo, pericarp, and endosperm are disclosed in U.S. Pat. No. 6,225,529 and PCT International published application No. WO 00/12733. The disclosures of each of these are incorporated herein by reference in their entirety.

In some embodiments it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also PCT International published application No. WO 99/43819, herein incorporated by reference.

Of interest are promoters that are expressed locally at or near the site of pathogen infection. See, for example, Marineau et al. (1987) *Plant Mol Biol* 9:335-342; Matton et al. (1989) *Molecular Plant-Microbe Interactions* 2:325-331; Somsisch et al. (1986) *Proc Natl Acad Sci USA* 83:2427-2430; Somsisch et al. (1988) *Mol Gen Genet* 2:93-98; and Yang (1996) *Proc Natl Acad Sci USA* 93:14972-14977. See also, Chen et al. (1996) *Plant J* 10:955-966; Zhang et al. (1994) *Proc Natl Acad Sci USA* 91:2507-2511; Warner et al. (1993) *Plant J* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol Mol Plant Path* 41:189-200).

Additionally, as pathogens find entry into plants through wounds or insect damage, a wound-inducible promoter may be used in the constructions of the polynucleotides. Such wound-inducible promoters include potato proteinase inhibitor (pin II) gene (Ryan (1990) *Ann Rev Phytopath* 28:425-449; Duan et al. (1996) *Nature Biotech* 14:494-498); wun1 and wun2, U.S. Pat. No. 5,428,148; win1 and win2 (Stanford et al. (1989) *Mol Gen Genet* 215:200-208); system in (McGurl et al. (1992) *Science* 225:1570-1573); WIP1 (Rohmeier et al. (1993) *Plant Mol Biol* 22:783-792; Eckelkamp et al. (1993) *FEBS Lett* 323:73-76); MPI gene (Corderok et al. (1994) *Plant J* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc Natl Acad Sci USA* 88:10421-10425 and McNellis et al. (1998) *Plant J* 14(2):247-257) and tetracycline-inducible and tetracycline-repressible promoters (see, for example, Gatz et al. (1991) *Mol Gen Genet* 227:229-237, and U.S. Pat. Nos. 5,814,618 and 5,789,156), herein incorporated by reference.

Tissue-preferred promoters can be utilized to target enhanced expression of a sequence of interest within a particular plant tissue. Tissue-preferred promoters include Yamamoto et al. (1997) *Plant J* 12(2):255-265; Kawamata et al. (1997) *Plant Cell Physiol* 38(7):792-803; Hansen et al. (1997) *Mol Gen Genet* 254(3):337-343; Russell et al. (1997) *Transgenic Res* 6(2):157-168; Rinehart et al. (1996) *Plant Physiol* 112(3):1331-1341; Van Camp et al. (1996) *Plant Physiol* 112(2):525-535; Canevascini et al. (1996) *Plant Physiol* 112(2):513-524; Yamamoto et al. (1994) *Plant Cell Physiol* 35(5):773-778; Lam (1994) *Results Probl Cell Differ* 20:181-196; Orozco et al. (1993) *Plant Mol Biol* 23(6):1129-1138; Matsuoka et al. (1993) *Proc Natl Acad Sci USA* 90(20):

9586-9590; and Guevara-Garcia et al. (1993) *Plant J* 4(3): 495-505. Such promoters can be modified, if necessary, for weak expression.

Leaf-preferred promoters are known in the art. See, for example, Yamamoto et al. (1997) *Plant J* 12(2):255-265; Kwon et al. (1994) *Plant Physiol* 105:357-67; Yamamoto et al. (1994) *Plant Cell Physiol* 35(5):773-778; Gotor et al. (1993) *Plant J* 3:509-18; Orozco et al. (1993) *Plant Mol Biol* 23(6):1129-1138; and Matsuoka et al. (1993) *Proc Natl Acad Sci USA* 90(20):9586-9590. In addition, the promoters of cab and RUBISCO can also be used. See, for example, Simpson et al. (1958) *EMBO J* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol Biol* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol Biol* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi ((1991) *Plant Science* (Limerick) 79(1):69-76) describe their analysis of the promoters of the highly expressed rolC and rolD root-inducing genes of *Agrobacterium rhizogenes*. They concluded that enhancer and tissue-preferred DNA determinants are dissociated in those promoters. Teeri et al. ((1989) *EMBO J.* 8(2):343-350) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene. The TR1' gene, fused to nptII (neomycin phosphotransferase II) showed similar characteristics. Additional root-preferred promoters include the VfENOD-GRP3 gene promoter (Kuster et al. (1995) *Plant Mol Biol* 29(4):759-772); and rolB promoter (Capana et al. (1994) *Plant Mol Biol* 25(4):681-691. See also U.S. Pat. Nos. 5,837,876; 5,750,386; 5,633,363; 5,459,252; 5,401,836; 5,110,732; and 5,023,179. The phaseolin gene (Murai et al. (1983) Science 23:476-482 and Sengopta-Gopalen et al. (1988) *Proc Natl Acad Sci USA* 82:3320-3324.

Transformation protocols as well as protocols for introducing nucleotide sequences into plants may vary depending on the type of plant or plant cell, i.e., monocot or dicot, targeted for transformation. Suitable methods of introducing the DNA construct include microinjection (Crossway et al. (1986) *Biotechniques* 4:320-334; and U.S. Pat. No. 6,300,543), sexual crossing, electroporation (Riggs et al. (1986) *Proc Natl Acad Sci USA* 83:5602-5606), *Agrobacterium*-mediated transformation (Townsend et al., U.S. Pat. No. 5,563,055; and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann Rev Genet* 22:421-477; Sanford et al. (1987) *Particulate Science and Technology* 5:27-37 (onion); Christou et al. (1988) *Plant Physiol* 87:671-674 (soybean); Finer and McMullen (1991) *In Vitro Cell Dev Biol* 27P:175-182 (soybean); Singh et al. (1998) *Theor Appl Genet* 96:319-324 (soybean); Datta et al. (1990) *Biotechnology* 8:736-740 (rice); Klein et al. (1988) *Proc Natl Acad Sci USA* 85:4305-4309 (maize); Klein et al. (1988) *Biotechnology* 6:559-563 (maize); U.S. Pat. No. 5,240,855; U.S. Pat. No. 5,322,783; U.S. Pat. No. 5,324,646; Klein et al. (1988) *Plant Physiol* 91:440-444 (maize); Fromm et al. (1990) *Biotechnology* 8:833-839 (maize); Hooykaas-Van Slogteren et al. (1984) *Nature* 311:763-764; U.S. Pat. No. 5,736,369 (cereals); Bytebier et al. (1987) *Proc Natl Acad Sci USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor Appl Genet* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); and U.S. Pat. No. 5,736,369 (meristem transformation), all of which are herein incorporated by reference.

The nucleotide constructs may be introduced into plants by contacting plants with a virus or viral nucleic acids. Generally, such methods involve incorporating a nucleotide construct of the invention within a viral DNA or RNA molecule. Further, it is recognized that useful promoters encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

In some embodiments, transient expression may be desired. In those cases, standard transient transformation techniques may be used. Such methods include, but are not limited to viral transformation methods, and microinjection of DNA or RNA, as well other methods well known in the art.

The cells from the plants that have stably incorporated the nucleotide sequence may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic imparted by the nucleotide sequence of interest and/or the genetic markers contained within the target site or transfer cassette. Two or more generations may be grown to ensure that expression of the desired phenotypic characteristic is stably maintained and inherited and then seeds harvested to ensure expression of the desired phenotypic characteristic has been achieved.

Initial identification and selection of cells and/or plants comprising the DNA constructs may be facilitated by the use of marker genes. Gene targeting can be performed without selection if there is a sensitive method for identifying recombinants, for example if the targeted gene modification can be easily detected by PCR analysis, or if it results in a certain phenotype. However, in most cases, identification of gene targeting events will be facilitated by the use of markers. Useful markers include positive and negative selectable markers as well as markers that facilitate screening, such as visual markers. Selectable markers include genes carrying resistance to an antibiotic such as spectinomycin (e.g. the aada gene, Svab et al. (1990) *Plant Mol Biol* 14:197-205), streptomycin (e.g., aada, or SPT, Svab et al. (1990) *Plant Mol Biol* 14:197-205; Jones et al. (1987) *Mol Gen Genet* 210:86), kanamycin (e.g., nptII, Fraley et al. (1983) *Proc Natl Acad Sci USA* 80:4803-4807), hygromycin (e.g., HPT, Vanden Elzen et al. (1985) *Plant Mol Biol* 5:299), gentamycin (Hayford et al. (1988) *Plant Physiol* 86:1216), phleomycin, zeocin, or bleomycin (Hille et al. (1986) *Plant Mol Biol* 7:171), or resistance to a herbicide such as phosphinothricin (bar gene), or sulfonylurea (acetolactate synthase (ALS)) (Charest et al. (1990) *Plant Cell Rep* 8:643), genes that fulfill a growth requirement on an incomplete media such as HIS3, LEU2, URA3, LYS2, and TRP1 genes in yeast, and other such genes known in the art. Negative selectable markers include cytosine deaminase (codA) (Stougaard (1993) *Plant J.* 3:755-761), tms2 (DePicker et al. (1988) *Plant Cell Rep* 7:63-66), nitrate reductase (Nussame et al. (1991) *Plant J* 1:267-274), SU1 (O'Keefe et al. (1994) *Plant Physiol.* 105:473-482), aux-2 from the Ti plasmid of *Agrobacterium*, and thymidine kinase. Screenable markers include fluorescent proteins such as green fluorescent protein (GFP) (Chalfie et al. (1994) *Science* 263:802; U.S. Pat. No. 6,146,826; U.S. Pat. No. 5,491,084; and WO 97/41228), reporter enzymes such as β-glucuronidase (GUS) (Jefferson (1987) *Plant Mol Biol Rep* 5:387; U.S. Pat. No. 5,599,670; U.S. Pat. No. 5,432,081), β-galactosidase (lacZ), alkaline phosphatase (AP), glutathione S-transferase (GST) and luciferase (U.S. Pat. No. 5,674,713; Ow et al. (1986) *Science* 234:856-859), visual markers like anthocyanins such as CRC (Ludwig et al. (1990) *Science* 247:449-450) R gene family (e.g. Lc, P, S), A, C, R-nj, body and/or eye color genes in *Drosophila*, coat color genes in mammalian systems, and others known in the art.

One or more markers may be used in order to select and screen for gene targeting events. One common strategy for gene disruption involves using a target modifying polynucleotide in which the target is disrupted by a promoterless selectable marker. Since the selectable marker lacks a promoter, random integration events are unlikely to lead to transcription of the gene. Gene targeting events will put the selectable marker under control of the promoter for the target gene. Gene targeting events are identified by selection for expression of the selectable marker. Another common strategy utilizes a positive-negative selection scheme. This scheme utilizes two selectable markers, one that confers resistance (R+) coupled with one that confers a sensitivity (S+), each with a promoter. When this polynucleotide is randomly inserted, the resulting phenotype is R+/S+. When a gene targeting event is generated, the two markers are uncoupled and the resulting phenotype is R+/S−. Examples of using positive-negative selection are found in Thykjær et al. (1997) *Plant Mol Biol* 35:523-530; and PCT International published application No. WO 01/66717, which are herein incorporated by reference.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al. (1982) *Molecular Cloning* (Cold Spring Harbor Laboratory Press, Cold Spring Harbor, N.Y.); Sambrook et al. (1989) *Molecular Cloning*, 2nd Ed. (Cold Spring Harbor Laboratory Press, Cold Spring Harbor, N.Y.); Sambrook and Russell (2001) *Molecular Cloning*, 3rd Ed. (Cold Spring Harbor Laboratory Press, Cold Spring Harbor, N.Y.); Ausubel et al. (1992) *Current Protocols in Molecular Biology* (John Wiley & Sons, including periodic updates); Glover (1985) *DNA Cloning* (IRL Press, Oxford); Anand (1992) *Techniques for the Analysis of Complex Genomes* (Academic Press); Guthrie and Fink (1991) *Guide to Yeast Genetics and Molecular Biology* (Academic Press); Harlow and Lane (1988) *Antibodies*, (Cold Spring Harbor Laboratory Press, Cold Spring Harbor, N.Y.); Jakoby and Pastan, eds. (1979) "Cell Culture" *Methods in Enzymology* Vol. 58 (Academic Press, Inc., Harcourt Brace Jovanovich (NY)); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Hogan et al., *Manipulating the Mouse Embryo*, (Cold Spring Harbor Laboratory Press, Cold Spring Harbor, N.Y., 1986); Westerfield, M., *The zebrafish book. A guide for the laboratory use of zebrafish (Danio rerio)*, (4th Ed., Univ. of Oregon Press, Eugene, 2000); *Methods in Arabidopsis Research* (C. Koncz et al., eds, World Scientific Press, Co., Inc., River Edge, Minn., 1992); *Arabidopsis: A Laboratory Manual* (D. Weigel and J. Glazebrook, eds., Cold Spring Harbor Laboratory Press, Cold Spring Harbor, N.Y., 2002).

EXAMPLES

The following are non-limiting examples intended to illustrate the invention. Although the present invention has been described in some detail by way of illustration and example for purposes of clarity of understanding, it will be obvious that certain changes and modifications may be practiced within the scope of the appended claims. For example, any of the pre-miRNAs and miRNAs described herein can be used in place of the pre-miRNAs and miRNAs used in the examples. Examples 1-15 are derived from PCT International published application Nos. WO 2005/052170 and WO 2005/035769 and from U.S. published application Nos. US 2005/0138689 and US 2005/0120415, each incorporated herein by reference.

Example 1

The example describes the identification of a microRNA

The following experiments are carried out on the *Arabidopsis thaliana* Col-0 ecotype. Plants are grown in long days (16 h light, 8 h dark) under cool white light at 22° C.

*Arabidopsis* plants are transformed by a modified version of the floral dip method, in which *Agrobacterium* cell suspension is applied to plants by direct watering from above. The T-DNA vector used, pHSbarENDs, contained four copies of the CAMV 35S enhancer adjacent to the right border, an arrangement similar to that described by Weigel et al. (*Plant Physiol.* 122:1003-1013, 2000). Transformed plants are selected with glufosinate (BASTA) and screened for flowering time, which resulted in the identification of the early-flowering EAT-D mutant. A single T-DNA cosegregating with early flowering is identified in EAT-D, and TAIL-PCR is performed to amplify sequences adjacent to the left and right borders of the T-DNA. To identify transcripts upregulated in the EAT-D mutant, Northern blots containing RNA extracted from wild type (Col-0) and EAT-D plants is probed. Probes for the genes At5g04270 and At5g04280 (GenBank NC_003076) do not detect any difference between wild type and EAT-D, whereas a probe from the intergenic region identifies an ~1.4 kb transcript that is expressed at significantly higher levels in EAT-D than in wild type.

To isolate the full-length EAT cDNA, 5'- and 3'-RACE-PCR is performed with a GeneRacer kit (Invitrogen) that selects for 5'-capped mRNAs. Reverse transcription is carried out using an oligo-dT primer, and PCR utilized a gene-specific primer (SEQ ID NO:45 5'-CTGTGCTCACGATCT-TGTTGTTCTTGATC-3') paired with the 5' kit primer, or a second gene-specific primer (SEQ ID NO:46 5'-GTCGGCG-GATCCATGGAAGAAAGCTCATC-5') paired with the 3' kit primer.

The *Arabidopsis* EAT-D (Early Activation Tagged—Dominant) mutant is identified in an activation tagging population (Weigel et al. (2000) *Plant Physiol* 122:1003-1013). As evidenced by visual inspection and by measuring rosette leaf number (Table 2), the EAT-D mutant flowers extremely early. In addition, EAT-D displays floral defects that are virtually identical to those observed for strong apetala2 (ap2) mutant alleles (Bowman et al. (1991) *Development* 112:1-20), including the complete absence of petals and the transformation of sepals to carpels. This ap2-like phenotype is only observed in EAT-D homozygotes, whereas both EAT-D heterozygotes and homozygotes are early flowering, indicating that the flowering time phenotype is more sensitive to EAT-D dosage than the ap2-like floral phenotype.

TABLE 2

Rosette leaf numbers for *Arabidopsis* lines

| Genotype | rosette leaf no. | floral phenotype |
|---|---|---|
| Col-0 | 11.4 +/− 1.2 | wild type |
| EAT-D | 3.1 +/− 0.8 | ap2 |
| EAT-OX | 2.0 +/− 0.2 | ap2 + additional |
| eatdel | 11.1 +/− 1.1 | wild type |
| miR172a1-OX | 2.1 +/− 0.3 | ap2 + additional |
| LAT-D | 22.5 +/− 2.1 | wild type |
| At2g28550-OX | 28.6 +/− 3.6 | wild type |
| 5-60120 | 10.2 +/− 1.4 | wild type |
| 2-28550 | 8.7 +/− 0.6 | wild type |
| 5-60120; 2-28550 | 6.0 +/− 0.8 | wild type |

The activation-tagged T-DNA insert in EAT-D is mapped to chromosome 5, in between the annotated genes At5g04270 and At5g04280. 5'- and 3'-RACE PCR is then used with primers located within this region to identify a 1.4 kb transcript (SEQ ID NO:1), which is named EAT, that is upregulated in EAT-D. When the 1.4 kb EAT cDNA is fused to the constitutive CAMV 35S promoter and the resultant 35S::EAT construct is introduced into wild type (Col-0) plants by *Agrobacterium*-mediated transformation (Clough and Bent (1998) *Plant J* 16:735-743), the 35S::EAT transformants display the identical early-flowering and ap2-like phenotypes seen for EAT-D (Table 1). Many of the 35S::EAT transformants occasionally display additional defects, including stigmatic papillae on cauline leaf margins and the formation of a complete or partial flower rather than a secondary inflorescence in the axils of cauline leaves. Ectopic expression of the EAT gene in 35S::EAT plants, therefore, affects both flowering time and the specification of floral organ identity.

The EAT gene produces a 1417-nucleotide noncoding RNA that is predicted to be 5'-capped and polyadenylated, based on the RACE-PCR methodology. BLASTN and BLASTX searches of several databases with the EAT cDNA do not reveal extensive nucleotide or predicted amino acid sequence identity between EAT and any other gene. However, a 21-nucleotide (nt) (SEQ ID NO:4) stretch in the middle of the EAT transcript is identified that is identical to miR172a-2, a recently identified miRNA (Park et al. (2002) *Curr Biol* 12:1484-1495). To confirm the functional importance of the miR172a-2 sequence within the EAT cDNA, a mutant form of EAT is generated in which the miR172a-2 sequence is deleted, and a construct consisting of this mutant EAT cDNA, eatdel, is made driven by the 35S promoter. Transgenic plants carrying this 35S::eatdel construct flower with the same number of leaves as wild-type and had normal flowers (Table 1), indicating that the miR172a-2 sequence is necessary to confer both the flowering time and floral organ identity phenotypes seen in EAT-overexpressing lines.

As noted by Park et al. (2002) *Curr Biol* 12:1484-1495), the 21-nt miR172a-2 miRNA has the potential to form an RNA duplex with a sequence near the 3' end of the coding region of AP2 (Table 3).

TABLE 3

Putative 21-nt miR172a-2/AP2 RNA duplex

| Sequence | Duplex | SEQ ID NO: |
|---|---|---|
| AP2 RNA | 5'-CUGCAGCAUCAUCAGGAUUCU-3' | 47 |
| EAT miRNA | 3'-UACGUCGUAGUAGU<u>U</u>CUAAGA-5' | 48 |

The GU wobble in the duplex is underlined.

This particular region of the AP2 gene is poorly conserved at the nucleotide level among the AP2 family; nevertheless, the AP2 sequence (SEQ ID NO:49) that is complementary to miR172a-2 is found in a similar location in three other *Arabidopsis* AP2 family members, At5g60120 (SEQ ID NO:50), At2g28550 (SEQ ID NO:51), At5g67180 (SEQ ID NO:52). In addition, the sequence can be found at the corresponding positions of the maize AP2 genes indeterminate spikelet1 (Chuck et al. (1998) *Genes Dev* 12:1145-1154) (IDS1 (SEQ ID NO:53)) and glossy15 (Moose and Sisco (1996) *Genes Dev* 10:3018-3027) (GL15 (SEQ ID NO:54)), and in AP2 family members from many other plant species, including soybean, rice, wheat, tomato and pea (not shown). The alignment of three *Arabidopsis* and two maize AP2 family members is shown in Table 4 below.

TABLE 4

Alignment of AP2 21-nt region (black bar) and surrounding sequence (SEQ ID NO:)

| | | |
|---|---|---|
| AP2 | ACCAAGTGTTGACAAATGCTGCAGCATCATCAGGATTCTCTCCTCATCATCACAATCAG | (49) |
| At5g60120 | CACCGCCACTGTTTTCAAATGCAGCATCATCAGGATTCTCACTCTCAGCTACACGCCCT | (50) |
| At2q28550 | CACCATTGTTCTCAGTTGCAGCAGCATCATCAGGATTCTCACATTTCCGGCCACAACCT | (51) |
| At5g67180 | GAAATCGAGTGGTGGGAATGGCAGCATCATCAGGATTCTCTCCTCAACCTTCCCCTTAC | (52) |
| IDS1 | ACGTGCCGTTGCACCACTCTGCAGCATCATCAGGATTCTCTACCGCCGCCGGGGCCAAC | (53) |
| GL15 | ACGCCAGCAGCGCCGCCGCTGCAGCATCATCAGGATTCCCACTGTGGCAGCTGGGTGCG | (54) |

There is an additional copy of the miR172a-2 miRNA in the *Arabidopsis* genome on chromosome 2 (miR172a-1, FIG. 2d), and miR172a-2 is highly similar to three other *Arabidopsis* loci. Like the miR172a-2 miRNA, all four reiterations of the sequence are in intergenic regions, i.e. in between the *Arabidopsis* genes currently annotated in GenBank. In addition, the sequence is found in ESTs from tomato, potato and soybean, and four copies were found in the genomic sequence of rice.

Example 2

This example describes the construction of expression vectors

To overexpress the EAT gene, primers containing XhoI sites (SEQ ID NO:55 5'-GACTACTCGAGCACCTCT-CACTCCCTTTCTCTAAC-3' and SEQ ID NO:56 5'-GAC-TACTCGAGGTTCTCAAGTTGAGCACTTGAAAAC-3') are designed to amplify the entire EAT gene from Col-0 DNA. The PCR product is digested with XhoI and inserted into a modified pBluescriptSK+ vector (Stratagene, La Jolla, Calif.) that lacked BamHI and HindIII sites, to generate EATX4 (SEQ ID NO:44). To generate the 35S::EAT transformants, the XhoI-cut EAT gene is inserted into the binary vector pBE851 in between a CAMV 35S promoter and b-phaseolin terminator, and Col-0 was transformed by floral dip. To generate the eatdel construct, two oligonucleotides are synthesized (SEQ ID NO:57 5'-GATCCATGGAAGAAAGCTCAT CTGTCGTTGTTTGTAGGCGCAGCACCAT-TAAGATTCACATGGAAATTGATAAATAC-3' and SEQ ID NO:58 5'-CCTAAATTAGGGTTTTGATATGTATAT-TCAACAATCGACG GCTACAAATACCTAA-3') that completely recreated the BamHI/HindIII fragment of the EAT cDNA except that it lacked the 21 nt miR172a-2 sequence located within the fragment. These two oligos are annealed to their synthesized complementary strands (SEQ ID NO:59 5'-TAG GGTATTTATCAATTTCCATGTGAATCT-TAATGGTGCTGCGCCTACAAACAACGACAG ATGAGCTTTCTTCCATG-3' and SEQ ID NO:60 5'-AGCTTTAGGTATTTGTAGCCGTC GATTGT-TGAATATACATATCAAAACCCTAATT-3') and ligated to EATX4 that had been digested with BamHI and HindIII, in a trimolecular ligation reaction. This resulted in the replacement of 159 bp of wild-type EAT sequence with the 138 bp mutant sequence. The eatdel cDNA is then subcloned into pBE851 and transformed as described above. BASTA is used to select in plants for both the EAT and eatdel overexpression constructs.

To test whether another member of the miR172 family, miR172a-1, would confer a phenotype similar to that of miR172a-2, a construct containing the 35S promoter fused to the genomic region surrounding miR172a-1 is generated. Plants containing the 35S::miR172a-1 construct flower early and display an ap2 phenotype (Table 1), indicating that miR172a-1 behaves in an identical manner to miR172a-2 when overexpressed.

Figure 1:
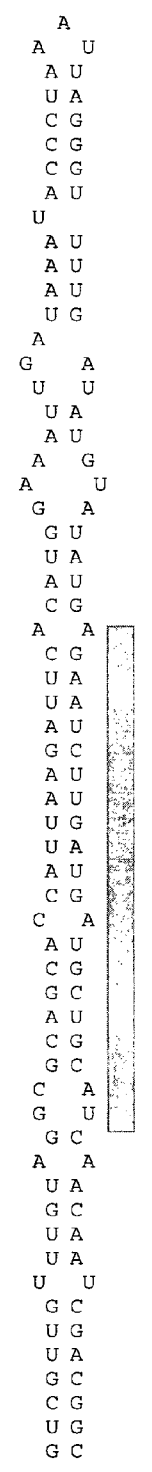

All of the miR172 miRNA family members are located within a sequence context that allows an RNA hairpin to form (FIG. 1). Presumably this hairpin is the substrate which is subsequently cleaved by a plant Dicer homolog to generate the mature miRNA. The location of the miRNA within the hairpin, i.e. on the 3' side of the stem, is conserved amongst all the members of the miR172 family, and this may reflect a structural requirement for processing of this particular miRNA family. The 21-nt miR172a-2 miRNA, therefore, is predicted to be a member of a family of miRNAs that have the capacity to regulate a subset of AP2 genes by forming an RNA duplex with a 21-nt cognate sequence in these genes.

Example 3

The example describes the analysis of microRNA expression and AP2 expression

Total RNA is isolated from wild type and EAT-D whole plants that had already flowered, using TRIZOL reagent (Sigma). 50 mg of each RNA is subjected to electrophoresis on a 15% TBE-Urea Criterion gel (BioRad), electroblotted onto Hybond-N+ filter paper (Amersham) using a TransBlot-SD apparatus (BioRad). The filter is then hybridized at 37° C. overnight in UltraHyb-Oligo buffer (Ambion) with 32P-labeled oligos. The oligos are 30-mers that corresponded to either the sense or antisense strands of the miR172a-2 miRNA, with 4-5 nt of flanking sequence on each side. The filter is washed twice at 37° C., in buffer containing 2× SSC and 0.5% SDS. For S1 analysis, probe is made by end-labeling an oligo (SEQ ID NO:61) (5'-ATGCAGCATCATCAA-GATTCTCATATACAT-3') with T4 polynucleotide kinase and 32P. Hybridization and processing of S1 reactions are carried out using standard protocols. For developmental analysis of miR172a-2 and miR172a-1, total RNA is isolated from plants at the various stages and tissues indicated in Example 4, using an Rneasy kit (Qiagen). RT-PCR is carried out using standard protocols, and utilized oligos specific for sequences adjacent to miR172a-2 (SEQ ID NO:62) (5'-GTCGGCGGATCCATGG AAGAAAGCTCATC-3' and (SEQ ID NO:63) 5'-CAAAGATCGATCCAGACTTCAAT-CAA TATC-3') or sequences adjacent to miR172a-1 (SEQ ID NO:64) (5'-TAATTTCCGGAGCCAC GGTCGTTGTTG-3' and (SEQ ID NO:65) 5'-AATAGTCGTTGATTGCCGATG-CAGCATC-3'). Oligos used to amplify the ACT11 (Actin) transcript were: (SEQ ID NO:66) 5'-ATGGCAGATGGT-GAAGACATTCAG-3', and (SEQ ID NO:67) 5'-GAAG- CACTTCCTGTG GACTATTGATG-3'. RT-PCR analysis of AP2 is performed on RNA from floral buds, and utilized the following oligos: (SEQ ID NO:68) 5'-TTTCCGGGCAG-CAGCAACATTGGTAG-3', and (SEQ ID NO:69) 5'-GT-TCGCCTAAGTTAACAAGAGGATTTAGG-3'. Oligos used to amplify the ANT transcript are: (SEQ ID NO:70) 5'-GAT-CAACTTCAATGACTAACTCTG GTTTTC-3', and (SEQ ID NO:71) 5'-GTTATAGAGAGATTCATTCTGTTTCA-CATG-3'.

Immunoblot analysis of AP2 is performed on proteins extracted from floral buds. Following electrophoresis on a 10% SDS-PAGE gel, proteins are transferred to a Hybond-P membrane (Amersham) and incubated with an antibody specific for AP2 protein (aA-20, Santa Cruz Biotechnology). The blot is processed using an ECL-plus kit (Amersham).

Northern analysis using probes both sense and antisense to the miR172a-2 miRNA identifies a small single-stranded RNA of 21-25 nucleotides accumulating to much higher levels in EAT-D mutant plants relative to wild type. The small amount of transcript seen in wild type presumably represents endogenous levels of not only the miR172a-2 miRNA but also its family members, which are similar enough to cross-hybridize with the probe. The predicted miR172a-2 hairpin is 117 nt in length (FIG. 1), a small amount of an ~100 nt transcript accumulating is detected in EAT-D, this likely represents partially processed miR172a-2 hairpin precursor. S1 nuclease mapping of the miR172a-2 miRNA provides independent confirmation of the 5' end of miR172a-2 reported by Park et al. ((2002) *Curr Biol* 12:1484-1495).

Example 4

The example describes the developmental pattern of EAT miRNA expression.

To address the wild-type expression pattern of miR172a-2 separate from its other *Arabidopsis* family members, RT-PCR is used to specifically detect a fragment of the 1.4 kb EAT full-length precursor transcript containing miR172a-2. EAT precursor transcript expression is temporally regulated, with little or no transcript detected two days after germination, and progressively more steady-state transcript accumulation seen as the plant approaches flowering. The precursor transcript of miR172a-1 shows a similar temporal pattern of expression. Both miR172a-2 and miR172a-1 precursor transcripts continue to be expressed after flowering has occurred, and accumulate in both leaves and floral buds. Expression of the precursors for the other miR172 family members is not detected, perhaps due to their exclusive expression in tissue types not included in this analysis, or because their precursor transcripts are too transient to detect. The temporal expression pattern seen for miR172a-2 and miR172a-1 is reminiscent of that observed for let-7 and lin-4, two miRNAs that control developmental timing in *C. elegans* (Feinbaum and Ambros (1999) *Dev Biol* 210:87-95; Reinhart et al. (2000) *Nature* 403:901-906).

Example 5

The levels of miR172 in various flowering time mutants are assessed, in an attempt to position miR172 within the known flowering time pathways. The levels of miR172 are not altered in any of the mutants tested, and the levels of the EAT transcript are identical in plants grown in long days versus plants grown in short days.

Example 6

The example describes evaluation of protein expression

Immunoblot analysis indicates that AP2 protein is reduced 3.5-fold in the EAT-D mutant relative to wild type, whereas the AP2 transcript is unaffected. This data suggests that the miR172a-2 miRNA negatively regulates AP2 by translational inhibition. The predicted near-perfect complementarity between the miR172a-2 miRNA and the AP2 target site would be predicted to trigger AP2 miRNA cleavage by the RNA interference (RNAi) pathway (Llave et al. (2002) *Plant Cell* 14:1605-1619; Hutvagner and Zamore (2002) *Science* 297:2056-2060). Indeed, others have proposed that many plant miRNAs enter the RNAi pathway exclusively due to their near-perfect complementarity to putative targets (Rhoades et al. (2002) *Cell* 110:513-520). While there is no evidence regarding the GU wobble base pair in the predicted miR172a-2/AP2 RNA duplex, it is conserved in all predicted duplexes between miR172 family members and their AP2 targets. Regardless of the mechanism, it is apparent from the AP2 expression data and the observed phenotype of EAT-D that AP2 is a target of negative regulation by miR172a-2, at least when miR172a-2 is overexpressed.

Example 7

In the same genetic screen that identified the early-flowering EAT-D mutant, an activation-tagged late-flowering mutant, called LAT-D, is identified. The LAT-D mutant displays no additional phenotypes besides late flowering (Table 1), and the late-flowering phenotype cosegregates with a single T-DNA insertion. Sequence analysis of the T-DNA insert in LAT-D indicates that the 4x35S enhancer is located approximately 5 kb upstream of At2g28550, which is one of the AP2-like target genes that are potentially regulated by miR172. RT-PCR analysis using primers specific for At2g28550 indicates that the transcript corresponding to this gene is indeed expressed at higher levels in the LAT-D mutant relative to wild type. To confirm that overexpression of At2g28550 causes late flowering, a genomic region containing the entire At2g28550 coding region (from start to stop codon) is fused to the 35S promoter, and transgenic plants containing this construct are created. Transgenic 35S::At2g28550 plants flower later than wild type plants, and are slightly later than the LAT-D mutant (Table 1). This late flowering phenotype is observed in multiple independent transformants.

The fact that overexpression of At2g28550 causes late flowering suggests that miR172 promotes flowering in part by downregulating At2g28550. However, because miR172 appears to affect protein rather than transcript accumulation of its target genes, and because there is not an antibody to the At2g28550 gene product, this regulation is tested indirectly via a genetic cross. A plant heterozygous for LAT-D is crossed to a plant homozygous for EAT-D, such that all F1 progeny would contain one copy of EAT-D and 50% of the F1 progeny would also have one copy of LAT-D. F1 progeny are scored for the presence or absence of the LAT-D allele by PCR, and also are scored for flowering time. All of the F1 plants are early flowering, regardless of whether or not they contained a copy of the LAT-D allele, indicating that EAT-D is epistatic to LAT-D. This result is consistent with the idea that miR172a-2, which is overexpressed in EAT-D, directly downregulates At2g28550, which is overexpressed in LAT-D.

Example 8

To assess the effects of reducing At2g28550 function, plants containing a T-DNA insertion in the At2g28550 gene are identified. In addition, a T-DNA mutant for At2g60120, a closely related AP2-like gene that also contains the miR172 target sequence, is identified. Plants homozygous for either the At2g28550 insert or the At5g60120 insert are slightly early flowering relative to wild type (Table 1). The two mutants are crossed, and the double mutant is isolated by PCR genotyping. The At2g28550/At5g60120 double mutant is earlier flowering than either individual mutant (Table 1), suggesting that the genes have overlapping function. The early flowering phenotype of the At2g28550/At5g60120 double mutant is consistent with the idea that the early flowering phenotype of miR172-overexpressing lines is due to down-regulation of several AP2-like genes, including At2g28550 and At5g60120. Interestingly, the At2g28550/At5g60120 double mutant is not as early as miR172-overexpressing lines (c.f. EAT-OX, Table 1), which suggests that other AP2-like targets of miR172, for example AP2 itself or At5g67180, also contribute to flowering time control. Because ap2 mutants are not early flowering, any potential negative regulation of flowering by AP2 must be normally masked by genetic redundancy.

Example 9

This example describes a method of target selection and method to design DNA constructs to generate miRNAs using the constructs of SEQ ID NOS: 3 and 44. Any sequence of interest can be selected for silencing by miRNA generated using the following method:

1. Choose a region from the coding strand in a gene of interest to be the target sequence. Typically, choose a region of about 10-50 nucleotides found in a similar location to the region targeted by EAT in AP2-like genes, which are regions about 100 nt upstream of the stop codon. The exact location of the target, however, does not appear to be critical. It is recommended to choose a region that has ~50% GC and is of high sequence complexity, i.e. no repeats or long polynucleotide tracts. It is also recommended that the chosen region ends with a T or A, such that the complementary miRNA will start with an A or U. This is to help ensure a lower stability at the 5' end of the miRNA in its double-stranded Dicer product form (Schwartz, et al. (2003) *Cell* 115:199-208). For example, in the miR172a-2 precursor, the miRNA sequence starts with an A, and many other miRNAs start with a U.

2. To use the construct of SEQ ID NO:3, create a 21 nucleotide sequence complementary to the 21 nt target region (miRNA). Optionally, change a C in the miRNA to a T, which will generate a GU wobble with the target sequence, which mimics the GU wobble seen in EAT.

3. Create the 21 nucleotide "backside" sequence of the hairpin. This will be substantially complementary to the miRNA from step 2. Note, this backside sequence will also be substantially identical to the target sequence. Typically, introduce a few mismatches to make some bulges in the stem of the hairpin that are similar to the bulges in the original EAT hairpin. Optionally, introduce an A at the 3' end of the backside, to create mismatch at the 5' end of the miRNA. This last step may help ensure lower stability at the 5' end of the miRNA in its double-stranded Dicer product form (Schwartz et al. (2003) *Cell* 115:199-208).

4. Replace the 21 nucleotide miRNA sequence and the 21 nucleotide "backside" sequence in the EAT BamHI/HindIII DNA construct (SEQ ID NO:3) with the new miRNA and "backside" sequences from steps 2 and 3.

5. Use MFOLD (GCG, Accelrys, San Diego, Calif.), or an equivalent program, to compare the new hairpin from Step 4 with the original hairpin. Generally, the sequence substantially replicate the structure of the original hairpin (FIG. 1). It is predicted that the introduced bulges need not be exactly identical in length, sequence or position to the original. Examine the miRNA sequence in the hairpin for the relative stability of the 5' and 3' ends of the predicted dsRNA product of Dicer.

6. Generate four synthetic oligonucleotides of 76-77 nucleotides in length to produce two double-stranded fragments which comprise the BamHI and HindIII restriction sites, and a 4 nucleotide overhang to facilitate directional ligation which will recreate the BamHI/HindIII fragment. Design of the overhang can be done by one of skill in the art, the current example uses the 4 nucleotide region of positions 79-82 (CCTA) of SEQ ID NO:3. Hence, for example:

Oligo 1 will have an unpaired BamHI site at the 5' end, and will end with the nucleotide at position 78 of SEQ ID NO:3.

Oligo 2 will have the nucleotides of position 79-82 (CCTA) unpaired at the 5' end, and will terminate just before the HindIII site (or positions 151-154 in SEQ ID NO:3).

Oligo 3 will be essentially complementary to Oligo 1, (nucleotides 5-78 of SEQ ID NO:3), and will terminate with 4 nucleotides complementary to nucleotides 1-4 (CCTA) of Oligo 2.

Oligo 4 will be essentially complementary to Oligo 2 beginning at the nucleotide of position 5, and will terminate with the HindIII site at the 3' end.

Anneal the oligonucleotides to generate two fragments to be used in a subsequence ligation reaction with the plasmid sequence.

Optionally, two synthetic oligonucleotides comprising attB sequences can be synthesized and annealed to create an attB-flanked miRNA precursor that is then integrated into a vector using recombinational cloning (GATEWAY, InVitrogen Corp., Carlsbad, Calif.).

7. Ligate the two DNA fragments from Step 6 in a trimolecular ligation reaction with a plasmid cut with BamHI/HindIII. The current example uses the modified pBluescript SK+ plasmid of SEQ ID NO:44, which comprises the 1.4 kb EAT sequence of SEQ ID NO:1, digested with BamHI/HindIII and gel purified away from the small fragment using standard molecular biological techniques. The new designed miRNA to the gene of interest has replaced the previous miRNA.

If an attB-flanked sequence is used from Step 6, the BP and LR recombination reactions (GATEWAY, InVitrogen Corp., Carlsbad, Calif.) can be used to insert the modified hairpin into a destination vector comprising the full-length miR172a-2 precursor.

8. The plasmid from Step 7, subject to any other preparations or modifications as needed, is used to transform the target organism using techniques appropriate for the target.

9. Silencing of the target gene can be assessed using techniques well-known in the art, for example, Northern blot analysis, immunoblot analysis if the target gene of interest encodes a polypeptide, and any phenotypic screens relevant to the target gene, for example flowering time, or floral morphology.

Example 10

Described in this example are methods one may use for introduction of a polynucleotide or polypeptide into a plant cell.

A. Maize Particle-Mediated DNA Delivery

A DNA construct can be introduced into maize cells capable of growth on suitable maize culture medium. Such competent cells can be from maize suspension culture, callus culture on solid medium, freshly isolated immature embryos or meristem cells. Immature embryos of the Hi-II genotype can be used as the target cells. Ears are harvested at approximately 10 days post-pollination, and 1.2-1.5 mm immature embryos are isolated from the kernels, and placed scutellum-side down on maize culture medium.

The immature embryos are bombarded from 18-72 hours after being harvested from the ear. Between 6 and 18 hours prior to bombardment, the immature embryos are placed on medium with additional osmoticum (MS basal medium, Musashige and Skoog (1962) *Physiol Plant* 15:473-497, with 0.25 M sorbitol). The embryos on the high-osmotic medium are used as the bombardment target, and are left on this medium for an additional 18 hours after bombardment.

For particle bombardment, plasmid DNA (described above) is precipitated onto 1.8 mm tungsten particles using standard CaCl2-spermidine chemistry (see, for example, Klein et al. (1987) *Nature* 327:70-73). Each plate is bombarded once at 600 PSI, using a DuPont Helium Gun (Lowe et al. (1995) *Bio/Technol* 13:677-682). For typical media formulations used for maize immature embryo isolation, callus initiation, callus proliferation and regeneration of plants, see Armstrong (1994) In *The Maize Handbook*, M. Freeling and V. Walbot, eds. Springer Verlag, NY, pp 663-671.

Within 1-7 days after particle bombardment, the embryos are moved onto N6-based culture medium containing 3 mg/l of the selective agent bialaphos. Embryos, and later callus, are transferred to fresh selection plates every 2 weeks. The calli developing from the immature embryos are screened for the desired phenotype. After 6-8 weeks, transformed calli are recovered.

B. Soybean Transformation

Soybean embryogenic suspension cultures are maintained in 35 ml liquid media SB196 or SB172 in 250 ml Erlenmeyer flasks on a rotary shaker, 150 rpm, 26 C with cool white fluorescent lights on 16:8 hr day/night photoperiod at light intensity of 30-35 uE/m2s. Cultures are subcultured every two weeks by inoculating approximately 35 mg of tissue into 35 ml of fresh liquid media. Alternatively, cultures are initiated and maintained in 6-well Costar plates.

SB 172 media is prepared as follows: (per liter), 1 bottle Murashige and Skoog Medium (Duchefa # M 0240), 1 ml B5 vitamins 1000× stock, 1 ml 2,4-D stock (Gibco 11215-019), 60 g sucrose, 2 g MES, 0.667 g L-Asparagine anhydrous (GibcoBRL 11013-026), pH 5.7. SB 196 media is prepared as follows: (per liter) 10 ml MS FeEDTA, 10 ml MS Sulfate, 10 ml FN-Lite Halides, 10 ml FN-Lite P,B,Mo, 1 ml B5 vitamins 1000× stock, 1 ml 2,4-D, (Gibco 11215-019), 2.83 g KNO3, 0.463 g (NH4)2SO4, 2 g MES, 1 g Asparagine Anhydrous, Powder (Gibco 11013-026), 10 g Sucrose, pH 5.8. 2,4-D stock concentration 10 mg/ml is prepared as follows: 2,4-D is solubilized in 0.1 N NaOH, filter-sterilized, and stored at −20° C. B5 vitamins 1000× stock is prepared as follows: (per 100 ml)—store aliquots at −20° C., 10 g myo-inositol, 100 mg nicotinic acid, 100 mg pyridoxine HCl, 1 g thiamin.

Soybean embryogenic suspension cultures are transformed with various plasmids by the method of particle gun bombardment (Klein et al. (1987) *Nature* 327:70). To prepare tissue for bombardment, approximately two flasks of suspension culture tissue that has had approximately 1 to 2 weeks to recover since its most recent subculture is placed in a sterile 60×20 mm petri dish containing 1 sterile filter paper in the bottom to help absorb moisture. Tissue (i.e. suspension clusters approximately 3-5 mm in size) is spread evenly across each petri plate. Residual liquid is removed from the tissue with a pipette, or allowed to evaporate to remove excess moisture prior to bombardment. Per experiment, 4-6 plates of tissue are bombarded. Each plate is made from two flasks.

To prepare gold particles for bombardment, 30 mg gold is washed in ethanol, centrifuged and resuspended in 0.5 ml of sterile water. For each plasmid combination (treatments) to be used for bombardment, a separate micro-centrifuge tube is prepared, starting with 50 µl of the gold particles prepared above. Into each tube, the following are also added; 5 µl of plasmid DNA (at 1 µg/µl), 50 µl CaCl2, and 20 µl 0.1 M spermidine. This mixture is agitated on a vortex shaker for 3 minutes, and then centrifuged using a microcentrifuge set at 14,000 RPM for 10 seconds. The supernatant is decanted and the gold particles with attached, precipitated DNA are washed twice with 400 µl aliquots of ethanol (with a brief centrifugation as above between each washing). The final volume of 100% ethanol per each tube is adjusted to 40 µl, and this particle/DNA suspension is kept on ice until being used for bombardment.

Immediately before applying the particle/DNA suspension, the tube is briefly dipped into a sonicator bath to disperse the particles, and then 5 µL of DNA prep is pipetted onto each flying disk and allowed to dry. The flying disk is then placed into the DuPont Biolistics PDS1000/HE. Using the DuPont Biolistic PDS1000/HE instrument for particle-mediated DNA delivery into soybean suspension clusters, the following settings are used. The membrane rupture pressure is 1100 psi. The chamber is evacuated to a vacuum of 27-28 inches of mercury. The tissue is placed approximately 3.5 inches from the retaining/stopping screen (3rd shelf from the bottom). Each plate is bombarded twice, and the tissue clusters are rearranged using a sterile spatula between shots.

Following bombardment, the tissue is re-suspended in liquid culture medium, each plate being divided between 2 flasks with fresh SB196 or SB172 media and cultured as described above. Four to seven days post-bombardment, the medium is replaced with fresh medium containing a selection agent. The selection media is refreshed weekly for 4 weeks and once again at 6 weeks. Weekly replacement after 4 weeks may be necessary if cell density and media turbidity is high.

Four to eight weeks post-bombardment, green, transformed tissue may be observed growing from untransformed, necrotic embryogenic clusters. Isolated, green tissue is removed and inoculated into 6-well microtiter plates with liquid medium to generate clonally-propagated, transformed embryogenic suspension cultures.

Each embryogenic cluster is placed into one well of a Costar 6-well plate with 5 mls fresh SB196 media with selection agent. Cultures are maintained for 2-6 weeks with fresh media changes every 2 weeks. When enough tissue is available, a portion of surviving transformed clones are subcultured to a second 6-well plate as a back-up to protect against contamination.

To promote in vitro maturation, transformed embryogenic clusters are removed from liquid SB196 and placed on solid agar media, SB 166, for 2 weeks. Tissue clumps of 2-4 mm size are plated at a tissue density of 10 to 15 clusters per plate. Plates are incubated in diffuse, low light (<10 µE) at 26+/−1° C. After two weeks, clusters are subcultured to SB 103 media for 3-4 weeks.

SB 166 is prepared as follows: (per liter), 1 pkg. MS salts (Gibco/BRL—Cat#11117-017), 1 ml B5 vitamins 1000× stock, 60 g maltose, 750 mg MgCl2 hexahydrate, 5 g activated charcoal, pH 5.7, 2 g gelrite. SB 103 media is prepared as follows: (per liter), 1 pkg. MS salts (Gibco/BRL—Cat#11117-017), 1 ml B5 vitamins 1000× stock, 60 g maltose, 750 mg MgCl2 hexahydrate, pH 5.7, 2 g gelrite. After 5-6 week maturation, individual embryos are desiccated by placing embryos into a 100×15 petri dish with a 1 cm² portion of the SB103 media to create a chamber with enough humidity to promote partial desiccation, but not death.

Approximately 25 embryos are desiccated per plate. Plates are sealed with several layers of parafilm and again are placed in a lower light condition. The duration of the desiccation step is best determined empirically, and depends on size and quantity of embryos placed per plate. For example, small embryos or few embryos/plate require a shorter drying period, while large embryos or many embryos/plate require a longer drying period. It is best to check on the embryos after about 3 days, but proper desiccation will most likely take 5 to 7 days. Embryos will decrease in size during this process.

Desiccated embryos are planted in SB 71-1 or MSO medium where they are left to germinate under the same culture conditions described for the suspension cultures. When the plantlets have two fully-expanded trifoliate leaves, germinated and rooted embryos are transferred to sterile soil and watered with MS fertilizer. Plants are grown to maturity for seed collection and analysis. Healthy, fertile transgenic plants are grown in the greenhouse.

SB 71-1 is prepared as follows: 1 bottle Gamborg's B5 salts w/sucrose (Gibco/BRL—Cat#21153-036), 10 g sucrose, 750 mg MgCl2 hexahydrate, pH 5.7, 2 g gelrite. MSO media is prepared as follows: 1 pkg Murashige and Skoog salts (Gibco 11117-066), 1 ml B5 vitamins 1000× stock, 30 g sucrose, pH 5.8, 2 g Gelrite.

Example 11

This example describes the design and synthesis of miRNA targets and hairpins directed to various gene targets found in maize, soy, and/or *Arabidopsis*, using the method described in Example 9.

A. Targeting *Arabidopsis* AGAMOUS, At4g18960

The miRNA sequence of SEQ ID NO:4 is selected and designed. The sequence is put into the BamHI/HindIII hairpin cassette by annealing the synthetic oligonucleotides of SEQ ID NOS: 12-15, and ligating them into the BamHI/HindIII backbone fragment of SEQ ID NO:44.

*Arabidopsis thaliana* Col-0 is transformed and grown as described in Example 1. After transformation with a vector comprising the miRNA of SEQ ID NO:4, 88% of the transformants exhibit a mutant AGAMOUS (ag) floral phenotype, characterized by the conversion of stamens to petals in whorl 3, and carpels to another ag flower in whorl 4 (Bowman, et al. (1991) *The Plant Cell* 3:749-758). The mutant phenotype varies between transformants, with approximately ⅓ exhibiting a strong ag phenotype, ⅓ exhibiting an intermediate ag phenotype, and ⅓ exhibiting a weak ag phenotype. Gel electrophoresis and Northern Blot analysis of small RNAs isolated from the transformants demonstrates that the degree of the mutant ag phenotype is directly related to the level of antiAG miRNA, with the strongest phenotype having the highest accumulation of the processed miRNA (~21 nt).

B. Targeting *Arabidopsis* Apetela3 (AP3), At3g54340

Two miRNA targets from AP3 are selected and oligonucleotides designed.

The miRNA sequence of SEQ ID NO:5 is selected and designed. The sequence is put into the BamHI/HindIII hairpin cassette by annealing the synthetic oligonucleotides of SEQ ID NOS: 16-19, and ligating them into the BamHI/HindIII backbone fragment of SEQ ID NO:44.

The miRNA sequence of SEQ ID NO:6 is selected and designed. The sequence is put into the BamHI/HindIII hairpin cassette by annealing the synthetic oligonucleotides of SEQ ID NOS: 20-23, and ligating them into the BamHI/HindIII backbone fragment of SEQ ID NO:44.

*Arabidopsis thaliana* Col-0 is transformed and grown as described in Example 1. After transformation with a vector comprising the miRNA of SEQ ID NO:5, the transformants have novel leaf and floral phenotypes, but do not exhibit any mutant AP3 phenotype. Gel electrophoresis and Northern analysis of RNA isolated from 2 week old rosette leaf tissue from the transformants demonstrates that the highest accumulation of the processed miRNA (~21 nt) corresponds to the "backside" strand of the precursor, which evidently silences a different target sequence to produce the novel leaf and floral phenotypes.

A new target sequence is selected, with the correct asymmetry in order for the miRNA target strand to be selected during incorporation into RISC (Schwartz et al. (2003) *Cell* 115:199-208). The miRNA sequence of SEQ ID NO:6 is selected and designed. The sequence is put into the BamHI/HindIII hairpin cassette by annealing the synthetic oligonucleotides of SEQ ID NOS: 20-23, and ligating them into the BamHI/HindIII backbone fragment of SEQ ID NO:44. Greater than 90% of the transformants show silencing for the AP3 gene, as demonstrated by floral phenotype and electrophoretic analysis. An approximately 21 nt miRNA (antiAP3b) is detected at high levels in the transgenic plants, and not in wild type control plants. RT-PCR analysis confirmed that the amount of AP3 transcript is reduced in the transformants, as compared to wild type control plants.

C. Targeting Maize Phytoene Desaturase

Two miRNA targets from phytoene desaturase (PDS) are selected and oligonucleotides designed.

The miRNA sequence of SEQ ID NO:7 is selected and designed. The sequence is put into the BamHI/HindIII hairpin cassette by annealing the synthetic oligonucleotides of SEQ ID NOS: 24-27, and ligating them into the BamHI/HindIII backbone fragment of SEQ ID NO:44.

The miRNA sequence of SEQ ID NO:8 is selected and designed. The sequence is put into the BamHI/HindIII hairpin cassette by annealing the synthetic oligonucleotides of SEQ ID NOS: 28-31, and ligating them into the BamHI/HindIII backbone fragment of SEQ ID NO:44.

D. Targeting Maize Phytic Acid biosynthetic Enzymes

Three maize phytic acid biosynthetic enzyme gene targets are selected and miRNA and oligonucleotides designed. Inositol polyphosphate kinase-2 polynucleotides are disclosed in PCT International published application No. WO 02/059324, herein incorporated by reference. Inositol 1,3,4-trisphosphate 5/6-kinase polynucleotides are disclosed in PCT International published application No. WO 03/027243, herein incorporated by reference. Myo-inositol 1-phosphate synthase polynucleotides are disclosed in PCT International published application No. WO 99/05298, herein incorporated by reference.

Inositol Polyphosphate Kinase-2 (IPPK2)

The miRNA sequence of SEQ ID NO:9 is selected and designed. The sequence is put into the BamHI/HindIII hairpin cassette by annealing the synthetic oligonucleotides of SEQ ID NOS: 32-35, and ligating them into the BamHI/HindIII backbone fragment of SEQ ID NO:44.

Inositol 1,3,4-trisphosphate 5/6-kinase-5 (ITPK5)

The miRNA sequence of SEQ ID NO:10 is selected and designed. The sequence is put into the BamHI/HindIII hairpin cassette by annealing the synthetic oligonucleotides of SEQ ID NOS: 36-39, and ligating them into the BamHI/HindIII backbone fragment of SEQ ID NO:44.

Myo-Inositol 1-Phosphate Synthase (mi1ps)

The miRNA sequence of SEQ ID NO:11 is selected and designed. The sequence is put into the BamHI/HindIII hairpin cassette by annealing the synthetic oligonucleotides of SEQ ID NOS: 40-43, and ligating them into the BamHI/HindIII backbone fragment of SEQ ID NO:44.

E. Targeting Soy Apetela2-Like Sequences (AP2)

The same EAT (miR172a-2) construct, comprising SEQ ID NO:1, used for *Arabidopsis* transformation is used to transform soybean. This construct has a miRNA template sequence which encodes the miRNA of SEQ ID NO:48. The construct is created using a PCR amplification of miR172a-2 precursor sequence from *Arabidopsis*, restriction digestion, and ligation as described in Example 2.

Soybean tissue is transformed and grown essentially as described in Example 10. After transformation, 42% of the transformants exhibit a mutant phenotype, characterized by the conversion of sepals to leaves. Plants exhibiting the strongest phenotypes are sterile, and produce no seed. Both the homeotic conversion of the organs and the effects on fertility are similar to that seen for ap2 mutant alleles in *Arabidopsis*. Small RNA gel electrophoresis and Northern analysis, probed with an oligonucleotide probe antisense to miR172, shows accumulation of miR172 in the transgenic lines. A small amount of endogenous soy miR172 is also detected in the soy control line. The degree of the mutant phenotype is directly related to the level of miRNA, with the strongest phenotype having the highest accumulation of the processed miRNA (~21 nt).

F. Targeting *Arabidopsis* AP2-Like Genes

The miRNA sequence of SEQ ID NO:72 is selected and designed. The sequence is put into the attB hairpin cassette by annealing the synthetic oligonucleotides of SEQ ID NOS: 73-74, and performing the BP recombination reaction (GATEWAY) to generate the attL intermediate. This intermediate is used in the LR reaction to recombine with the destination vector, generally described in Example 12, comprising the EAT full-length precursor containing attR sites, and negative selection markers in place of the hairpin. The product of this reaction comprises the miR172a-2 precursor hairpin cassette flanked by attR sites (i.e., the hairpin replaces the marker cassette).

G. Targeting *Arabidopsis* Fatty Acid Desaturase (FAD2)

The miRNA sequence of SEQ ID NO:75 is selected and designed based on the sequence of NM_112047 (At3g12120). The sequence is put into the attB hairpin cassette by annealing the synthetic oligonucleotides of SEQ ID NOS: 76-77, and performing the BP recombination reaction (GATEWAY) to generate the attL intermediate. This intermediate is used in the LR reaction to recombine with the destination vector, generally described in Example 12, comprising the EAT full-length precursor containing attR sites, and negative selection markers in place of the hairpin. The product of this reaction comprises the FAD2 miRNA precursor hairpin cassette flanked by attR sites (i.e., the hairpin replaces the marker cassette). The effect of the anti-FAD2 miRNA can be determined by fatty acid analysis to determine the change in the fatty acid profile, for example, see Wu et al. (1997) *Plant Physiol.* 113:347-356, herein incorporated by reference.

H. Targeting *Arabidopsis* Phytoene Desaturase (PDS)

The miRNA sequence of SEQ ID NO:78 is selected and designed based on the sequence of NM_202816 (At4g14210). The sequence is put into the attB hairpin cassette by annealing the synthetic oligonucleotides of SEQ ID NOS: 79-80, and performing the BP recombination reaction (GATEWAY) to generate the attL intermediate. This intermediate is used in the LR reaction to recombine with the destination vector, generally described in Example 12, comprising the EAT full-length precursor containing attR sites, and negative selection markers in place of the hairpin. The product of this reaction comprises the PDS miRNA precursor hairpin cassette flanked by attR sites (i.e., the hairpin replaces the marker cassette). Transgenic plants containing the antiPDS construct are photobleached upon gennination in greater than about 90% of the lines, indicating silencing of PDS.

Example 12

This example describes the construction of expression vectors using recombinational cloning technology.

The vector described in Example 2 (SEQ ID NO:44) is modified to incorporate att recombination sites to facilitate recombinational cloning using GATEWAY technology (Invitrogen, Carlsbad, Calif.). The BamHI/HindIII segment is replaced with a sequence comprising in the following order: attR1-CAM-ccdB-attR2. Upon recombination (BP+LR) with oligos containing attB sites flanking the miRNA hairpin precursor construct, the selectable markers are replaced by the miRNA hairpin precursor.

Example 13

This example, particularly Table 5, summarizes the target sequences and oligos used for miRNA silencing constructs as described in the examples.

TABLE 5

| Organism | Target gene | miRNA name | miRNA template | Precursor oligos SEQ ID NOS |
|---|---|---|---|---|
| Arabidopsis | AP2-like | miR172-a2 | SEQ ID NO: 86 | 55-56 (PCR) |
| | none | EATdel | none | 57-60 |
| | AGAMOUS | antiAG | SEQ ID NO: 4 | 12-15 |
| | APETELA3 (a) | antiAP3a | SEQ ID NO: 5 | 16-19 |
| | APETELA3 (b) | antiAP3b | SEQ ID NO: 6 | 20-23 |
| Corn | PDS1 | antiPDS1 | SEQ ID NO: 7 | 24-27 |
| | PDS2 | antiPDS1 | SEQ ID NO: 8 | 28-31 |
| | IPPK2 | antiIPPK2 | SEQ ID NO: 9 | 32-35 |
| | ITPK5 | antiITPK5 | SEQ ID NO: 10 | 36-39 |
| | MI1PS | antiMI1PS | SEQ ID NO: 11 | 40-43 |
| Soybean | AP2-like | miR172a-2 | SEQ ID NO: 86 | 55-56 (PCR) |
| Arabidopsis | AP2-like | miR172a-2 | SEQ ID NO: 72 | 73-74 |
| | FAD2 | antiFAD2 | SEQ ID NO: 75 | 76-77 |
| | PDS | antiAtPDS | SEQ ID NO: 78 | 79-80 |

TABLE 5-continued

| Organism | Target gene | miRNA name | miRNA template | Precursor oligos SEQ ID NOS |
|---|---|---|---|---|
| Corn | miR172b | miR172 | SEQ ID NO: 92 | 91 |
|  | PDS | antiZmPDS | SEQ ID NO: 95 | 94 |

Example 14

This example describes the identification and isolation of genomic corn miR172 precursors.

The Genome Survey Sequence (GSS) database of the National Center for Biotechnology Information (NCBI) is searched using the 21 nt miR172a-2 sequence in order to identify genomic corn sequences containing miR172 precursor sequence. Several corn miR172 precursors are identified, and named miR172a-miR172e (SEQ ID NOS: 81-85) as summarized in Table 6. Each sequence is imported into Vector NTI (InVitrogen, Carlsbad, Calif.) and contig analyses done. The analysis identifies four distinct loci, each with a unique consensus sequence. A region of about 200 nucleotides surrounding the miRNA sequence from each locus is examined for secondary structure folding using RNA Structure software (Mathews et al. (2004) *Proc Natl Acad Sci USA* 101:7287-7292, herein incorporated by reference). The results of this analysis identifies the hairpin precursors of each of the corn sequences miR172a-e.

TABLE 6

Corn miR172 precursors and positions of hairpin, & miRNA duplex components

| Precursor | NCBI ID | Corn Line | SEQ ID NO: | Length | Hairpin | Backside | miRNA |
|---|---|---|---|---|---|---|---|
| miR172a | CG090465 | B73 | 81 | 907 | 508-598 | 512-532 | 574-594 |
| miR172b | BZ401521 and BZ4011525 | B73 (both) | 82 | 1128 | 551-654 | 567-587 | 620-640 |
| miR172c | CG247934 | B73 | 83 | 912 | 230-400 | 250-270 | 364-384 |
| miR172d | CG097860 and BZ972414 | B73 | 84 | 1063 | 351-520 | 361-381 | 466-486 |
| miR172e | CG065885 and CC334589 | B73 (both) | 85 | 1738 | 913-1072 | 931-951 | 1033-1053 |

Oligonucleotides are designed in order amplify miR172a or miR172b from a B73 genomic corn library, these primers also add restriction enzyme recognition sites in order to facilitate cloning (BamHI or EcoRV). Alternatively, PCR primers designed to create att sites for recombinational cloning could be used. After PCR amplification, the products are isolated, purified, and confirmed by sequence analysis. Once confirmed, these sequences are inserted into a construct comprising the corn ubiquitin (UBI) promoter. This construct can be used for further transformation vector construction, for example, with the addition of att sites, the GATEWAY system can be used.

The following PCR primers are used to amplify a sequence comprising the hairpin precursor of corn miR172a

```
Forward primer (SEQ ID NO:87):
5' GGATCCTCTGCACTAGTGGGGTTATT 3'

Reverse primer (SEQ ID NO:88):
5' GATATCTGCAACAGTTTACAGGCGTT 3'
```

The following PCR primers are used to amplify a sequence comprising the hairpin precursor of corn miR172b

```
Forward primer: (SEQ ID NO:89)
5' GGATCCCATGATATAGATGATGCTTG 3'

Reverse primer (SEQ ID NO:90):
5' GATATCAAGAGCTGAGGACAAGTTTT 3'
```

Example 15

This example describes the design and synthesis of miRNA targets and hairpins directed to various gene targets found in maize, for use with the corn miR172b miRNA precursor.

A. miR172b Target in Corn

Similar to the *Arabidopsis* EAT examples, the corn miR172b hairpin precursor will be tested by overexpression in corn. The precursor sequence comprising the miRNA template is shown in SEQ ID NO:91. The miRNA is shown in SEQ ID NO:92, and the backside of the miRNA duplex is shown in SEQ ID NO:93. A double-stranded DNA molecule comprising the miRNA precursor and restriction enzyme overhangs, for BamHI and KpnI, is created by annealing the oligonucleotides of SEQ ID NOS: 97 and 98.

B. Phytoene Desaturase (PDS)

An oligonucleotide comprising the miRNA template is shown in SEQ ID NO:94. The miRNA directed to PDS is shown in SEQ ID NO:92, and the backside of the miRNA duplex is shown in SEQ ID NO:93. A double-stranded DNA molecule comprising the miRNA precursor and restriction enzyme overhangs, for BamHI and KpnI, is created by annealing the oligonucleotides of SEQ ID NOS: 99 and 100.

The oligonucleotides of this example can be inserted into vectors for transformation of corn using standard cloning techniques, including restriction digestion and ligation, and/or recombinational cloning such as GATEWAY.

Example 16

This example describes the materials and methods used for Examples 17-19.

Plasmid Constructs

A fragment of 276 base pairs containing the entire sequence of *Arabidopsis* miR159a (see below) was cloned by PCR amplification using primers CACC-miR159a-prec: 5' CACCACAGTTTGCTTATGTCGGATCC 3' (SEQ ID NO:101) and miR159a-Xma: 5' TGACCCGGGATGTA-GAGCTCCCTTCAATCC 3' (SEQ ID NO:102). The miR159a-Xma contains 18 of 21 nucleotides of the mature miR159a (bold) and an introduced XmaI site (italic). The PCR fragment was cloned in the pENTR/SD/D-TOPO vector (Invitrogen) according to manufacturers directions to obtain pENTR-miR159a-prec.

The Gateway recombination system was used to transfer the pre-miR159a sequence to the plant binary vector pK2GW7, which contains two copies of the 35S promoter and a NOS terminator to generate pK2-pre-miR159a.

Mutagenesis of pre-miR159a was performed by PCR with the following oligonucleotides.

5'-miR-PDS[159a]: 5' ATAGATCTTGATCTGACGATG-GAAGAAGAGATCCTAAC T TTTCAAA 3' (SEQ ID NO:103; This oligonucleotide contains a natural Bgl II site (italic) and the miR-PDS[159a]* sequence (bold)).

3'-miR-PDS[159a]: 5' TGACCCGGGATGAAGAGATC-CCATATTTCCAAA 3' SEQ ID NO:104; This oligonucleotide contains point mutations in the miR159a sequence (bold) to increase its complementarity to the PDS miRNA sequence, based on available *N. benthamiana* PDS miRNA partial sequence (Genbank AJ571700, see below)).

PCR amplification of the miR159a precursor using the above primers and pENTR-miR159a-prec DNA as template generated a DNA fragment that was digested with BglII and XmaI to be re-inserted into pENTR-pre-miR159a, to generate pENTR-pre-miR-PDS[159a]. Gateway system procedures were used again to transfer the miR-PDS[159a] precursor to pK2GW7 and generate pK2-pre-miR-PDS[159a].

The miR-PDS[169g] was cloned as follows. An *Arabidopsis* genomic fragment of 222 base pairs containing the miR169g sequence (see below) was amplified using primers miR169g-For 5' CACCAATGATGATTACGATGATGAGAGTC 3' (SEQ ID NO:105), and miR169g-Rev 5' CAAAGTTTGAT-CACGATTCATGA 3' (SEQ ID NO:106). The resulting PCR fragment was introduced into pENTR/D-TOPO vector (Invitrogen) to obtain pENTR-pre-miR169g. The pre-miR169g sequence was then transferred into binary vectors pBADC and pB2GW7 using the Gateway system to generate pBA-pre-miR169g and pB2-pre-miR169g.

Two miR-PDS[169g] precursors were created using pENTR-pre-miR169g as template and the Quick-change Mutagenesis kit from Stratagene. pENTR-pre-miR-PDSa[169g] was made by using the following oligonucleotides:

```
                                      (SEQ ID NO:107)
miR169^PDSa:  5' GAGAATGAGGTTGAGTTTAGTCTGACTTGGCCAG
                 TTTTTTTACCAATG 3',
and
                                      (SEQ ID NO:108)
miR169^PDSa*: 5' CTGATTCTGGTGTTGGCCAAGTCAGACTAAACTC
                 TGTTTCCTTCTC 3'.
``` pENTR-pre-miR-PDSb[169g] was produced by using the oligonucleotides:

```
                                      (SEQ ID NO:109)
miR169^PDSb:  5' GAGAATGAGGTTGATCTCTTTCCAGTCTTCAGGG
                 TTTTTTTACCAATG 3',
and
                                      (SEQ ID NO:110)
miR169^PDSb*: 5' GATTCTGGTGTCCTGAAGACTGGAAAGAGATCTG
                 TTTCCTTCTCTTC 3'.
```

The two mutagenized miR-PDS[169g] precursors above were then transferred into plant binary vectors pBADC and pB2GW7 to generate pBA-pre-miR-PDSa[169g], pB2-pre-miR-PDSa[169g]; pBA-pre-miR-PDSb[169g], and pB2-pre-miR-PDSb[169g].

Precursors for artificial miRNAs that target *N. benthamiana* rbcS transcripts (pENTR-pre-miR-rbcS[159a]-A) were produced using similar procedures as those described for pENTR-miR-PDS[159a] using the following primers and cloned into pK2GW7:

```
                                      (SEQ ID NO:111)
MrbcSA-S: 5' TCTGACGATGGAAGTTCCTCGCCCGACATTCGAAAATG
             AGTTGA 3',
and
                                      (SEQ ID NO:112)
MrbcSA-R: 5' AAACCCGGGATGTTCCTCGCCCGGAATTCGAAAGAGAG
             TAAAAG 3'.
```

All cloned sequences were confirmed by DNA sequencing.

Precursor Sequences Used miR159a precursor template sequence (276 bp)

```
                                           (SEQ ID NO:113)
ACAGTTTGCTTATGTCGGATCCATAATATATTTGACAAGATACTTTGTTT

TTCGATAGATCTTGATCTGACGATGGAAG TAGAGCTCCT TAAAGTTCAAA

CATGAGTTGAGCAGGGTAAAGAAAAGCTGCTAAGCTATGGATCCCATAAG

CCCTAATCCTTGTAAAGTAAAAAAGGATTTGGTTATATGGATTGCATATC

TCAGGAGCTTTAACTTGCCCTTTAATGGCTTTTACTCTTC *TTTGGATTGA*

*AGGGAGCTCTA*CATCCCGGGTC
```
(Sequence of the pre-miR159a cloned. Sequences of miR159a* and miR159a (italic) are shown in bold. Nucleotides changed in miR-PDS[159a] are underlined.)

miR-159a mature template

```
5' TTTGGATTGAAGGGAGCTCTA 3'      (SEQ ID NO:114)
``` miR-PDS[159a] mature template

```
                                           (SEQ ID NO:115)
    5' TTTGGA a a t A t GGGAt CTCT t 3'
``` miR169g precursor template sequence 0.3 kb (222 bp)

```
                                           (SEQ ID NO:116)
AATGATGATTACGATGATGAGAGTCTCTAGTTGTATCAGAGGGTCTTGCA

TGGAAGAATAGAGAATGAGGTT*TTTGGATTGA*GTTTTTT

TACCAATGAATCTAATTAACTGATTCTGGTG TCCGGCAAGTTGACCTTGG

CTCTGTTTCCTTCTCTTCTTTTGGATGTCAGACTCCAAGATATCTATCAT

CATGAATCGTGATCAAACTTTG
```
(Sequence of the pre-miR169g fragment (0.3 kb) cloned. Sequences of miR169g (italic) and miR169g* are shown in bold. Nucleotides changed in miR-PDS[169g] are underlined.)

miR169g mature template

```
5' GAGCCAAGGATGACTTGCCGG 3'      (SEQ ID NO:117)
``` miR-PDSa[169g] mature template

```
                                           (SEQ ID NO:118)
    5' GAG t t t AG t c TGACTTG gC c a 3'
``` miR169g mature template

```
5' GAGCCAAGGATGACTTGCCGG 3'      (SEQ ID NO: 119)
``` miR-PDSb[169g] mature template (SEQ ID NO:120)
5' GA tC t c t t t c c a g t c T t C aGG 3' miR169g precursor template sequence 2.0 kb (2474 bp)

(SEQ ID NO:121)
AAGCTTTGATCTTTAGCTCTTTGCCAAAGCTTCTTTTGATTTTTCTATTT
CTCTAATCTATCCATTGACCATTTGGGGTGATGATATTCTTCAATTTATG
TTGTTGTTTATTGCCCATCCACAGACCCACGTTTGATTTGTTTAATCAAA
ATATATAAACTGACAGTTGTGCCACTAGTCACTTGCCAATTAAGCATTCC
AAAGCTCCTTCCTTTACATTAGTATCAAGTGAGACTAGCACAAGCTTTTA
AGTCCAGATAAAAGCCCCATGGAAGGGAAGCTTTCAAGAACGAGATTTA
ACCGTAAAACCCAATTTCGATTTCCGCTAATAATTTGGATCCAAAAATCT
AGACAAAATCTGATAAAATTAGACAAAGAAATGGATAAAACCCCAAAACC
CATAATCGTCGTTGTTCTTGTTTGCTTCAATATCACTCTTTCCCCTCCAA
CGAGTTAGTTAGAGTGACGTGGCAGCTGAACTAGATTTGGAGTAACGGGA
TAGATTACCCATAAAGCCCAATAATGATCATTACGTGAGACATAACTTGC
TTAGATAACCTCATTTTATGGGCTTAGATGGGGTCTCTAGTGTTAGTCAT
AAGCTCTTAAATACCATTTCTAGTTATATATCAATCTTTAGCTTGGAATT
GGATCGTTGTCCTATAGTAAAAAAACTTTTACTATTTTATGTTAGCAATC
CCACTTAACATTCAATATGTTTAAAATGAAAGAGTTTACCAAAAGGAAAG
AAAAAAAGGTTGGTAATGAATTTATCTAATCGGATACGATATTTCATAAT
CTAATGATGGGATCTATCAATAAATAGAATCAAAGTTAACTTTAACGCTT
TTGTTACCTGTTTTCTTTCTTTAGCAATTAATATTAAACGAGTTTTAGTA
ATATAAATATGTTTCCAGTTATATACCAAACTTTATGTAATATTCATAAG
CTTGCCAAAATTTACAAGAGTTTTTGGAACGCGCACAAAATTCTCATATA
TTTCTTACCCAAAAATAAATTTTTTTTTTTTTTTACTTGTTTATAATCC
TATATGAACATTGCTCATCTTCCCCATTTGATGGTAATTTTTCTATTCCT
ATATGTAATTAAATCCTAACTAATGAAATTGAAAACATAATTTGAAGATA
ATCAATCCTAATATCTCCCGTCTTAGATCTATTTAAATGGTCTTATTTAA
TTTCCTATATTTTGGCCTAATTATTTATTTGATATAGTGAATTTATGGAA
GCTTCATGTTGATGGAATAAAACCGGCTTATCCCAATTAATCGATCGGGA
GCTATAACACAAATCGAAACTCTAGTAGCTATAAAGAGTGTGTAATAGCT
TTGGATCACATGTATTACTATTTATTTACTAGCTCGTGCAACAATTGGCT
TTGGGAAAAAATTTATTTACTAGTACTCCCCCTTCACAATGTGATGAGTC
TCCAAATGATATATTCTCAACCCAAAGGACAATCTGAAATTTTCAATATA
TATTCCATTTTATCCGCAACATTTGAAATTTGTGGCAATGTTTTTAAAAA
GACTATTTATAAAGAATCTTTCTAAATTGTTTCTACGACAATCGATAACA
CCTTTTGTTGATCAACCCCACACAAGACTATGATTCCAATCCTAAGAAAC
ATACGACACGTGGATTTTTATGTCACACTAGTACGATGCGTCGATGCCTT
CAGAGTACGAATATTATTCACATAAAATTCTTATTCGAATTTGATAATAT
AAGGTCAGCCAATCTTTTAAAGTAATTATATTCTTCAATATACGGTTGTG
GTCAAAATTCCATTTTATTTTGTAGCTTGCATGCACTACTAGTTTAAAAC
CATGCATGGATTTATTGCATATAATAACATTATATGAATTTTCAATTAAA
TTAATCCACACATTTCCCATTTCAATATGCCTATAAATACCTTCATCACG
AGTATGACAAGATCACAAGACAAGAAAAGAAAGGTAGAGAAAACATGATA
ATGATGATTACGATGATGAGAGTCTCTAGTTGTATCAGAGGGTCTTGCAT
GGAAGAATAGAGAATGAGGTT*TTTGGATTGA*GTTTTTTT
ACCAATGAATCTAATTAACTGATTCTGGTG**TCCGGCAAGTTGACCTTGGC
T**CTGTTTCCTTCTCTTCTTTTGGATGTCAGACTCCAAGATATCTATCATC
ATGAATCGTGATCAAACTTTGTAATTTCATTGAAATGTATTTTTTCTTGAT
GCGAATTTTTTGGCTTACGGTTTTTCGATTTGAATGATCAGATTTTTGTT
TTTGCACTCAAACTATAGTTTCACTTAGGTTCTATTTTTTTCAGGTTTAT
GAATGATAAAACAAGTAAGATTTTATGCTAGTTTTAGTTCATTTTTCGAT
TCAAATTCAAACATCTTGGTTTTGGTTTAGTTAAGTTTGATTTTTCAAGT
CAAATGCTATGTTTTCTTGT
(Sequence of the pre-miR169g fragment (2.0 kb) cloned. Sequences of miR169g (italic) and miR169g* are shown in bold.)

Target Gene Sequences Used:
Nicotiana benthamiana PDS Sequences:

5'end probe sequence (corresponding to Le-PDS pos. 1-268, see FIG. 15A):

(SEQ ID NO: 122)
ATGCCTCAAATTGGACTTGTTTCTGCTGTTAACTTGAGAGTCCAAGGTAG

TTCAGCTTATCTTTGGAGCTCGAGGTCGTCTTCTTTGGGAACTGAAAGTC

GAGATGGTTGCTTGCAAAGGAATTCGTTATGTTTTGCTGGTAGCGAATCA

ATGGGTCATAAGTTAAAGATTCGTACTCCCCATGCCACGACCAGAAGATT

GGTTAAGGACTTGGGGCCTTTAAAGGTCGTATGCATTGATTATCCAAGAC

CAGAGCTGGACAATACAG

Partial+5'RACE fragment. Assembled sequence from partial Nicotiana benthamiana PDS sequence (Genbank AJ571700) and 5'RACE experiments (corresponding to Le-PDS pos. 858-1514, see FIG. 15A).

(SEQ ID NO:123)
GGCACTCAACTTTATAAACCCTGACGAGCTTTCGATGCAGTGCATTTTGA

TTGCTTTGAACAGATTTCTTCAGGAGAAACATGGTTCAAAAATGGCCTTT

TTAGATGGTAACCCTCCTGAGAGACTTTGCATGCCGATTGTGGAACATAT

TGAGTCAAAAGGTGGCCAAGTCAGACTAAACTCACGAATAAAAAAGATCG

AGCTGAATGAGGATGGAAGTGTCAAATGTTTTATACTGAATAATGGCAGT

ACAATTAAAGGAGATGCTTTTGTGTTTGCCACTCCAGTGGATATCTTGAA

GCTTCTTTTG*AGGGAGCTCTA*CCATATTTCCAAAAGTTGG

AGAAGCTAGTGGGAGTTCCTGTGATAAATGTCCATATATGGTTTG

ACAGAAAACTGAAGAACACATCTGATAATCTGCTCTTCAGCAGAA

GCCCGTTGCTCAGTGTGTACGCTGACATGTCTGTTACATGTAAGG

AATATTACAACCCCAATCAGTCTATGTTGGAATTGGTATTTGCAC

CCGCAGAAGAGTGGATAAATCGTAGTGACTCAGAAATTATTGATG

CTACAATGAAGGAACTAGCGAAGCTTTTCCCTGATGAAATTTCGG

CAGATCAGAGCAAAGCAAAAATATTGAAGTACCATGT
(Sequences targeted by miR-PDSa[169g] (bold), mir-PDSb[169g] (bold and italic) and miR-PDS[159a] (underlined) are indicated.)

Nicotiana benthamiana rbcS sequences (Bolded nucleotides in all six rbcS gene sequences correspond to the sequence targeted by miR-rbcS[159a]-A):

rbcS1 (Genbank accessions: CN748904: 56-633 bp, CN748069: 419-end)

(SEQ ID NO: 124)
GGAGAAAGAGAAACTTTCTGTCTTAAGAGTAATTAGCAATGGCTTCCTCA

GTTCTTCCTCAGCAGCAGTTGCCACCCGCAGCAATGTTGCTCAAGCTAA

CATGGTTGCACCTTTCACAGGTCTTAAGTCTGCTGCCTCATTCCCTGTTT

CAAGAAAGCAAAACCTTGACATCACTTCCATTGCCAGCAACGGCGGAAGA

GTGCAATGCATGCAGGTGTGGCCACCAATTAACATGAAGAAGTATGAGAC

TCTCTCATACCTTCCCGATTTGAGCCAGGAGCAATTGCTCTCCGAAATTG

AGTACCTTTTGAAAAATGGATGGGTTCCTTGCTTGGAATTCGAGACTGAG

AAAGGATTTGTCTACCGTGAACACCACAAGTCACCAGGATACTATGATGG

CAGATACTGGACCATGTGGAAGCTACCTATGTTCGGATGCACTGATGCCA

CCCAAGTGTTGGCTGAGGTGGGAGAGGCGAAGAAGGAATACCCACAGGCC

TGGGTCCGTATCATTGGATTTGACAACGTGCGTCAAGTGCAGTGCATCAG

TTTCATTGCCTCCAAGCCTGACGGCTACTGAGTTTCATATTAGGACAACT

TACCCTATTGTCTGTCTTTAGGGGCAGTTTGTTTGAAATGTTACTTAGCT rbcS2 (Genbank accessions: CN748495: 3-552 b, CN748945: 364-575 b)

(SEQ ID NO:125)
TCTTTCTGTCTTAAGTGTAATTAACAATGGCTTCCTCAGTTCTTTCCTCA

GCAGCAGTTGCCACCCGCAGCAATGTTGCTCAAGCTAACATGGTTGCACC

TTTCACTGGTCTTAAGTCAGCTGCCTCGTTCCCTGTTTCAAGGAAGCAAA

ACCTTGACATCACTTCCATTGCCAGCAACGGCGGAAGAGTGCAATGCATG

CAGGTGTGGCCACCAATTAACAAGAAGAAGTACGAGACTCTCTCATACCT

TCCTGATCTGAGCGTGGAGCAATTGCTTAGCGAAATTGAGTACCTCTTGA

AAAATGGATGGGTTCCTTGCTTGGAATTCGAGACTGAGCGCGGATTTGTC

TACCGTGAACACCACAAGTCACCGGGATACTATGACGGCAGATACTGGAC

CATGTGGAAGTTGCCTATGTTCGGATGCACTGATGCCACCCAAGTGTTGG

CCGAGGTGGAAGAGGCGAAGAAGGCATACCCACAGGCCTGGATCCGTATT

ATTGGATTCGACAACGTGCGTCAAGTGCAGTGCATCAGTTTCATTGCCTA

CAAGCCAGAAGGCTACTAAGTTTCATATTAGGACAACTTACCCTATTGTC

CGACTTTAGGGGCAATTTGTTTGAAATGTTACTTGGCTTCTTTTTTTTTT

AATTTTCCCACAAAAACTGTTTATGTTTCCTACTTTCTATTCGGTGTATG

TTTTTGCATTCCTACCAAGTTATGAGACCTAATAACTATGATTTGGTGCT

TTGTTTGTAAAT rbcS3 (Genbank accessions: CN746374: 22-108 b, CN748757: 156-175 b, CN748929: 158-309 b, CN748913: 319-489 b, CN748777: 485-603 b, CN748188: 453-529 b)

(SEQ ID NO:126)
TAGCAATAGCTTTAAGCTTAGAAATTATTTTCAGAAATGGCTTCCTCAGT

TATGTCCTCAGCAGCTGCTGTTGCGACCGGCGCCAATGCTGCTCAAGCCA

ACATGGTTGCACCCTTCACTGGCCTCAAGTCCGCCTCCTCCTTCCCTGTT

ACCAGGAAACAAAACCTTGACATTACCTCCATTGCTAGCAATGGTGGAAG

AGTTCAATGCATGCAGGTGTGGCCACCAATTAACATGAAGAAGTACGAGA

CACTCTCATACCTTCCTGATTTGAGCCAGGAGCAATTGCTTAGTGAAGTT

GAGTACCTTTTGAAAAATGGATGGGTTCCTTGCTTGGAATTCGAGACTGA

GCGTGGATTCGTCTACCGTGAACACCACAACTCACCAGGATACTACGATG

GCAGATACTGGACCATGTGGAAGTTGCCCATGTTCGGGTGCACTGATGCC

ACTCAGGTGTTGGCTGAGGTCGAGGAGGCAAAGAAGGCTTACCCACAAGC

CTGGGTTAGAATCATTGGATTCGACAACGTCCGTCAAGTGCAATGCATCA

GTTTTATCGCCTCCAAGCCAGAAGGCTACTAAAATCTCCATTTTTAAGGC rbcS4 (Genbank accessions CN748906: 9-607 b, CN747257: 629-709b)

(SEQ ID NO:127)
AATGGCTTCCTCAGTTATGTCCTCAGCTGCCGCTGTTGCCACCGGCGCCA

ATGCTGCTCAAGCCAGTATGGTTGCACCTTTCACTGGCCTCAAGTCCGCA

ACCTCCTTCCCTGTTTCCAGAAAACAAAACCTTGACATTACTTCCATTGC

TAGCAACGGCGGAAGAGTTCAATGCATGCAGGTGTGGCCACCAATTAACA

AGAAGAAGTACGAGACACTCTCATACCTTCCCGATTTGAGCCAGGAGCAA

TTGCTTAGTGAAGTTGAGTACCTGTTGAAAAATGGATGGGTTCCTTGCTT

GGAATTCGAGACTGAGCGTGGATTCGTCTACCGTGAACACCACAGCTCAC

CAGGATATTATGATGGCAGATACTGGACCATGTGGAAGTTGCCCATGTTC

GGGTGCACTGATGCCACTCAGGTGTTGGCTGAGGTCGAGGAGGCAAAGAA

GGCTTACCCACAAGCCTGGGTTAGAATCATTGGATTCGACAATGTCCGTC

AAGTGCAATGCATCAGTTTCATCGCCTACAAGCCAGAAGGCTACTAGAAT

CTCCATTTTTAAGGCAACTTATCGTATGTGTTCCCCGGAGAAACTGTTTT

GGTTTTTCCTGCTTCATTATATTATTCAATGTATGTTTTTGAATTCCAAT

CAAGGTTATGAGAACTAATAATGACATTTAATTTGTTTCTTTTCTATATA rbcS5 (Genbank accession: CN744712: 16-713 b)

(SEQ ID NO:128)
TAAATAATTAATTGCAACAATGGCTTCCTCTGTGATTTCCTCAGCTGCTG

CCGTTGCCACCGGCGCTAATGCTGCTCAAGCCAGCATGGTTGCACCCTTC

ACTGGCCTCAAATCTGCTTCCTCCTTCCCTGTTACCAGAAAACAAAACCT

TGACATTACATCCATTGCTAGCAATGGTGGAAGAGTCCAATGCATGCAGG

TGTGGCCACCAATTAACATGAAGAAGTACGAGACACTCTCATACCTTCCT

GATTTGAGCCAGGAGCAATTGCTTAGTGAAGTTGAGTATCTTTTGAAAAA

TGGATGGGTTCCTTGCTTGGAATTCGAGACTGAGCGTGGATTTGTCTACC

GTGAACATCACAGCTCACCAGGATACTACGATGGCAGATACTGGACCATG

TGGAAGTTGCCCATGTTCGGGTGCACTGATGCCACTCAGGTGTTGGCTGA

GGTCGAGGAGGCAAAGAAGGCTTACCCACAAGCCTGGGTTAGAATCATTG

GATTCGACAACGTCCGTCAAGTGCAATGCATCAGTTTTATCGCCTCCAAG

CCAGAAGGCTACTAAAATCTCCATTTTTAAGGCAACTTATCGTATGTGTT

CCCCGGAGAAACTGTTTTGGTTTTCCTGCTTCATTATATTATTCAATGTA

TGTTTTGAATTCCAATCAAGGTTATGAGAACTAATAATGACATTTAA rbcS6 (Genbank accessions: CN745030: 14-123 b, CN748077: 1-523 b)

(SEQ ID NO:129)
GCACGAGGCTTCCTCAGTTATGTCCTCAGCTGCCGCTGTTTCCACCGGCG

CCAATGCTGTTCAAGCCAGCATGGTCGCACCCTTCACTGGCCTCAAGGCC

GCCTCCTCCTTCCCGGTTTCCAGGAAACAAAACCTTGACATTACTTCCAT

-continued

```
TGCTAGAAATGGTGGAAGAGTCCAATGCATGCAGGTGTGGCCGCCAATTA

ACAAGAAGAAGTACGAGACACTCTCATACCTTCCTGATTTGAGCGTGGAG

CAATTGCTTAGCGAAATTGAGTACCTTTTGAAAAATGGATGGGTTCCTTG

CTTGGAATTCGAGACTGAGCATGGATTCGTCTACCGTGAACACCACCACT

CACCAGGATACTACGATGGCAGATACTGGACGATGTGGAAGTTGCCCATG

TTCGGGTGCACCGATGCCACTCAGGTCTTGGCTGAGGTAGAGGAGGCCAA

GAAGGCTTACCCACAAGCCTGGGTCAGAATCATTGGATTCGACAACGTCC

GTCAAGTGCAATGCATCAGTTTCATCGCCTACAAGCCCGAAGGCTATTAA

AATCTCCATTTTTAGGACAGCTTACCCTATGTATTCAGGGGAAGTTTGTT

TGAATTCTCCTGGAGAAACTGTTTTGGTTTTCCTTTGTTTTAATCTTCTT

TCTATTATATTTTTGGATTTTACTCAAGTTTATAAGAACTAATAATAATC

ATTTGTTTCGTTACTAAAAAAAAAAAA
```

Infiltration of *N. benthamiana* with *Agrobacterium tumefaciens*

Infiltration with *A. tumefaciens* carrying appropriate plasmids was carried out as follows. Cells were grown to exponential phase in the presence of appropriate antibiotics and 40 μM acetosyringone. They were harvested by centrifugation, resuspended in 10 mM MgCl$_2$ containing 150 μM acetosyringone and incubated at room temperature for 2 hrs without agitation. Infiltration was performed by using a syringe without needle applied to the abaxial side of leaves. After 1, 2, or 3 days leaf tissue was collected, frozen and ground in liquid nitrogen before RNA extraction.

Northern Blot Hybridizations

Leaves from *Nicotiana benthamiana* were used to extract total RNA using the Trizol reagent (Invitrogen). 10-20 μg total RNA were resolved in a 15% polyacrylamide/1×TBE (8.9 mM Tris, 8.9 mM Boric Acid, 20 mM EDTA)/8 M urea gel and blotted to a Hybond-N+ membrane (Amersham). DNA oligonucleotides with the exact reverse-complementary sequence to miRNAs were end-labeled with $^{32}$P-γ-ATP and T4 polynucleotide kinase (New England Biolabs) to generate high specific activity probes. Hybridization was carried out using the ULTRAHyb-Oligo solution according to the manufacturer's directions (Ambion, Tex.), and signals were detected by autoradiography. In each case, the probe contained the exact antisense sequence of the expected miRNA to be detected.

Northern blot hybridizations to detect PDS mRNA abundance were performed according to standard procedures. The 5' end probe corresponded to a fragment of *N. benthamiana* PDS gene reported before (Guo et al. (2003) *Plant J* 34:383-392) equivalent to the tomato PDS gene sequence positions 1-268 (Genbank X59948, see above). The 3'end probe corresponded to a fragment obtained by 5'RACE and equivalent to the tomato PDS gene sequence positions 1192-1514.

5' RACE

To identify the products of miRNA-directed cleavage the First Choice RLM-RACE Kit (Ambion) was used in 5' RACE experiments, except that total RNA (2 μg) was used for direct ligation to the RNA adapter without further processing of the RNA sample. Subsequent steps were according to the manufacturer's directions. Oligonucleotide sequences for nested PCR amplification of PDS cleavage fragment were:

```
3'Nb-PDS1
5' CCACTCTTCTGCAGGTGCAAAAACC 3'    (SEQ ID NO:130)

3'Nb-PDS2
5' ACATGGTACTTCAATATTTTGCTTTGC 3'  (SEQ ID NO:131)

3'Nb-PDS3
5' GATCTTTGTAAAGGCCGACAGGGTTCAC 3' (SEQ ID NO:132)
```

All three primers were designed based on available sequence information for the tomato PDS gene since the complete *N. bethamiana* PDS gene sequence has not been published.

PCR fragments obtained from 5'RACE experiments were cloned in the pCR4 vector (Invitrogen) and analyzed by DNA sequencing of individual clones.

RT-PCR

First strand cDNA was synthesized form 5 μg total RNA using an oligo-dT primer (Sigma) and Ready-To-Go You-Prime First-strand beads (Amersham Biosciences). Amounts of first strand cDNA were normalized by PCR using primers for EF1α (Nishihama et al. (2002) *Cell* 109:87-99). To amplify DNA fragments of rbcS cDNAs, the following primers were used.

```
NBrbcs5:1/2-F:    5' TTCCTCAGTTCTTTCCTCAGCAGCAGTTG 3'      (SEQ ID NO:133)

rbcS3-F:          5' CTCAGTTATGTCCTCAGCAGCTGC 3'           (SEQ ID NO:134)

rbcS4/6-F:        5' TCCTCAGTTATGTCCTCAGCTGCC 3'           (SEQ ID NO:135)

NBrbcS5-F:        5' TGTGATTTCCTCAGCTGCTGCC 3'             (SEQ ID NO:136)

NBrbcs1 rev2:     5' AACTCAGTAGCCGTCAGGCTTGG 3'            (SEQ ID NO:137)

NBrbcs2 rev2:     5' AATATGAAACTTAGTAGCCTTCTGGCTTGT 3'     (SEQ ID NO:138)

NBrbcs3/4/5 rev1: 5' GTTTCTCCGGGGAACACATACGA 3'            (SEQ ID NO:139)

NBrbcs6 rev1:     5' AAACAAACTTCCCCTGAATACATAGGG 3'        (SEQ ID NO:140)
```

Example 17

This example describes the design of an artificial microRNA to cleave the phytoene desaturase (PDS) mRNAs of *Nicotiana benthamiana*.

*Arabidopsis* miRNAs identified so far have been shown to target different mRNAs, and a significant number encodes transcription factors (Bartel (2004) *Cell* 116:281-297; Wang et al. (2004) *Genome Biol* 5:R65; Rhoades et al. (2002) *Cell* 110:513-520). Base-pairing of plant miRNAs to their target mRNAs is almost perfect and results in cleavage of the RNA molecule as has been shown for several examples (Jones-Rhoades and Bartel (2004) *Mol Cell* 14:787-799), resulting in silencing of gene expression. Alternatively, miRNA interaction with the target mRNA can result in inhibition of translation rather than mRNA cleavage as shown for miR172 of *Arabidopsis* (Aukerman and Sakai (2003) *Plant Cell* 15:2730-2741; Chen (2004) *Science* 303:2022-2025).

In an effort to design artificial miRNAs that can inhibit the expression of particular genes, we sought to modify the sequence of a known miRNA to target an mRNA of choice.

Figure 11A:
FIGS. 11A-11C show an artificial microRNA (miRNA) designed to cleave the phytoene desaturase (PDS) miRNAs of *Nicotiana benthamiana*.
Figure 11B:
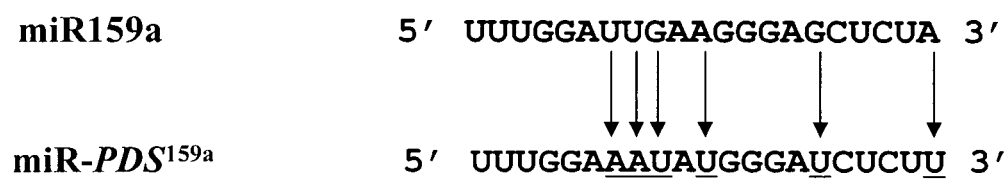

The *Arabidopsis* miR159 has been shown to target a set of MYB transcription factors. Base-pairing of miR159 to its target mRNAs is almost perfect and results in cleavage of the RNA molecule (Achard et al. (2004) *Development* 131:3357-3365; Palatnik et al. (2003) *Nature* 425:257-263). There are three genomic sequences (MIR159a, MIR159b, MIR159c) with the potential to encode miR159. The natural promoter and precise precursor sequence of miR159 are not known, nor is it known whether microRNA genes are transcribed by DNA polymerase II or III. We decided to use as precursor sequence a DNA fragment of 276 bp that contains the *Arabidopsis* miR159a. This precursor sequence, which is called pre-miR159a was placed downstream of a 35S promoter and flanked at the 3' end by a polyA addition sequence of the nopaline synthase gene (FIG. 11A). We decided to use the *N. benthamiana* phytoene desaturase (PDS) gene as a target to see whether we can design an artificial microRNA to cleave its mRNA and thereby compromise its expression. We compared the sequence of At-miR159a to that of PDS to find the best match between the two sequences. For one particular region of the PDS mRNA we found that only 6 base changes are sufficient to convert miR159a into a miRNA capable to perfectly base-pair to PDS mRNA (FIG. 11B). We called this sequence miR-PDS$^{159a}$.

To generate pre-miR-PDS$^{159a}$, PCR techniques were used to introduce point mutations in both miR159a and the miR159a* sequence (the RNA sequence located in the opposite arm to the miRNA within the precursor sequence) in the context of the *Arabidopsis* pre-miR159a. The resulting precursor was placed under the control of the strong cauliflower mosaic virus (CaMV) 35S promoter and expressed in *N. benthamiana* by infiltration of *Agrobacterium tumefaciens* containing the appropriate constructs.

Figure 11C:
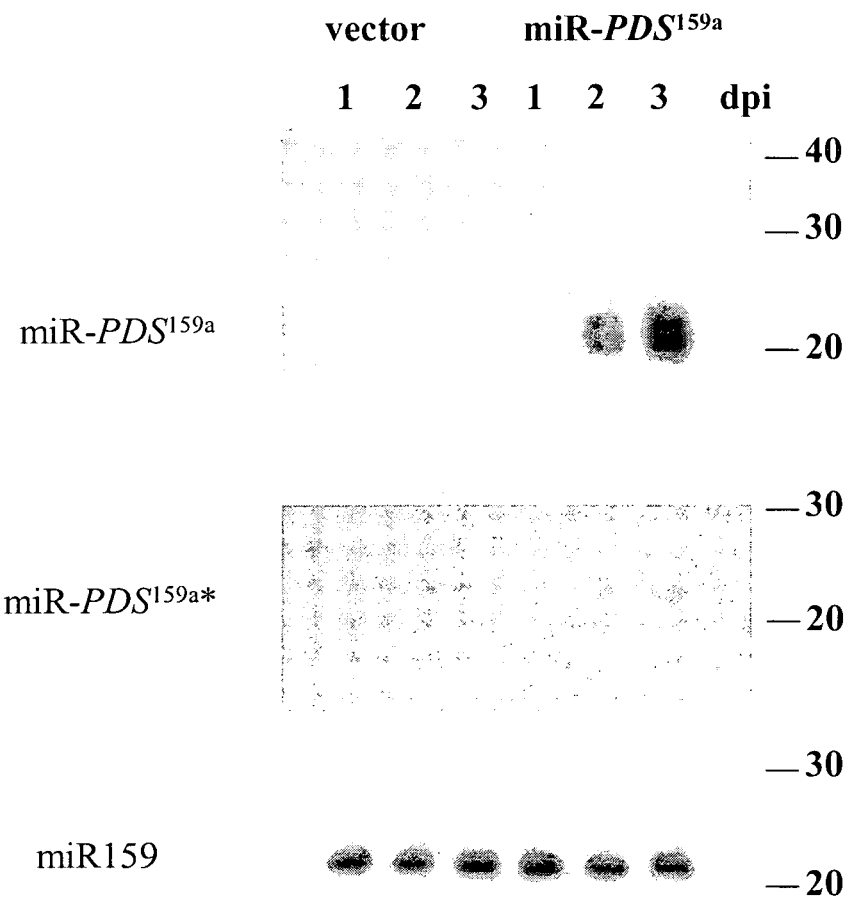

Expression of the *Arabidopsis* pre-miR-PDS$^{159a}$ in *N. benthamiana* was first analyzed to confirm that the mutations introduced in its sequence did not affect its processing and maturation of miR-PDS$^{159a}$. Northern blot analysis showed that 2 to 3 days after infiltration miR-PDS$^{159a}$ is clearly expressed (FIG. 11C), accumulating to levels comparable to endogenous miR159. Biogenesis of known miRNAs includes the generation of the almost complementary miRNA* which is short-lived and accumulates to very low levels when compared to those of the actual miRNA. Consistently, the presence of miR-PDS$^{159a}$* was detected but its abundance was significantly lower than that of miR-PDS$^{159a}$ (FIG. 11C, middle panel). Expression of endogenous miR159 was unchanged under these conditions and served as both a loading and probe-specificity control (FIG. 11B, bottom panel). In addition, this result indicates that expression of an artificial miRNA based on the *Arabidopsis* miRNA precursor does not affect expression of the endogenous *N. benthamiana* miR159. Finally, these findings imply that the enzymatic machinery for processing of natural microRNA precursors is not rate limiting and can process artificial precursors with great efficiency.

Figure 12A:
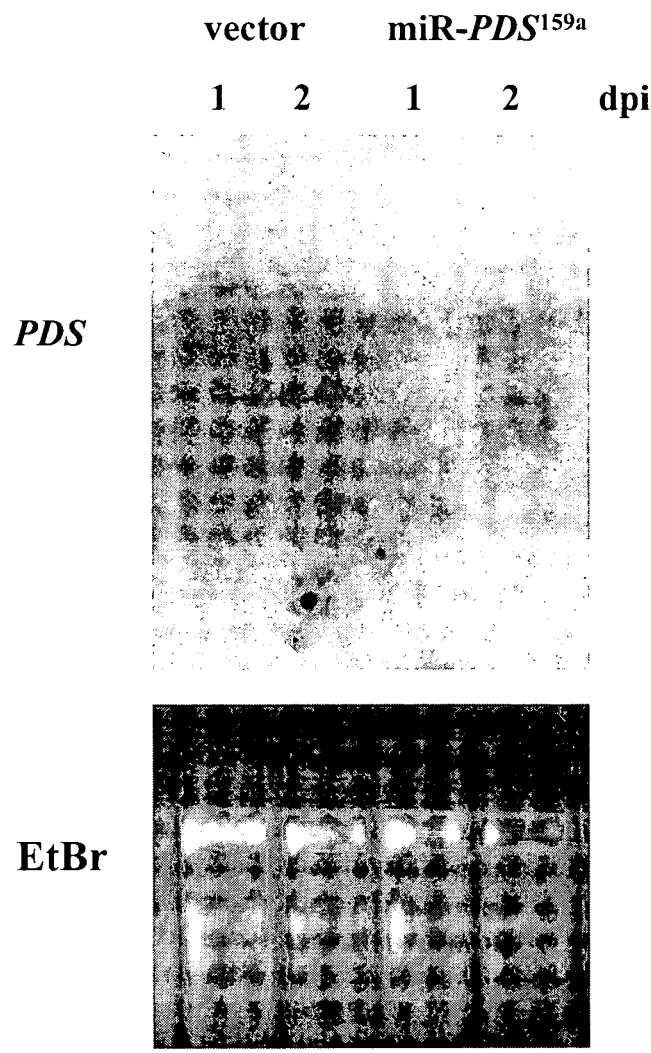
FIGS. 12A-12B show that miR-PDS$^{159a}$ (SEQ ID NO:142) causes PDS miRNA (SEQ ID NO:143) cleavage.
Figure 12B:
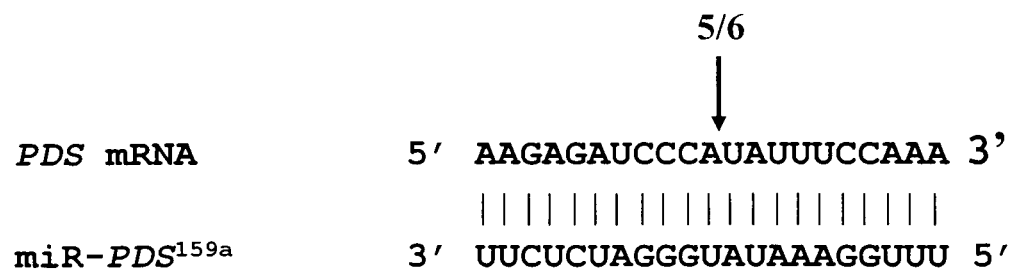

We next determined whether expression of miR-PDS$^{159a}$ resulted in the expected cleavage of the endogenous PDS mRNA. Northern blot hybridization of the samples expressing miR-PDS$^{159a}$ showed a clear reduction in PDS mRNA levels (FIG. 12A). To further establish the mechanism of PDS mRNA reduction we set to define: (1) whether the PDS miRNA is cleaved by miR-PDS$^{159a}$ and contains a diagnostic 5' phosphate, and (2) whether the cleavage point corresponds to the predicted site, based on the PDS mRNA:miR-PDS$^{159a}$ base-pairing interaction. To this end, 5'RACE experiments were performed. We found that the 5'-end sequence of 5 out of 6 independent clones mapped the site of cleavage after the tenth nucleotide counting from the 5' end of miR-PDS$^{159a}$. The location of the cleavage site correlates perfectly with published work with other miRNA targets (Jones-Rhoades and Bartel (2004) *Mol Cell* 14:787-799).

The results demonstrate that the reduction of PDS mRNA levels was caused by accurate cleavage directed by miR-PDS$^{159a}$.

Example 18

This example demonstrates that microRNA-directed cleavage of PDS mRNA can be produced from a different microRNA precursor.

To show that expression of artificial miRNAs is not restricted to the use of pre-miR159a we have designed a different miR-PDS based on a putative precursor sequence containing the *Arabidopsis* miR169g to generate two different miR-PDS$^{169g}$ (FIG. 13A). During the design of the expression vector for miR169g, we noticed that a construct containing only the stem-loop precursor of 222 bp resulted in higher accumulation of the mature miRNA than a construct containing the entire 2.0 kb intergenic region including the miR169g gene (FIG. 13B). Based on this result we decided to continue our mutagenesis of miRNA sequences using exclusively short precursor vectors. Examination of the PDS mRNA with the miR169g sequence revealed a region in the mRNA sequence susceptible for miRNA cleavage, different from that found for miR-PDS$^{159a}$. Seven point mutations turn miR169g into a microRNA capable of base-pairing perfectly to the PDS miRNA (miR-PDSa$^{169g}$, FIG. 13A). As shown before for the miR159a-based miR-PDS, transient expression of miR-PDSa$^{169g}$ in *N. benthamiana* is easily detected (FIG. 13C). In addition, to test whether the entire miRNA can be changed independently of its original sequence, we have generated miR-PDSb$^{169g}$ (FIG. 13A and FIG. 13C), which targets a different region in the PDS mRNA selected irrespective of its homology to the original miR169g. Using both miR-PDSa$^{169g}$ and miR-PDSb$^{169g}$ we could detect cleavage of the PDS mRNA, as determined by 5'RACE analysis (FIG. 13D) and a reduction in PDS mRNA levels as determined by Northern blot analysis (FIG. 13E).

These results show that a different miRNA precursor can be used to target degradation of PDS mRNA and importantly, that the sequence of the original miRNA can be extensively changed to design an artificial one.

Example 19

This example demonstrates microRNA-directed specific cleavage of *Nicotiana benthamiana* rbcS mRNAs.

To show that this approach can be used to target other genes different from PDS, we have introduced point mutations in miR159a to target the different members of the Rubisco small subunit (rbcS) gene family of *N. benthamiana*. We searched for rbcS EST transcripts present in publicly available databases and found that at least 6 different rbcS transcripts are expressed in *N. benthamiana*. Nucleotide sequences of the coding region of these rbcS transcripts were over 90% identical to each other, and allowed us to design miR-rbsS$^{159a}$-A, which targets all members of the gene family. Here, the sequence introduced in miR159a was not guided by the minimal number of changes that would target rbsS but reflected the need to target a specific region common to all rbsS mRNAs and thus included several changes. In this way, we have generated one miRNA that targets all six rbcS mRNAs (miR-rbcS$^{159a}$-A, FIG. 14A).

As in the previous examples, we have detected efficient expression of the miR-rbsS$^{159a}$-A (FIG. 14B), but due to the high degree of homology among the members of this family, distinct rbsS mRNAs have been difficult to detect by Northern blot analysis. Instead, we have used semi-quantitative RT-PCR to determine the levels of mRNAs in plants infiltrated with *Agrobacterium* strains containing the miR-rbcS$^{159a}$-A construct. Compared to leaves infiltrated with the empty binary vector (C in FIG. 14C), mRNA accumulation for rbcS genes 1, 2 and 3 was reduced while for rbcS genes 4, 5 and 6 it could not be detected in samples infiltrated with a miR-rbcS$^{159a}$-A construct (A in FIG. 14C). These results indicate that the artificial miRNA targeted all the rbcS mRNAs it was intended for, although the efficiency in each case varied. Finally, the presence of the artificial miRNA did not interfere with expression of other plant genes such as EF1α (FIG. 14C, bottom panel).

Figure 15A:
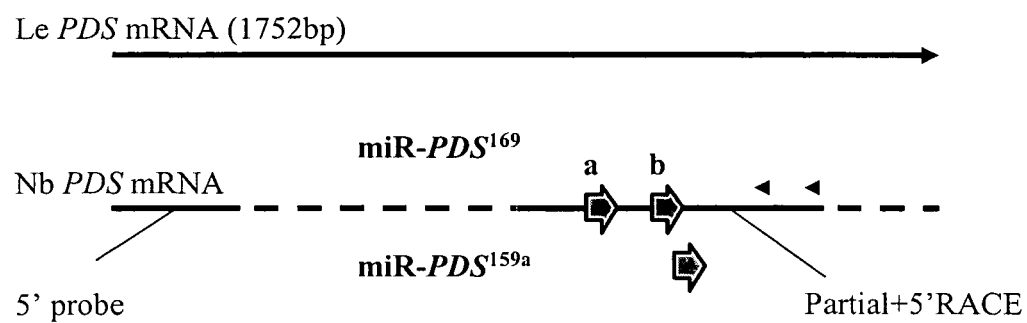
FIGS. 15A-15B show the schematic representation of the genes and relevant sequences used in the work shown in FIGS. 11-14.
Figure 15B:
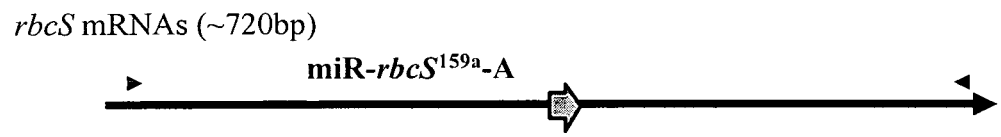

The artificial miRNAs presented here are distributed along three different locations in PDS mRNA (summarized in FIG. 15A), and have been used to target 2 different genes (PDS and rbcS, FIG. 15A and FIG. 15B). This range of use is also reflected in the flexibility of the miRNA sequences, as the artificial miRNAs show that almost every nucleotide position can be changed (FIG. 16). Changes in miR159a to create two artificial miRNAs retained only 8 positions unchanged (FIG. 16A). In the case of miR169g this number was reduced to only three positions (FIG. 16B). Moreover, when the mutations in both miRNAs are analyzed together, only the first two nucleotide positions remain untouched. This suggests that every position along the miRNA sequence can be changed, adding to the advantages of using artificial miRNAs for gene silencing.

Example 20

This example demonstrates that artificial miRNACPC$^{159a}$ inhibits root hair development in *Arabidopsis*.

Figure 17:
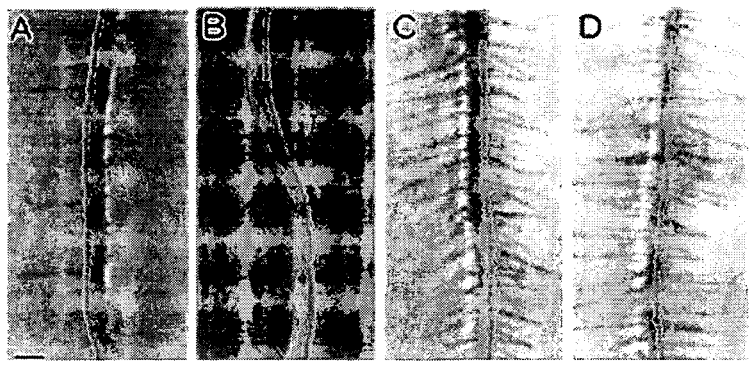
FIG. 17 shows development of *Arabidopsis* root hairs in wildtype, mutant and transgenic plants. Panel A: Wild type root shows many root hair structures. Panel B: Very few root hair in cpc mutant. Panel C: 35S::CPC plants show more root hairs. Panel D: More root hair in gl2 mutant. This figure is taken from Wada et al. ((2002) *Development* 129:5409-5419).

Root epidermal cells differentiate root-hair cells and hairless cells. Only root-hair epidermal cells are able to develop into root hair. In *Arabidopsis* roots, among a total of 16-22 cell files, 8 symmetrically positioned cell files are root-hair cells and all others are hairless cell files. CAPRICE (CPC), a MYB like protein, positively regulates root hair development by negatively regulating GLABRA2 (GL2), which promotes root epidermal cells differentiation into hairless cells. In cpc mutant, GL2 causes most epidermal cells to differentiate into root hairless cells, and consequently, very few cells are able develop root hair. Roots of the gl2 mutant or wild type transgenic plants over-expressing CPC, produce more root hairs compared to wild type roots (FIG. 17; Wada et al. (2002) *Development* 129:5409-5419).

CPC is a good candidate for investigations on the utility of artificial miRNAs to silence or suppress gene function because the loss-of-function phenotype of CPC appears at a very early stage during seedling development, does not cause lethality and is easy to observe. Using pre-miRNA159 as a backbone two artificial pre-miRNAs, pre-miRCPC1$^{159a}$ and pre-miRCPC3$^{159a}$ were designed to target different regions of the CPC mRNA. Mature miRCPC1$^{159a}$ and miRCPC3$^{159a}$ are complementary to the sequences located in nt 233-253 and nt 310-330, respectively, of the CPC messenger RNA. The nucleotide sequences for the precursor and mature miRNAs are as follows.

miRCPC1$^{159a}$ precursor template:

(SEQ ID NO: 151)
5'acagtttgcttatgtcggatccataatatatttgacaagatactttgt ttttcgatagatcttgatctgacgatggaagaagaggtgagtaatgttga aacatgagttgagcagggtaaagaaaagctgctaagctatggatcccata agccctaatccttgtaaagtaaaaaaggatttggttatatggattgcata tctcaggagctttaacttgccctttaatggcttttactcttctttcgata ctactcacctcttcatcccgggtca 3'.

miRCPC1$^{159a}$ mature template:

5' tttcgatactactcacctctt 3'.   (SEQ ID NO:152)

miRCPC3$^{159a}$ precursor template:

(SEQ ID NO:153)
5'acagtttgcttatgtcggatccataatatatttgacaagatactttgt ttttcgatagatcttgatctgacgatggaagctcgttggcgacaggtggg agcatgagttgagcagggtaaagaaaagctgctaagctatggatcccata agccctaatccttgtaaagtaaaaaaggatttggttatatggattgcata tctcaggagctttaacttgccctttaatggcttttactcttcctcccacc tgacgccaacgagcatcccgggtca 3'.

miRCPC3$^{159a}$ mature template: 5' ctcccacctgacgccaacgag 3' (SEQ ID NO:154).

These two artificial pre-miRNAs were cloned into a vector which contains a constitutive 35S promoter for expression of these precursors. Northern blot analysis of *Nicotinana benthamiana* leaves infiltrated by *Agrobacteria* carrying 35S::per-miRCPC1$^{159a}$ or 35S::pre-miRCPC3$^{159a}$ constructs indicated successful production of mature miRCPC1$^{159a}$ and miRCPC3$^{159a}$.

*Arabidopsis thaliana* plants were transformed by *Agrobacteria* carrying XVE::pre-miRCPC1$^{159a}$ or 35S::pre-miRCPC1$^{159a}$, and many transgenic lines were obtained. T$_1$ seeds of XVE::pre-miRCPC1$^{159a}$ plants were geminated on antibiotic selection medium containing kanamycin and resistant transgenic seedlings were transferred to MS medium with or without β-estradiol, an inducer of the XVE system. T$_1$ transgenic lines carrying XVE::pre-miR159 were used as a control. Pre-miR159 is the backbone used to construct the artificial pre-miRCPC1$^{159a}$.

Figure 18:
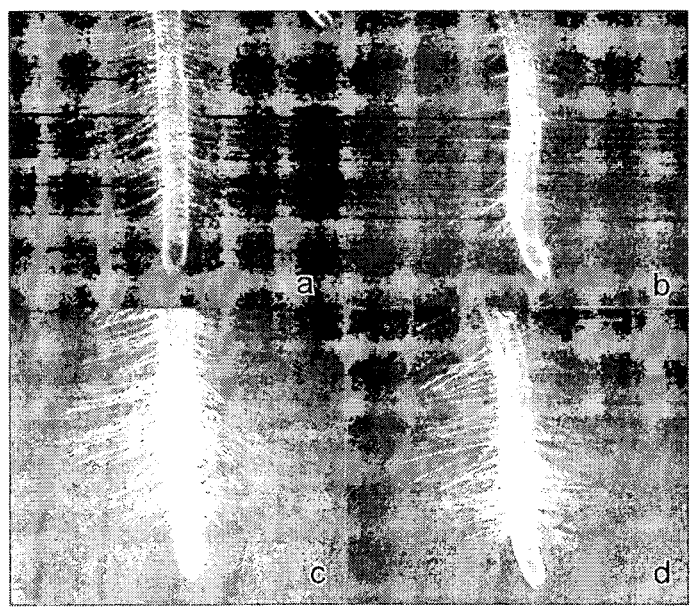
FIG. 18 shows *Arabidopsis* root hair development in transgenic plants. Panel a: XVE::pre-miRCPC1$^{159a}$ without inducer (estradiol). Panel b: XVE::pre-miRCPC1$^{159a}$ with inducer (estradiol). Panel c: XVE::pre-miR159a without inducer (estradiol). Panel d: XVE::pre-miR159a with inducer (estradiol).

No difference in root hair development between XVE::pre-miR159 seedlings grown on medium with or without inducer (FIG. 18, panels c and d) was seen. By contrast, XVE::pre-miRCPC1$^{159a}$ seedlings grown on medium with β-estradiol clearly developed fewer root hairs (FIG. 18, panel b) than those grown without inducer (FIG. 18, panel a).

T$_1$ seedlings of transgenic *Arabidopsis* seedlings carrying 35S::pre-miRCPC1$^{159a}$, 35S::pre-miR159 and 35S::pre-miRP69$^{159a}$ were investigated and similar results were obtained as the XVE inducible lines. T$_1$ seeds of transgenic lines were geminated on a BASTA-selective medium and two-week old seedlings were transferred to MS medium plates placed vertically in a tissue culture room. In this experiment, two negative controls were used: transgenic lines carrying 35S::pre-miR159 and those carrying 35S::pre-miRP69[159a]. The latter was designed using pre-miR159 as a backbone to produce an artificial pre-miRP69[159a] targeting nt 214-234 of the P69 mRNA of turnip yellow mosaic virus (TYMV; Bozarth et al. (1992) *Virology* 187:124-130). The nucleotide sequences for the precursor and mature miRNAs are as follows.

miRP69[159a] precursor template:

```
                                     (SEQ ID NO: 155)
5'acagtttgcttatgtcggatccataatatatttgacaagatactttgt ttttcgatagatcttgatctgacgatggaagccacaagacaatcgagact ttcatgagttgagcagggtaaagaaaagctgctaagctatggatcccata agccctaatccttgtaaagtaaaaaaggatttggttatatggattgcata tctcaggagctttaacttgcccttaaatggcttttactcttcaaagtctc gattgtcttgtggcatcccgggtca 3'
``` miRP69[159a] mature template:

```
5' aaagtctcgattgtcttgtgg 3'.    (SEQ ID NO:156)
```

Figure 19:
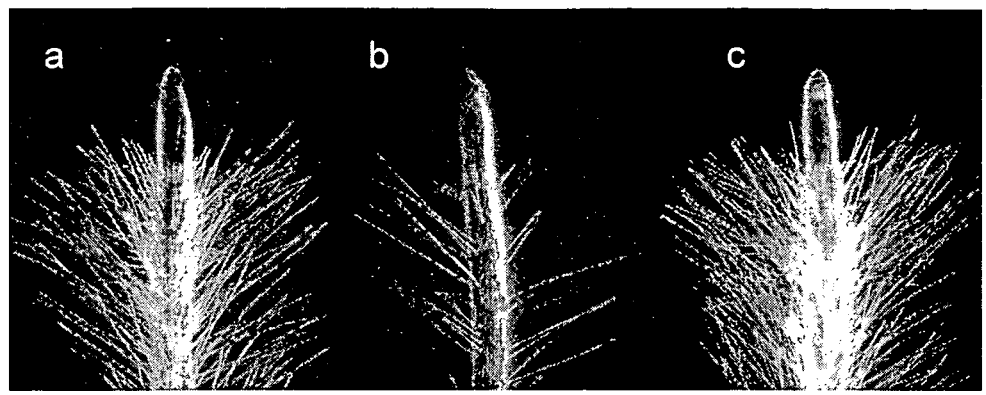
FIG. 19 shows *Arabidopsis* root hair development in transgenic plants. Panel a: 35S::pre-miR159. Panel b: 35S::pre-miRCPC1$^{159a}$. Panel c: 35S::pre-miRP69$^{159a}$.

Seedlings of both types of transgenic plants developed abundant root hair as wild type plants (FIG. 19, panels a and c). By contrast, among 30 independent 35S::pre-miRCPC1[159a] lines, 18 lines showed clearly fewer root hair (FIG. 19, panel b) compared to negative control plants (FIG. 19 panels a and c).

Figure 20:
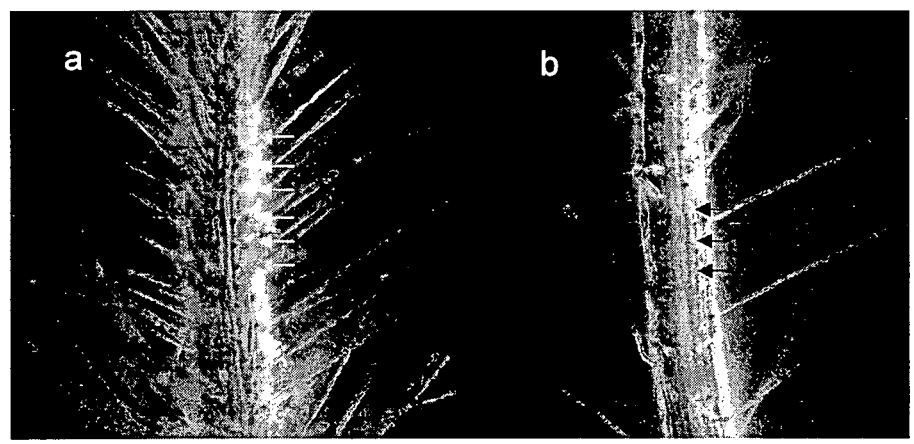
FIG. 20 shows *Arabidopsis* root hair development in transgenic plants. Panel a: 35S::pre-miR159. Panel b: 35S::pre-miRCPC1$^{159a}$.

In negative control transgenic plants (35S::pre-miR159 and pre-miRP69[159a]), all root-hair file cells in the epidermis of the root tip region were able to develop root hairs (FIG. 20, panel a; see arrows). However, in transgenic lines carrying 35S::pre-miRCPC1[159a] many cells in root-hair files were unable to produce root hairs (FIG. 20, panel b; see arrows). These results indicate that the artificial miRCPC1[159a] is able to induce cleavage of the endogenous CPC mRNA to cause a loss function of the CPC gene function and inhibit root hair development.

Example 21

This example describes one embodiment of a process for the designing a polymeric pre-miRNA.

Figure 21A:
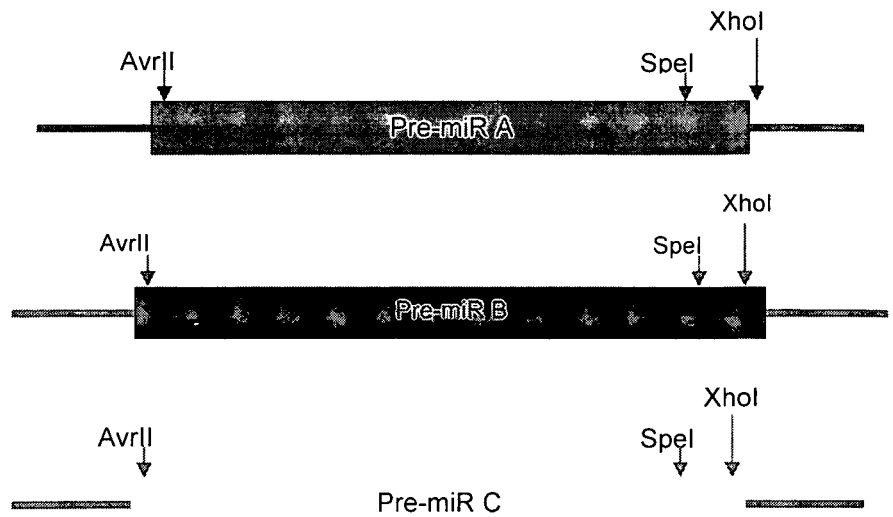

Step 1: Different pre-miRNAs are amplified by PCR to include an AvrII site in the 5' end and to include an SpeI site and an XhoI site in the 3' end Each pre-miRNA is then cloned into a vector, such as pENTR/SD/D-TOPO (Invitrogen) to produce, for example, pENTR/pre-miRA, pENTR/pre-miRB and pENTR/pre-miRC (FIG. 21A).

Figure 21B:
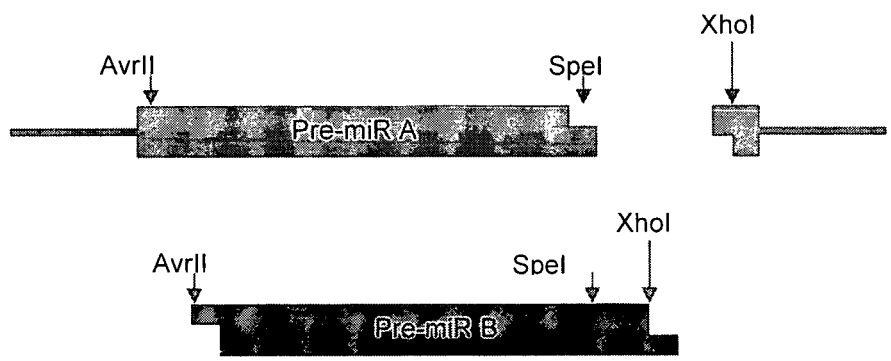

Step 2: The pENTR/pre-miRA is digested with the restriction enzymes SpeI and XhoI. The restriction enzymes AvrII and XhoI are used to digest the pENTR/pre-miRB vector (FIG. 21B). Opened vector pENTR/pre-miRA and DNA fragment of pre-miRB are collected and purified for further steps.

Figure 21C:
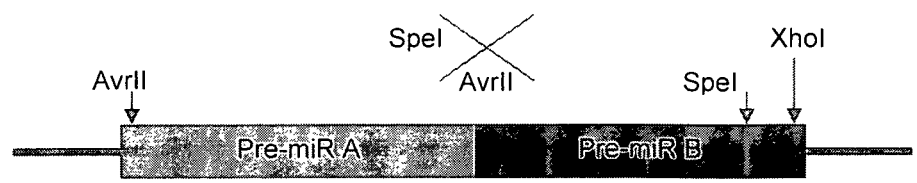

Step 3: The opened vector pENTR/pre-miRA and DNA fragment of pre-miRB from step 2 are ligated to generate dimeric pre-miRA-B (FIG. 21C). Because of compatible cohesive ends of AvrII and SpeI, the pre-miRB fragment can be inserted into the opened pENTR/pre-miRA and both AvrII and SpeI sites will disappear after ligation (FIG. 21C).

Step 4: The pENTR/pre-miRA-B is digested by with the restriction enzymes SpeI and XhoI, and pENTR/pre-miRC is digested with the restriction enzymes AvrII and XhoI (FIG. 21D). Opened vector pENTR/pre-miRA-B and DNA fragment of pre-miRC are collected and purified for further steps.

Step 5: The opened vector pENTR/pre-miRA-B and DNA fragment of pre-miRC from step 4 are ligated to generated triple pre-miRNA-B-C (FIG. 21E).

In this manner, or using functionally equivalent restriction enzymes polymeric pre-miRNAs containing more pre-miRNA units can be prepared. As many pre-miRNAs as desired can be linked together in this fashion, with the only limitation being the ultimate size of the transcript. It is well known that transcripts of 8-10 kb can be produced in plants. Thus, it is possible to form a multimeric pre-miRNA molecule containing from 2-30 or more, for example from 3-40 or more, for example from 3-45 and more, and for further example, multimers of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or more pre-miRNAs.

Example 22

This example demonstrates the successful processing of a dimeric pre-iRNA to two mature miRNAs.

Artificial pre-miRPDS1[169g] and pre-miRCPC3[159a] were linked to form dimeric precursor, pre-miRPDS1[169g]-CPC3[159a] as described in Example 21. This dimeric miRNA precursor was cloned into a vector in which 35S promoter drives expression of the pre-miRPDS1[169g]-CPC3[159a] (FIG. 22). The nucleotide sequences for the precursor and mature miRNAs are as follows.

miRPDS1[169g] precursor template:

```
                                     (SEQ ID NO: 157)
5'aatgatgattacgatgatgagagtctctagttgtatcagagggtcttg catggaagaatagagaatgaggttgagtttagtctgacttggccagtttt tttaccaatgaatctaattaactgattctggtgttggccaagtcagacta aactctgtttccttctcttcttttggatgtcagactccaagatatctatc atcatgaatcgtgatcaaactttg 3'.
``` miRPDS1[169g] mature template:

```
5' gagtttagtctgacttggcca 3'.    (SEQ ID NO: 158)
``` miRPDS1[169g]-CPC3[159a] precursor template:

```
                                     (SEQ ID NO:159)
5'cacctaggaatgatgattacgatgatgagagtctctagttgtatcaga gggtcttgcatggaagaatagagaatgaggttgagtttagtctgacttgg ccagttttttaccaatgaatctaattaactgattctggtgttggccaag tcagactaaactcgtttccttctcttcttttggatgtcagactccaagat atctatcatcatgaatcgtgatcaaactttgaagggtgggcgactaggac agtttgcttatgtcggatccataatatatttgacaagatactttgttttt cgatagatcttgatctgacgatggaagctcgttggcgacaggtgggagca tgagttgagcagggtaaagaaaagctgctaagctatggatcccataagcc
```

-continued
ctaatccttgtaaagtaaaaaaggatttggttatatggattgcatatctc aggagctttaacttgccctttaatggcttttactcttcctcccacctgac gccaacgagcatcccgggtcaaagggtgggcgactagtctagactcgagt att 3'.

Northern blotting analysis of tobacco *Nicotiana benthamiana* levies, infiltrated by *Agrobacteria* carrying different constructs of 35S::pre-miRPDS1[169g], 35S::pre-miRCPC3[159a] and 35S::pre-miRPDS[169g]-CPC3[159a], indicates that mature miRPDS[169g] and CPC3[159a] were successfully produced from the dimeric miRNA precursor (FIGS. 23A and 23B). In this experiment, treatment 1 is 35S::pre-miRPDS1[169g], treatment 2 is 35S::miRCPC3[159a] and treatment 3 is 35S::pre-miRPDS[169g]-CPC3[159a]. When miRPDS1[169g] anti sense DNA oligo as probe, both 1 and 3 treatments showed signals that proved the dimeric precursor was able to produce matured miRPDS1[169g]. When the probe is miRCPC3[159a] anti sense DNA oligo, signal in treatment 3 confirmed the ability of pre-miRpDS[169g]-CPC3[159a] to generate mature miRCPC3[159a].

Example 23

Design of Anti-Viral miRNAs

Since viral gene silencing suppressors are used to counteract host defense, we reasoned that compromising the production of these suppressors by the expression of specific miRNAs would be an effective mechanism to confer resistance or tolerance to plant viruses (Roth et al. (2004) *Virus Res* 102: 97-108). This principle is demonstrated by using TuMV as an example.

HC-Pro and P69 are plant PTGS suppressors encoded by TuMV and TYMV, respectively (Anandalakshmi et al. (1998) *Proc Natl Acad Sci USA* 95:13079-13084; Chen et al. (2004) *Plant Cell* 16:1302-1313; Kasschau and Carrington (1998) *Cell* 95:461-470). Using these two viral suppressor genes as targets, artificial miRNAs were designed with sequence complementarity to their coding sequences. The coding sequence for HC-Pro is SEQ ID NO:188, and the coding sequence for P69 is SEQ ID NO:189.

Figure 24:
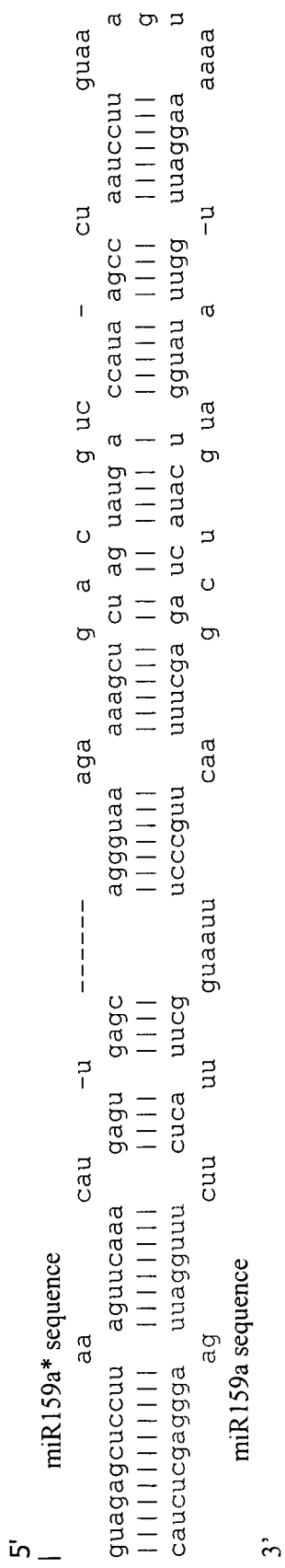
FIG. 24 shows the structure of the miR159a precursor (SEQ ID NO:161).

At-miR159a is strongly expressed in most *Arabidopsis* organs and at high levels. Similar high level expression was also found in other plants species such as corn and tobacco. For these reasons, the miR159a precursor (pre-miR159a) was used as a backbone to generate artificial miRNAs. Pre-miR159a, a 184 nt stem-loop RNA, produces mature miR159a (5'-uuuggauugaagggagcucua-3'; SEQ ID NO:160) from the base of its stem near the 3'end. This base stem sequence is the miR159a sequence and the complementary strand is called miR159a* sequence (FIG. 24; SEQ ID NO:161). To design artificial miRNA, the miR159a sequence was replaced by a sequence 5'-acuugcucacgcacucgacug-3' (SEQ ID NO:162), which is complementary to the viral sequence encoding HC-P from 2045 to 2065 of the TuMV genome sequence. The miR159a* sequence was also altered to maintain the stem structure. For more efficient miRNA processing and convenient manipulation of the artificial miRNA precursor, a 78 bp sequence cloned from the genome sequence upstream of pre-miR159 was added to the 5'end of this artificial miRNA precursor. This primary miRNA-like artificial miRNA precursor was called pre-miRHC-P[159a]. Its DNA sequence follows.

Pre-miRHC-P[159a]

(SEQ ID NO:163)
5'CAGTTTGCTTATGTCGGATCCATAATATATTTGACAAGATACTTTGTT

TTTCGATAGATCTTGATCTGACGATGGAAGCAGTCGAGTGCGTGAGCAAG

TCATGAGTTGAGCAGGGTAAAGAAAAGCTGCTAAGCTATGGATCCCATAA

GCCCTAATCCTTGTAAAGTAAAAAAGGATTTGGTTATATGGATTGCATAT

CTCAGGAGCTTTAACTTGCCCTTTAATGGCTTTTACTCTTCACTTGCTCA

CGCACTCGACTGC 3'

Using the same method, pre-miRP69[159a] was also constructed. Pre-miRP69[159a] was predicted to generate mature artificial miRNA P69[159a], 5'-aaagucucgauugucuugugg-3' (SEQ ID NO:164), to target the P69 gene of TYMV. Its DNA sequence follows.

Pre-miR P69[159a]

(SEQ ID NO:165)
5'CAGTTTGCTTATGTCGGATCCATAATATATTTGACAAGATACTTTGTT

TTTCGATAGATCTTGATCTGACGATGGAAGCCACAAGACAATCGAGACTT

TCATGAGTTGAGCAGGGTAAAGAAAAGCTGCTAAGCTATGGATCCCATAA

GCCCTAATCCTTGTAAAGTAAAAAAGGATTTGGTTATATGGATTGCATAT

CTCAGGAGCTTTAACTTGCCCTTTAATGGCTTTTACTCTTCAAAGTCTCG

ATTGTCTTGTGGC 3'

Example 24

Expression of pre-miRHC-P[159a] and pre-miRP69[159a] in *Nicotiana benthamiana*

Replacement of the miR159 and miR159* sequences in the pre-miR159 may possibly effect RNA folding structure which is believed to be important for miRNA biosynthesis. A tobacco transient expression system was used to check whether these two artificial miRNA precursors can produce the desired miRNAs. Agrobacterial cells containing plasmids with 35S::pre-miR-HC-Pro[159a], 35S::pre-miR-P69[159a], 35S::HC-Pro, 35S::P69, and XVE: pre-miR-P69[159a] were used to infiltrate *N. benthamiana* leaves (Llave et al. (2000) *Proc Natl Acad Sci USA* 97:13401-13406; Voinnet et al. (2000) *Cell* 103:157-167).

One ml of stationary phase growth culture of *Agrobacteria tumefaciens* carrying different constructs were cultured overnight in 50 ml LB medium containing 100 mg/l spectinomycin and 50 mg/l kanamycin and cells were collected by centrifugation at 4,000 rpm for 10 minutes. Bacterial pellets were re-suspended in 50 ml 10 mM $MgCl_2$ solution with 75 µl of 100 mM acetosyringone. After incubation at room temperature for 3 hr without shaking, the Agrobacterial suspensions were infiltrated into leaves of *N. bethamiana* by a syringe. Two days later, total RNA was extracted from the infiltrated leaves using the trizol reagent (Invitogen) and analyzed by northern blot hybridizations (Guo et al. (2005) *Plant Cell* 17:1376-1386; Wang et al. (2004) *Genome Biol* 5:R65). Samples of 20 µg total RNA were analyzed by electrophoresis on a 15% polyacrylamide gel and blotted to a Hybond-N+ membrane (Amersham). DNA oligonucleotides with exact complementary sequence to miR-HC-Pro[159a] or pre-miR-P69[159a] were end-labeled with [γ-$^{32}$P]-ATP and T4 polynucleotide kinase to generate high specific activity probe. Hybridization was carried out using the ULTRA-Hyb Oligo solution according to the manufacturer's directions (Ambion) and signals were detected by autoradiography.

Northern blot analyses of miR-HC-Pro$^{159a}$ were performed with three different treatments: (1) Agrobacterial cells with 35S::pre-miR-HC-Pro$^{159a}$, (2) Agrobacterial cells with 35S::HC-Pro, and (3) Agrobacterial cells with 35S::pre-miR-HC-Pro$^{159a}$ and 35S::HC-Pro. The results are shown in FIG. 25.

Figure 25:
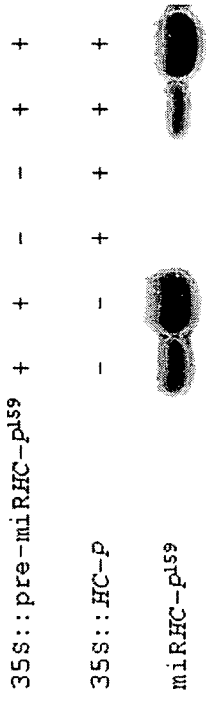
FIG. 25 shows Northern blot analysis of miR-HC-Pro$^{159a}$ were performed with three different treatments: (1) Agrobacterial cells with 35S::pre-miR-HC-Pro$^{159a}$, (2) Agrobacterial cells with 35S::HC-Pro, and (3) Agrobacterial cells with 35S::pre-miR-HC-Pro$^{159a}$ and 35S::HC-Pro.

Note that mature miR-HC-Pro$^{159a}$ signals were detected in all treatments with 35S::pre-miR-HC-Pro$^{159a}$ (column 1, 2, 5, 6 of FIG. 25). No signal was detected when leaves were infiltrated with the 35S::HC-Pro construct only (column 3 and 4 of FIG. 25). This result indicates that the artificial pre-miR-HC-Pro$^{159a}$ can generate mature miR-HC-Pro$^{159a}$ in the plant cell.

In the case of miR-P69, 4 different treatments were performed: (1) Agrobacterial cells carrying 35S::pre-miR-P69$^{159a}$, (2) Agrobacterial cells carrying XVE::pre-miR-P69$^{159a}$, (3) Agrobacterial cells carrying 35S::P69, and (4) Agrobacterial cells carrying 35S::pre-miR-P69$^{159a}$ and 35S::P-69. Note that the XVE system is a transcriptional inducible system responsive to β-estradiol (Zuo et al. (2001) *Nature Biotechnol* 19(2):157-61).

Figure 26:
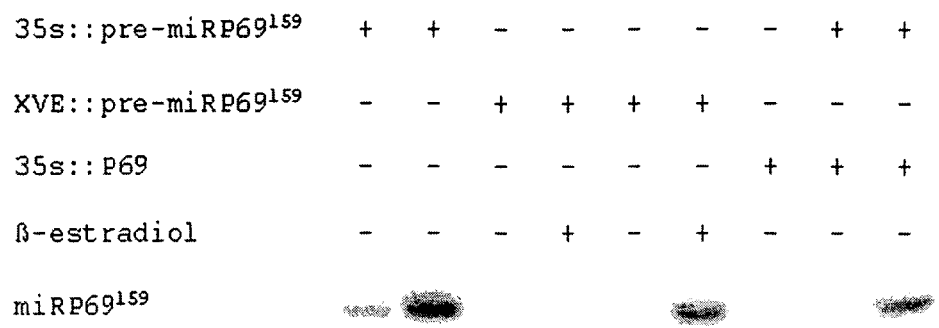
FIG. 26 shows Northern blot analysis of miR-P69, 4 different treatments were performed: (1) Agrobacterial cells carrying 35S::pre-miR-P69$^{159a}$, (2) Agrobacterial cells XVE::pre-miR-P69$^{159a}$, (3) Agrobacterial cells carrying 35S::P69, and (4) Agrobacterial cells carrying 35S::pre-miR-P69$^{159a}$ and 35S::P-69.

The Northern blot results (FIG. 26) showed that mature miR-P69$^{159a}$ was detectable only in leaves infiltrated with 35S::pre-miR-P69$^{159a}$ and XVE::pre-miR-P69$^{159a}$ plus inducer (column 1, 2, 4, 6, 8, and 9 of FIG. 26). Leaves infiltrated with 35S::P69 and XVE::pre-miRP69$^{159a}$ without inducer can not produce miR-P69$^{159a}$ (column 3, 5, and 7 of FIG. 26). Together, these results indicate that artificial pre-miR-P69$^{159a}$ can be successfully used to generate mature miR-P69$^{159a}$.

Example 25

Stable *Arabidopsis* Transgenic Lines with High Artificial miRNAs Expression Levels Constructs containing 35S::pre-miR-HC-Pro$^{159a}$ or 35S::pre-miR-P69$^{159a}$ was transformed into *Arabidopsis* Col-0 ecotype mediated by *Agrobacteria* using the floral dip method (Clough and Bent (1998) *Plant J* 16:735-43).

Figure 27:
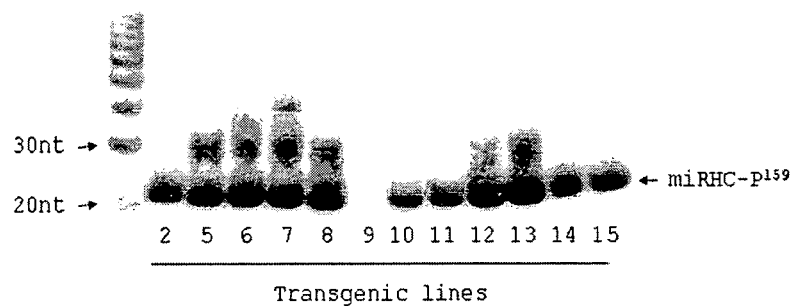
FIG. 27 shows Northern blot analysis of mature artificial miRNA levels for randomly picked $T_2$ 35S::pre-miRHC-Pro$^{159a}$ transgenic lines (plants). The $T_2$ plants are known to be transgenic because they were first selected on Kan-containing medium to remove WT. The $T_2$ plants are either heterozygous (one copy) or homozygous (two copies), and the ratio should be about 2:1.
Figure 28:
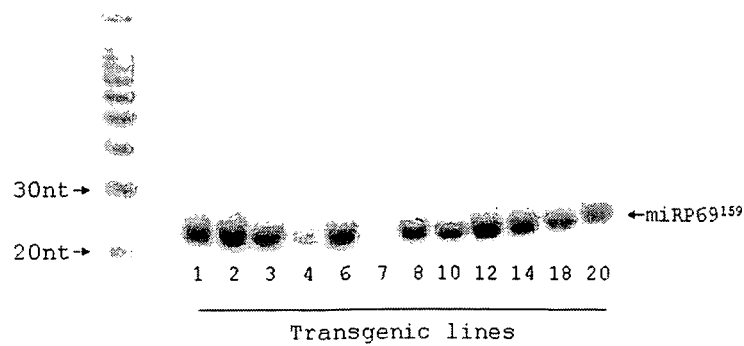
FIG. 28 shows Northern blot analysis of mature artificial miRNA levels for randomly picked $T_2$ 35S::pre-miR-P69$^{159a}$ transgenic lines (plants).

Transgenic seedlings were selected on selection medium (MS salts 4.3 g/l+Sucrose 10 g/l+Basta10 mg/l+Carbenicilin 200 mg/l+Agar 8 g/l). Twelve different 35S::pre-miR-HC-Pro$^{159a}$ or 35S::pre-miR-P69$^{159a}$ T$_2$ transgenic lines were randomly picked and used to analyze mature artificial miRNA levels by northern blots. Among 12 transgenic 35S::pre-miRHC-Pro$^{159a}$ lines, 11 lines showed high levels of expression of miRHC-Pro$^{159a}$ (FIG. 27). In *Arabidopsis* transgenic 35S::pre-miR-P69$^{159a}$ plants, all T$_2$ lines tested showed miR-P69$^{159a}$ signals and 10 lines showed high expression levels (FIG. 28).

Example 26

TuMV Virus Challenge of WT and Transgenic Plants

Inoculation of WT and Transgenic *Arabidopsis* Lines with the TuMV

*N. benthamiana* leaves were inoculated with Turnip mosaic virus (TuMV) (Chen et al. (2003) *Plant Dis* 87:901-905) and two weeks later tissues were extracted in 1:20 (wt/vol) dilution in 0.05 M potassium phosphate buffer (pH 7.0). This extract was used as a viral inoculum. T$_2$ plants of 35S::miR-HC-Pro$^{159a}$ transgenic *Arabidopsis* lines were grown in a greenhouse for 4 weeks (5 to 6 leaves stage) before inoculation. Plants were dusted with 600-mesh Carborundum on the first to fourth leaf and gently rubbed with 200 μl inoculum. Wild type *Arabidopsis thaliana* (col-0) plants and transgenic plants expressing 35S::miR-P69$^{159a}$ were used as controls. Inoculated plants were kept in a temperature-controlled greenhouse (23° C. to 28° C.) and symptom development was monitored daily for 2 weeks.

Enzyme-Linked Immunosorbent Assay (ELISA)

Leaf disks (a total of 0.01 g) from different systemic leaves of each plant infected with TuMV were taken 14 dpi (days post infection), and assayed by indirect enzyme-linked immunosorbent assay (ELISA) using a polyclonal antiserum to TuMV coat protein (CP) (Chen et al. (2003) *Plant Dis* 87:901-905) and goat anti-rabbit immunoglobulin G conjugated with alkaline phosphatase. The substrate p-nitrophenyl phosphate was used for color development. Results were recorded by measuring absorbance at 405 nm using Tunable Microplate Reader (VersaMax, Molecular Devices Co., CA).

Western Blot Analysis

Western blot analysis was conducted using the rabbit antiserum to TuMV CP (Chen et al. (2003) *Plant Dis* 87:901-905) and goat anti-rabbit immunoglobulin G conjugated with alkaline phosphatase. Systemic leaves from *Arabidopsis* plants were homogenized in 20 volumes (wt/vol) of denaturation buffer (50 mM Tris-HCl, pH 6.8, 4% SDS, 2% 2-mercaptoethanol, 10% glycerol, and 0.001% bromophenol blue). Extracts were heated at 100° C. for 5 min and centrifuged at 8,000×g for 3 min to pellet plant debris. Total protein of each sample (15 μl) was loaded on 12% polyacryamide gels, separated by SDS-polyacrylamide gel electrophoresis, and subsequently transferred onto PVDF membrane (immobilon-P, Millipore, Bedford, Mass.) using an electro transfer apparatus (BioRad). The membranes were incubated with polyclonal rabbit antiserum to TuMV CP as primary antibodies and peroxidase-conjugated secondary antibodies (Amersham Biosciences) before visualization of immunoreactive proteins using ECL kits (Amersham Biosciences). Gels were stained with coomassie-blue R250 and levels of the large subunit of RUBISCO (55 kd) were used as loading controls.

Figure 29:
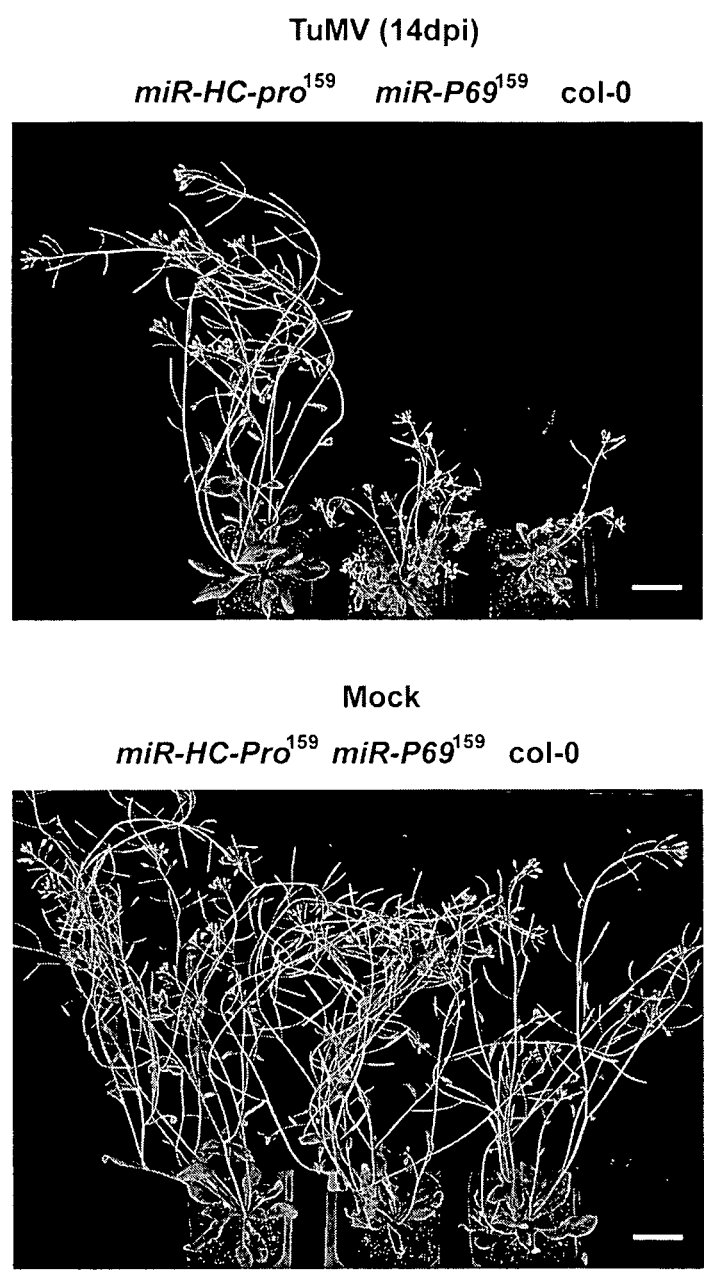
FIG. 29 shows that $T_2$ transgenic plants expressing miR-HC-Pro$^{159a}$ artificial miRNA are resistant to TuMV infection. Photographs were taken 2 weeks (14 days after infection) after inoculation. $T_2$ transgenic plants expressing miR-HC-Pro$^{159a}$ (line #11.

It was found that transgenic plants expressing miR-HC-Pro$^{159a}$ artificial miRNA are resistant to TuMV infection (FIG. 29). Photographs were taken 2 weeks (14 days after infection) after inoculation. Plants expressing miR-HC-Pro$^{159a}$ (line #11; FIG. 33B) developed normal inflorescences whereas WT plants and transgenic plants expressing miR-P69$^{159a}$ (line #1; FIG. 33B) showed viral infection symptoms.

Figure 30:
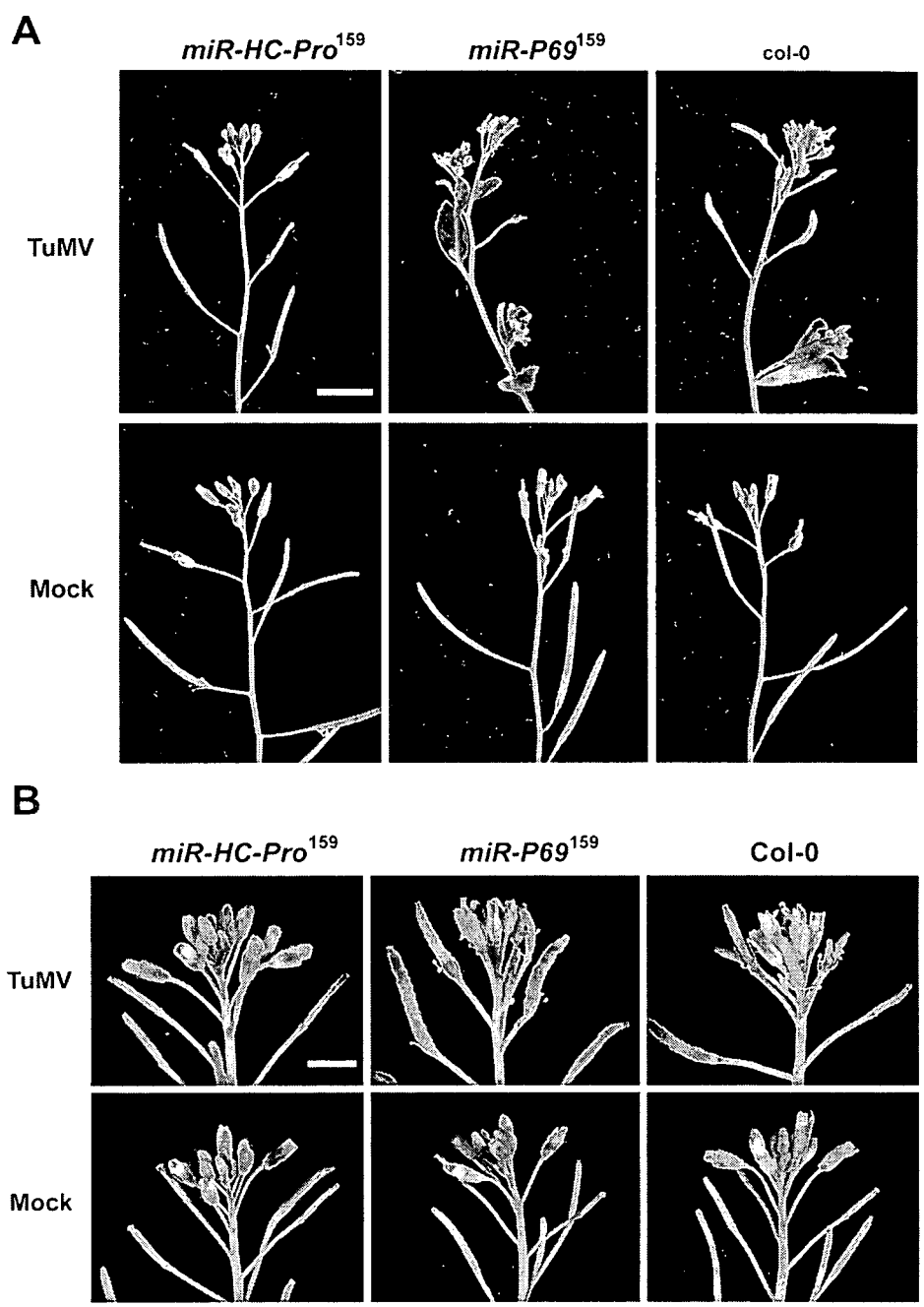
FIG. 30 shows symptoms of inflorescences caused by TuMV infection. (Top panel) Fourteen days after TuMV infection, $T_2$ transgenic miR-P69$^{159a}$ plants (line #1) and col-0 plants showed shorter internodes between flowers in inflorescences, whereas $T_2$ miR-HC-Pro$^{159a}$ transgenic plant (line #11) displayed normal inflorescence development. The bar represents 1 cm. (Bottom panel) Close-up views of inflorescences on TuMV-infected *Arabidopsis* plants. $T_2$ transgenic miR-P69$^{159a}$ plants (line #1) and col-0 plants showed senescence and pollination defects whereas $T_2$ transgenic miR-HC-Pro$^{159a}$ plants (line #11) showed normal flower and silique development. For mock-infection, plants were inoculated with buffer only. The bar represents 0.2 cm.

Fourteen days after TuMV infection, miR-P69$^{159a}$ (line #1) and col-0 plants showed shorter internodes between flowers in inflorescences, whereas miR-HC-Pro$^{159a}$ transgenic plant (line #11) displayed normal inflorescence development (FIG. 30, upper panel). Close-up views of inflorescences on TuMV-infected *Arabidopsis* plants. miR-P69$^{159a}$ (line #1) and col-0 plants showed senescence and pollination defects whereas miR-HC-Pro$^{159a}$ plants (line #11) showed normal flower and silique development (FIG. 30, bottom panel). For mock-infection, plants were inoculated with buffer only.

Figure 31:
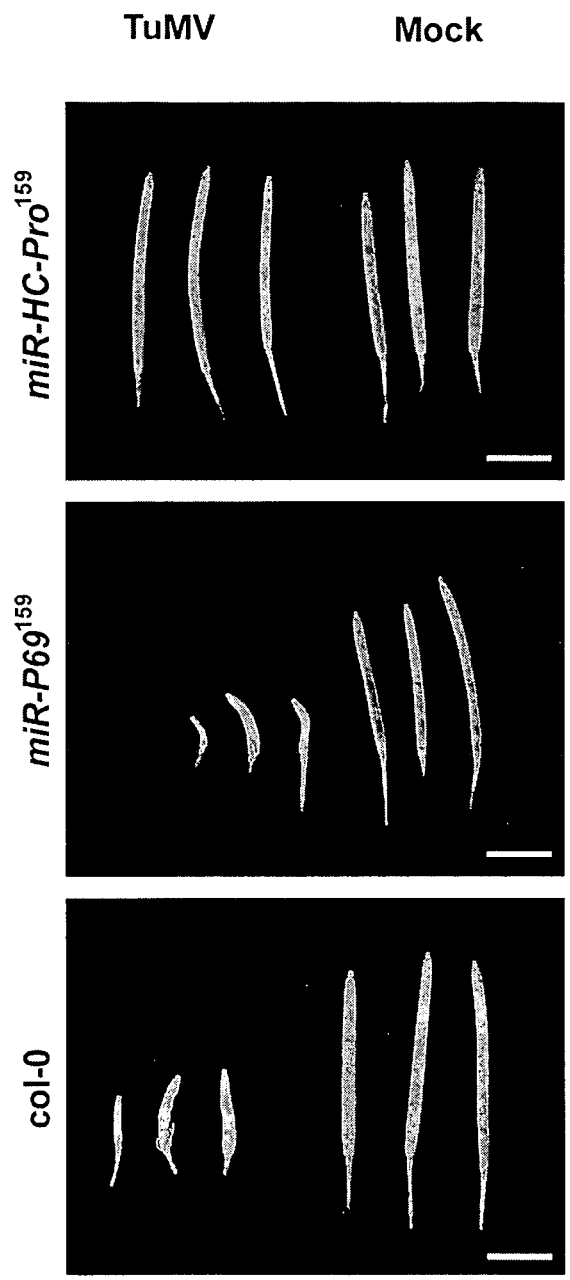
FIG. 31 shows symptoms of siliques caused by TuMV infection. In TuMV-infected $T_2$ transgenic miR-P69$^{159a}$ plants (line #1) and WT (col-0) plants, siliques were small and mal-developed. $T_2$ transgenic miR-HC-Pro$^{159a}$ plants (line #11) were resistant to TuMV infection and showed normal silique development. Buffer-inoculated plants (mock-inculated) were used as controls. The bar represents 0.5 cm.

In TuMV-infected miR-P69$^{159a}$ (line #1) and WT (col-0) plants, siliques were small and mal-developed. miR-HC-Pro$^{159a}$ plants (line #11) were resistant to TuMV infection and showed normal silique development (FIG. 31). Buffer-inoculated plants (mock-inculated) were used as controls.

Figure 32:
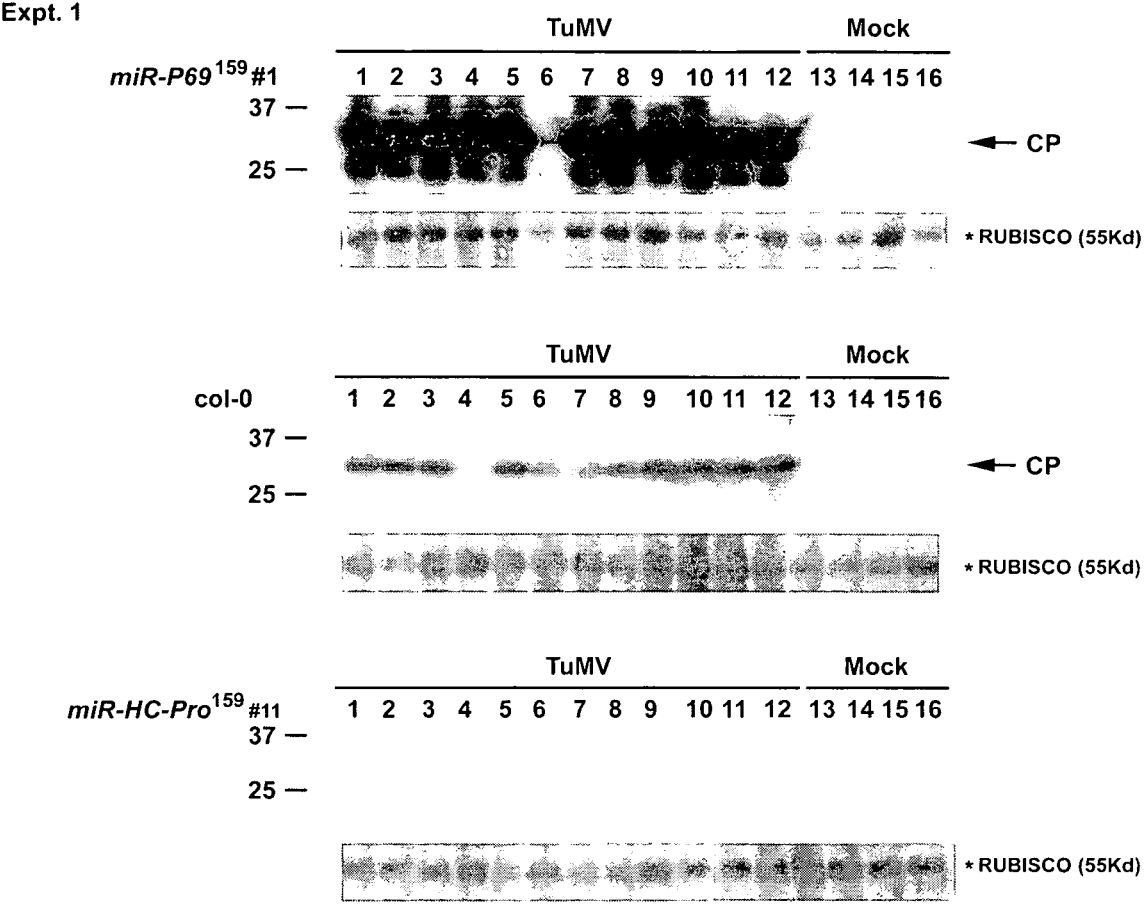
FIG. 32 shows Western blot analysis of TuMV coat protein (CP) levels in leaves of different transgenic and WT plants.

Two independent experiments were performed to examine the resistance of various transgenic miR-HC-Pro$^{159a}$ and WT plants to TuMV infection. Experiment 1: Sixteen individual plants of a $T_2$ transgenic line (line #11 of miR-HC-Pro$^{159a}$ plant and line #1 of miR-P69$^{159a}$ plant) were used. Twelve individual plants were inoculated with virus whereas 4 individual plants were inoculated with buffer as control (MOCK). After 2 weeks system leaves were collected for western blot analyses using an antibody against TuMV CP. No TuMV CP was detected in miR-HC-Pro$^{159a}$ transgenic plants, whereas, TuMV CP was highly expressed in miR-P69$^{159a}$ and WT col-0 plants (FIG. 32). The large subunit (55 kd) of RUBISCO was used as a loading control. Note that no CP was detected in lane 6 (top panel) and lane 4 (middle panel) likely due to failed virus inoculation. These plants had no symptoms. The results of the infectivity assay are shown in Table 7.

TABLE 7

Infectivity Assay of Transgenic *Arabidopsis* of the miR-HC-Pro$^{159a}$ and miR-P69$^{159a}$ Challenged with TuMV Inocula

| Transgenic line | Number of seedlings | | | Resistant rate (%) |
| --- | --- | --- | --- | --- |
| | Resistant | Susceptible | Total | |
| miR-HC-Pro$^{159a}$ #11 | 12 | 0 | 12 | 100 |
| miR-P69$^{159a}$ #1 | 1 | 11 | 12 | 8.3 |
| col-0 | 1 | 11 | 12 | 8.3 |

Experiment 2: The following transgenic lines and WT plants were used. (1) 35S::miR-HC-Pro$^{159a}$ plants: line #10 (12 plants inoculated with TuMV and 4 with buffer); line #11 (12 plants inoculated with TuMV and 4 with buffer); line #12 (9 plants inoculated with TuMV and 4 with buffer); line #13 (10 plants inoculated with TuMV and 4 with buffer). (2) 35S::miR-P69$^{159a}$ plants: line #1 (8 plants inoculated with TuMV and 4 with buffer); line #2 (7 plants inoculated with TuMV and 4 with buffer); line #3 (9 plants inoculated with TuMV and 4 with buffer); line 7 (5 plants inoculated with TuMV and 4 with buffer).

Western blot results of a representative plant from each transgenic line are shown in FIG. 33, panel A. Levels of the large subunit (55 kd) of RUBISCO were used as loading controls. All plants expressing 35S::miR-HC-Pro$^{159a}$ were resistant to the virus and did not show any visible symptoms nor expressed any TuMV CP. All WT plants and 35S::miR-P69$^{159a}$ plants showed TuMV infection symptoms and expressed high levels of TuMV CP. All mock-infected plants were normal and did not express any TuMV CP. Expression of artificial miRNA in miR-HC-Pro$^{159a}$ and miR-P69$^{159a}$ transgenic *Arabidopsis* is shown in FIG. 33, panel B. The results of the infectivity assay are shown in Table 8.

TABLE 8

Infectivity Assay of Transgenic *Arabidopsis* of the miR-HC-Pro$^{159a}$ and miR-P69$^{159a}$ Challenged with TuMV Inocula

| Transgenic line | Number of seedlings | | | Resistant rate (%) |
| --- | --- | --- | --- | --- |
| | Resistant | Susceptible | Total | |
| miR-HC-Pro$^{159a}$ #10 | 12 | 0 | 12 | 100 |
| miR-HC-Pro$^{159a}$ #11 | 12 | 0 | 12 | 100 |
| miR-HC-Pro$^{159a}$ #12 | 9 | 0 | 9 | 100 |
| miR-HC-Pro$^{159a}$ #13 | 10 | 0 | 10 | 100 |
| miR-P69$^{159a}$ #1 | 0 | 8 | 8 | 0 |
| col-0 | 1 | 11 | 12 | 8.3 |

Fourteen days after infection with TuMV, samples of systemic leaves were collected and extracts assayed by ELISA. The results are means of ELISA readings of 9 or 12 plants from two different experiments. The results (FIG. 34) show that the miR-HC-Pro$^{159a}$ plants were completely resistant to TuMV infection. The readings were taken after 30 min of substrate hydrolysis.

Example 27

Production of More than One Synthetic miRNAs from Same Transcript Using Homo-Polymeric pre-miRNAs Polymeric pre-miRNAs are artificial miRNA precursors consisting of more than one miRNA precursor units. They can either be hetero-polymeric with different miRNA precursors, or homo-polymeric containing several units of the same miRNA precursor. In previous Examples, it has been demonstrated that hetero-polymeric pre-miRNAs are able to produce different mature artificial miRNAs. For example, pre-miR-PDS1$^{169g}$-CPC3$^{159a}$, which is a dimer comprising of pre-miR-CPC3$^{159a}$ and pre-miR-PDS1$^{169g}$ can produce mature miR-PDS1$^{169g}$ and miR-CPC3$^{159a}$ when expressed in plant cells. Here, the use of homo-polymeric miRNA precursors to produce different mature artificial miRNAs is described.

Pre-miR-P69$^{159a}$ and pre-miR-HC-Pro$^{159a}$ were generated from the pre-miR159a backbone. They are derived from the same miRNA precursor. They were linked together to form a homo-dimeric pre-miRNA, pre-miR-P69$^{159a}$-HC-Pro$^{159a}$. The DNA sequence follows.

Pre-miRP69$^{159a}$-HC-P$^{159a}$ (SEQ ID NO:166)
5'cagtttgcttatgtcggatccataatatatttgacaagatactttgtt tttcgatagatcttgatctgacgatggaagccacaagacaatcgagactt tcatgagttgagcagggtaaagaaaagctgctaagctatggatcccataa gccctaatccttgtaaagtaaaaaaggatttggttatatggattgcatat ctcaggagctttaacttgcccttaatggcttttactcttcAAAGTCTCG

ATTGTCTTGTGGc*ATCCCGGGTCAAAGGGTGGGCGACTAGGA*cagtttgc ttatgtcggatccataatatatttgacaagatactttgttttcgataga tcttgatctgacgatggaagcagtcgagtgcgtgagcaagtcatgagttg agcagggtaaagaaaagctgctaagctatggatcccataagccctaatcc ttgtaaagtaaaaaaggatttggttatatggattgcatatctcaggagct ttaacttgcccttaatggcttttactcttc*ACTTGCTCACGCACTCGAC*

*TGc* 3'

The sequences in lower case text are At-miR159 backbone. The sequence in bold text is miR-P69$^{159a}$. The sequence in italic text is miR-HC-Pro$^{159a}$. The sequence in bold italic text is the linker sequence.

Figure 35:
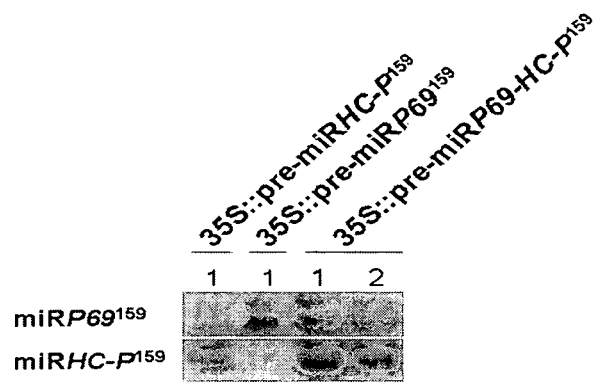
FIG. 35 shows Northern blot analysis of pre-miR-P69$^{159a}$, pre-miR-HC-Pro$^{159a}$ and pre-miR-P69$^{159a}$-HC-Pro$^{159a}$ demonstrating that homo-dimeric miRNA precursor, pre-miR-P69$^{159a}$-HC-Pro$^{159a}$, can produce mature miR-P69$^{159a}$ and miR-HC-Pro$^{159a}$.

A tobacco transient expression system was used to check whether this homo-dimeric miRNA precursor can produce the desired mature miR-P69$^{159a}$ and miR-HC-Pro$^{159a}$. In this experiment, three treatments were performed: (1) *Agrobacteria* with 35S::pre-miR-P69$^{159a}$, (2) *Agrobacteria* with 35S::pre-miR-HC-Pro$^{159a}$, and (3) *Agrobacteria* with 35:: pre-miR-P69$^{159a}$-HC-Pro$^{159a}$. Northern analysis indicated that homo-dimeric miRNA precursor, pre-miR-P69$^{159a}$-HC-Pro$^{159a}$, can produce mature miR-P69$^{159a}$ and miR-HC-Pro$^{159a}$ (FIG. 35).

Example 28

Expression of miRNAs from pre-miRNAs Inserted in Intronic Sequences

During RNA splicing, introns are released from primary RNA transcripts and therefore can potentially serve as precursors for miRNAs. In this example, the insertion of pre-miRNAs into such intronic sequences to produce artificial miRNAs is described.

Most introns begin with the sequence 5'-GU-3' and end with the sequence 5'-AG-3'. These sequences are referred to as the splicing donor and splicing acceptor site, respectively. In addition to these sequences, the branch site which is located within introns is also important for intron maturation. Without the branch site, an intron can not be excised and released from the primary RNA transcript. A branch site is located 20-50 nt upstream of the splicing acceptor site. Distances between the splice donor site and the branch site are largely variable among different introns. For this reason, it was decided to insert artificial pre-miRNAs in between these two sites, i.e., the splice donor site and the branch site, of introns.

The *Arabidopsis* CARPRICE (CPC) gene contains three exons and two introns. Following the consensus sequence of the branch site 5'-CU(A/G)A(C/U)-3', where A is conserved in all transcripts, two branch sites located in 128 to 132 nt (intron 1) and 722 to 726 nt (intron 2) downstream of the start codon are predicted. Sequences from 111 to 114 nt and from 272 to 697 nt, located in intron 1 and in intron 2, respectively, were replaced by artificial miRNA precursors containing the miR159a backbone. The DNA sequence follows.

CPC Genome Sequence (SEQ ID NO:167)
atgtttcgttcagacaaggcggaaaaaatggataaacgacgacggagaca gagcaaagccaaggcttcttgttccgaagGTCTGATTTCTCTTTGTTTCT

CTCTATATCTTTTTGATCGGTTTGAGT*AGGGAGCTCTA*TTTGTATGTTTG

TTTCGCAGaggtgagtagtatcgaatgggaagctgtgaagatgtcagaag aagaagaagatctcatttctcggatgtataaactcgttggcgacagGTTA

GAGACTCTTTCTCTCTCGATCCATCTTGTTGCTTTCTCTTTTTTTGGTC

TTTCATGTTTTGTCGAATCTGCTTAGATTTTGATCTCAAAGTCGGTCGTT

TATTTATGCATTTTCTTGGTTTTTCTATTATATTATTGGGTCTAACTTAC

CGAGCTGTCAATGACTGTGTTCAGCCTGATTTTTGATCTTGTTATTATTC

TCTGTTTTTGTTTTAGTTGTTCAAATAGCAAAACCTAATCAAGATTTCG

TTTTCAGTTTCTTTTTTTATATATGATTCTTTAGCAAAACATATTCTTAA

TTTATGTCAGAACTCACTTTGGCTAGTTTGGTTCAATTTTGATTACAGCA

TGTTTGTATGAAGTCAAAGTGTAAATTACGATTTTGGTTCGGTTCCATAG

AATTTTAACCGAATTACAAACTTTATGCGGTTTTTATCGGAATAAAAGGT

ATTTGGTTAAGTGTAAGTTCCTCAACA*GAGCCAAGGATGACTTGCCGG*

TGTTAGCCTATCCTACGTGGCGCGTAGgtgggagttgatcgccggaagga tcccgggacggacgccggaggagatagagagatattggcttatgaaacac ggcgtcgttttgccaacagacgaagagacttttttaggaaatga The sequences in lower case are exons. The sequences in bold italic text are branch sites. The sequences in bold were replaced by artificial pre-miRNAs. Intron sequences include sequences in normal text, bold text and bold italic text.

Figure 36:
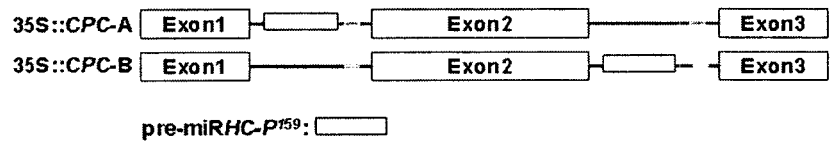
FIG. 36 shows constructs in which miR-HC-Pro$^{159a}$ is placed in either intron 1 or intron 2 of the CPC gene.
Figure 37:
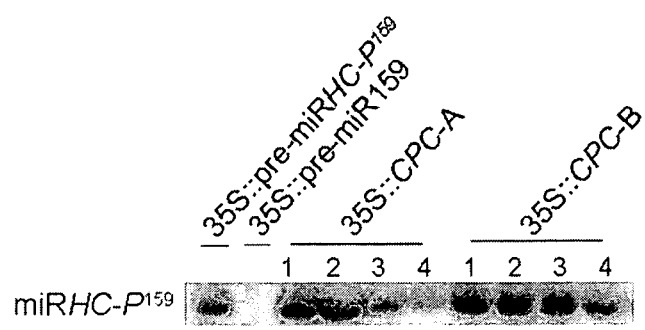
FIG. 37 shows Northern blot analysis of the constructs of FIG. 36 and demonstrates that intron 1 and intron 2 of the CPC transcript can be used to produce artificial miRNAs.

Constructs 35S::CPC-A and 35S::CPC-B were generated to check whether intron 1 or intron 2 of the unspliced CPC transcript can be used to insert artificial pre-miRNA for the production of artificial miRNAs. In the CPC-A construct, pre-miR-HC-Pro$^{159a}$ was inserted into intron 1 with no change in intron 2. In CPC-B, pre-miR-HC-Pro$^{159a}$ was inserted into intron 2 with no change in intron 1 (FIG. 36). Agrobacterial cells carrying 35S::CPC-A, 35S::CPC-B, 35S::pre-miR-HC-Pro$^{159a}$, and 35::pre-miR159a were infiltrated into *N. benthamiana* leaves for transient expression. Northern blot hybridizations using a probe complementary to miR-HC-Pro$^{159a}$ showed that in 4 separate experiments leaf samples infiltrated with CPC-A and CPC-B expressed miR-HC-Pro$^{159a}$ (FIG. 37). This result demonstrates that both intron 1 and intron 2 of the CPC transcript can be used to produce artificial miRNAs.

Figure 38:
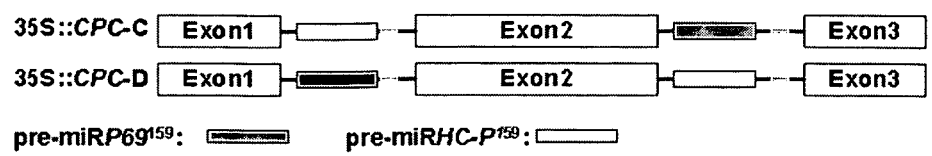
FIG. 38 shows constructs in which pre-miR-HC-Pro[159a] is placed in either intron 1 or intron 2 and pre-miR-P69[159], is placed in either intron 2 or intron 1 of the CPC gene.
Figure 39:
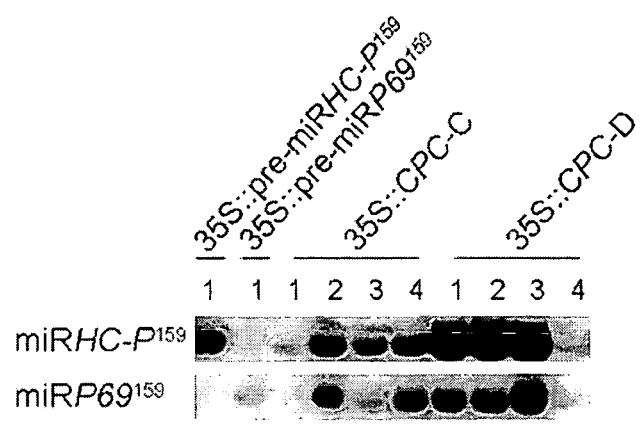
FIG. 39 shows Northern blot analysis of the constructs of FIG. 38 and demonstrates that it is possible to use CPC introns to produce two different artificial miRNAs simultaneously in one transcript.

Constructs 35S::CPC-C and 35S::CPC-D were generated to determine the possibility of producing miRNAs in both introns. In CPC-C, pre-miR-HC-Pro$^{159a}$ was inserted into intron 1 and pre-miR-P69$^{159a}$ into intron 2. In CPC-D, pre-miR-P69$^{159a}$ was inserted into intron 1 and pre-miR-HC-Pro$^{159a}$ into intron 2 (FIG. 38). Agrobacterial cells carrying 35S::CPC-C, 35S::CPC-D, 35S::pre-miR-HC-P$^{159a}$, and 35S::pre-miR-P69$^{159a}$ were infiltrated into *N. benthamiana* leaves for transient expression. FIG. 39 shows northern blot results of four independent experiments. Note that all of the four samples show signals corresponding to miR-HC-Pro$^{159a}$ miRNA and miR-P69$^{159a}$ although the signal in sample 1 is weak (FIG. 39, 1 of 35S::CPC-C). This weak signal could be due to a lower transient expression efficiency in this particular sample. A similar situation was encountered in sample 4 of the 35S::CPC-D experiment. These results demonstrate that it is possible to use CPC introns to produce two different artificial miRNAs simultaneously in one transcript.

The above examples are provided to illustrate the invention but not to limit its scope. Other variants of the invention will be readily apparent to one of ordinary skill in the art and are encompassed by the appended claims. For example, in the Examples described above, pre-miR159a and pre-miR169g were used to generate artificial pre-miRNAs. However, other pre-miRNAs, such as described herein, could be used in place of pre-miR159a and pre-miR169g. All publications, patents, patent applications, and computer programs cited herein are hereby incorporated by reference. It will also be appreciated that in this specification and the appended claims, the singular forms of "a," "an" and "the" include plural reference unless the context clearly dictates otherwise. It will further be appreciated that in this specification and the appended claims, The term "comprising" or "comprises" is intended to be open-ended, including not only the cited elements or steps, but further encompassing any additional elements or steps.

What is claimed:

1. A method of obtaining a disease resistant plant by down regulating a target sequence of a plant virus or plant viroid in a plant, consisting of:

(a) transforming a plant cell susceptible to infection by the plant virus or plant viroid with a nucleic acid construct comprising a promoter functional in a plant cell operably linked to a polynucleotide, wherein the polynucleotide encodes one or more modified miRNA precursors, wherein each modified miRNA precursor comprises a fragment of a plant miRNA primary transcript that is modified in the miRNA sequence and the miRNA complementary sequence, wherein the plant miRNA primary transcript is a plant miR159 primary transcript, further wherein each modified miRNA precursor is capable of forming a first double-stranded RNA or a hairpin, wherein each modified miRNA is an miRNA modified to be (i) fully complementary to a target sequence, (ii) fully complementary to a target sequence except for GU base pairing or (iii) fully complementary to a target sequence in the first ten nucleotides counting from the 5' end of the miRNA, wherein the target sequence of each modified miRNA is the same or different, and wherein at least one target sequence encodes a gene silencing suppressor of a plant virus or plant viroid and wherein the modified miRNA sequence targeting said gene silencing suppressor consists of (i) the nucleotide sequence of SEQ ID NO:162 or (ii) a nucleotide sequence that is at least 90% identical to the nucleotide sequence of SEQ ID NO:162;

(b) obtaining a transgenic plant from the transformed plant cell of (a);

(c) expressing the nucleic acid construct in the transgenic plant of (b) for a time sufficient to produce each modified miRNA, wherein each modified miRNA binds to its target sequence to form a second double-stranded RNA which is cleaved thereby down regulating the target sequence; and (d) selecting a transgenic plant of (c) that is resistant to a plant virus or plant viroid, wherein the plant virus or plant viroid comprises the at least one target sequence that encodes the gene silencing suppressor and wherein the resistant transgenic plant shows no symptoms of infection.

2. The method of claim 1, wherein the cell is from a plant selected from the group consisting of corn, wheat, rice, barley, oats, sorghum, millet, sunflower, safflower, cotton, soy, canola, alfalfa, *Arabidopsis*, and tobacco.

3. The method of claim 1, wherein the modified miRNA is a plant miRNA modified to be fully complementary to the target sequence.

4. The method of claim 1, wherein the promoter is a pathogen-inducible promoter.

5. The method of claim 1, wherein the nucleic acid construct encodes two or more modified miRNA precursor sequences.

6. The method of claim 5, wherein the nucleic acid construct encodes a hetero-polymeric precursor miRNA or a homo-polymeric precursor miRNA.

7. The method of claim 1, wherein the nucleic acid construct is inserted into an intron of a gene or transgene of the plant cell.

8. The method of claim 3, wherein the cell is from a plant selected from the group consisting of corn, wheat, rice, barley, oats, sorghum, millet, sunflower, safflower, cotton, soy, canola, alfalfa, *Arabidopsis*, and tobacco.

9. The method of claim 2, wherein the plant miRNA is from a plant selected from the group consisting of *Arabidopsis*, tomato, soybean, rice, and corn.

10. The method of claim 3, wherein the promoter is a pathogen-inducible promoter.

11. The method of claim 3, wherein the nucleic acid construct encodes two or more modified miRNA precursor sequences.

12. The method of claim 4, wherein the nucleic acid construct encodes two or more modified miRNA precursor sequences.

13. The method of claim 1, wherein the nucleotide sequence (ii) is at least 95% identical to the nucleotide sequence of SEQ ID NO:162.

14. The method of claim 13, wherein the nucleic acid construct encodes two or more modified miRNA precursor sequences.

15. The method of claim 11, wherein the nucleic acid construct encodes a hetero-polymeric precursor miRNA or a homo-polymeric precursor miRNA.

16. The method of claim 12, wherein the nucleic acid construct encodes a hetero-polymeric precursor miRNA or a homo-polymeric precursor miRNA.

17. The method of claim 14, wherein the nucleic acid construct encodes a hetero-polymeric precursor miRNA or a homo-polymeric precursor miRNA.

18. The method of claim 3, wherein the nucleic acid construct is inserted into an intron of a gene or transgene of the cell.

19. The method of claim 4, wherein the cell is from a plant selected from the group consisting of corn, wheat, rice, barley, oats, sorghum, millet, sunflower, safflower, cotton, soy, canola, alfalfa, *Arabidopsis*, and tobacco.

20. The method of claim 4, wherein the nucleic acid construct is inserted into an intron of a gene or transgene of the cell.

21. The method of claim 5, wherein the cell is from a plant selected from the group consisting of corn, wheat, rice, barley, oats, sorghum, millet, sunflower, safflower, cotton, soy, canola, alfalfa, *Arabidopsis*, and tobacco.

22. The method of claim 6, wherein the cell is from a plant selected from the group consisting of corn, wheat, rice, barley, oats, sorghum, millet, sunflower, safflower, cotton, soy, canola, alfalfa, *Arabidopsis*, and tobacco.

23. The method of claim 5, wherein the nucleic acid construct is inserted into an intron of a gene or transgene of the cell.

24. The method of claim 7, wherein the cell is from a plant selected from the group consisting of corn, wheat, rice, barley, oats, sorghum, millet, sunflower, safflower, cotton, soy, canola, alfalfa, *Arabidopsis*, and tobacco.

25. The method of claim 13, wherein the cell is from a plant selected from the group consisting of corn, wheat, rice, barley, oats, sorghum, millet, sunflower, safflower, cotton, soy, canola, alfalfa, *Arabidopsis*, and tobacco.

26. The method of claim 13, wherein the promoter is a pathogen-inducible promoter.

27. The method of claim 13, wherein the nucleic acid construct is inserted into an intron of a gene or transgene of the cell.

28. The method of claim 8, wherein the plant miRNA is from a plant selected from the group consisting of *Arabidopsis*, tomato, soybean, rice, and corn.

29. The method of claim 19, wherein the plant miRNA is from a plant selected from the group consisting of *Arabidopsis*, tomato, soybean, rice, and corn.

30. The method of claim 21, wherein the plant miRNA is from a plant selected from the group consisting of *Arabidopsis*, tomato, soybean, rice, and corn.

31. The method of claim 22, wherein the plant miRNA is from a plant selected from the group consisting of *Arabidopsis*, tomato, soybean, rice, and corn.

32. The method of claim 24, wherein the plant miRNA is from a plant selected from the group consisting of *Arabidopsis*, tomato, soybean, rice, and corn.

33. The method of claim 25, wherein the plant miRNA is from a plant selected from the group consisting of *Arabidopsis*, tomato, soybean, rice, and corn.

* * * * *